US012758601B2

(12) United States Patent
Partlo et al.

(10) Patent No.: US 12,758,601 B2
(45) Date of Patent: Oct. 13, 2026

(54) ONCOLYTIC ADENOVIRUS WITH REPLICATION SELECTIVITY BASED ON STATUS OF P53 TRANSCRIPTIONAL ACTIVITY

(71) Applicant: Salk Institute for Biological Studies, La Jolla, CA (US)

(72) Inventors: William Partlo, San Diego, CA (US); Clodagh O'Shea, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 879 days.

(21) Appl. No.: 18/151,081

(22) Filed: Jan. 6, 2023

(65) Prior Publication Data

US 2023/0218690 A1 Jul. 13, 2023

Related U.S. Application Data

(63) Continuation of application No. PCT/US2021/040580, filed on Jul. 6, 2021.

(60) Provisional application No. 63/048,499, filed on Jul. 6, 2020.

(51) Int. Cl.
*A61K 35/761* (2015.01)
*C12N 7/00* (2006.01)

(52) U.S. Cl.
CPC .............. *A61K 35/761* (2013.01); *C12N 7/00* (2013.01); *C12N 2710/10321* (2013.01); *C12N 2710/10332* (2013.01); *C12N 2830/005* (2013.01); *C12N 2830/008* (2013.01); *C12N 2830/15* (2013.01)

(58) Field of Classification Search
None
See application file for complete search history.

(56) References Cited

U.S. PATENT DOCUMENTS

| | | | |
|---|---|---|---|
| 9,217,160 | B2 | 12/2015 | O'Shea et al. |
| 9,885,090 | B2 | 2/2018 | O'Shea et al. |
| 9,913,866 | B2 | 3/2018 | O'Shea et al. |
| 11,077,156 | B2 | 8/2021 | O'Shea et al. |
| 11,130,968 | B2 | 9/2021 | O'Shea et al. |
| 2017/0202893 | A1 | 7/2017 | O'Shea et al. |

FOREIGN PATENT DOCUMENTS

| | | | |
|---|---|---|---|
| EP | 3604548 | 2/2020 | |
| WO | WO 2002/012524 | 2/2002 | |
| WO | WO-2016049201 A1 * | 3/2016 | ............. A61P 35/00 |
| WO | WO 2017/147269 | 8/2017 | |
| WO | WO 2018/218240 | 11/2018 | |
| WO | WO 2018/220207 | 12/2018 | |
| WO | WO 2019/199859 | 10/2019 | |
| WO | WO 2022/010949 | 1/2022 | |

OTHER PUBLICATIONS

Partlo W. Engineered Adenovirus for Selective Replication in Tumors and Druggable Control of Virus Progression. https://escholarship.org/uc/item/2k3957sr, UC San Diego Electronic Theses and Dissertations. 2018. (Year: 2018).*

Shen Y, Kitzes G, Nye JA, Fattaey A, Hermiston T. Analyses of single-amino-acid substitution mutants of adenovirus type 5 E1B-55K protein. J Virol. May 2001;75(9):4297-307. (Year: 2001).*

Email and metadata from UC San Diego Library evidencing the embargo of: Partlo, "Engineered Adenovirus for Selective Replication in Tumors and Druggable Control of Virus Progress," Dissertation, University of California San Diego, ProQuest ID: Partlo_ucsd_0033D_17604, 2018, until Jun. 30, 2021 (2 pages).

Howe et al., "Matching complementing functions of transformed cells with stable expression of selected viral genes for production of E1-deleted adenovirus vectors," *Virology* 345:220-230, 2005.

Yew et al., "Adenovirus E1B oncoprotein tethers a transcriptional repression domain to p53," *Genes Dev* 8(2):190-202, 1994.

Gossen and Bujard, "Tight control of gene expression in mammalian cells by tetracycline-responsive promoters," *Proc Natl Acad Sci USA*, 89:5547-5551, 1992.

Huang et al., "Oncolytic Adenovirus Programmed by Synthetic Gene Circuit for Cancer Immunotherapy," *Nature Comm*, vol. 10:1-15, 2019.

International Search Report and Written Opinion for PCT/US2021/040580, dated Sep. 8, 2021, 9 pages.

International Search Report and Written Opinion for PCT/US2021/040586, dated Oct. 6, 2021, 11 pages.

Lyer et al., "Two-step transcriptional amplification as a method for imaging reporter gene expression using weak promoters," *Proc Natl Acad Sci USA*, 98(25):14595-14600, 2001.

Partlo, "Engineered Adenovirus for Selective Replication in Tumors and Druggable Control of Virus Progress," Dissertation, University of California San Diego, ProQuest ID: Partlo_ucsd_0033D_17604, 2018, embargoed until Jul. 6, 2020.

Partlo, "Progress Toward Engineered Adenovirus for Selective Replication in Tumors and Druggable Control of Virus Progression," Oral Presentation, Jan. 26, 2018.

Zhou et al., "A New Vector System with Inducible E2a Cell Line for Production of Higher Titer and Safer Adenoviral Vectors," *Virol.*, vol. 275:348-357, 2000.

* cited by examiner

*Primary Examiner* — Nicole Kinsey White
*Assistant Examiner* — Ruixue Wang
(74) *Attorney, Agent, or Firm* — Klarquist Sparkman, LLP

(57) ABSTRACT

Oncolytic adenoviruses capable of selectively replicating in tumor cells deficient in p53 transcriptional activity are described. Recombinant adenovirus genomes that encode the p53-selective adenoviruses are also described. The recombinant adenoviruses and adenovirus genomes, or compositions thereof, can be used, for example, to reduce or inhibit tumor progression, or reduce tumor volume in a subject with a tumor having dysregulated p53 activity.

23 Claims, 16 Drawing Sheets

Specification includes a Sequence Listing.

SEQUENCE LISTING

```
Sequence total quantity: 16
SEQ ID NO: 1           moltype = DNA  length = 36299
FEATURE                Location/Qualifiers
misc_feature           1..36299
                       note = Synthetic adenovirus genome (CMBT-1065)
source                 1..36299
                       mol_type = other DNA
                       organism = synthetic construct
SEQUENCE: 1
catcatcaat aatatacctt attttggatt gaagccaata tgataatgag gggtggagt  60
ttgtgacgtg gcgcggggcg tgggaacggg gcgggtgacg tagtagtgtg gcggaagtgt  120
gatgttgcaa gtgtggcgga acacatgtaa gcgacggatg tggcaaaagt gacgtttttg  180
gtgtgcgccg gtgtacacag gaagtgacaa ttttcgcgcg gttttaggcg gatgttgtag  240
taaatttggg cgtaaccgag taagatttgg ccattttcgc gggaaaactg aataagagga  300
agtgaaatct gaataatttt gtgttactca tagcgcgtaa tatttgtcta gggccgcggg  360
gactttgacc gtttacgtgg agactcgccc aggtgttttt ctcaggtgtt ttccgcgttc  420
cgggtcaaag ttggcgtttt attattatag tcagctgacg tgtagtgtat ttatacccgg  480
tgagttcctc aagaggccac tcttgagtgc cagcgagtag agttttctcc tccgagccgc  540
tccgacaccg ggactgaaaa tgagacatat tatctgccac ggaggtgtta ttaccgaaga  600
aatggccgcc agtcttttgg accagctgat cgaagaggta ctggctgata atcttccacc  660
tcctagccat tttgaaccac ctacccttca cgaactgtat gatttagacg tgacggcccc  720
cgaagatccc aacgaggagg cggtttcgca gatttttccc gactctgtaa tgttggcggt  780
gcaggaaggg attgacttac tcacttttcc gccggcgccc ggttctccgg agccgcctca  840
cctttcccgg cagcccgagc agccggagca gagagccttg ggtccggttt ctatgccaaa  900
ccttgtaccg gaggtgatcg atcttacctg ccacgaggct ggctttccac ccagtgacga  960
cgaggatgaa gagggtgagg agtttgtgtt agattatgtg gagcaccccg ggcacggttg  1020
caggtcttgt cattatcacc ggaggaatac gggggaccca gatattatgt gttcgctttg  1080
ctatatgagg acctgtggca tgtttgtcta cagtaagtga aaattatggg cagtgggtga  1140
tagagtggtg ggtttggtgt ggtaattttt tttttaattt ttacagtttt gtggtttaaa  1200
gaattttgta ttgtgatttt tttaaaaggt cctgtgtctg aacctgagcc tgagcccgag  1260
ccagaaccgg agcctgcaag acctacccgc cgtcctaaaa tggcgcctgc tatcctgaga  1320
cgcccgacat cacctgtgtc tagagaatgc aatagtagta cggatagctg tgactccggt  1380
ccttctaaca cacctcctga gatacacccg gtggtcccgc tgtgccccat taaaccagtt  1440
gccgtgagag ttggtgggcg tcgccaggct gtggaatgta tcgaggactt gcttaacgag  1500
cctgggcaac ctttggactt gagctgtaaa cgccccaggc cataaggtgt aaacctgtga  1560
```

-continued

```
ttgcgtgtgt ggttaacgcc tttgtttgct gaatgagttg atgtaagttt aataaagggt  1620
gagataatgt ttaacttgca tggcgtgtta aatggggcgg ggcttaaagg gtatataatg  1680
cgccgtgggc taatcttggt tacatctgac ctcatggagg cttgggagtg tttggaagat  1740
ttttctgctg tgcgtaactt gctggaacag agctctaaca gtacctcttg gttttggagg  1800
tttctgtggg gctcatccca ggcaaagtta gtctgcagaa ttaaggagga ttacaagtgg  1860
gaatttgaag agcttttgaa atcctgtggt gagctgtttg attctttgaa tctgggtcac  1920
caggcgcttt tccaagagaa ggtcatcaag actttggatt tttccacacc ggggcgcgct  1980
gcggctgctg ttgctttttt gagttttata aaggataaat ggagcgaaga aacccatctg  2040
agcggggggt acctgctgga ttttctggcc atgcatctgt ggagagcggt tgtgagacac  2100
aagaatcgcc tgctactgtt gtcttccgtc cgcccggcga taataccgac ggaggagcag  2160
cagcagcagc aggaggaagc caggcggcgg cggcaggagc agagcccatg gaacccgaga  2220
gccggcctgg accctcggga atgaatgttg tacaggtggc tgaactgtat ccagaactga  2280
gacgcatttt gacaattaca gaggatgggc aggggctaaa gggggtaaag agggagcggg  2340
gggcttgtga ggctacagag gaggctagga atctagcttt tagcttaatg accagacacc  2400
gtcctgagtg tattactttt caacagatca aggataattg cgctaatgag cttgatctgc  2460
tggcgcagaa gtattccata gagcagctga ccacttactg gctgcagcca ggggatgatt  2520
ttgaggaggc tattagggta tatgcaaagg tggcacttag gccagattgc aagtacaaga  2580
tcagcaaact tgtaaatatc aggaattgtt gctacatttc tgggaacggg gccgaggtgg  2640
agatagatac ggaggatagg gtggccttta gatgtagcat gataaatatg tggccggggg  2700
tgcttggcat ggacggggtg gttattatga atgtaaggtt tactggcccc aattttagcg  2760
gtacggtttt cctggccaat accaacctta tcctacacgg tgtaagcttc tatgggttta  2820
acaatacctg tgtggaagcc tggaccgatg taagggttcg gggctgtgcc ttttactgct  2880
gctggaaggg ggtggtgtgt cgccccaaaa gcagggcttc aattaagaaa tgcctctttg  2940
aaaggtgtac cttgggtatc ctgtctgagg gtaactccag ggtgcgccac aatgtggcct  3000
ccgactgtgg ttgcttcatg ctagtgaaaa gcgtggctgt gattaagcat aacatggtat  3060
gtggcaactg cgaggacagg gcctctcaga tgctgacctg ctcggacggc aactgtcacc  3120
tgctgaagac cattcacgta gccagccact ctcgcaaggc ctggccagtg tttgagcata  3180
acatactgac ccgctgttcc ttgcatttgg gtaacaggag gggggtgttc ctaccttacc  3240
aatgcaattt gagtcacact aagatattgc ttgagcccga gagcatgtcc aaggtgaacc  3300
tgaacggggt gtttgacatg accatgaaga tctggaaggt gctgaggtac gatgagaccc  3360
gcaccaggtg cagaccctgc gagtgtggcg gtaaacatat taggaaccag cctgtgatgc  3420
tggatgtgac cgaggagctg aggcccgatc acttggtgct ggcctgcacc cgcgctgagt  3480
ttggctctag cgatgaagat acagattgag gtactgaaat gtgtgggcgt ggcttaaggg  3540
tgggaaagaa tatataaggt gggggtctta tgtagttttg tatctgtttt gcagcagccg  3600
ccgccgccca acttttctat acaaagttgt aatgagcacc aactcgtttg atggaagcat  3660
tgtgagctca tatttgacaa cgcgcatgcc cccatgggcc ggggtgcgtc agaatgtgat  3720
gggctccagc attgatggtc gccccgtcct gcccgcaaac tctactacct tgacctacga  3780
gaccgtgtct ggaacgccgt tggagactgc agcctccgcc gccgcttcag ccgctgcagc  3840
caccgcccgc gggattgtga ctgactttgc tttcctgagc ccgcttgcaa gcagtgcagc  3900
ttcccgttca tccgcccgcg atgacaagtt gacggctctt ttggcacaat tggattcttt  3960
gacccgggaa cttaatgtcg tttctcagca gctgttggat ctgcgccagc aggtttctgc  4020
cctgaaggct tcctcccctc ccaatgcggt ttaaaacata aataaaaaac cagactctgt  4080
ttggatttgg atcaagcata agtgtcttgc tgtctttatt taggggtttt gcgcgcgcgg  4140
taggcccggg accagcggtc tcggtcgttg agggtcctgt gtattttttc caggacgtgg  4200
taaaggtgac tctggatgtt cagatacatg ggcataagcc cgtctctggg gtggaggtag  4260
caccactgca gagcttcatg ctgcggggtg gtgttgtaga tgatccagtc gtagcaggag  4320
cgctgggcgt ggtgcctaaa aatgtctttc agtagcaagc tgattgccag gggcaggccc  4380
ttggtgtaag tgtttacaaa gcggttaagc tgggatgggt gcatacgtgg ggatatgaga  4440
tgcatcttgg actgtatttt taggttggct atgttcccag ccatatccct ccggggattc  4500
atgttgtgca gaaccaccag cacagtgtat ccggtgcact tgggaaattt gtcatgtagc  4560
ttagaaggaa atgcgtggaa gaacttggag acgcccttgt gacctccaag attttccatg  4620
cattcgtcca taatgatggc aatgggccca cgggcggcgg cctgggcgaa gatatttctg  4680
ggatcactaa cgtcatagtt gtgttccagg atgagatcgt cataggccat ttttacaaag  4740
cgcgggcgga gggtgccaga ctgcggtata atggttccat ccggcccagg ggcgtagtta  4800
ccctcacaga tttgcatttc ccacgctttg agttcagatg gggggatcat gtctacctgc  4860
ggggcgatga agaaaacggt ttccggggta ggggagatca gctgggaaga aagcaggttc  4920
ctgagcagct gcgacttacc gcagccggtg ggcccgtaaa tcacacctat taccgggtgc  4980
aactggtagt taagagagct gcagctgccg tcatccctga gcaggggggc cacttcgtta  5040
agcatgtccc tgactcgcat gttttccctg accaaatccg ccagaaggcg ctcgccgccc  5100
agcgatagca gttcttgcaa ggaagcaaag tttttcaacg gtttgagacc gtccgccgta  5160
ggcatgcttt tgagcgtttg accaagcagt tccaggcggt cccacagctc ggtcacctgc  5220
tctacggcat ctcgatccag catatctcct cgtttcgcgg gttggggcgg ctttcgctgt  5280
acggcagtag tcggtgctcg tccagacggg ccagggtcat gtctttccac gggcgcaggg  5340
tcctcgtcag cgtagtctgg gtcacggtga aggggtgcgc tccgggctgc gcgctggcca  5400
gggtgcgctt gaggctggtc ctgctggtgc tgaagcgctg ccggtcttcg ccctgcgcgt  5460
cggccaggta gcatttgacc atggtgtcat agtccagccc ctccgcggcg tggcccttgg  5520
cgcgcagctt gcccttggag gaggcgccgc acgaggggca gtgcagactt ttgagggcgt  5580
agagcttggg cgcgagaaat accgattccg gggagtaggc atccgcgccg caggccccgc  5640
agacggtctc gcattccacg agccaggtga gctctggccg ttcggggtca aaaaccaggt  5700
ttcccccatg ctttttgatg cgtttcttac ctctggtttc catgagccgg tgtccacgct  5760
cggtgacgaa aaggctgtcc gtgtccccgt atacagactt gagaggcctg tcctcgagcg  5820
gtgttccgcg gtcctcctcg tatagaaact cggaccactc tgagacaaag gctcgcgtcc  5880
aggccagcac gaaggaggct aagtgggagg ggtagcggtc gttgtccact agggggtcca  5940
ctcgctccag ggtgtgaaga cacatgtcgc cctcttcggc atcaaggaag gtgattggtt  6000
tgtaggtgta ggccacgtga ccgggtgttc ctgaaggggg gctataaaag gggggtgggg  6060
cgcgttcgtc ctcactctct tccgcatcgc tgtctgcgag ggccagctgt tggggtgagt  6120
actccctctg aaaagcgggc atgacttctg cgctaagatt gtcagtttcc aaaaacgagg  6180
aggatttgat attcacctgg cccgcggtga tgcctttgag ggtggccgca tccatctggt  6240
cagaaaagac aatctttttg ttgtcaagct tggtggcaaa cgacccgtag agggcgttgg  6300
```

```
acagcaactt ggcgatggag cgcagggttt ggtttttgtc gcgatcggcg cgctccttgg  6360
ccgcgatgtt tagctgcacg tattcgcgcg caacgcaccg ccattcggga aagacggtgg  6420
tgcgctcgtc gggcaccagg tgcacgcgcc aaccgcggtt gtgcagggtg acaaggtcaa  6480
cgctggtggc tacctctccg cgtaggcgct cgttggtcca gcagaggcgg ccgcccttgc  6540
gcgagcagaa tggcggtagg gggtctagct gcgtctcgtc cggggggtct gcgtccacgg  6600
taaagacccc gggcagcagg cgcgcgtcga agtagtctat cttgcatcct tgcaagtcta  6660
gcgcctgctg ccatgcgcgg gcggcaagcg cgcgctcgta tgggttgagt gggggacccc  6720
atggcatggg gtgggtgagc gcggaggcgt acatgccgca aatgtcgtaa acgtagaggg  6780
gctctctgag tattccaaga tatgtagggt agcatcttcc accgcggatg ctggcgcgca  6840
cgtaatcgta tagttcgtgc gagggagcga ggaggtcggg accgaggttg ctacgggcgg  6900
gctgctctgc tcggaagact atctgcctga agatggcatg tgagttggat gatatggttg  6960
gacgctggaa gacgttgaag ctggcgtctg tgagacctac cgcgtcacgc acgaaggagg  7020
cgtaggagtc gcgcagcttg ttgaccagct cggcggtgac ctgcacgtct agggcgcagt  7080
agtccagggt ttccttgatg atgtcatact tatcctgtcc cttttttttc cacagctcgc  7140
ggttgaggac aaactcttcg cggtctttcc agtactcttg gatcggaaac ccgtcggcct  7200
ccgaacggta agagcctagc atgtagaact ggttgacggc ctggtaggcg cagcatccct  7260
tttctacggg tagcgcgtat gcctgcgcgg ccttccggag cgaggtgtgg gtgagcgcaa  7320
aggtgtccct gaccatgact ttgaggtact ggtatttgaa gtcagtgtcg tcgcatccgc  7380
cctgctccca gagcaaaaag tccgtgcgct ttttggaacg cggatttggc agggcgaagg  7440
tgacatcgtt gaagagtatc tttcccgcgc gaggcataaa gttgcgtgtg atgcggaagg  7500
gtcccggcac ctcggaacgg ttgttaatta cctgggcggc gagcacgatc tcgtcaaagc  7560
cgttgatgtt gtggcccaca atgtaaagtt ccaagaagcg cgggatgccc ttgatggaag  7620
gcaatttttt aagttcctcg taggtgagct cttcagggga gctgagcccg tgctctgaaa  7680
gggcccagtc tgcaagatga gggttggaag cgacgaatga gctccacagg tcacgggcca  7740
ttagcatttg caggtggtcg cgaaaggtcc taaactggcg acctatggcc atttttctg  7800
gggtgatgca gtagaaggta agcgggtctt gttcccagcg gtcccatcca aggttcgcgg  7860
ctaggtctcg cgcggcagtc actagaggct catctccgcc gaacttcatg accagcatga  7920
agggcacgag ctgcttccca aaggccccca tccaagtata ggtctctaca tcgtaggtga  7980
caaagagacg ctcggtgcga ggatgcgagc cgatcgggaa gaactggatc tcccgccacc  8040
aattggagga gtggctattg atgtggtgaa agtagaagtc cctgcgacgg gccgaacact  8100
cgtgctggct tttgtaaaaa cgtgcgcagt actggcagcg gtgcacgggc tgtacatcct  8160
gcacgaggtt gacctgacga ccgcgcacaa ggaagcagag tgggaatttg agcccctcgc  8220
ctggcgggtt tggctggtgg tcttctactt cggctgcttg tccttgaccg tctggctgct  8280
cgaggggagt tacggtggat cggaccacca cgccgcgcga gcccaaagtc cagatgtccg  8340
cgcgcggcgg tcggagcttg atgacaacat cgcgcagatg ggagctgtcc atggtctgga  8400
gctcccgcgg cgtcaggtca ggcgggagct cctgcaggtt tacctcgcat agacgggtca  8460
gggcgcgggc tagatccagg tgatacctaa tttccagggg ctggttggtg gcggcgtcga  8520
tggcttgcaa gaggccgcat ccccgcggcg cgactacggt accgcgcggc gggcggtggg  8580
ccgcgggggt gtccttggat gatgcatcta aaagcggtga cgcgggcgag cccccggagg  8640
taggggggc tccggacccg ccgggagagg gggcaggggc acgtcggcgc cgcgcgcggg  8700
caggagctgg tgctgcgcgc gtaggttgct ggcgaacgcg acgacgcggc ggttgatctc  8760
ctgaatctgg cgcctctgcg tgaagacgac gggcccggtg agcttgagcc tgaaagagag  8820
ttcgacagaa tcaatttcgg tgtcgttgac ggcggcctgg cgcaaaatct cctgcacgtc  8880
tcctgagttg tcttgatagg cgatctcggc catgaactgc tcgatctctt cctcctggag  8940
atctccgcgt ccggctcgct ccacggtggc ggcgaggtcg ttggaaatgc gggccatgag  9000
ctgcgagaag gcgttgaggc ctccctcgtt ccagacgcgg ctgtagacca cgcccccttc  9060
ggcatcgcgg gcgcgcatga ccacctgcgc gagattgagc tccacgtgcc gggcgaagac  9120
ggcgtagttt cgcaggcgct gaaagaggta gttgagggtg gtggcggtgt gttctgccac  9180
gaagaagtac ataacccagc gtcgcaacgt ggattcgttg atatccccca aggcctcaag  9240
gcgctccatg gcctcgtaga agtccacggc gaagttgaaa aactgggagt tgcgcgccga  9300
cacggttaac tcctcctcca gaagacggat gagctcggcg acagtgtcgc gcacctcgcg  9360
ctcaaaggct acaggggcct cttcttcttc ttcaatctcc tcttccataa gggcctcccc  9420
ttcttcttct tctggcggcg gtgggggagg ggggacacgg cggcgacgac ggcgcaccgg  9480
gaggcggtcg acaaagcgct cgatcatctc cccgcggcga cggcgcatgg tctcggtgac  9540
ggcgcggccg ttctcgcggg ggcgcagttg gaagacgccg cccgtcatgt cccggttatg  9600
ggttggcggg gggctgccat gcggcaggga tacggcgcta acgatgcatc tcaacaattg  9660
ttgtgtaggt actccgccgc cgagggacct gagcgagtcc gcatcgaccg gatcggaaaa  9720
cctctcgaga aaggcgtcta accagtcaca gtcgcaaggt aggctgagca ccgtggcggg  9780
cggcagcggg cggcggtcgg ggttgtttct ggcggaggtg ctgctgatga tgtaattaaa  9840
gtaggcggtc ttgagacggc ggatggtcga cagaagcacc atgtccttgg gtccggcctg  9900
ctgaatgcgc aggcggtcgg ccatgcccca ggcttcgttt tgacatcggc gcaggtcttt  9960
gtagtagtct tgcatgagcc tttctaccgg cacttcttct tctccttcct cttgtcctgc  10020
atctcttgca tctatcgctg cggcggcggc ggagtttggc cgtaggtggc gccctcttcc  10080
tcccatgcgt gtgaccccga agcccctcat cggctgaagc agggctaggt cggcgacaac  10140
gcgctcggct aatatggcct gctgcacctg cgtgagggta gactggaagt catccatgtc  10200
cacaaagcgg tggtatgcgc ccgtgttgat ggtgtaagtg cagttggcca taacggacca  10260
gttaacggtc tggtgacccg gctgcgagag ctcggtgtac ctgagacgcg agtaagccct  10320
cgagtcaaat acgtagtcgt tgcaagtccg caccaggtac tggtatccca ccaaaaagtg  10380
cggcggcggc tggcggtaga ggggccagcg tagggtggcc ggggctccgg gggcgagatc  10440
ttccaacata aggcgatgat atccgtagat gtacctggac atccaggtga tgccggcggc  10500
ggtggtggag gcgcgcggaa agtcgcggac gcggttccag atgttgcgca gcggcaaaaa  10560
gtgctccatg gtcgggacgc tctggccggt caggcgcgcg caatcgttga cgctctagac  10620
cgtgcaaaag gagagcctgt aagcgggcac tcttccgtgg tctggtggat aaattcgcaa  10680
gggtatcatg gcggacgacc ggggttcgag ccccgtatcc ggccgtccgc cgtgatccat  10740
gcggttaccg cccgcgtgtc gaacccaggt gtgcgacgtc agacaacggg ggagtgctcc  10800
ttttggcttc cttccaggcg cggcggctgc tgcgctagct tttttggcca ctggccgcgc  10860
gcagcgtaag cggttaggct ggaaagcgaa agcattaagt ggctcgctcc ctgtagccgg  10920
agggttattt tccaagggtt gagtcgcggg acccccggtt cgagtctcgg accggccgga  10980
ctgcggcgaa cgggggtttg cctccccgtc atgcaagacc ccgcttgcaa attcctccgg  11040
```

-continued

```
aaacagggac gagccccttt tttgcttttc ccagatgcat ccggtgctgc ggcagatgcg  11100
ccccccctcct cagcagcggc aagagcaaga gcagcggcag acatgcaggg caccctcccc  11160
tcctcctacc gcgtcaggag gggcgacatc cgcggttgac gcggcagcag atggtgatta  11220
cgaacccccg cggcgccggg cccggcacta cctggacttg gaggagggcg agggcctggc  11280
gcggctagga gcgccctctc ctgagcggta cccaagggtg cagctgaagc gtgatacgcg  11340
tgaggcgtac gtgccgcggc agaacctgtt tcgcgaccgc gagggagagg agcccgagga  11400
gatgcgggat cgaaagttcc acgcagggcg cgagctgcgg catggcctga atcgcgagcg  11460
gttgctgcgc gaggaggact ttgagcccga cgcgcgaacc gggattagtc ccgcgcgcgc  11520
acacgtggcg gccgccgacc tggtaaccgc atacgagcag acggtgaacc aggagattaa  11580
ctttcaaaaa agctttaaca accacgtgcg tacgcttgtg gcgcgcgagg aggtggctat  11640
aggactgatg catctgtggg actttgtaag cgcgctggag caaaacccaa atagcaagcc  11700
gctcatggcg cagctgttcc ttatagtgca gcacagcagg gacaacgagg cattcaggga  11760
tgcgctgcta aacatagtag agcccgaggg ccgctggctg ctcgatttga taaacatcct  11820
gcagagcata gtggtgcagg agcgcagctt gagcctggct gacaaggtgg ccgccatcaa  11880
ctattccatg cttagcctgg gcaagtttta cgcccgcaag atataccata ccccttacgt  11940
tcccatagac aaggaggtaa agatcgaggg gttctacatg cgcatggcgc tgaaggtgct  12000
taccttgagc gacgacctgg gcgtttatcg caacgagcgc atccacaagg ccgtgagcgt  12060
gagccggcgg cgcgagctca gcgaccgcga gctgatgcac agcctgcaaa gggccctggc  12120
tggcacgggc agcggcgata gagaggccga gtcctacttt gacgcgggcg ctgacctgcg  12180
ctgggcccca agccgacgcg ccctggaggc agctggggcc ggacctgggc tggcggtggc  12240
acccgcgcgc gctggcaacg tcggcggcgt ggaggaatat gacgaggacg atgagtacga  12300
gccagaggac ggcgagtact aagcggtgat gtttctgatc agatgatgca agacgcaacg  12360
gacccggcgg tgcgggcggc gctgcagagc cagccgtccg gccttaactc cacggacgac  12420
tggcgccagg tcatggaccg catcatgtcg ctgactgcgc gcaatcctga cgcgttccgg  12480
cagcagccgc aggccaaccg gctctccgca attctggaag cggtggtccc ggcgcgcgca  12540
aaccccacgc acgagaaggt gctggcgatc gtaaacgcgc tggccgaaaa cagggccatc  12600
cggcccgacg aggccggcct ggtctacgac gcgctgcttc agcgcgtggc tcgttacaac  12660
agcggcaacg tgcagaccaa cctggaccgg ctggtggggg atgtgcgcga ggccgtggcg  12720
cagcgtgagc gcgcgcagca gcagggcaac ctgggctcca tggttgcact aaacgccttc  12780
ctgagtacac agcccgccaa cgtgccgcgg ggacaggagg actacaccaa ctttgtgagc  12840
gcactgcggc taatggtgac tgagacaccg caaagtgagg tgtaccagtc tgggccagac  12900
tattttttcc agaccagtag acaaggcctg cagaccgtaa acctgagcca ggctttcaaa  12960
aacttgcagg ggctgtgggg ggtgcgggct cccacaggcg accgcgcgac cgtgtctagc  13020
ttgctgacgc ccaactcgcg cctgttgctg ctgctaatag cgcccttcac ggacagtggc  13080
agcgtgtccc gggacacata cctaggtcac ttgctgacac tgtaccgcga ggccataggt  13140
caggcgcatg tggacgagca tactttccag gagattacaa gtgtcagccg cgcgctgggg  13200
caggaggaca cgggcagcct ggaggcaacc ctaaactacc tgctgaccaa ccggcggcag  13260
aagatcccct cgttgcacag tttaaacagc gaggaggagc gcattttgcg ctacgtgcag  13320
cagagcgtga gccttaacct gatgcgcgac ggggtaacgc ccagcgtggc gctggacatg  13380
accgcgcgca acatggaacc gggcatgtat gcctcaaacc ggccgtttat caaccgccta  13440
atggactact tgcatcgcgc ggccgccgtg aaccccgagt atttcaccaa tgccatcttg  13500
aacccgcact ggctaccgcc ccctggtttc tacaccgggg gattcgaggt gcccgagggt  13560
aacgatggat tcctctggga cgacatagac gacagcgtgt tttccccgca accgcagacc  13620
ctgctagagt tgcaacagcg cgagcaggca gaggcggcgc tgcgaaagga aagcttccgc  13680
aggccaagca gcttgtccga tctaggcgct gcggccccgc ggtcagatgc tagtagccca  13740
tttccaagct tgatagggtc tcttaccagc actcgcacca cccgcccgcg cctgctgggc  13800
gaggaggagt acctaaacaa ctcgctgctg cagccgcagc gcgaaaaaaa cctgcctccg  13860
gcatttccca acaacgggat agagagccta gtggacaaga tgagtagatg gaagacgtac  13920
gcgcaggagc acagggacgt gccaggcccg cgcccgccca cccgtcgtca aaggcacgac  13980
cgtcagcggg gtctggtgtg ggaggacgat gactcggcag acgacagcag cgtcctggat  14040
ttgggaggga gtggcaaccc gtttgcgcac cttcgcccca ggctggggag aatgttttaa  14100
aaaaaaaaaa gcatgatgca aaataaaaaa ctcaccaagg ccatggcacc gagcgttggt  14160
tttcttgtat tccccttagt atgcggcgcg cggcgatgta tgaggaaggt cctcctccct  14220
cctacgagag tgtggtgagc gcggcgccag tggcggcggc gctgggttct cccttcgatg  14280
ctcccctgga cccgccgttt gtgcctccgc ggtacctgcg gcctaccggg gggagaaaca  14340
gcatccgtta ctctgagttg gcacccctat tcgacaccac ccgtgtgtac ctggtggaca  14400
acaagtcaac ggatgtggca tccctgaact accagaacga ccacagcaac tttctgacca  14460
cggtcattca aaacaatgac tacagcccgg gggaggcaag cacacagacc atcaatcttg  14520
acgaccggtc gcactggggc ggcgacctga aaaccatcct gcataccaac atgccaaatg  14580
tgaacgagtt catgtttacc aataagttta aggcgcgggt gatggtgtcg cgcttgccta  14640
ctaaggacaa tcaggtggag ctgaaatacg agtgggtgga gttcacgctg cccgagggca  14700
actactccga gaccatgacc atagacctta tgaacaacgc gatcgtggag cactacttga  14760
aagtgggcag acagaacggg gttctggaaa gcgacatcgg ggtaaagttt gacacccgca  14820
acttcagact ggggtttgac cccgtcactg gtcttgtcat gcctggggta tatacaaacg  14880
aagccttcca tccagacatc attttgctgc caggatgcgg ggtggacttc acccacagcc  14940
gcctgagcaa cttgttgggc atccgcaagc ggcaaccctt ccaggagggc tttaggatca  15000
cctacgatga tctggagggt ggtaacattc ccgcactgtt ggatgtggac gcctaccagg  15060
cgagcttgaa agatgacacc gaacagggcg ggggtggcgc aggcggcagc aacagcagtg  15120
gcagcggcgc ggaagagaac tccaacgcgg cagccgcggc aatgcagccg gtggaggaca  15180
tgaacgatca tgccattcgc ggcgacacct ttgccacacg ggctgaggag aagcgcgctg  15240
aggccgaagc agcggccgaa gctgccgccc ccgctgcgca acccgaggtc gagaagcctc  15300
agaagaaacc ggtgatcaaa cccctgacag aggacagcaa gaaacgcagt tacaacctaa  15360
taagcaatga cagcaccttc acccagtacc gcagctggta ccttgcatac aactacggcg  15420
accctcagac cggaatccgc tcatggaccc tgctttgcac tcctgacgta acctgcggct  15480
cggagcaggt ctactggtcg ttgccagaca tgatgcaaga ccccgtgacc ttccgctcca  15540
cgcgccagat cagcaacttt ccggtggtgg gcgccgagct gttgcccgtg cactccaaga  15600
gcttctacaa cgaccaggcc gtctactccc aactcatccg ccagtttacc tctctgaccc  15660
acgtgttcaa tcgctttccc gagaaccaga ttttggcgcg cccgccagcc cccaccatca  15720
ccaccgtcag tgaaaacgtt cctgctctca cagatcacgg gacgctaccg ctgcgcaaca  15780
```

-continued

```
gcatcggagg agtccagcga gtgaccatta ctgacgccag acgccgcacc tgcccctacg  15840
tttacaaggc cctgggcata gtctcgccgc gcgtcctatc gagccgcact ttttgagcaa  15900
gcatgtccat ccttatatcg cccagcaata acacaggctg gggcctgcgc ttcccaagca  15960
agatgtttgg cggggccaag aagcgctccg accaacaccc agtgcgcgtg cgcgggcact  16020
accgcgcgcc ctggggcgcg cacaaacgcg gccgcactgg gcgcaccacc gtcgatgacg  16080
ccatcgacgc ggtggtggag gaggcgcgca actacacgcc cacgccgcca ccagtgtcca  16140
cagtggacgc ggccattcag accgtggtgc gcggagcccg gcgctatgct aaaatgaaga  16200
gacggcggag gcgcgtagca cgtcgccacc gccgccgacc cggcactgcc gcccaacgcg  16260
cggcggcggc cctgcttaac cgcgcacgtc gcaccggccg acgggcggcc atgcgggccg  16320
ctcgaaggct ggccgcgggt attgtcactg tgccccccag gtccaggcga cgagcggccg  16380
ccgcagcagc cgcggccatt agtgctatga ctcagggtcg caggggcaac gtgtattggg  16440
tgcgcgactc ggttagcggc ctgcgcgtgc ccgtgcgcac ccgcccccog cgcaactaga  16500
ttgcaagaaa aaactactta gactcgtact gttgtatgta tccagcggcg gcggcgcgca  16560
acgaagctat gtccaagcgc aaaatcaaag aagagatgct ccaggtcatc gcgccggaga  16620
tctatggccc cccgaagaag gaagagcagg attacaagcc ccgaaagcta aagcgggtca  16680
aaaagaaaaa gaaagatgat gatgatgaac ttgacgacga ggtggaactg ctgcacgcta  16740
ccgcgcccag gcgacgggta cagtggaaag gtcgacgcgt aaaacgtgtt ttgcgacccg  16800
gcaccaccgt agtctttacg cccggtgagc gctccacccg cacctacaag cgcgtgtatg  16860
atgaggtgta cggcgacgag gacctgcttg agcaggccaa cgagcgcctc ggggagtttg  16920
cctacggaaa gcggcataag gacatgctgg cgttgccgct ggacgagggc aacccaacac  16980
ctagcctaaa gcccgtaaca ctgcagcagg tgctgcccgc gcttgcaccg tccgaagaaa  17040
agcgcggcct aaagcgcgag tctggtgact tggcacccac cgtgcagctg atggtaccca  17100
agcgccagcg actggaagat gtcttggaaa aaatgaccgt ggaacctggg ctggagcccg  17160
aggtccgcgt gcggccaatc aagcaggtgg cgccgggact gggcgtgcag accgtggacg  17220
ttcagatacc cactaccagt agcaccagta ttgccaccgc cacagagggc atggagacac  17280
aaacgtcccc ggttgcctca gcggtggcgg atgccgcggt gcaggcggtc gctgcggccg  17340
cgtccaagac ctctacggag gtgcaaacgg acccgtggat gtttcgcgtt tcagcccccc  17400
ggcgcccgcg cggttcgagg aagtacggcg ccgccagcgc gctactgccc gaatatgccc  17460
tacatccttc cattgcgcct acccccggct atcgtggcta cacctaccgc cccagaagac  17520
gagcaactac ccgacgccga accaccactg gaacccgccg ccgccgtcgc cgtcgccagc  17580
ccgtgctggc cccgatttcc gtgcgcaggg tggctcgcga aggaggcagg accctggtgc  17640
tgccaacagc gcgctaccac cccagcatcg tttaaaagcc ggtctttgtg gttcttgcag  17700
atatggccct cacctgccgc ctccgtttcc cggtgccggg attccgagga agaatgcacc  17760
gtaggagggg catggccggc cacggcctga cgggcggcat gcgtcgtgcg caccaccggc  17820
ggcggcgcgc gtcgcaccgt cgcatgcgcg gcggtatcct gcccctcctt attccactga  17880
tcgccgcggc gattggcgcc gtgcccggaa ttgcatccgt ggccttgcag gcgcagagac  17940
actgattaaa aacaagttgc atgtggaaaa atcaaaataa aaagtctgga ctctcacgct  18000
cgcttggtcc tgtaactatt ttgtagaatg gaagacatca actttgcgtc tctggccccg  18060
cgacacggct cgcgcccgtt catgggaaac tggcaagata tcggcaccag caatatgagc  18120
ggtggcgcct tcagctgggg ctcgctgtgg agcggcatta aaaatttcgg ttccaccgtt  18180
aagaactatg gcagcaaggc ctggaacagc agcacaggcc agatgctgag ggataagttg  18240
aaagagcaaa atttccaaca aaaggtggta gatggcctgg cctctggcat tagcggggtg  18300
gtggacctgg ccaaccaggc agtgcaaaat aagattaaca gtaagcttga tccccgccct  18360
cccgtagagg agcctccacc ggccgtggag acagtgtctc cagaggggcg tggcgaaaag  18420
cgtccgcgcc ccgacaggga agaaactctg gtgacgcaaa tagacgagcc tccctcgtac  18480
gaggaggcac taaagcaagg cctgcccacc acccgtccca tcgcgcccat ggctaccgga  18540
gtgctgggcc agcacacacc cgtaacgctg gacctgcctc cccccgccga cacccagcag  18600
aaacctgtgc tgccaggccc gaccgccgtt gttgtaaccc gtcctagccg cgcgtccctg  18660
cgccgcgccg ccagcggtcc gcgatcgttg cggcccgtag ccagtggcaa ctggcaaagc  18720
acactgaaca gcatcgtggg tctgggggtg caatccctga agcgccgacg atgcttctga  18780
atagctaacg tgtcgtatgt gtgtcatgta tgcgtccatg tcgccgccag aggagctgct  18840
gagccgccgc gcgcccgctt tccaagatgg ctaccccttc gatgatgccg cagtggtctt  18900
acatgcacat ctcgggccag gacgcctcgg agtacctgag ccccgggctg gtgcagtttg  18960
cccgcgccac cgagacgtac ttcagcctga ataacaagtt tagaaacccc acggtggcgc  19020
ctacgcacga cgtgaccaca gaccggtccc agcgtttgac gctgcggttc atccctgtgg  19080
accgtgagga tactgcgtac tcgtacaagg cgcggttcac cctagctgtg ggtgataacc  19140
gtgtgctgga catggcttcc acgtactttg acatccgcgg cgtgctggac aggggcccta  19200
cttttaagcc ctactctggc actgcctaca acgccctggc tcccaagggt gccccaaatc  19260
cttgcgaatg ggatgaagct gctactgctc ttgaaataaa cctagaagaa gaggacgatg  19320
acaacgaaga cgaagtagac gagcaagctg agcagcaaaa aactcacgta tttgggcagg  19380
cgccttattc tggtataaat attacaaagg agggtattca aataggtgtc gaaggtcaaa  19440
cacctaaata tgccgataaa acatttcaac ctgaacctca aataggagaa tctcagtggt  19500
acgaaactga aattaatcat gcagctggga gagtccttaa aaagactacc ccaatgaaac  19560
catgttacgg ttcatatgca aaacccacaa atgaaaatgg agggcaaggc attcttgtaa  19620
agcaacaaaa tggaaagcta gaaagtcaag tggaaatgca atttttctca actactgagg  19680
cgaccgcagg caatggtgat aacttgactc ctaaagtggt attgtacagt gaagatgtag  19740
atatagaaac cccagacact catatttctt acatgcccac tattaaggaa ggtaactcac  19800
gagaactaat gggccaacaa tctatgccca acaggcctaa ttacattgct tttaggaca  19860
attttattgg tctaatgtat tacaacagca cgggtaatat gggtgttctg gcgggccaag  19920
catcgcagtt gaatgctgtt gtagatttgc aagacagaaa cacagagctt tcataccagc  19980
ttttgcttga ttccattggt gatagaacca ggtacttttc tatgtggaat caggctgttg  20040
acagctatga tccagatgtt agaattattg aaaatcatgg aactgaagat gaacttccaa  20100
attactgctt tccactggga ggtgtgatta atacagagac tcttaccaag gtaaaaccta  20160
aaacaggtca ggaaaatgga tgggaaaaag atgctacaga attttcagat aaaaatgaaa  20220
taagagttgg aaataatttt gccatggaaa tcaatctaaa tgccaacctg tggagaaatt  20280
tcctgtactc caacatagcg ctgtatttgc ccgacaagct aaagtacagt ccttccaacg  20340
taaaaatttc tgataaccca aacacctacg actacatgaa caagcgagtg gtggctcccg  20400
ggttagtgga ctgctacatt aaccttggag cacgctggtc ccttgactat atggacaacg  20460
tcaacccatt taaccaccac cgcaatgctg gcctgcgcta ccgctcaatg ttgctgggca  20520
```

-continued

```
atggtcgcta tgtgcccttc cacatccagg tgcctcagaa gttctttgcc attaaaaacc  20580
tccttctcct gccgggctca tacacctacg agtggaactt caggaaggat gttaacatgg  20640
ttctgcagag ctccctagga aatgacctaa gggttgacgg agccagcatt aagtttgata  20700
gcatttgcct ttacgccacc ttcttcccca tggcccacaa caccgcctcc acgcttgagg  20760
ccatgcttag aaacgacacc aacgaccagt cctttaacga ctatctctcc gccgccaaca  20820
tgctctaccc tatacccgcc aacgctacca acgtgcccat atccatcccc tcccgcaact  20880
gggcggcttt ccgcggctgg gccttcacgc gccttaagac taaggaaacc ccatcactgg  20940
gctcgggcta cgacccttat tacacctact ctggctctat accctaccta gatggaacct  21000
tttacctcaa ccacaccttt aagaaggtgg ccattacctt tgactcttct gtcagctggc  21060
ctggcaatga ccgcctgctt acccccaacg agtttgaaat taagcgctca gttgacgggg  21120
agggttacaa cgttgcccag tgtaacatga ccaaagactg gttcctggta caaatgctag  21180
ctaactataa cattggctac cagggcttct atatcccaga gagctacaag gaccgcatgt  21240
actccttctt tagaaacttc cagcccatga gccgtcaggt ggtggatgat actaaataca  21300
aggactacca acaggtgggc atcctacacc aacacaacaa ctctggattt gttggctacc  21360
ttgcccccac catgcgcgaa ggacaggcct accctgctaa cttcccctat ccgcttatag  21420
gcaagaccgc agttgacagc attacccaga aaaagtttct ttgcgatcgc accctttggc  21480
gcatcccatt ctccagtaac tttatgtcca tgggcgcact cacagacctg ggccaaaacc  21540
ttctctacgc caactccgcc cacgcgctag acatgacttt tgaggtggat cccatggacg  21600
agcccaccct tctttatgtt ttgtttgaag tctttgacgt ggtccgtgtg caccagccgc  21660
accgcggcgt catcgaaacc gtgtacctgc gcacgccctt ctcggccggc aacgccacaa  21720
cataaagaag caagcaacat caacaacagc tgccgccatg ggctccagtg agcaggaact  21780
gaaagccatt gtcaaagatc ttggttgtgg gccatatttt ttgggcacct atgacaagcg  21840
ctttccaggc tttgtttctc cacacaagct cgcctgcgcc atagtcaata cggccggtcg  21900
cgagactggg ggcgtacact ggatggcctt tgcctggaac ccgcactcaa aaacatgcta  21960
cctctttgag ccctttggct tttctgacca gcgactcaag caggtttacc agtttgagta  22020
cgagtcactc ctgcgccgta gcgccattgc ttcttccccc gaccgctgta taacgctgga  22080
aaagtccacc caaagcgtac aggggcccaa ctcggccgcc tgtggactat tctgctgcat  22140
gtttctccac gcctttgcca actggcccca aactcccatg gatcacaacc ccaccatgaa  22200
ccttattacc ggggtaccca actccatgct caacagtccc caggtacagc ccaccctgcg  22260
tcgcaaccag gaacagctct acagcttcct ggagcgccac tcgccctact tccgcagcca  22320
cagtgcgcag attaggagcg ccacttcttt ttgtcacttg aaaaacatgt aaaaataatg  22380
tactagagac actttcaata aaggcaaatg cttttatttg tacactctcg ggtgattatt  22440
tacccccacc cttgccgtct gcgccgtttc cttctcctat aggcagaaaa agatcatgga  22500
gtcagtcgag aagaaggaca gcctaaccgc cccctctgag ttcgccacca ccgcctccac  22560
cgatgccgcc aacgcgccta ccaccttccc cgtcgaggca cccccgcttg aggaggagga  22620
agtgattatc gagcaggacc caggttttgt aagcgaagac gacgaggacc gctcagtacc  22680
aacagaggat aaaaagcaag accaggacaa cgcagaggca aacgaggaac aagtcgggcg  22740
gggggacgaa aggcatggcg actacctaga tgtgggagac gacgtgctgt tgaagcatct  22800
gcagcgccag tgcgccatta tctgcgacgc gttgcaagag cgcagcgatg tgcccctcgc  22860
catagcggat gtcagccttg cctacgaacg ccacctattc tcaccgcgcg taccccccaa  22920
acgccaagaa aacggcacat gcgagcccaa cccgcgcctc aacttctacc ccgtatttgc  22980
cgtgccagag gtgcttgcca cctatcacat ctttttccaa aactgcaaga tacccctatc  23040
ctgccgtgcc aaccgcagcc gagcggacaa gcagctggcc ttgcggcagg gcgctgtcat  23100
acctgatatc gcctcgctca acgaagtgcc aaaaatcttt gagggtcttg gacgcgacga  23160
gaagcgcgcg gcaaacgctc tgcaacagga aaacagcgaa aatgaaagtc actctggagt  23220
gttggtggaa ctcgagggtg acaacgcgcg cctagccgta ctaaaacgca gcatcgaggt  23280
cacccacttt gcctacccgg cacttaacct acccccccaag gtcatgagca cagtcatgag  23340
tgagctgatc gtgcgccgtg cgcagcccct ggagagggat gcaaatttgc aagaacaaac  23400
agaggagggc ctacccgcag ttggcgacga gcagctagcg cgctggcttc aaacgcgcga  23460
gcctgccgac ttggaggagc gacgcaaact aatgatggcc gcagtgctcg ttaccgtgga  23520
gcttgagtgc atgcagcggt tctttgctga cccggagatg cagcgcaagc tagaggaaac  23580
attgcactac acctttcgac agggctacgt acgccaggcc tgcaagatct ccaacgtgga  23640
gctctgcaac ctggtctcct accttggaat tttgcacgaa aaccgccttg ggcaaaacgt  23700
gcttcattcc acgctcaagg gcgaggcgcg ccgcgactac gtccgcgact gcgtttactt  23760
atttctatgc tacacctggc agacggccat gggcgtttgg cagcagtgct tggaggagtg  23820
caacctcaag gagctgcaga aactgctaaa gcaaaacttg aaggacctat ggacggcctt  23880
caacgagcgc tccgtggccg cgcacctggc ggacatcatt ttccccgaac gcctgcttaa  23940
aaccctgcaa cagggtctgc cagacttcac cagtcaaagc atgttgcaga actttaggaa  24000
ctttatccta gagcgctcag gaatcttgcc cgccacctgc tgtgcacttc ctagcgactt  24060
tgtgcccatt aagtaccgcg aatgccctcc gccgctttgg ggccactgct accttctgca  24120
gctagccaac taccttgcct accactctga cataatggaa gacgtgagcg gtgacggtct  24180
actggagtgt cactgtcgct gcaacctatg caccccgcac cgctccctgg tttgcaattc  24240
gcagctgctt aacgaaagtc aaattatcgg tacctttgag ctgcagggtc cctcgcctga  24300
cgaaaagtcc gcggctccgg ggttgaaact cactccgggg ctgtggacgt cggcttacct  24360
tcgcaaattt gtacctgagg actaccacgc ccacgagatt aggttctacg aagaccaatc  24420
ccgcccgcct aatgcggagc ttaccgcctg cgtcattacc cagggccaca ttcttggcca  24480
attgcaagcc atcaacaaag cccgccaaga gtttctgcta cgaaagggac gggggggttta  24540
cttggacccc cagtccggcg aggagctcaa cccaatcccc ccgccgccgc agccctatca  24600
gcagcagccg cgggcccttg cttcccagga tggcacccaa aaagaagctg cagctgccgc  24660
cgccacccac ggacgaggag gaatactggg acagtcaggc agaggaggtt ttggacgagg  24720
aggaggagga catgatggaa gactgggaga gcctagacga ggaagcttcc gaggtcgaag  24780
aggtgtcaga cgaaacaccg tcaccctcgg tcgcattccc ctcgccggcg ccccagaaat  24840
cggcaaccgg ttccagcatg gctacaacct ccgctcctca ggcgccgccg gcactgcccg  24900
ttcgccgacc caaccgtaga tgggacacca ctggaaccag ggccggtaag tccaagcagc  24960
cgccgccgtt agcccaagag caacaacagc gccaaggcta ccgctcatgg cgcgggcaca  25020
agaacgccat agttgcttgc ttgcaagact gtgggggcaa catctccttc gcccgccgct  25080
ttcttctcta ccatcacggc gtggccttcc cccgtaacat cctgcattac taccgtcatc  25140
tctacagccc atactgcacc ggcggcagcg gcagcaacag cagcggccac acagaagcaa  25200
aggcgaccgg atagcaagac tctgacaaag cccaagaaat ccacagcggc ggcagcagca  25260
```

```
ggaggaggag cgctgcgtct ggcgcccaac gaacccgtat cgacccgcga gcttagaaac  25320
aggatttttc ccactctgta tgctatattt caacagagca ggggccaaga acaagagctg  25380
aaaataaaaa acaggtctct gcgatccctc acccgcagct gcctgtatca caaaagcgaa  25440
gatcagcttc ggcgcacgct ggaagacgcg gaggctctct tcagtaaata ctgcgcgctg  25500
actcttaagg actagtttcg cgccctttct caaatttaag cgcgaaaact acgtcatctc  25560
cagcggccac acccggcgcc agcacctgtc gtcagcgcca tttcaacttt gtatacaaaa  25620
gttgtgatga gcaaggaaat tcccacgccc tacatgtgga gttaccagcc acaaatggga  25680
cttgcggctg gagctgccca agactactca acccgaataa actacatgag cgcgggaccc  25740
cacatgatat cccgggtcaa cggaatacgc gcccaccgaa accgaattct cctggaacag  25800
gcggctatta ccaccacacc tcgtaataac cttaatcccc gtagttggcc cgctgccctg  25860
gtgtaccagg aaagtcccgc tcccaccact gtggtacttc ccagagacgc ccaggccgaa  25920
gttcagatga ctaactcagg ggcgcagctt gcgggcggct ttcgtcacag ggtgcggtcg  25980
cccgggcagg gtataactca cctgacaatc agagggcgag gtattcagct caacgacgag  26040
tcggtgagct cctcgcttgg tctccgtccg gacgggacat ttcagatcgg cggcgccggc  26100
cgctcttcat tcacgcctcg tcaggcaatc ctaactctgc agacctcgtc ctctgagccg  26160
cgctctggag gcattggaac tctgcaattt attgaggagt ttgtgccatc ggtctacttt  26220
aacccctttct cgggacctcc cggccactat ccggatcaat ttattcctaa ctttgacgcg  26280
gtaaaggact cggcggacgg ctacgactga ctctatgtgg gatatgctcc agcgctacaa  26340
ccttgaagtc aggcttcctg gatgtcagca tctgactttg gccagcacct gtcccgcgga  26400
tttgttccag tccaactaca gcgacccacc ctaacagaga tggtgagcaa gggcgaggag  26460
gataacatgg ccatcatcaa ggagttcatg cgcttcaagg tgcacatgga gggctccgtg  26520
aacggccacg agttcgagat cgagggcgag ggcgagggcc gcccctacga gggcacccag  26580
accgccaagc tgaaggtgac caagggtggc cccctgccct tcgcctggga catcctgtcc  26640
cctcagttca tgtacggctc caaggcctac gtgaagcacc ccgccgacat ccccgactac  26700
ttgaagctgt ccttccccga gggcttcaag tgggagcgcg tgatgaactt cgaggacggc  26760
ggcgtggtga ccgtgaccca ggactcctcc ctgcaggacg gcgagttcat ctacaaggtg  26820
aagctgcgcg gcaccaactt cccctccgac ggccccgtaa tgcagaagaa gaccatgggc  26880
tgggaggcct cctccgagcg gatgtacccc gaggacggcg ccctgaaggg cgagatcaag  26940
cagaggctga agctgaagga cggcggccac tacgacgctg aggtcaagac cacctacaag  27000
gccaagaagc ccgtgcagct gcccggcgcc tacaacgtca acatcaagtt ggacatcacc  27060
tcccacaacg aggactacac catcgtggaa cagtacgaac gcgccgaggg ccgccactcc  27120
accggcggca tggacgagct gtacaaggga agcggagcta ctaacttcag cctgctgaag  27180
caggctggtg acgtcgagga gaatcctggc ccaatggtga tgaccaacac aaccaacgcg  27240
gccgccgcta ccggacttac atctaccaca aatacacccc aagtttctgc ctttgtcaat  27300
aactgggata acttgggcat gtggtggttc tccatagcgc ttatgtttgt atgccttatt  27360
attatgtggc tcatctgctg cctaaagcgc aaacgcgccc gaccacccat ctatagtccc  27420
atcattgtgc tacacccaaa caatgatgga atccatagat tggacggact gaaacacatg  27480
ttcttttctc ttacagtatg attaaatgag actaataaaa aaaaataata aagcatcact  27540
tacttaaaat cagttagcaa atttctgtcc agtttattca gcagcacctc cttgccctcc  27600
tcccagctct ggtattgcag cttcctcctg gctgcaaact ttctccacaa tctaaatgga  27660
atgtcagttt cctcctgttc ctgtccatcc gcacccacta tcttcatgtt gttgcagatg  27720
aagcgcgcaa gaccgtctga agataccttc aaccccgtgt atccatatga cacggaaacc  27780
ggtcctccaa ctgtgccttt tcttactcct ccctttgtat cccccaatgg gtttcaagag  27840
agtcccccctg gggtactctc tttgcgccta tccgaacctc tagttacctc caatggcatg  27900
cttgcgctca aaatgggcaa cggcctctct ctggacgagg ccggcaacct tacctcccaa  27960
aatgtaacca ctgtgagccc acctctcaaa aaaaccaagt caaacataaa cctggaaata  28020
tctgcacccc tcacagttac ctcagaagcc ctaactgtgg ctgccgccgc acctctaatg  28080
gtcgcgggca acacactcac catgcaatca caggccccgc taaccgtgca cgactccaaa  28140
cttagcattg ccacccaagg acccctcaca gtgtcagaag gaaagctagc cctgcaaaca  28200
tcaggccccc tcaccaccac cgatagcagt acccttacta tcactgcctc acccccctcta  28260
actactgcca ctggtagctt gggcattgac ttgaaagagc ccatttatac acaaaatgga  28320
aaactaggac taaagtacgg ggctcctttg catgtaacag acgacctaaa cactttgacc  28380
gtagcaactg gtccaggtgt gactattaat aatacttcct tgcaaactaa agttactgga  28440
gccttgggtt ttgattcaca aggcaatatg caacttaatg tagcaggagg actaaggatt  28500
gattctcaaa acagacgcct tatacttgat gttagttatc cgtttgatgc tcaaaaccaa  28560
ctaaatctaa gactaggaca gggccctctt tttataaact cagcccacaa cttggatatt  28620
aactacaaca aaggccttta cttgtttaca gcttcaaaca attccaaaaa gcttgaggtt  28680
aacctaagca ctgccaaggg gttgatgttt gacgctacag ccatagccat taatgcagga  28740
gatgggcttg aatttggttc acctaatgca ccaaacacaa atcccctcaa aacaaaaatt  28800
ggccatggcc tagaatttga ttcaaacaag gctatggttc ctaaactagg aactggcctt  28860
agttttgaca gcacaggtgc cattacagta ggaaacaaaa ataatgataa gctaactttg  28920
tggaccacac cagctccatc tcctaactgt agactaaatg cagagaaaga tgctaaactc  28980
actttggtct taacaaaatg tggcagtcaa atacttgcta cagtttcagt tttggctgtt  29040
aaaggcagtt tggctccaat atctggaaca gttcaaagtg ctcatcttat tataagattt  29100
gacgaaaatg gagtgctact aaacaattcc ttcctggacc cagaatattg gaactttaga  29160
aatggagatc ttactgaagg cacagcctat acaaacgctg ttggatttat gcctaaccta  29220
tcagcttatc caaaatctca cggtaaaact gccaaaagta acattgtcag tcaagtttac  29280
ttaaacggag acaaaactaa acctgtaaca ctaaccatta cactaaacgg tacacaggaa  29340
acaggagaca caactccaag tgcatactct atgtcatttt catgggactg gtctggccac  29400
aactacatta atgaaatatt tgccacatcc tcttacactt tttcatacat tgcccaagaa  29460
taaagcaata gcatcacaaa tttcacaaat aaagcattat tttagttatt aatagtaatc  29520
aattacgggg tcattagttc atagcccata tatggagttc cgcgttacat aacttacggt  29580
aaatggcccg cctggctgac cgcccaacga cccccgccca ttgacgtcaa taatgacgta  29640
tgttcccata gtaacgccaa tagggacttt ccattgacgt caatgggtgg agtatttacg  29700
gtaaactgcc cacttggcag tacatcaagt gtatcatatg ccaagtacgc cccctattga  29760
cgtcaatgac ggtaaatggc ccgcctggca ttatgcccag tacatgacct tatgggactt  29820
tcctacttgg cagtacatct acgtattagt catcgctatt accatggtga tgcggttttg  29880
gcagtacatc aatgggcgtg gatagcggtt tgactcacgg ggatttccaa gtctccaccc  29940
cattgacgtc aatgggagtt tgttttggca ccaaaatcaa cgggactttc caaaatgtcg  30000
```

-continued

```
taacaactcc gccccattga cgcaaatggg cggtaggcgt gtacggtggg aggtctatat  30060
aagcatccct atcagtgata gagatcagat ctccctatca gtgatagaga gctgttttga  30120
cctccataga agacaccggg accgatccag cctccggact ctagcgttta aacttaagct  30180
tggtacccgg ggatcctcta gggcctctga gctattccag aagtagtgaa gaggcttttt  30240
tggaggccta ggcttttgca aaaagctccg gatcgatcct gagacaccat ggccagtcgg  30300
gaagaggagc agcgcgaaac cacccccgag cgcggacgcg gtgcggcgcg acgtccccca  30360
accatggagg acgtgtcgtc cccgtccccg tcgccgccgc ctccccgggc gcccccaaaa  30420
aagcggatga ggcggcgtat cgagtccgag gacgaggaag actcatcaca agacgcgctg  30480
gtgccgcgca cacccagccc gcggccatcg acctcggcgg cggatttggc cattgcgccc  30540
aagaagaaaa agaagcgccc ttctcccaag cccgagcgcc cgccatcacc agaggtaatc  30600
gtggacagcg aggaagaaag agaagatgtg gcgctacaaa tggtgggttt cagcaaccca  30660
ccggtgctaa tcaagcatgg caaaggaggt aagcgcacag tgcggcggct gaatgaagac  30720
gacccagtgg cgcgtggtat gcggacgcaa gaggaagagg aagagcccag cgaagcggaa  30780
agtgaaatta cggtgatgaa cccgctgagt gtgccgatcg tgtctgcgtg ggagaagggc  30840
atggaggctg cgcgcgcgct gatggacaag taccacgtgg ataacgatct aaaggcgaac  30900
ttcaaactac tgcctgacca agtggaagct ctggcggccg tatgcaagac ctggctgaac  30960
gaggagcacc gcgggttgca gctgaccttc accagcaaca agacctttgt gacgatgatg  31020
gggcgattcc tgcaggcgta cctgcagtcg tttgcagagg tgacctacaa gcatcacgag  31080
cccacgggct gcgcgttgtg gctgcaccgc tgcgctgaga tcgaaggcga gcttaagtgt  31140
ctacacggaa gcattatgat aaataaggag cacgtgattg aaatggatgt gacgagcgaa  31200
aacgggcagc gcgcgctgaa ggagcagtct agcaaggcca agatcgtgaa gaaccggtgg  31260
ggccgaaatg tggtgcagat ctccaacacc gacgcaaggt gctgcgtgca cgacgcggcc  31320
tgtccggcca atcagttttc cggcaagtct tgcggcatgt tcttctctga aggcgcaaag  31380
gctcaggtgg cttttaagca gatcaaggct tttatgcagg cgctgtatcc taacgcccag  31440
accgggcacg gtcacctttt gatgccacta cggtgcgagt gcaactcaaa gcctgggcac  31500
gcgccctttt tgggaaggca gctaccaaag ttgactccgt tcgccctgag caacgcggag  31560
gacctggacg cggatctgat ctccgacaag agcgtgctgg ccagcgtgca ccacccggcg  31620
ctgatagtgt tccagtgctg caaccctgtg tatcgcaact cgcgcgcgca gggcggaggc  31680
cccaactgcg acttcaagat atcggcgccc gacctgctaa acgcgttggt gatggtgcgc  31740
agcctgtgga gtgaaaactt caccgagctg ccgcggatgg ttgtgcctga gtttaagtgg  31800
agcactaaac accagtatcg caacgtgtcc ctgccagtgg cgcatagcga tgcgcggcag  31860
aacccctttg atttttaaaa taaacaagtt aacaacaaca caaaaaataat gctttatttc  31920
tcgagagctt gatgccaggc aagtccaggc aggccaggca agtccaggca ggccaggcaa  31980
gtccaggcag gccaggcaag tccaggcagg ccaggcaagt ccaggcaggc caggcaagtc  32040
caggcaggcc aggcaagtcc aggcaggcca ggcaagtcca ggcaggccag gcaagtccag  32100
gcaggccagg caagtccagg cagggccagg caagtccagg caggccaggc aagtccaggc  32160
aggccaggca agtccaggca ggatcgaatt aagctttagg cgtgtacggt gggcgcctat  32220
aaaagcagag ctcgtttagt gaaccgtcag atcgcctgga gcaattccac aacacttttg  32280
tcttatacca actttccgta ccacttccta ccctcgtaaa cctggagacg ccatccacgc  32340
tgttttgacc tccatagaag acaccgggac cgatccagcc tccggtcgac cgatcctgat  32400
tcaccatgtc tagactggac aagagcaaag tcataaactc tgctctggaa ttactcaatg  32460
aagtcggtat cgaaggcctg acgacaagga aactcgctca aaagctggga gttgagcagc  32520
ctaccctgta ctggcacgtg aagaacaagc gggccctgct cgatgccctg gcaatcgaga  32580
tgctggacag gcatcatacc cacttctgcc ccctggaagg cgagtcatgg caagactttc  32640
tgcggaacaa cgccaagtca ttccgctgtg ctctcctctc acatcgcgac ggggctaaag  32700
tgcatctcgg cacccgccca acagagaaac agtacgaaac cctggaaaat cagctcgcgt  32760
tcctgtgtca gcaaggcttc tccctggaga acgcactgta cgctctgtcc gccgtgggcc  32820
actttacact gggctgcgta ttggaggatc aggagcatca agtagcaaaa gaggaaagag  32880
agacacctac caccgattct atgcccccac ttctgagaca agcaattgag ctgttcgacc  32940
atcagggagc cgaacctgcc ttccttttcg gcctggaact aatcatatgt ggcctggaga  33000
aacagctaaa gtgcgaaagc ggctccgcgt acagcggatc ccgggaattc agatcttatt  33060
aataaacaag ttaacaacaa cacaaaaata atgctttatt taatcgtggc aaatccacta  33120
taataaaaga atcgtttgtg ttatgtttca acgtgtttat ttttcaattg cagaaaattt  33180
cgaatcattt ttcattcagt agtatagccc caccaccaca tagcttatac agatcaccgt  33240
acctcaactt tgtataataa agttgtaatc aaactcacag aaccctagta ttcaacctgc  33300
cacctccctc ccaacacaca gagtacacag tcctttctcc ccggctggcc ttaaaaagca  33360
tcatatcatg ggtaacagac atattcttag gtgttatatt ccacacggtt tcctgtcgag  33420
ccaaacgctc atcagtgata ttaataaact ccccgggcag ctcacttaag ttcatgtcgc  33480
tgtccagctg ctgagccaca ggctgctgtc caacttgcgg ttgcttaacg ggcggcgaag  33540
gagaagtcca cgcctacatg ggggtagagt cataatcgtg catcaggata gggcggtggt  33600
gctgcagcag cgcgcgaata aactgctgcc gccgccgctc cgtcctgcag gaatacaaca  33660
tggcagtggt ctcctcagcg atgattcgca ccgcccgcag cataaggcgc cttgtcctcc  33720
gggcacagca gcgcaccctg atctcactta aatcagcaca gtaactgcag cacagcacca  33780
caatattgtt caaaatccca cagtgcaagg cgctgtatcc aaagctcatg gcggggacca  33840
cagaacccac gtggccatca taccacaagc gcaggtagat taagtggcga cccctcataa  33900
acacgctgga cataaacatt acctcttttg gcatgttgta attcaccacc tcccggtacc  33960
atataaacct ctgattaaac atggcgccat ccaccaccat cctaaaccag ctggccaaaa  34020
cctgcccgcc ggctatacac tgcagggaac cgggactgga acaatgacag tggagagccc  34080
aggactcgta accatggatc atcatgctcg tcatgatatc aatgttggca caacacaggc  34140
acacgtgcat acacttcctc aggattacaa gctcctcccg cgttagaacc atatcccagg  34200
gaacaaccca ttcctgaatc agcgtaaatc ccacactgca gggaagacct cgcacgtaac  34260
tcacgttgtg cattgtcaaa gtgttacatt cgggcagcag cggatgatcc tccagtatgg  34320
tagcgcgggt ttctgtctca aaaggaggta gacgatccct actgtacgga gtgcgccgag  34380
acaaccgaga tcgtgttggt cgtagtgtca tgccaaatgg aacgccggac gtagtcatat  34440
ttcctgaagc aaaaccaggt gcgggcgtga caaacagatc tgcgtctccg gtctcgccgc  34500
ttagatcgct ctgtgtagta gttgtagtat atccactctc tcaaagcatc caggcgcccc  34560
ctggcttcgg gttctatgta aactccttca tgcgccgctg ccctgataac atccaccacc  34620
gcagaataag ccacacccag ccaacctaca cattcgttct gcgagtcaca cacgggagga  34680
gcgggaagag ctggaagaac catgtttttt tttttattcc aaaagattat ccaaaacctc  34740
```

```
aaaatgaaga tctattaagt gaacgcgctc ccctccggtg gcgtggtcaa actctacagc  34800
caaagaacag ataatggcat ttgtaagatg ttgcacaatg gcttccaaaa ggcaaacggc  34860
cctcacgtcc aagtggacgt aaaggctaaa cccttcaggg tgaatctcct ctataaacat  34920
tccagcacct tcaaccatgc ccaaataatt ctcatctcgc caccttctca atatatctct  34980
aagcaaatcc cgaatattaa gtccggccat tgtaaaaatc tgctccagag cgccctccac  35040
cttcagcctc aagcagcgaa tcatgattgc aaaaattcag gttcctcaca gacctgtata  35100
agattcaaaa gcggaacatt aacaaaaata ccgcgatccc gtaggtccct tcgcagggcc  35160
agctgaacat aatcgtgcag gtctgcacgg accagcgcgg ccacttcccc gccaggaacc  35220
atgacaaaag aacccacact gattatgaca cgcatactcg gagctatgct aaccagcgta  35280
gccccgatgt aagcttgttg catgggcggc gatataaaat gcaaggtgct gctcaaaaaa  35340
tcaggcaaag cctcgcgcaa aaaagaaagc acatcgtagt catgctcatg cagataaagg  35400
caggtaagct ccggaaccac cacagaaaaa gacaccattt ttctctcaaa catgtctgcg  35460
ggtttctgca taaacacaaa ataaaataac aaaaaaacat ttaaacatta gaagcctgtc  35520
ttacaacagg aaaaacaacc cttataagca taagacggac tacggccatg ccggcgtgac  35580
cgtaaaaaaa ctggtcaccg tgattaaaaa gcaccaccga cagctcctcg gtcatgtccg  35640
gagtcataat gtaagactcg gtaaacacat caggttgatt cacatcggtc agtgctaaaa  35700
agcgaccgaa atagcccggg ggaatacata cccgcaggcg tagagacaac attacagccc  35760
ccataggagg tataacaaaa ttaataggag agaaaaacac ataaacacct gaaaaaccct  35820
cctgcctagg caaaatagca ccctcccgct ccagaacaac atacagcgct tccacagcgg  35880
cagccataac agtcagcctt accagtaaaa aagaaaacct attaaaaaaa caccactcga  35940
cacggcacca gctcaatcag tcacagtgta aaaaagggcc aagtgcagag cgagtatata  36000
taggactaaa aaatgacgta acggttaaag tccacaaaaa acacccagaa aaccgcacgc  36060
gaacctacgc ccagaaacga aagccaaaaa acccacaact tcctcaaatc gtcacttccg  36120
ttttcccacg ttacgtcact tcccatttta agaaaactac aattcccaac acatacaagt  36180
tactccgccc taaaacctac gtcacccgcc ccgttcccac gccccgcgcc acgtcacaaa  36240
ctccaccccc tcattatcat attggcttca atccaaaata aggtatatta ttgatgatg   36299

SEQ ID NO: 2            moltype = DNA  length = 36299
FEATURE                 Location/Qualifiers
misc_feature            1..36299
                        note = Synthetic adenovirus genome (CMBT-1066)
source                  1..36299
                        mol_type = other DNA
                        organism = synthetic construct
SEQUENCE: 2
catcatcaat aatatacctt attttggatt gaagccaata tgataatgag ggggtggagt  60
ttgtgacgtg gcgcggggcg tgggaacggg gcgggtgacg tagtagtgtg gcggaagtgt  120
gatgttgcaa gtgtggcgga acacatgtaa gcgacggatg tggcaaaagt gacgtttttg  180
gtgtgcgccg gtgtacacag gaagtgacaa ttttcgcgcg gttttaggcg gatgttgtag  240
taaatttggg cgtaaccgag taagatttgg ccattttcgc gggaaaactg aataagagga  300
agtgaaatct gaataatttt gtgttactca tagcgcgtaa tatttgtcta gggccgcggg  360
gactttgacc gtttacgtgg agactcgccc aggtgttttt ctcaggtgtt ttccgcgttc  420
cgggtcaaag ttggcgtttt attattatag tcagctgacg tgtagtgtat ttatacccgg  480
tgagttcctc aagaggccac tcttgagtgc cagcgagtag agttttctcc tccgagccgc  540
tccgacaccg ggactgaaaa tgagacatat tatctgccac ggaggtgtta ttaccgaaga  600
aatggccgcc agtcttttgg accagctgat cgaagaggta ctggctgata atcttccacc  660
tcctagccat tttgaaccac ctacccttca cgaactgtat gatttagacg tgacggcccc  720
cgaagatccc aacgaggagg cggtttcgca gatttttccc gactctgtaa tgttggcggt  780
gcaggaaggg attgacttac tcacttttcc gccggcgccc ggttctccgg agccgcctca  840
cctttcccgg cagcccgagc agccggagca gagagccttg ggtccggttt ctatgccaaa  900
ccttgtaccg gaggtgatcg atcttacctg ccacgaggct ggctttccac ccagtgacga  960
cgaggatgaa gagggtgagg agtttgtgtt agattatgtg gagcaccccg ggcacggttg  1020
caggtcttgt cattatcacc ggaggaatac gggggaccca gatattatgt gttcgctttg  1080
ctatatgagg acctgtggca tgtttgtcta cagtaagtga aaattatggg cagtgggtga  1140
tagagtggtg ggtttggtgt ggtaattttt tttttaattt ttacagtttt gtggtttaaa  1200
gaattttgta ttgtgatttt tttaaaaggt cctgtgtctg aacctgagcc tgagcccgag  1260
ccagaaccgg agcctgcaag acctacccgc cgtcctaaaa tggcgcctgc tatcctgaga  1320
cgcccgacat cacctgtgtc tagagaatgc aatagtagta cggatagctg tgactccggt  1380
ccttctaaca cacctcctga gatacacccg gtggtcccgc tgtgccccat taaaccagtt  1440
gccgtgagag ttggtgggcg tcgccaggct gtggaatgta tcgaggactt gcttaacgag  1500
cctgggcaac ctttggactt gagctgtaaa cgccccaggc cataaggtgt aaacctgtga  1560
ttgcgtgtgt ggttaacgcc tttgtttgct gaatgagttg atgtaagttt aataaagggt  1620
gagataatgt ttaacttgca tggcgtgtta aatggggcgg ggcttaaagg gtatataatg  1680
cgccgtgggc taatcttggt tacatctgac ctcatggagg cttgggagtg tttggaagat  1740
ttttctgctg tgcgtaactt gctggaacag agctctaaca gtacctcttg gttttggagg  1800
tttctgtggg gctcatccca ggcaaagtta gtctgcagaa ttaaggagga ttacaagtgg  1860
gaatttgaag agcttttgaa atcctgtggt gagctgtttg attctttgaa tctgggtcac  1920
caggcgcttt tccaagagaa ggtcatcaag actttggatt tttccacacc ggggcgcgct  1980
gcggctgctg ttgctttttt gagttttata aaggataagt ggagcgaaga aacccatctg  2040
agcggggggt acctgctgga ttttctggcc atgcatctgt ggagagcggt tgtgagacac  2100
aagaatcgcc tgctactgtt gtcttccgtc cgcccggcga taataccgac ggaggagcag  2160
cagcagcagc aggaggaagc caggcggcgg cggcaggagc agagcccatg gaacccgaga  2220
gccggcctgg accctcggga atgaatgttg tacaggtggc tgaactgtat ccagaactga  2280
gacgctagtt gacaattaca gaggatgggc aggggctaaa gggggtaaag agggagcggg  2340
gggcttgtga ggctacagag gaggctagga atctagcttt tagcttaatg accagacacc  2400
gtcctgagtg tattactttt caacagatca aggataattg cgctaatgag cttgatctgc  2460
tggcgcagaa gtattccata gagcagctga ccacttactg gctgcagcca ggggatgatt  2520
ttgaggaggc tattagggta tatgcaaagg tggcacttag gccagattgc aagtacaaga  2580
tcagcaaact tgtaaatatc aggaattgtt gctacatttc tgggaacggg gccgaggtgg  2640
```

-continued

```
agatagatac ggaggatagg gtggccttta gatgtagcat gataaatatg tggccggggg  2700
tgcttggcat ggacggggtg gttattatga atgtaaggtt tactggcccc aattttagcg  2760
gtacggtttt cctggccaat accaacctta tcctacacgg tgtaagcttc tatgggttta  2820
acaatacctg tgtggaagcc tggaccgatg taagggttcg gggctgtgcc ttttactgct  2880
gctggaaggg ggtggtgtgt cgccccaaaa gcagggcttc aattaagaaa tgcctctttg  2940
aaaggtgtac cttgggtatc ctgtctgagg gtaactccag ggtgcgccac aatgtggcct  3000
ccgactgtgg ttgcttcatg ctagtgaaaa gcgtggctgt gattaagcat aacatggtat  3060
gtggcaactg cgaggacagg gcctctcaga tgctgacctg ctcggacggc aactgtcacc  3120
tgctgaagac cattcacgta gccagccact ctcgcaaggc ctggccagtg tttgagcata  3180
acatactgac ccgctgttcc ttgcatttgg gtaacaggag gggggtgttc ctaccttacc  3240
aatgcaattt gagtcacact aagatattgc ttgagcccga gagcatgtcc aaggtgaacc  3300
tgaacggggt gtttgacatg accatgaaga tctggaaggt gctgaggtac gatgagaccc  3360
gcaccaggtg cagaccctgc gagtgtggcg gtaaacatat taggaaccag cctgtgatgc  3420
tggatgtgac cgaggagctg aggcccgatc acttggtgct ggcctgcacc cgcgctgagt  3480
ttggctctag cgatgaagat acagattgag gtactgaaat gtgtgggcgt ggcttaaggg  3540
tgggaaagaa tatataaggt gggggtctta tgtagttttg tatctgtttt gcagcagccg  3600
ccgccgccca acttttctat acaaagttgt aatgagcacc aactcgtttg atggaagcat  3660
tgtgagctca tatttgacaa cgcgcatgcc cccatgggcc ggggtgcgtc agaatgtgat  3720
gggctccagc attgatggtc gccccgtcct gcccgcaaac tctactacct tgacctacga  3780
gaccgtgtct ggaacgccgt tggagactgc agcctccgcc gccgcttcag ccgctgcagc  3840
caccgcccgc gggattgtga ctgactttgc tttcctgagc ccgcttgcaa gcagtgcagc  3900
ttcccgttca tccgcccgcg atgacaagtt gacggctctt ttggcacaat tggattcttt  3960
gacccgggaa cttaatgtcg tttctcagca gctgttggat ctgcgccagc aggtttctgc  4020
cctgaaggct tcctcccctc ccaatgcggt ttaaaacata aataaaaaac cagactctgt  4080
ttggatttgg atcaagcata agtgtcttgc tgtctttatt taggggtttt gcgcgcgcgg  4140
taggcccggg accagcggtc tcggtcgttg agggtcctgt gtattttttc caggacgtgg  4200
taaaggtgac tctggatgtt cagatacatg ggcataagcc cgtctctggg gtggaggtag  4260
caccactgca gagcttcatg ctgcggggtg gtgttgtaga tgatccagtc gtagcaggag  4320
cgctgggcgt ggtgcctaaa aatgtctttc agtagcaagc tgattgccag gggcaggccc  4380
ttggtgtaag tgtttacaaa gcggttaagc tgggatgggt gcatacgtgg ggatatgaga  4440
tgcatcttgg actgtatttt taggttggct atgttcccag ccatatccct ccggggattc  4500
atgttgtgca gaaccaccag cacagtgtat ccggtgcact tgggaaattt gtcatgtagc  4560
ttagaaggaa atgcgtggaa gaacttggag acgcccttgt gacctccaag attttccatg  4620
cattcgtcca taatgatggc aatgggccca cgggcggcgg cctgggcgaa gatatttctg  4680
ggatcactaa cgtcatagtt gtgttccagg atgagatcgt cataggccat ttttacaaag  4740
cgcgggcgga gggtgccaga ctgcggtata atggttccat ccggcccagg ggcgtagtta  4800
ccctcacaga tttgcatttc ccacgctttg agttcagatg gggggatcat gtctacctgc  4860
ggggcgatga agaaaacggt ttccggggta ggggagatca gctgggaaga aagcaggttc  4920
ctgagcagct gcgacttacc gcagccggtg ggcccgtaaa tcacacctat taccgggtgc  4980
aactggtagt taagagagct gcagctgccg tcatccctga gcaggggggc cacttcgtta  5040
agcatgtccc tgactcgcat gttttccctg accaaatccg ccagaaggcg ctcgccgccc  5100
agcgatagca gttcttgcaa ggaagcaaag tttttcaacg gtttgagacc gtccgccgta  5160
ggcatgcttt tgagcgtttg accaagcagt tccaggcggt cccacagctc ggtcacctgc  5220
tctacggcat ctcgatccag catatctcct cgtttcgcgg gttggggcgg ctttcgctgt  5280
acggcagtag tcggtgctcg tccagacggg ccagggtcat gtctttccac gggcgcaggg  5340
tcctcgtcag cgtagtctgg gtcacggtga aggggtgcgc tccgggctgc gcgctggcca  5400
gggtgcgctt gaggctggtc ctgctggtgc tgaagcgctg ccggtcttcg ccctgcgcgt  5460
cggccaggta gcatttgacc atggtgtcat agtccagccc ctccgcggcg tggcccttgg  5520
cgcgcagctt gcccttggag gaggcgccgc acgaggggca gtgcagactt ttgagggcgt  5580
agagcttggg cgcgagaaat accgattccg gggagtaggc atccgcgccg caggccccgc  5640
agacggtctc gcattccacg agccaggtga gctctggccg ttcggggtca aaaaccaggt  5700
ttcccccatg ctttttgatg cgtttcttac ctctggtttc catgagccgg tgtccacgct  5760
cggtgacgaa aaggctgtcc gtgtccccgt atacagactt gagaggcctg tcctcgagcg  5820
gtgttccgcg gtcctcctcg tatagaaact cggaccactc tgagacaaag gctcgcgtcc  5880
aggccagcac gaaggaggct aagtgggagg ggtagcggtc gttgtccact agggggtcca  5940
ctcgctccag ggtgtgaaga cacatgtcgc cctcttcggc atcaaggaag gtgattggtt  6000
tgtaggtgta ggccacgtga ccgggtgttc ctgaaggggg gctataaaag gggtgggggg  6060
cgcgttcgtc ctcactctct tccgcatcgc tgtctgcgag ggccagctgt tggggtgagt  6120
actccctctg aaaagcgggc atgacttctg cgctaagatt gtcagtttcc aaaaacgagg  6180
aggatttgat attcacctgg cccgcggtga tgcctttgag ggtggccgca tccatctggt  6240
cagaaaagac aatctttttg ttgtcaagct tggtggcaaa cgacccgtag agggcgttgg  6300
acagcaactt ggcgatggag cgcagggttt ggtttttgtc gcgatcggcg cgctccttgg  6360
ccgcgatgtt tagctgcacg tattcgcgcg caacgcaccg ccattcggga aagacggtgg  6420
tgcgctcgtc gggcaccagg tgcacgcgcc aaccgcggtt gtgcagggtg acaaggtcaa  6480
cgctggtggc tacctctccg cgtaggcgct cgttggtcca gcagaggcgg ccgcccttgc  6540
gcgagcagaa tggcggtagg gggtctagct gcgtctcgtc cgggggggtct gcgtccacgg  6600
taaagacccc gggcagcagg cgcgcgtcga agtagtctat cttgcatcct tgcaagtcta  6660
gcgcctgctg ccatgcgcgg gcggcaagcg cgcgctcgta tgggttgagt gggggacccc  6720
atggcatggg gtgggtgagc gcggaggcgt acatgccgca aatgtcgtaa acgtagaggg  6780
gctctctgag tattccaaga tatgtagggt agcatcttcc accgcggatg ctggcgcgca  6840
cgtaatcgta tagttcgtgc gagggagcga ggaggtcggg accgaggttg ctacgggcgg  6900
gctgctctgc tcggaagact atctgcctga agatggcatg tgagttggat gatatggttg  6960
gacgctggaa gacgttgaag ctggcgtctg tgagacctac cgcgtcacgc acgaaggagg  7020
cgtaggagtc gcgcagcttg ttgaccagct cggcggtgac ctgcacgtct agggcgcagt  7080
agtccagggt ttccttgatg atgtcatact tatcctgtcc cttttttttc cacagctcgc  7140
ggttgaggac aaactcttcg cggtctttcc agtactcttg gatcggaaac ccgtcggcct  7200
ccgaacggta agagcctagc atgtagaact ggttgacggc ctggtaggcg cagcatccct  7260
tttctacggg tagcgcgtat gcctgcgcgg ccttccggag cgaggtgtgg gtgagcgcaa  7320
aggtgtccct gaccatgact ttgaggtact ggtatttgaa gtcagtgtcg tcgcatccgc  7380
```

-continued

```
cctgctccca gagcaaaaag tccgtgcgct ttttggaacg cggatttggc agggcgaagg  7440
tgacatcgtt gaagagtatc tttcccgcgc gaggcataaa gttgcgtgtg atgcggaagg  7500
gtcccggcac ctcggaacgg ttgttaatta cctgggcggc gagcacgatc tcgtcaaagc  7560
cgttgatgtt gtggcccaca atgtaaagtt ccaagaagcg cgggatgccc ttgatggaag  7620
gcaatttttt aagttcctcg taggtgagct cttcagggga gctgagcccg tgctctgaaa  7680
gggcccagtc tgcaagatga gggttggaag cgacgaatga gctccacagg tcacgggcca  7740
ttagcatttg caggtggtcg cgaaaggtcc taaactggcg acctatggcc atttttctg  7800
gggtgatgca gtagaaggta agcgggtctt gttcccagcg gtcccatcca aggttcgcgg  7860
ctaggtctcg cgcggcagtc actagaggct catctccgcc gaacttcatg accagcatga  7920
agggcacgag ctgcttccca aaggccccca tccaagtata ggtctctaca tcgtaggtga  7980
caaagagacg ctcggtgcga ggatgcgagc cgatcgggaa gaactggatc tcccgccacc  8040
aattggagga gtggctattg atgtggtgaa agtagaagtc cctgcgacgg gccgaacact  8100
cgtgctggct tttgtaaaaa cgtgcgcagt actggcagcg gtgcacgggc tgtacatcct  8160
gcacgaggtt gacctgacga ccgcgcacaa ggaagcagag tgggaatttg agcccctcgc  8220
ctggcgggtt tggctggtgg tcttctactt cggctgcttg tccttgaccg tctggctgct  8280
cgagggggagt tacggtggat cggaccacca cgccgcgcga gcccaaagtc cagatgtccg  8340
cgcgcggcgg tcggagcttg atgacaacat cgcgcagatg ggagctgtcc atggtctgga  8400
gctcccgcgg cgtcaggtca ggcgggagct cctgcaggtt tacctcgcat agacgggtca  8460
gggcgcgggc tagatccagg tgatacctaa tttccagggg ctggttggtg gcggcgtcga  8520
tggcttgcaa gaggccgcat ccccgcggcg cgactacggt accgcgcggc gggcggtggg  8580
ccgcgggggt gtccttggat gatgcatcta aaagcggtga cgcgggcgag cccccggagg  8640
taggggggc tccggacccg ccgggagagg gggcaggggc acgtcggcgc cgcgcgcggg  8700
caggagctgg tgctgcgcgc gtaggttgct ggcgaacgcg acgacgcggc ggttgatctc  8760
ctgaatctgg cgcctctgcg tgaagacgac gggcccggtg agcttgagcc tgaaagagag  8820
ttcgacagaa tcaatttcgg tgtcgttgac ggcggcctgg cgcaaaatct cctgcacgtc  8880
tcctgagttg tcttgatagg cgatctcggc catgaactgc tcgatctctt cctcctggag  8940
atctccgcgt ccggctcgct ccacggtggc ggcgaggtcg ttggaaatgc gggccatgag  9000
ctgcgagaag gcgttgaggc ctccctcgtt ccagacgcgg ctgtagacca cgcccccttc  9060
ggcatcgcgg gcgcgcatga ccacctgcgc gagattgagc tccacgtgcc gggcgaagac  9120
ggcgtagttt cgcaggcgct gaaagaggta gttgagggtg gtggcggtgt gttctgccac  9180
gaagaagtac ataacccagc gtcgcaacgt ggattcgttg atatccccca aggcctcaag  9240
gcgctccatg gcctcgtaga agtccacggc gaagttgaaa aactgggagt tgcgcgccga  9300
cacggttaac tcctcctcca gaagacggat gagctcggcg acagtgtcgc gcacctcgcg  9360
ctcaaaggct acaggggcct cttcttcttc ttcaatctcc tcttccataa gggcctcccc  9420
ttcttcttct tctggcggcg gtgggggagg ggggacacgg cggcgacgac ggcgcaccgg  9480
gaggcggtcg acaaagcgct cgatcatctc cccgcggcga cggcgcatgg tctcggtgac  9540
ggcgcggccg ttctcgcggg ggcgcagttg gaagacgccg cccgtcatgt cccggttatg  9600
ggttggcggg gggctgccat gcggcaggga tacggcgcta acgatgcatc tcaacaattg  9660
ttgtgtaggt actccgccgc cgagggacct gagcgagtcc gcatcgaccg gatcggaaaa  9720
cctctcgaga aaggcgtcta accagtcaca gtcgcaaggt aggctgagca ccgtggcggg  9780
cggcagcggg cggcggtcgg ggttgtttct ggcggaggtg ctgctgatga tgtaattaaa  9840
gtaggcggtc ttgagacggc ggatggtcga cagaagcacc atgtccttgg gtccggcctg  9900
ctgaatgcgc aggcggtcgg ccatgcccca ggcttcgttt tgacatcggc gcaggtcttt  9960
gtagtagtct tgcatgagcc tttctaccgg cacttcttct tctccttcct cttgtcctgc  10020
atctcttgca tctatcgctg cggcggcggc ggagtttggc cgtaggtggc gccctcttcc  10080
tcccatgcgt gtgaccccga agcccctcat cggctgaagc agggctaggt cggcgacaac  10140
gcgctcggct aatatggcct gctgcacctg cgtgagggta gactggaagt catccatgtc  10200
cacaaagcgg tggtatgcgc ccgtgttgat ggtgtaagtg cagttggcca taacggacca  10260
gttaacggtc tggtgacccg gctgcgagag ctcggtgtac ctgagacgcg agtaagccct  10320
cgagtcaaat acgtagtcgt tgcaagtccg caccaggtac tggtatccca ccaaaaagtg  10380
cggcggcggc tggcggtaga ggggccagcg tagggtggcc ggggctccgg gggcgagatc  10440
ttccaacata aggcgatgat atccgtagat gtacctggac atccaggtga tgccggcggc  10500
ggtggtggag gcgcgcggaa agtcgcggac gcggttccag atgttgcgca gcggcaaaaa  10560
gtgctccatg gtcgggacgc tctggccggt caggcgcgcg caatcgttga cgctctagac  10620
cgtgcaaaag gagagcctgt aagcgggcac tcttccgtgg tctggtggat aaattcgcaa  10680
gggtatcatg gcggacgacc ggggttcgag ccccgtatcc ggccgtccgc cgtgatccat  10740
gcggttaccg cccgcgtgtc gaacccaggt gtgcgacgtc agacaacggg ggagtgctcc  10800
ttttggcttc cttccaggcg cggcggctgc tgcgctagct tttttggcca ctggccgcgc  10860
gcagcgtaag cggttaggct ggaaagcgaa agcattaagt ggctcgctcc ctgtagccgg  10920
agggttattt tccaagggtt gagtcgcggg acccccggtt cgagtctcgg accggccgga  10980
ctgcggcgaa cgggggtttg cctccccgtc atgcaagacc ccgcttgcaa attcctccgg  11040
aaacagggac gagccccttt tttgcttttc ccagatgcat ccggtgctgc ggcagatgcg  11100
ccccctcct cagcagcggc aagagcaaga gcagcggcag acatgcaggg caccctcccc  11160
tcctcctacc gcgtcaggag gggcgacatc cgcggttgac gcggcagcag atggtgatta  11220
cgaacccccg cggcgccggg cccggcacta cctggacttg gaggagggcg agggcctggc  11280
gcggctagga gcgccctctc ctgagcggta cccaagggtg cagctgaagc gtgatacgcg  11340
tgaggcgtac gtgccgcggc agaacctgtt tcgcgaccgc gagggagagg agcccgagga  11400
gatgcgggat cgaaagttcc acgcagggcg cgagctgcgg catggcctga atcgcgagcg  11460
gttgctgcgc gaggaggact ttgagcccga cgcgcgaacc gggattagtc ccgcgcgcgc  11520
acacgtggcg gccgccgacc tggtaaccgc atacgagcag acggtgaacc aggagattaa  11580
ctttcaaaaa agctttaaca accacgtgcg tacgcttgtg gcgcgcgagg aggtggctat  11640
aggactgatg catctgtggg actttgtaag cgcgctggag caaaacccaa atagcaagcc  11700
gctcatggcg cagctgttcc ttatagtgca gcacagcagg gacaacgagg cattcaggga  11760
tgcgctgcta aacatagtag agcccgaggg ccgctggctg ctcgatttga taaacatcct  11820
gcagagcata gtggtgcagg agcgcagctt gagcctggct gacaaggtgg ccgccatcaa  11880
ctattccatg cttagcctgg gcaagtttta cgcccgcaag atataccata ccccttacgt  11940
tcccatagac aaggaggtaa agatcgaggg gttctacatg cgcatggcgc tgaaggtgct  12000
taccttgagc gacgacctgg gcgtttatcg caacgagcgc atccacaagg ccgtgagcgt  12060
gagccggcgg cgcgagctca gcgaccgcga gctgatgcac agcctgcaaa gggccctggc  12120
```

-continued tggcacgggc agcggcgata gagaggccga gtcctacttt gacgcgggcg ctgacctgcg 12180
ctgggcccca agccgacgcg ccctggaggc agctggggcc ggacctgggc tggcggtggc 12240
acccgcgcgc gctggcaacg tcggcggcgt ggaggaatat gacgaggacg atgagtacga 12300
gccagaggac ggcgagtact aagcggtgat gtttctgatc agatgatgca agacgcaacg 12360
gacccggcgg tgcgggcggc gctgcagagc cagccgtccg gccttaactc cacggacgac 12420
tggcgccagg tcatggaccg catcatgtcg ctgactgcgc gcaatcctga cgcgttccgg 12480
cagcagccgc aggccaaccg gctctccgca attctggaag cggtggtccc ggcgcgcgca 12540
aaccccacgc acgagaaggt gctggcgatc gtaaacgcgc tggccgaaaa cagggccatc 12600
cggcccgacg aggccggcct ggtctacgac gcgctgcttc agcgcgtggc tcgttacaac 12660
agcggcaacg tgcagaccaa cctggaccgg ctggtggggg atgtgcgcga ggccgtggcg 12720
cagcgtgagc gcgcgcagca gcagggcaac ctgggctcca tggttgcact aaacgccttc 12780
ctgagtacac agcccgccaa cgtgccgcgg ggacaggagg actacaccaa ctttgtgagc 12840
gcactgcggc taatggtgac tgagacaccg caaagtgagg tgtaccagtc tgggccagac 12900
tattttttcc agaccagtag acaaggcctg cagaccgtaa acctgagcca ggctttcaaa 12960
aacttgcagg ggctgtgggg ggtgcgggct cccacaggcg accgcgcgac cgtgtctagc 13020
ttgctgacgc ccaactcgcg cctgttgctg ctgctaatag cgcccttcac ggacagtggc 13080
agcgtgtccc gggacacata cctaggtcac ttgctgacac tgtaccgcga ggccataggt 13140
caggcgcatg tggacgagca tactttccag gagattacaa gtgtcagccg cgcgctgggg 13200
caggaggaca cgggcagcct ggaggcaacc ctaaactacc tgctgaccaa ccggcggcag 13260
aagatcccct cgttgcacag tttaaacagc gaggaggagc gcattttgcg ctacgtgcag 13320
cagagcgtga gccttaacct gatgcgcgac ggggtaacgc ccagcgtggc gctggacatg 13380
accgcgcgca acatggaacc gggcatgtat gcctcaaacc ggccgtttat caaccgccta 13440
atggactact tgcatcgcgc ggccgccgtg aaccccgagt atttcaccaa tgccatcttg 13500
aacccgcact ggctaccgcc ccctggtttc tacaccgggg gattcgaggt gcccgagggt 13560
aacgatggat tcctctggga cgacatagac gacagcgtgt tttccccgca accgcagacc 13620
ctgctagagt tgcaacagcg cgagcaggca gaggcggcgc tgcgaaagga aagcttccgc 13680
aggccaagca gcttgtccga tctaggcgct gcggccccgc ggtcagatgc tagtagccca 13740
tttccaagct tgatagggtc tcttaccagc actcgcacca cccgcccgcg cctgctgggc 13800
gaggaggagt acctaaacaa ctcgctgctg cagccgcagc gcgaaaaaaa cctgcctccg 13860
gcatttccca acaacgggat agagagccta gtggacaaga tgagtagatg gaagacgtac 13920
gcgcaggagc acagggacgt gccaggcccg cgcccgccca cccgtcgtca aaggcacgac 13980
cgtcagcggg gtctggtgtg ggaggacgat gactcggcag acgacagcag cgtcctggat 14040
ttgggaggga gtggcaaccc gtttgcgcac cttcgcccca ggctggggag aatgttttaa 14100
aaaaaaaaaa gcatgatgca aaataaaaaa ctcaccaagg ccatggcacc gagcgttggt 14160
tttcttgtat tccccttagt atgcggcgcg cggcgatgta tgaggaaggt cctcctccct 14220
cctacgagag tgtggtgagc gcggcgccag tggcggcggc gctgggttct cccttcgatg 14280
ctcccctgga cccgccgttt gtgcctccgc ggtacctgcg gcctaccggg gggagaaaca 14340
gcatccgtta ctctgagttg gcacccctat tcgacaccac ccgtgtgtac ctggtggaca 14400
acaagtcaac ggatgtggca tccctgaact accagaacga ccacagcaac tttctgacca 14460
cggtcattca aaacaatgac tacagcccgg gggaggcaag cacacagacc atcaatcttg 14520
acgaccggtc gcactggggc ggcgacctga aaaccatcct gcataccaac atgccaaatg 14580
tgaacgagtt catgtttacc aataagttta aggcgcgggt gatggtgtcg cgcttgccta 14640
ctaaggacaa tcaggtggag ctgaaatacg agtgggtgga gttcacgctg cccgagggca 14700
actactccga gaccatgacc atagacctta tgaacaacgc gatcgtggag cactacttga 14760
aagtgggcag acagaacggg gttctggaaa gcgacatcgg ggtaaagttt gacacccgca 14820
acttcagact ggggtttgac cccgtcactg gtcttgtcat gcctggggta tatacaaacg 14880
aagccttcca tccagacatc attttgctgc caggatgcgg ggtggacttc acccacagcc 14940
gcctgagcaa cttgttgggc atccgcaagc ggcaaccctt ccaggagggc tttaggatca 15000
cctacgatga tctggagggt ggtaacattc ccgcactgtt ggatgtggac gcctaccagg 15060
cgagcttgaa agatgacacc gaacagggcg ggggtggcgc aggcggcagc aacagcagtg 15120
gcagcggcgc ggaagagaac tccaacgcgg cagccgcggc aatgcagccg gtggaggaca 15180
tgaacgatca tgccattcgc ggcgacacct ttgccacacg ggctgaggag aagcgcgctg 15240
aggccgaagc agcggccgaa gctgccgccc ccgctgcgca acccgaggtc gagaagcctc 15300
agaagaaacc ggtgatcaaa cccctgacag aggacagcaa gaaacgcagt tacaacctaa 15360
taagcaatga cagcaccttc acccagtacc gcagctggta ccttgcatac aactacggcg 15420
accctcagac cggaatccgc tcatggaccc tgctttgcac tcctgacgta acctgcggct 15480
cggagcaggt ctactggtcg ttgccagaca tgatgcaaga ccccgtgacc ttccgctcca 15540
cgcgccagat cagcaacttt ccggtggtgg gcgccgagct gttgcccgtg cactccaaga 15600
gcttctacaa cgaccaggcc gtctactccc aactcatccg ccagtttacc tctctgaccc 15660
acgtgttcaa tcgctttccc gagaaccaga ttttggcgcg cccgccagcc cccaccatca 15720
ccaccgtcag tgaaaacgtt cctgctctca cagatcacgg gacgctaccg ctgcgcaaca 15780
gcatcggagg agtccagcga gtgaccatta ctgacgccag acgccgcacc tgcccctacg 15840
tttacaaggc cctgggcata gtctcgccgc gcgtcctatc gagccgcact ttttgagcaa 15900
gcatgtccat ccttatatcg cccagcaata acacaggctg gggcctgcgc ttcccaagca 15960
agatgtttgg cggggccaag aagcgctccg accaacaccc agtgcgcgtg cgcgggcact 16020
accgcgcgcc ctggggcgcg cacaaacgcg gccgcactgg gcgcaccacc gtcgatgacg 16080
ccatcgacgc ggtggtggag gaggcgcgca actacacgcc cacgccgcca ccagtgtcca 16140
cagtggacgc ggccattcag accgtggtgc gcggagcccg gcgctatgct aaaatgaaga 16200
gacggcggag gcgcgtagca cgtcgccacc gccgccgacc cggcactgcc gcccaacgcg 16260
cggcggcggc cctgcttaac cgcgcacgtc gcaccggccg acgggcggcc atgcgggccg 16320
ctcgaaggct ggccgcgggt attgtcactg tgccccccag gtccaggcga cgagcggccg 16380
ccgcagcagc cgcggccatt agtgctatga ctcagggtcg caggggcaac gtgtattggg 16440
tgcgcgactc ggttagcggc ctgcgcgtgc ccgtgcgcac ccgcccccg cgcaactaga 16500
ttgcaagaaa aaactactta gactcgtact gttgtatgta tccagcggcg gcggcgcgca 16560
acgaagctat gtccaagcgc aaaatcaaag aagagatgct ccaggtcatc gcgccggaga 16620
tctatggccc cccgaagaag gaagagcagg attacaagcc ccgaaagcta aagcgggtca 16680
aaaagaaaaa gaaagatgat gatgatgaac ttgacgacga ggtggaactg ctgcacgcta 16740
ccgcgcccag gcgacgggta cagtggaaag gtcgacgcgt aaaacgtgtt ttgcgacccg 16800
gcaccaccgt agtctttacg cccggtgagc gctccacccg cacctacaag cgcgtgtatg 16860

```
atgaggtgta cggcgacgag gacctgcttg agcaggccaa cgagcgcctc ggggagtttg  16920
cctacggaaa gcggcataag gacatgctgg cgttgccgct ggacgagggc aacccaacac  16980
ctagcctaaa gcccgtaaca ctgcagcagg tgctgcccgc gcttgcaccg tccgaagaaa  17040
agcgcggcct aaagcgcgag tctggtgact tggcacccac cgtgcagctg atggtaccca  17100
agcgccagcg actggaagat gtcttggaaa aaatgaccgt ggaacctggg ctggagcccg  17160
aggtccgcgt gcggccaatc aagcaggtgg cgccgggact gggcgtgcag accgtggacg  17220
ttcagatacc cactaccagt agcaccagta ttgccaccgc cacagagggc atggagacac  17280
aaacgtcccc ggttgcctca gcggtggcgg atgccgcggt gcaggcggtc gctgcggccg  17340
cgtccaagac ctctacggag gtgcaaacgg acccgtggat gtttcgcgtt tcagcccccc  17400
ggcgcccgcg cggttcgagg aagtacggcg ccgccagcgc gctactgccc gaatatgccc  17460
tacatccttc cattgcgcct acccccggct atcgtggcta cacctaccgc cccagaagac  17520
gagcaactac ccgacgccga accaccactg gaacccgccg ccgccgtcgc cgtcgccagc  17580
ccgtgctggc cccgatttcc gtgcgcaggg tggctcgcga aggaggcagg accctggtgc  17640
tgccaacagc gcgctaccac cccagcatcg tttaaaagcc ggtctttgtg gttcttgcag  17700
atatggccct cacctgccgc ctccgtttcc cggtgccggg attccgagga agaatgcacc  17760
gtaggagggg catggccggc cacggcctga cgggcggcat gcgtcgtgcg caccaccggc  17820
ggcggcgcgc gtcgcaccgt cgcatgcgcg gcggtatcct gcccctcctt attccactga  17880
tcgccgcggc gattggcgcc gtgcccggaa ttgcatccgt ggccttgcag gcgcagagac  17940
actgattaaa aacaagttgc atgtggaaaa atcaaaataa aaagtctgga ctctcacgct  18000
cgcttggtcc tgtaactatt ttgtagaatg gaagacatca actttgcgtc tctggccccg  18060
cgacacggct cgcgcccgtt catgggaaac tggcaagata tcggcaccag caatatgagc  18120
ggtggcgcct tcagctgggg ctcgctgtgg agcggcatta aaaatttcgg ttccaccgtt  18180
aagaactatg gcagcaaggc ctggaacagc agcacaggcc agatgctgag ggataagttg  18240
aaagagcaaa atttccaaca aaaggtggta gatggcctgg cctctggcat tagcggggtg  18300
gtggacctgg ccaaccaggc agtgcaaaat aagattaaca gtaagcttga tccccgccct  18360
cccgtagagg agcctccacc ggccgtggag acagtgtctc cagaggggcg tggcgaaaag  18420
cgtccgcgcc ccgacaggga agaaactctg gtgacgcaaa tagacgagcc tccctcgtac  18480
gaggaggcac taaagcaagg cctgcccacc acccgtccca tcgcgcccat ggctaccgga  18540
gtgctgggcc agcacacacc cgtaacgctg gacctgcctc cccccgccga cacccagcag  18600
aaacctgtgc tgccaggccc gaccgccgtt gttgtaaccc gtcctagccg cgcgtccctg  18660
cgccgcgccg ccagcggtcc gcgatcgttg cggcccgtag ccagtggcaa ctggcaaagc  18720
acactgaaca gcatcgtggg tctgggggtg caatccctga agcgccgacg atgcttctga  18780
atagctaacg tgtcgtatgt gtgtcatgta tgcgtccatg tcgccgccag aggagctgct  18840
gagccgccgc gcgcccgctt tccaagatgg ctaccccttc gatgatgccg cagtggtctt  18900
acatgcacat ctcgggccag gacgcctcgg agtacctgag ccccgggctg gtgcagtttg  18960
cccgcgccac cgagacgtac ttcagcctga ataacaagtt tagaaacccc acggtggcgc  19020
ctacgcacga cgtgaccaca gaccggtccc agcgtttgac gctgcggttc atccctgtgg  19080
accgtgagga tactgcgtac tcgtacaagg cgcggttcac cctagctgtg ggtgataacc  19140
gtgtgctgga catggcttcc acgtactttg acatccgcgg cgtgctggac aggggcccta  19200
cttttaagcc ctactctggc actgcctaca acgccctggc tcccaagggt gccccaaatc  19260
cttgcgaatg ggatgaagct gctactgctc ttgaaataaa cctagaagaa gaggacgatg  19320
acaacgaaga cgaagtagac gagcaagctg agcagcaaaa aactcacgta tttgggcagg  19380
cgccttattc tggtataaat attacaaagg agggtattca aataggtgtc gaaggtcaaa  19440
cacctaaata tgccgataaa acatttcaac ctgaacctca aataggagaa tctcagtggt  19500
acgaaactga aattaatcat gcagctggga gagtccttaa aaagactacc ccaatgaaac  19560
catgttacgg ttcatatgca aaacccacaa atgaaaatgg agggcaaggc attcttgtaa  19620
agcaacaaaa tggaaagcta gaaagtcaag tggaaatgca atttttctca actactgagg  19680
cgaccgcagg caatggtgat aacttgactc ctaaagtggt attgtacagt gaagatgtag  19740
atatagaaac cccagacact catatttctt acatgcccac tattaaggaa ggtaactcac  19800
gagaactaat gggccaacaa tctatgccca acaggcctaa ttacattgct tttagggaca  19860
attttattgg tctaatgtat tacaacagca cgggtaatat gggtgttctg gcgggccaag  19920
catcgcagtt gaatgctgtt gtagatttgc aagacagaaa cacagagctt tcataccagc  19980
ttttgcttga ttccattggt gatagaacca ggtacttttc tatgtggaat caggctgttg  20040
acagctatga tccagatgtt agaattattg aaaatcatgg aactgaagat gaacttccaa  20100
attactgctt tccactggga ggtgtgatta atacagagac tcttaccaag gtaaaaccta  20160
aaacaggtca ggaaaatgga tgggaaaaag atgctacaga attttcagat aaaaatgaaa  20220
taagagttgg aaataatttt gccatggaaa tcaatctaaa tgccaacctg tggagaaatt  20280
tcctgtactc caacatagcg ctgtatttgc ccgacaagct aaagtacagt ccttccaacg  20340
taaaaatttc tgataaccca aacacctacg actacatgaa caagcgagtg gtggctcccg  20400
ggttagtgga ctgctacatt aaccttggag cacgctggtc ccttgactat atggacaacg  20460
tcaacccatt taaccaccac cgcaatgctg gcctgcgcta ccgctcaatg ttgctgggca  20520
atggtcgcta tgtgcccttc cacatccagg tgcctcagaa gttctttgcc attaaaaacc  20580
tccttctcct gccgggctca tacacctacg agtggaactt caggaaggat gttaacatgg  20640
ttctgcagag ctccctagga aatgacctaa gggttgacgg agccagcatt aagtttgata  20700
gcatttgcct ttacgccacc ttcttcccca tggcccacaa caccgcctcc acgcttgagg  20760
ccatgcttag aaacgacacc aacgaccagt cctttaacga ctatctctcc gccgccaaca  20820
tgctctaccc tatacccgcc aacgctacca acgtgcccat atccatcccc tcccgcaact  20880
gggcggcttt ccgcggctgg gccttcacgc gccttaagac taaggaaacc ccatcactgg  20940
gctcgggcta cgacccttat tacacctact ctggctctat accctaccta gatggaacct  21000
tttacctcaa ccacaccttt aagaaggtgg ccattacctt tgactcttct gtcagctggc  21060
ctggcaatga ccgcctgctt acccccaacg agtttgaaat taagcgctca gttgacgggg  21120
agggttacaa cgttgcccag tgtaacatga ccaaagactg gttcctggta caaatgctag  21180
ctaactataa cattggctac cagggcttct atatcccaga gagctacaag gaccgcatgt  21240
actccttctt tagaaacttc cagcccatga gccgtcaggt ggtggatgat actaaataca  21300
aggactacca acaggtgggc atcctacacc aacacaacaa ctctggattt gttggctacc  21360
ttgcccccac catgcgcgaa ggacaggcct accctgctaa cttcccctat ccgcttatag  21420
gcaagaccgc agttgacagc attacccaga aaaagtttct ttgcgatcgc accctttggc  21480
gcatcccatt ctccagtaac tttatgtcca tgggcgcact cacagacctg ggccaaaacc  21540
ttctctacgc caactccgcc cacgcgctag acatgacttt tgaggtggat cccatggacg  21600
```

-continued

```
agcccaccct tctttatgtt ttgtttgaag tctttgacgt ggtccgtgtg caccagccgc  21660
accgcggcgt catcgaaacc gtgtacctgc gcacgccctt ctcggccggc aacgccacaa  21720
cataaagaag caagcaacat caacaacagc tgccgccatg ggctccagtg agcaggaact  21780
gaaagccatt gtcaaagatc ttggttgtgg gccatatttt ttgggcacct atgacaagcg  21840
ctttccaggc tttgtttctc cacacaagct cgcctgcgcc atagtcaata cggccggtcg  21900
cgagactggg ggcgtacact ggatggcctt tgcctggaac ccgcactcaa aaacatgcta  21960
cctctttgag ccctttggct tttctgacca gcgactcaag caggtttacc agtttgagta  22020
cgagtcactc ctgcgccgta gcgccattgc ttcttccccc gaccgctgta taacgctgga  22080
aaagtccacc caaagcgtac aggggcccaa ctcggccgcc tgtggactat tctgctgcat  22140
gtttctccac gcctttgcca actggcccca aactcccatg gatcacaacc ccaccatgaa  22200
ccttattacc ggggtaccca actccatgct caacagtccc caggtacagc ccaccctgcg  22260
tcgcaaccag gaacagctct acagcttcct ggagcgccac tcgcccttact tccgcagcca  22320
cagtgcgcag attaggagcg ccacttcttt ttgtcacttg aaaaacatgt aaaaataatg  22380
tactagagac actttcaata aaggcaaatg cttttatttg tacactctcg ggtgattatt  22440
taccccccacc cttgccgtct gcgccgtttc cttctcctat aggcagaaaa agatcatgga  22500
gtcagtcgag aagaaggaca gcctaaccgc cccctctgag ttcgccacca ccgcctccac  22560
cgatgccgcc aacgcgccta ccaccttccc cgtcgaggca cccccgcttg aggaggagga  22620
agtgattatc gagcaggacc caggttttgt aagcgaagac gacgaggacc gctcagtacc  22680
aacagaggat aaaaagcaag accaggacaa cgcagaggca aacgaggaac aagtcgggcg  22740
gggggacgaa aggcatggcg actacctaga tgtgggagac gacgtgctgt tgaagcatct  22800
gcagcgccag tgcgccatta tctgcgacgc gttgcaagag cgcagcgatg tgcccctcgc  22860
catagcggat gtcagccttg cctacgaacg ccacctattc tcaccgcgcg taccccccaa  22920
acgccaagaa aacggcacat gcgagcccaa cccgcgcctc aacttctacc ccgtatttgc  22980
cgtgccagag gtgcttgcca cctatcacat ctttttccaa aactgcaaga tacccctatc  23040
ctgccgtgcc aaccgcagcc gagcggacaa gcagctggcc ttgcggcagg gcgctgtcat  23100
acctgatatc gcctcgctca acgaagtgcc aaaaatcttt gagggtcttg gacgcgacga  23160
gaagcgcgcg gcaaacgctc tgcaacagga aaacagcgaa aatgaaagtc actctggagt  23220
gttggtggaa ctcgagggtg acaacgcgcg cctagccgta ctaaaacgca gcatcgaggt  23280
cacccacttt gcctacccgg cacttaacct accccccaag gtcatgagca cagtcatgag  23340
tgagctgatc gtgcgccgtg cgcagcccct ggagagggat gcaaatttgc aagaacaaac  23400
agaggagggc ctacccgcag ttggcgacga gcagctagcg cgctggcttc aaacgcgcga  23460
gcctgccgac ttggaggagc gacgcaaact aatgatggcc gcagtgctcg ttaccgtgga  23520
gcttgagtgc atgcagcggt tctttgctga cccggagatg cagcgcaagc tagaggaaac  23580
attgcactac acctttcgac agggctacgt acgccaggcc tgcaagatct ccaacgtgga  23640
gctctgcaac ctggtctcct accttggaat tttgcacgaa aaccgccttg ggcaaaacgt  23700
gcttcattcc acgctcaagg gcgaggcgcg ccgcgactac gtccgcgact gcgtttactt  23760
atttctatgc tacacctggc agacggccat gggcgtttgg cagcagtgct tggaggagtg  23820
caacctcaag gagctgcaga aactgctaaa gcaaaacttg aaggacctat ggacggcctt  23880
caacgagcgc tccgtggccg cgcacctggc ggacatcatt ttccccgaac gcctgcttaa  23940
aaccctgcaa cagggtctgc cagacttcac cagtcaaagc atgttgcaga actttaggaa  24000
ctttatccta gagcgctcag gaatcttgcc cgccacctgc tgtgcacttc ctagcgactt  24060
tgtgcccatt aagtaccgcg aatgccctcc gccgctttgg ggccactgct accttctgca  24120
gctagccaac taccttgcct accactctga cataatggaa gacgtgagcg gtgacggtct  24180
actggagtgt cactgtcgct gcaacctatg caccccgcac cgctccctgg tttgcaattc  24240
gcagctgctt aacgaaagtc aaattatcgg tacctttgag ctgcagggtc cctcgcctga  24300
cgaaaagtcc gcggctccgg ggttgaaact cactccgggg ctgtggacgt cggcttacct  24360
tcgcaaattt gtacctgagg actaccacgc ccacgagatt aggttctacg aagaccaatc  24420
ccgcccgcct aatgcggagc ttaccgcctg cgtcattacc cagggccaca ttcttggcca  24480
attgcaagcc atcaacaaag cccgccaaga gtttctgcta cgaaagggac gggggggttta  24540
cttggacccc cagtccggcg aggagctcaa cccaatcccc ccgccgccgc agccctatca  24600
gcagcagccg cgggcccttg cttcccagga tggcacccaa aaagaagctg cagctgccgc  24660
cgccacccac ggacgaggag gaatactggg acagtcaggc agaggaggtt ttggacgagg  24720
aggaggagga catgatggaa gactgggaga gcctagacga ggaagcttcc gaggtcgaag  24780
aggtgtcaga cgaaacaccg tcaccctcgg tcgcattccc ctcgccggcg ccccagaaat  24840
cggcaaccgg ttccagcatg gctacaacct ccgctcctca ggcgccgccg gcactgcccg  24900
ttcgccgacc caaccgtaga tgggacacca ctggaaccag ggccggtaag tccaagcagc  24960
cgccgccgtt agcccaagag caacaacagc gccaaggcta ccgctcatgg cgcgggcaca  25020
agaacgccat agttgcttgc ttgcaagact gtgggggcaa catctccttc gcccgccgct  25080
ttcttctcta ccatcacggc gtggccttcc cccgtaacat cctgcattac taccgtcatc  25140
tctacagccc atactgcacc ggcggcagcg gcagcaacag cagcggccac acagaagcaa  25200
aggcgaccgg atagcaagac tctgacaaag cccaagaaat ccacagcggc ggcagcagca  25260
ggaggaggag cgctgcgtct ggcgcccaac gaacccgtat cgacccgcga gcttagaaac  25320
aggatttttc ccactctgta tgctatattt caacagagca ggggccaaga acaagagctg  25380
aaaataaaaa acaggtctct gcgatccctc acccgcagct gcctgtatca caaaagcgaa  25440
gatcagcttc ggcgcacgct ggaagacgcg gaggctctct tcagtaaata ctgcgcgctg  25500
actcttaagg actagtttcg cgccctttct caaatttaag cgcgaaaact acgtcatctc  25560
cagcggccac acccggcgcc agcacctgtc gtcagcgcca tttcaacttt gtatacaaaa  25620
gttgtgatga gcaaggaaat tcccacgccc tacatgtgga gttaccagcc acaaatggga  25680
cttgcggctg gagctgccca agactactca acccgaataa actacatgag cgcgggaccc  25740
cacatgatat cccgggtcaa cggaatacgc gcccaccgaa accgaattct cctggaacag  25800
gcggctatta ccaccacacc tcgtaataac cttaatcccc gtagttggcc cgctgccctg  25860
gtgtaccagg aaagtcccgc tcccaccact gtggtacttc ccagagacgc ccaggccgaa  25920
gttcagatga ctaactcagg ggcgcagctt gcgggcggct ttcgtcacag ggtgcggtcg  25980
cccgggcagg gtataactca cctgacaatc agagggcgag gtattcagct caacgacgag  26040
tcggtgagct cctcgcttgg tctccgtccg gacgggacat ttcagatcgg cggcgccggc  26100
cgctcttcat tcacgcctcg tcaggcaatc ctaactctgc agacctcgtc ctctgagccg  26160
cgctctggag gcattggaac tctgcaattt attgaggagt ttgtgccatc ggtctacttt  26220
aacccttct cgggacctcc cggccactat ccggatcaat ttattcctaa ctttgacgcg  26280
gtaaaggact cggcggacgg ctacgactga ctctatgtgg gatatgctcc agcgctacaa  26340
```

```
ccttgaagtc aggcttcctg gatgtcagca tctgactttg gccagcacct gtcccgcgga  26400
tttgttccag tccaactaca gcgacccacc ctaacagaga tggtgagcaa gggcgaggag  26460
gataacatgg ccatcatcaa ggagttcatg cgcttcaagg tgcacatgga gggctccgtg  26520
aacggccacg agttcgagat cgagggcgag ggcgagggcc gcccctacga gggcacccag  26580
accgccaagc tgaaggtgac caagggtggc cccctgccct tcgcctggga catcctgtcc  26640
cctcagttca tgtacggctc caaggcctac gtgaagcacc ccgccgacat ccccgactac  26700
ttgaagctgt ccttccccga gggcttcaag tgggagcgcg tgatgaactt cgaggacggc  26760
ggcgtggtga ccgtgaccca ggactcctcc ctgcaggacg gcgagttcat ctacaaggtg  26820
aagctgcgcg gcaccaactt cccctccgac ggccccgtaa tgcagaagaa gaccatgggc  26880
tgggaggcct cctccgagcg gatgtacccc gaggacggcg ccctgaaggg cgagatcaag  26940
cagaggctga agctgaagga cggcggccac tacgacgctg aggtcaagac cacctacaag  27000
gccaagaagc ccgtgcagct gcccggcgcc tacaacgtca acatcaagtt ggacatcacc  27060
tcccacaacg aggactacac catcgtggaa cagtacgaac gcgccgaggg ccgccactcc  27120
accggcggca tggacgagct gtacaaggga agcggagcta ctaacttcag cctgctgaag  27180
caggctggtg acgtcgagga gaatcctggc ccaatggtga tgaccaacac aaccaacgcg  27240
gccgccgcta ccggacttac atctaccaca aatacacccc aagtttctgc ctttgtcaat  27300
aactgggata acttgggcat gtggtggttc tccatagcgc ttatgtttgt atgccttatt  27360
attatgtggc tcatctgctg cctaaagcgc aaacgcgccc gaccacccat ctatagtccc  27420
atcattgtgc tacacccaaa caatgatgga atccatagat tggacggact gaaacacatg  27480
ttcttttctc ttacagtatg attaaatgag actaataaaa aaaaataata aagcatcact  27540
tacttaaaat cagttagcaa atttctgtcc agtttattca gcagcacctc cttgccctcc  27600
tcccagctct ggtattgcag cttcctcctg gctgcaaact ttctccacaa tctaaatgga  27660
atgtcagttt cctcctgttc ctgtccatcc gcacccacta tcttcatgtt gttgcagatg  27720
aagcgcgcaa gaccgtctga agataccttc aaccccgtgt atccatatga cacggaaacc  27780
ggtcctccaa ctgtgccttt tcttactcct ccctttgtat cccccaatgg gtttcaagag  27840
agtccccctg gggtactctc tttgcgccta tccgaacctc tagttacctc caatggcatg  27900
cttgcgctca aaatgggcaa cggcctctct ctggacgagg ccggcaacct tacctcccaa  27960
aatgtaacca ctgtgagccc acctctcaaa aaaaccaagt caaacataaa cctggaaata  28020
tctgcacccc tcacagttac ctcagaagcc ctaactgtgg ctgccgccgc acctctaatg  28080
gtcgcgggca acacactcac catgcaatca caggccccgc taaccgtgca cgactccaaa  28140
cttagcattg ccacccaagg acccctcaca gtgtcagaag gaaagctagc cctgcaaaca  28200
tcaggccccc tcaccaccac cgatagcagt acccttacta tcactgcctc accccctcta  28260
actactgcca ctggtagctt gggcattgac ttgaaagagc ccatttatac acaaaatgga  28320
aaactaggac taaagtacgg ggctcctttg catgtaacag acgacctaaa cactttgacc  28380
gtagcaactg gtccaggtgt gactattaat aatacttcct tgcaaactaa agttactgga  28440
gccttgggtt ttgattcaca aggcaatatg caacttaatg tagcaggagg actaaggatt  28500
gattctcaaa acagacgcct tatacttgat gttagttatc cgtttgatgc tcaaaaccaa  28560
ctaaatctaa gactaggaca gggccctctt tttataaact cagcccacaa cttggatatt  28620
aactacaaca aaggccttta cttgtttaca gcttcaaaca attccaaaaa gcttgaggtt  28680
aacctaagca ctgccaaggg gttgatgttt gacgctacag ccatagccat taatgcagga  28740
gatgggcttg aatttggttc acctaatgca ccaaacacaa atcccctcaa aacaaaaatt  28800
ggccatggcc tagaatttga ttcaaacaag gctatggttc ctaaactagg aactggcctt  28860
agttttgaca gcacaggtgc cattacagta ggaaacaaaa ataatgataa gctaactttg  28920
tggaccacac cagctccatc tcctaactgt agactaaatg cagagaaaga tgctaaactc  28980
actttggtct taacaaaatg tggcagtcaa atacttgcta cagtttcagt tttggctgtt  29040
aaaggcagtt tggctccaat atctggaaca gttcaaagtg ctcatcttat tataagattt  29100
gacgaaaatg gagtgctact aaacaattcc ttcctggacc cagaatattg gaactttaga  29160
aatggagatc ttactgaagg cacagcctat acaaacgctg ttggatttat gcctaaccta  29220
tcagcttatc caaaatctca cggtaaaact gccaaaagta acattgtcag tcaagtttac  29280
ttaaacggag acaaaactaa acctgtaaca ctaaccatta cactaaacgg tacacaggaa  29340
acaggagaca caactccaag tgcatactct atgtcatttt catgggactg gtctggccac  29400
aactacatta atgaaatatt tgccacatcc tcttacactt tttcatacat tgcccaagaa  29460
taaagcaata gcatcacaaa tttcacaaat aaagcattat tttagttatt aatagtaatc  29520
aattacgggg tcattagttc atagcccata tatggagttc cgcgttacat aacttacggt  29580
aaatggcccg cctggctgac cgcccaacga cccccgccca ttgacgtcaa taatgacgta  29640
tgttcccata gtaacgccaa tagggacttt ccattgacgt caatgggtgg agtatttacg  29700
gtaaactgcc cacttggcag tacatcaagt gtatcatatg ccaagtacgc cccctattga  29760
cgtcaatgac ggtaaatggc ccgcctggca ttatgcccag tacatgacct tatgggactt  29820
tcctacttgg cagtacatct acgtattagt catcgctatt accatggtga tgcggttttg  29880
gcagtacatc aatgggcgtg gatagcggtt tgactcacgg ggatttccaa gtctccaccc  29940
cattgacgtc aatgggagtt tgttttggca ccaaaatcaa cgggactttc caaaatgtcg  30000
taacaactcc gccccattga cgcaaatggg cggtaggcgt gtacggtggg aggtctatat  30060
aagcatccct atcagtgata gagatcagat ctccctatca gtgatagaga gctgttttga  30120
cctccataga agacaccggg accgatccag cctccggact ctagcgttta aacttaagct  30180
tggtacccgg ggatcctcta gggcctctga gctattccag aagtagtgaa gaggcttttt  30240
tggaggccta ggcttttgca aaaagctccg gatcgatcct gagacaccat ggccagtcgg  30300
gaagaggagc agcgcgaaac cacccccgag cgcggacgcg gtgcggcgcg acgtccccca  30360
accatggagg acgtgtcgtc cccgtccccg tcgccgccgc ctccccgggc gcccccaaaa  30420
aagcggatga ggcggcgtat cgagtccgag gacgaggaag actcatcaca agacgcgctg  30480
gtgccgcgca cacccagccc gcggccatcg acctcggcgg cggatttggc cattgcgccc  30540
aagaagaaaa agaagcgccc ttctcccaag cccgagcgcc cgccatcacc agaggtaatc  30600
gtggacagcg aggaagaaag agaagatgtg gcgctacaaa tggtgggttt cagcaaccca  30660
ccggtgctaa tcaagcatgg caaaggaggt aagcgcacag tgcggcggct gaatgaagac  30720
gacccagtgg cgcgtggtat gcggacgcaa gaggaagagg aagagcccag cgaagcggaa  30780
agtgaaatta cggtgatgaa cccgctgagt gtgccgatcg tgtctgcgtg ggagaagggc  30840
atggaggctg cgcgcgcgct gatggacaag taccacgtgg ataacgatct aaaggcgaac  30900
ttcaaactac tgcctgacca agtggaagct ctggcggccg tatgcaagac ctggctgaac  30960
gaggagcacc gcgggttgca gctgaccttc accagcaaca agacctttgt gacgatgatg  31020
gggcgattcc tgcaggcgta cctgcagtcg tttgcagagg tgacctacaa gcatcacgag  31080
```

-continued cccacgggct gcgcgttgtg gctgcaccgc tgcgctgaga tcgaaggcga gcttaagtgt 31140
ctacacggaa gcattatgat aaataaggag cacgtgattg aaatggatgt gacgagcgaa 31200
aacgggcagc gcgcgctgaa ggagcagtct agcaaggcca agatcgtgaa gaaccggtgg 31260
ggccgaaatg tggtgcagat ctccaacacc gacgcaaggt gctgcgtgca cgacgcggcc 31320
tgtccggcca atcagttttc cggcaagtct tgcggcatgt tcttctctga aggcgcaaag 31380
gctcaggtgg cttttaagca gatcaaggct tttatgcagg cgctgtatcc taacgcccag 31440
accgggcacg gtcacctttt gatgccacta cggtgcgagt gcaactcaaa gcctgggcac 31500
gcgccctttt tgggaaggca gctaccaaag ttgactccgt tcgccctgag caacgcggag 31560
gacctggacg cggatctgat ctccgacaag agcgtgctgg ccagcgtgca ccacccggcg 31620
ctgatagtgt tccagtgctg caaccctgtg tatcgcaact cgcgcgcgca gggcggaggc 31680
cccaactgcg acttcaagat atcggcgccc gacctgctaa acgcgttggt gatggtgcgc 31740
agcctgtgga gtgaaaactt caccgagctg ccgcggatgg ttgtgcctga gtttaagtgg 31800
agcactaaac accagtatcg caacgtgtcc ctgccagtgg cgcatagcga tgcgcggcag 31860
aaccccttttg atttttaaaa taaacaagtt aacaacaaca caaaaataat gctttatttc 31920
tcgagagctt gatgccaggc aagtccaggc aggccaggca agtccaggca ggccaggcaa 31980
gtccaggcag gccaggcaag tccaggcagg ccaggcaagt ccaggcaggc caggcaagtc 32040
caggcaggcc aggcaagtcc aggcaggcca ggcaagtcca ggcaggccag gcaagtccag 32100
gcaggccagg caagtccagg cagggccagg caagtccagg caggccaggc aagtccaggc 32160
aggccaggca agtccaggca ggatcgaatt aagctttagg cgtgtacggt gggcgcctat 32220
aaaagcagag ctcgtttagt gaaccgtcag atcgcctgga gcaattccac aacacttttg 32280
tcttatacca actttccgta ccacttccta ccctcgtaaa cctggagacg ccatccacgc 32340
tgttttgacc tccatagaag acaccgggac cgatccagcc tccggtcgac cgatcctgat 32400
tcaccatgtc tagactggac aagagcaaag tcataaactc tgctctggaa ttactcaatg 32460
aagtcggtat cgaaggcctg acgacaagga aactcgctca aaagctggga gttgagcagc 32520
ctaccctgta ctggcacgtg aagaacaagc gggccctgct cgatgccctg gcaatcgaga 32580
tgctggacag gcatcatacc cacttctgcc ccctggaagg cgagtcatgg caagactttc 32640
tgcggaacaa cgccaagtca ttccgctgtg ctctcctctc acatcgcgac ggggctaaag 32700
tgcatctcgg cacccgccca acagagaaac agtacgaaac cctggaaaat cagctcgcgt 32760
tcctgtgtca gcaaggcttc tccctggaga acgcactgta cgctctgtcc gccgtgggcc 32820
actttacact gggctgcgta ttggaggatc aggagcatca agtagcaaaa gaggaaagag 32880
agacacctac caccgattct atgcccccac ttctgagaca agcaattgag ctgttcgacc 32940
atcagggagc cgaacctgcc ttccttttcg gcctggaact aatcatatgt ggcctggaga 33000
aacagctaaa gtgcgaaagc ggctccgcgt acagcggatc ccgggaattc agatcttatt 33060
aataaacaag ttaacaacaa cacaaaaata atgctttatt taatcgtggc aaatccacta 33120
taataaaaga atcgtttgtg ttatgtttca acgtgtttat ttttcaattg cagaaaattt 33180
cgaatcattt ttcattcagt agtatagccc caccaccaca tagcttatac agatcaccgt 33240
acctcaactt tgtataataa agttgtaatc aaactcacag aaccctagta ttcaacctgc 33300
cacctccctc ccaacacaca gagtacacag tcctttctcc ccggctggcc ttaaaaagca 33360
tcatatcatg ggtaacagac atattcttag gtgttatatt ccacacggtt tcctgtcgag 33420
ccaaacgctc atcagtgata ttaataaact ccccgggcag ctcacttaag ttcatgtcgc 33480
tgtccagctg ctgagccaca ggctgctgtc caacttgcgg ttgcttaacg ggcggcgaag 33540
gagaagtcca cgcctacatg gggtagagt cataatcgtg catcaggata gggcggtggt 33600
gctgcagcag cgcgcgaata aactgctgcc gccgccgctc cgtcctgcag gaatacaaca 33660
tggcagtggt ctcctcagcg atgattcgca ccgcccgcag cataaggcgc cttgtcctcc 33720
gggcacagca gcgcaccctg atctcactta aatcagcaca gtaactgcag cacagcacca 33780
caatattgtt caaaatccca cagtgcaagg cgctgtatcc aaagctcatg gcggggacca 33840
cagaacccac gtggccatca taccacaagc gcaggtagat taagtggcga cccctcataa 33900
acacgctgga cataaacatt acctcttttg gcatgttgta attcaccacc tcccggtacc 33960
atataaacct ctgattaaac atggcgccat ccaccaccat cctaaaccag ctggccaaaa 34020
cctgcccgcc ggctatacac tgcagggaac cgggactgga acaatgacag tggagagccc 34080
aggactcgta accatggatc atcatgctcg tcatgatatc aatgttggca caacacaggc 34140
acacgtgcat acacttcctc aggattacaa gctcctcccg cgttagaacc atatcccagg 34200
gaacaaccca ttcctgaatc agcgtaaatc ccacactgca gggaagacct cgcacgtaac 34260
tcacgttgtg cattgtcaaa gtgttacatt cgggcagcag cggatgatcc tccagtatgg 34320
tagcgcgggt ttctgtctca aaaggaggta gacgatccct actgtacgga gtgcgccgag 34380
acaaccgaga tcgtgttggt cgtagtgtca tgccaaatgg aacgccggac gtagtcatat 34440
ttcctgaagc aaaaccaggt gcgggcgtga caaacagatc tgcgtctccg gtctcgccgc 34500
ttagatcgct ctgtgtagta gttgtagtat atccactctc tcaaagcatc caggcgcccc 34560
ctggcttcgg gttctatgta aactccttca tgcgccgctg ccctgataac atccaccacc 34620
gcagaataag ccacacccag ccaacctaca cattcgttct gcgagtcaca cacgggagga 34680
gcgggaagag ctggaagaac catgtttttt tttttattcc aaaagattat ccaaaacctc 34740
aaaatgaaga tctattaagt gaacgcgctc ccctccggtg gcgtggtcaa actctacagc 34800
caaagaacag ataatggcat ttgtaagatg ttgcacaatg gcttccaaaa ggcaaacggc 34860
cctcacgtcc aagtggacgt aaaggctaaa cccttcaggg tgaatctcct ctataaacat 34920
tccagcacct tcaaccatgc ccaaataatt ctcatctcgc caccttctca atatatctct 34980
aagcaaatcc cgaatattaa gtccggccat tgtaaaaatc tgctccagag cgccctccac 35040
cttcagcctc aagcagcgaa tcatgattgc aaaaattcag gttcctcaca gacctgtata 35100
agattcaaaa gcggaacatt aacaaaaata ccgcgatccc gtaggtccct tcgcagggcc 35160
agctgaacat aatcgtgcag gtctgcacgg accagcgcgg ccacttcccc gccaggaacc 35220
atgacaaaag aacccacact gattatgaca cgcatactcg gagctatgct aaccagcgta 35280
gccccgatgt aagcttgttg catgggcggc gatataaaat gcaaggtgct gctcaaaaaa 35340
tcaggcaaag cctcgcgcaa aaaagaaagc acatcgtagt catgctcatg cagataaagg 35400
caggtaagct ccggaaccac cacagaaaaa gacaccattt ttctctcaaa catgtctgcg 35460
ggtttctgca taaacacaaa ataaaataac aaaaaaacat ttaaacatta gaagcctgtc 35520
ttacaacagg aaaaacaacc cttataagca taagacggac tacggccatg ccggcgtgac 35580
cgtaaaaaaa ctggtcaccg tgattaaaaa gcaccaccga cagctcctcg gtcatgtccg 35640
gagtcataat gtaagactcg gtaaacacat caggttgatt cacatcggtc agtgctaaaa 35700
agcgaccgaa atagcccggg ggaatacata cccgcaggcg tagagacaac attacagccc 35760
ccataggagg tataacaaaa ttaataggag agaaaaacac ataaacacct gaaaaaccct 35820

```
cctgcctagg caaaatagca ccctcccgct ccagaacaac atacagcgct tccacagcgg  35880
cagccataac agtcagcctt accagtaaaa aagaaaacct attaaaaaaa caccactcga  35940
cacggcacca gctcaatcag tcacagtgta aaaaagggcc aagtgcagag cgagtatata  36000
taggactaaa aaatgacgta acggttaaag tccacaaaaa acacccagaa aaccgcacgc  36060
gaacctacgc ccagaaacga aagccaaaaa acccacaact tcctcaaatc gtcacttccg  36120
ttttcccacg ttacgtcact tcccatttta agaaaactac aattcccaac acatacaagt  36180
tactccgccc taaaacctac gtcacccgcc ccgttcccac gccccgcgcc acgtcacaaa  36240
ctccaccccc tcattatcat attggcttca atccaaaata aggtatatta ttgatgatg   36299

SEQ ID NO: 3            moltype = DNA  length = 36299
FEATURE                 Location/Qualifiers
misc_feature            1..36299
                        note = Synthetic adenovirus genome (CMBT-1093)
source                  1..36299
                        mol_type = other DNA
                        organism = synthetic construct
SEQUENCE: 3
catcatcaat aatatacctt attttggatt gaagccaata tgataatgag ggggtggagt  60
ttgtgacgtg gcgcggggcg tgggaacggg gcgggtgacg tagtagtgtg gcggaagtgt  120
gatgttgcaa gtgtggcgga acacatgtaa gcgacggatg tggcaaaagt gacgtttttg  180
gtgtgcgccg gtgtacacag gaagtgacaa ttttcgcgcg gttttaggcg gatgttgtag  240
taaatttggg cgtaaccgag taagatttgg ccattttcgc gggaaaactg aataagagga  300
agtgaaatct gaataatttt gtgttactca tagcgcgtaa tatttgtcta gggccgcggg  360
gactttgacc gtttacgtgg agactcgccc aggtgttttt ctcaggtgtt ttccgcgttc  420
cgggtcaaag ttggcgtttt attattatag tcagctgacg tgtagtgtat ttatacccgg  480
tgagttcctc aagaggccac tcttgagtgc cagcgagtag agttttctcc tccgagccgc  540
tccgacaccg ggactgaaaa tgagacatat tatctgccac ggaggtgtta ttaccgaaga  600
aatggccgcc agtcttttgg accagctgat cgaagaggta ctggctgata atcttccacc  660
tcctagccat tttgaaccac ctacccttca cgaactgtat gatttagacg tgacggcccc  720
cgaagatccc aacgaggagg cggtttcgca gatttttccc gactctgtaa tgttggcggt  780
gcaggaaggg attgacttac tcacttttcc gccggcgccc ggttctccgg agccgcctca  840
cctttcccgg cagcccgagc agccggagca gagagccttg ggtccggttt ctatgccaaa  900
ccttgtaccg gaggtgatcg atcttacctg ccacgaggct ggctttccac ccagtgacga  960
cgaggatgaa gagggtgagg agtttgtgtt agattatgtg gagcaccccg ggcacggttg  1020
caggtcttgt cattatcacc ggaggaatac gggggaccca gatattatgt gttcgctttg  1080
ctatatgagg acctgtggca tgtttgtcta cagtaagtga aaattatggg cagtgggtga  1140
tagagtggtg ggtttggtgt ggtaattttt tttttaattt ttacagtttt gtggtttaaa  1200
gaattttgta ttgtgatttt tttaaaaggt cctgtgtctg aacctgagcc tgagcccgag  1260
ccagaaccgg agcctgcaag acctacccgc cgtcctaaaa tggcgcctgc tatcctgaga  1320
cgcccgacat cacctgtgtc tagagaatgc aatagtagta cggatagctg tgactccggt  1380
ccttctaaca cacctcctga gatacacccg gtggtcccgc tgtgccccat taaaccagtt  1440
gccgtgagag ttggtgggcg tcgccaggct gtggaatgta tcgaggactt gcttaacgag  1500
cctgggcaac ctttggactt gagctgtaaa cgcccccaggc cataaggtgt aaacctgtga  1560
ttgcgtgtgt ggttaacgcc tttgtttgct gaatgagttg atgtaagttt aataaagggt  1620
gagataatgt ttaacttgca tggcgtgtta aatggggcgg ggcttaaagg gtatataatg  1680
cgccgtgggc taatcttggt tacatctgac ctcatggagg cttgggagtg tttggaagat  1740
ttttctgctg tgcgtaactt gctggaacag agctctaaca gtacctcttg gttttggagg  1800
tttctgtggg gctcatccca ggcaaagtta gtctgcagaa ttaaggagga ttacaagtgg  1860
gaatttgaag agcttttgaa atcctgtggt gagctgtttg attctttgaa tctgggtcac  1920
caggcgcttt tccaagagaa ggtcatcaag actttggatt tttccacacc ggggcgcgct  1980
gcggctgctg ttgctttttt gagttttata aaggataaat ggagcgaaga aacccatctg  2040
agcgggggt acctgctgga ttttctggcc atgcatctgt ggagagcggt tgtgagacac  2100
aagaatcgcc tgctactgtt gtcttccgtc cgcccggcga taataccgac ggaggagcag  2160
cagcagcagc aggaggaagc caggcggcgg cggcaggagc agagcccatg gaacccgaga  2220
gccggcctgg accctcggga atgaatgttg tacaggtggc tgaactgtat ccagaactga  2280
gacgcatttt gacaattaca gaggatgggc aggggctaaa gggggtaaag agggagcggg  2340
gggcttgtga ggctacagag gaggctagga atctagcttt tagcttaatg accagacacc  2400
gtcctgagtg tattactttt caacagatca aggataattg cgctaatgag cttgatctgc  2460
tggcgcagaa gtattccata gagcagctga ccacttactg gctgcagcca ggggatgatt  2520
ttgaggaggc tattagggta tatgcaaagg tggcacttag gccagattgc aagtacaaga  2580
tcagcaaact tgtaaatatc aggaattgtt gctacatttc tgggaacggg gccgaggtgg  2640
agatagatac ggaggatagg gtggccttta gatgtagcat gataaatatg tggccggggg  2700
tgcttggcat ggacggggtg gttattatga atgtaaggtt tactggcccc aattttagcg  2760
gtacggtttt cctggccaat accaacctta tcctagccgg tgtaagcttc tatgggttta  2820
acaatacctg tgtggaagcc tggaccgatg taagggttcg gggctgtgcc ttttactgct  2880
gctggaaggg ggtggtgtgt cgccccaaaa gcagggcttc aattaagaaa tgcctctttg  2940
aaaggtgtac cttgggtatc ctgtctgagg gtaactccag ggtgcgccac aatgtggcct  3000
ccgactgtgg ttgcttcatg ctagtgaaaa gcgtggctgt gattaagcat aacatggtat  3060
gtggcaactg cgaggacagg gcctctcaga tgctgacctg ctcggacggc aactgtcacc  3120
tgctgaagac cattcacgta gccagccact ctcgcaaggc ctggccagtg tttgagcata  3180
acatactgac ccgctgttcc ttgcatttgg gtaacaggag gggggtgttc ctaccttacc  3240
aatgcaattt gagtcacact aagatattgc ttgagcccga gagcatgtcc aaggtgaacc  3300
tgaacggggt gtttgacatg accatgaaga tctggaaggt gctgaggtac gatgagaccc  3360
gcaccaggtg cagaccctgc gagtgtggcg gtaaacatat taggaaccag cctgtgatgc  3420
tggatgtgac cgaggagctg aggcccgatc acttggtgct ggcctgcacc cgcgctgagt  3480
ttggctctag cgatgaagat acagattgag gtactgaaat gtgtgggcgt ggcttaaggg  3540
tgggaaagaa tatataaggt gggggtctta tgtagttttg tatctgtttt gcagcagccg  3600
ccgccgccca actttctat acaaagttgt aatgagcacc aactcgtttg atggaagcat  3660
tgtgagctca tatttgacaa cgcgcatgcc cccatgggcc ggggtgcgtc agaatgtgat  3720
```

```
gggctccagc attgatggtc gccccgtcct gcccgcaaac tctactacct tgacctacga  3780
gaccgtgtct ggaacgccgt tggagactgc agcctccgcc gccgcttcag ccgctgcagc  3840
caccgcccgc gggattgtga ctgactttgc tttcctgagc ccgcttgcaa gcagtgcagc  3900
ttcccgttca tccgcccgcg atgacaagtt gacggctctt ttggcacaat tggattcttt  3960
gacccgggaa cttaatgtcg tttctcagca gctgttggat ctgcgccagc aggtttctgc  4020
cctgaaggct tcctcccctc ccaatgcggt ttaaaacata aataaaaaac cagactctgt  4080
ttggatttgg atcaagcata agtgtcttgc tgtctttatt taggggtttt gcgcgcgcgg  4140
taggcccggg accagcggtc tcggtcgttg agggtcctgt gtattttttc caggacgtgg  4200
taaaggtgac tctggatgtt cagatacatg ggcataagcc cgtctctggg gtggaggtag  4260
caccactgca gagcttcatg ctgcggggtg gtgttgtaga tgatccagtc gtagcaggag  4320
cgctgggcgt ggtgcctaaa aatgtctttc agtagcaagc tgattgccag gggcaggccc  4380
ttggtgtaag tgtttacaaa gcggttaagc tgggatgggt gcatacgtgg ggatatgaga  4440
tgcatcttgg actgtatttt taggttggct atgttcccag ccatatccct ccggggattc  4500
atgttgtgca gaaccaccag cacagtgtat ccggtgcact tgggaaattt gtcatgtagc  4560
ttagaaggaa atgcgtggaa gaacttggag acgcccttgt gacctccaag attttccatg  4620
cattcgtcca taatgatggc aatgggccca cgggcggcgg cctgggcgaa gatatttctg  4680
ggatcactaa cgtcatagtt gtgttccagg atgagatcgt cataggccat ttttacaaag  4740
cgcgggcgga gggtgccaga ctgcggtata atggttccat ccggcccagg ggcgtagtta  4800
ccctcacaga tttgcatttc ccacgctttg agttcagatg gggggatcat gtctacctgc  4860
ggggcgatga agaaaacggt ttccggggta ggggagatca gctgggaaga aagcaggttc  4920
ctgagcagct gcgacttacc gcagccggtg ggcccgtaaa tcacacctat taccgggtgc  4980
aactggtagt taagagagct gcagctgccg tcatccctga gcaggggggc cacttcgtta  5040
agcatgtccc tgactcgcat gttttccctg accaaatccg ccagaaggcg ctcgccgccc  5100
agcgatagca gttcttgcaa ggaagcaaag tttttcaacg gtttgagacc gtccgccgta  5160
ggcatgcttt tgagcgtttg accaagcagt tccaggcggt cccacagctc ggtcacctgc  5220
tctacggcat ctcgatccag catatctcct cgtttcgcgg gttggggcgg ctttcgctgt  5280
acggcagtag tcggtgctcg tccagacggg ccagggtcat gtctttccac gggcgcaggg  5340
tcctcgtcag cgtagtctgg gtcacggtga aggggtgcgc tccgggctgc gcgctggcca  5400
gggtgcgctt gaggctggtc ctgctggtgc tgaagcgctg ccggtcttcg ccctgcgcgt  5460
cggccaggta gcatttgacc atggtgtcat agtccagccc ctccgcggcg tggcccttgg  5520
cgcgcagctt gcccttggag gaggcgccgc acgaggggca gtgcagactt ttgagggcgt  5580
agagcttggg cgcgagaaat accgattccg gggagtaggc atccgcgccg caggccccgc  5640
agacggtctc gcattccacg agccaggtga gctctggccg ttcggggtca aaaaccaggt  5700
ttcccccatg ctttttgatg cgtttcttac ctctggtttc catgagccgg tgtccacgct  5760
cggtgacgaa aaggctgtcc gtgtccccgt atacagactt gagaggcctg tcctcgagcg  5820
gtgttccgcg gtcctcctcg tatagaaact cggaccactc tgagacaaag gctcgcgtcc  5880
aggccagcac gaaggaggct aagtgggagg ggtagcggtc gttgtccact agggggtcca  5940
ctcgctccag ggtgtgaaga cacatgtcgc cctcttcggc atcaaggaag gtgattggtt  6000
tgtaggtgta ggccacgtga ccgggtgttc ctgaaggggg gctataaaag ggggtggggg  6060
cgcgttcgtc ctcactctct tccgcatcgc tgtctgcgag ggccagctgt tggggtgagt  6120
actccctctg aaaagcgggc atgacttctg cgctaagatt gtcagtttcc aaaaacgagg  6180
aggatttgat attcacctgg cccgcggtga tgcctttgag ggtggccgca tccatctggt  6240
cagaaaagac aatctttttg ttgtcaagct tggtggcaaa cgacccgtag agggcgttgg  6300
acagcaactt ggcgatggag cgcagggttt ggtttttgtc gcgatcggcg cgctccttgg  6360
ccgcgatgtt tagctgcacg tattcgcgcg caacgcaccg ccattcggga aagacggtgg  6420
tgcgctcgtc gggcaccagg tgcacgcgcc aaccgcggtt gtgcagggtg acaaggtcaa  6480
cgctggtggc tacctctccg cgtaggcgct cgttggtcca gcagaggcgg ccgcccttgc  6540
gcgagcagaa tggcggtagg gggtctagct gcgtctcgtc cgggggggtct gcgtccacgg  6600
taaagacccc gggcagcagg cgcgcgtcga agtagtctat cttgcatcct tgcaagtcta  6660
gcgcctgctg ccatgcgcgg gcggcaagcg cgcgctcgta tgggttgagt gggggacccc  6720
atggcatggg gtgggtgagc gcggaggcgt acatgccgca aatgtcgtaa acgtagaggg  6780
gctctctgag tattccaaga tatgtagggt agcatcttcc accgcggatg ctggcgcgca  6840
cgtaatcgta tagttcgtgc gagggagcga ggaggtcggg accgaggttg ctacgggcgg  6900
gctgctctgc tcggaagact atctgcctga agatggcatg tgagttggat gatatggttg  6960
gacgctggaa gacgttgaag ctggcgtctg tgagacctac cgcgtcacgc acgaaggagg  7020
cgtaggagtc gcgcagcttg ttgaccagct cggcggtgac ctgcacgtct agggcgcagt  7080
agtccagggt ttccttgatg atgtcatact tatcctgtcc cttttttttc cacagctcgc  7140
ggttgaggac aaactcttcg cggtctttcc agtactcttg gatcggaaac ccgtcggcct  7200
ccgaacggta agagcctagc atgtagaact ggttgacggc ctggtaggcg cagcatccct  7260
tttctacggg tagcgcgtat gcctgcgcgg ccttccggag cgaggtgtgg gtgagcgcaa  7320
aggtgtccct gaccatgact ttgaggtact ggtatttgaa gtcagtgtcg tcgcatccgc  7380
cctgctccca gagcaaaaag tccgtgcgct ttttggaacg cggatttggc agggcgaagg  7440
tgacatcgtt gaagagtatc tttcccgcgc gaggcataaa gttgcgtgtg atgcggaagg  7500
gtcccggcac ctcggaacgg ttgttaatta cctgggcggc gagcacgatc tcgtcaaagc  7560
cgttgatgtt gtggcccaca atgtaaagtt ccaagaagcg cgggatgccc ttgatggaag  7620
gcaatttttt aagttcctcg taggtgagct cttcagggga gctgagcccg tgctctgaaa  7680
gggcccagtc tgcaagatga gggttggaag cgacgaatga gctccacagg tcacgggcca  7740
ttagcatttg caggtggtcg cgaaaggtcc taaactggcg acctatggcc atttttctg  7800
gggtgatgca gtagaaggta agcgggtctt gttcccagcg gtcccatcca aggttcgcgg  7860
ctaggtctcg cgcggcagtc actagaggct catctccgcc gaacttcatg accagcatga  7920
agggcacgag ctgcttccca aaggccccca tccaagtata ggtctctaca tcgtaggtga  7980
caaagagacg ctcggtgcga ggatgcgagc cgatcgggaa gaactggatc tcccgccacc  8040
aattggagga gtggctattg atgtggtgaa agtagaagtc cctgcgacgg gccgaacact  8100
cgtgctggct tttgtaaaaa cgtgcgcagt actggcagcg gtgcacgggc tgtacatcct  8160
gcacgaggtt gacctgacga ccgcgcacaa ggaagcagag tgggaatttg agcccctcgc  8220
ctggcgggtt tggctggtgg tcttctactt cggctgcttg tccttgaccg tctggctgct  8280
cgaggggagt tacggtggat cggaccacca cgccgcgcga gcccaaagtc cagatgtccg  8340
cgcgcggcgg tcggagcttg atgacaacat cgcgcagatg ggagctgtcc atggtctgga  8400
gctcccgcgg cgtcaggtca ggcgggagct cctgcaggtt tacctcgcat agacgggtca  8460
```

-continued

```
gggcgcgggc tagatccagg tgatacctaa tttccagggg ctggttggtg gcggcgtcga  8520
tggcttgcaa gaggccgcat ccccgcggcg cgactacggt accgcgcggc gggcggtggg  8580
ccgcgggggt gtccttggat gatgcatcta aaagcggtga cgcgggcgag cccccggagg  8640
taggggggc tccggacccg ccgggagagg gggcaggggc acgtcggcgc cgcgcgcggg  8700
caggagctgg tgctgcgcgc gtaggttgct ggcgaacgcg acgacgcggc ggttgatctc  8760
ctgaatctgg cgcctctgcg tgaagacgac gggcccggtg agcttgagcc tgaaagagag  8820
ttcgacagaa tcaatttcgg tgtcgttgac ggcggcctgg cgcaaaatct cctgcacgtc  8880
tcctgagttg tcttgatagg cgatctcggc catgaactgc tcgatctctt cctcctggag  8940
atctccgcgt ccggctcgct ccacggtggc ggcgaggtcg ttggaaatgc gggccatgag  9000
ctgcgagaag gcgttgaggc ctccctcgtt ccagacgcgg ctgtagacca cgcccccttc  9060
ggcatcgcgg gcgcgcatga ccacctgcgc gagattgagc tccacgtgcc gggcgaagac  9120
ggcgtagttt cgcaggcgct gaaagaggta gttgagggtg gtggcggtgt gttctgccac  9180
gaagaagtac ataacccagc gtcgcaacgt ggattcgttg atatccccca aggcctcaag  9240
gcgctccatg gcctcgtaga agtccacggc gaagttgaaa aactgggagt tgcgcgccga  9300
cacggttaac tcctcctcca gaagacggat gagctcggcg acagtgtcgc gcacctcgcg  9360
ctcaaaggct acaggggcct cttcttcttc ttcaatctcc tcttccataa gggcctcccc  9420
ttcttcttct tctggcggcg gtgggggagg ggggacacgg cggcgacgac ggcgcaccgg  9480
gaggcggtcg acaaagcgct cgatcatctc cccgcggcga cggcgcatgg tctcggtgac  9540
ggcgcggccg ttctcgcggg ggcgcagttg gaagacgccg cccgtcatgt cccggttatg  9600
ggttggcggg gggctgccat gcggcaggga tacggcgcta acgatgcatc tcaacaattg  9660
ttgtgtaggt actccgccgc cgagggacct gagcgagtcc gcatcgaccg gatcggaaaa  9720
cctctcgaga aaggcgtcta accagtcaca gtcgcaaggt aggctgagca ccgtggcggg  9780
cggcagcggg cggcggtcgg ggttgtttct ggcggaggtg ctgctgatga tgtaattaaa  9840
gtaggcggtc ttgagacggc ggatggtcga cagaagcacc atgtccttgg gtccggcctg  9900
ctgaatgcgc aggcggtcgg ccatgcccca ggcttcgttt tgacatcggc gcaggtcttt  9960
gtagtagtct tgcatgagcc tttctaccgg cacttcttct tctccttcct cttgtcctgc  10020
atctcttgca tctatcgctg cggcggcggc ggagtttggc cgtaggtggc gccctcttcc  10080
tcccatgcgt gtgaccccga agcccctcat cggctgaagc agggctaggt cggcgacaac  10140
gcgctcggct aatatggcct gctgcacctg cgtgagggta gactggaagt catccatgtc  10200
cacaaagcgg tggtatgcgc ccgtgttgat ggtgtaagtg cagttggcca taacggacca  10260
gttaacggtc tggtgacccg gctgcgagag ctcggtgtac ctgagacgcg agtaagccct  10320
cgagtcaaat acgtagtcgt tgcaagtccg caccaggtac tggtatccca ccaaaaagtg  10380
cggcggcggc tggcggtaga ggggccagcg tagggtggcc ggggctccgg gggcgagatc  10440
ttccaacata aggcgatgat atccgtagat gtacctggac atccaggtga tgccggcggc  10500
ggtggtggag gcgcgcggaa agtcgcggac gcggttccag atgttgcgca gcggcaaaaa  10560
gtgctccatg gtcgggacgc tctggccggt caggcgcgcg caatcgttga cgctctagac  10620
cgtgcaaaag gagagcctgt aagcgggcac tcttccgtgg tctggtggat aaattcgcaa  10680
gggtatcatg gcggacgacc ggggttcgag ccccgtatcc ggccgtccgc cgtgatccat  10740
gcggttaccg cccgcgtgtc gaacccaggt gtgcgacgtc agacaacggg ggagtgctcc  10800
ttttggcttc cttccaggcg cggcggctgc tgcgctagct tttttggcca ctggccgcgc  10860
gcagcgtaag cggttaggct ggaaagcgaa agcattaagt ggctcgctcc ctgtagccgg  10920
agggttattt tccaagggtt gagtcgcggg acccccggtt cgagtctcgg accggccgga  10980
ctgcggcgaa cgggggtttg cctccccgtc atgcaagacc ccgcttgcaa attcctccgg  11040
aaacagggac gagccccttt tttgcttttc ccagatgcat ccggtgctgc ggcagatgcg  11100
ccccctcct cagcagcggc aagagcaaga gcagcggcag acatgcaggg caccctcccc  11160
tcctcctacc gcgtcaggag gggcgacatc cgcggttgac gcggcagcag atggtgatta  11220
cgaacccccg cggcgccggg cccggcacta cctggacttg gaggagggcg agggcctggc  11280
gcggctagga gcgccctctc ctgagcggta cccaagggtg cagctgaagc gtgatacgcg  11340
tgaggcgtac gtgccgcggc agaacctgtt tcgcgaccgc gagggagagg agcccgagga  11400
gatgcgggat cgaaagttcc acgcagggcg cgagctgcgg catggcctga atcgcgagcg  11460
gttgctgcgc gaggaggact ttgagcccga cgcgcgaacc gggattagtc ccgcgcgcgc  11520
acacgtggcg gccgccgacc tggtaaccgc atacgagcag acggtgaacc aggagattaa  11580
ctttcaaaaa agctttaaca accacgtgcg tacgcttgtg gcgcgcgagg aggtggctat  11640
aggactgatg catctgtggg actttgtaag cgcgctggag caaaacccaa atagcaagcc  11700
gctcatggcg cagctgttcc ttatagtgca gcacagcagg gacaacgagg cattcaggga  11760
tgcgctgcta aacatagtag agcccgaggg ccgctggctg ctcgatttga taaacatcct  11820
gcagagcata gtggtgcagg agcgcagctt gagcctggct gacaaggtgg ccgccatcaa  11880
ctattccatg cttagcctgg gcaagtttta cgcccgcaag atataccata ccccttacgt  11940
tcccatagac aaggaggtaa agatcgaggg gttctacatg cgcatggcgc tgaaggtgct  12000
taccttgagc gacgacctgg gcgtttatcg caacgagcgc atccacaagg ccgtgagcgt  12060
gagccggcgg cgcgagctca gcgaccgcga gctgatgcac agcctgcaaa gggccctggc  12120
tggcacgggc agcggcgata gagaggccga gtcctacttt gacgcgggcg ctgacctgcg  12180
ctgggcccca agccgacgcg ccctggaggc agctggggcc ggacctgggc tggcggtggc  12240
acccgcgcgc gctggcaacg tcggcggcgt ggaggaatat gacgaggacg atgagtacga  12300
gccagaggac ggcgagtact aagcggtgat gtttctgatc agatgatgca agacgcaacg  12360
gacccggcgg tgcgggcggc gctgcagagc cagccgtccg gccttaactc cacggacgac  12420
tggcgccagg tcatggaccg catcatgtcg ctgactgcgc gcaatcctga cgcgttccgg  12480
cagcagccgc aggccaaccg gctctccgca attctggaag cggtggtccc ggcgcgcgca  12540
aaccccacgc acgagaaggt gctggcgatc gtaaacgcgc tggccgaaaa cagggccatc  12600
cggcccgacg aggccggcct ggtctacgac gcgctgcttc agcgcgtggc tcgttacaac  12660
agcggcaacg tgcagaccaa cctggaccgg ctggtggggg atgtgcgcga ggccgtggcg  12720
cagcgtgagc gcgcgcagca gcagggcaac ctgggctcca tggttgcact aaacgccttc  12780
ctgagtacac agcccgccaa cgtgccgcgg ggacaggagg actacaccaa ctttgtgagc  12840
gcactgcggc taatggtgac tgagacaccg caaagtgagg tgtaccagtc tgggccagac  12900
tattttttcc agaccagtag acaaggcctg cagaccgtaa acctgagcca ggctttcaaa  12960
aacttgcagg ggctgtgggg ggtgcgggct cccacaggcg accgcgcgac cgtgtctagc  13020
ttgctgacgc ccaactcgcg cctgttgctg ctgctaatag cgcccttcac ggacagtggc  13080
agcgtgtccc gggacacata cctaggtcac ttgctgacac tgtaccgcga ggccataggt  13140
caggcgcatg tggacgagca tactttccag gagattacaa gtgtcagccg cgcgctgggg  13200
```

```
caggaggaca cgggcagcct ggaggcaacc ctaaactacc tgctgaccaa ccggcggcag  13260
aagatcccct cgttgcacag tttaaacagc gaggaggagc gcattttgcg ctacgtgcag  13320
cagagcgtga gccttaacct gatgcgcgac ggggtaacgc ccagcgtggc gctggacatg  13380
accgcgcgca acatggaacc gggcatgtat gcctcaaacc ggccgtttat caaccgccta  13440
atggactact tgcatcgcgc ggccgccgtg aaccccgagt atttcaccaa tgccatcttg  13500
aacccgcact ggctaccgcc ccctggtttc tacaccgggg gattcgaggt gcccgagggt  13560
aacgatggat tcctctggga cgacatagac gacagcgtgt tttccccgca accgcagacc  13620
ctgctagagt tgcaacagcg cgagcaggca gaggcggcgc tgcgaaagga aagcttccgc  13680
aggccaagca gcttgtccga tctaggcgct gcggccccgc ggtcagatgc tagtagccca  13740
tttccaagct tgatagggtc tcttaccagc actcgcacca cccgcccgcg cctgctgggc  13800
gaggaggagt acctaaacaa ctcgctgctg cagccgcagc gcgaaaaaaa cctgcctccg  13860
gcatttccca acaacgggat agagagccta gtggacaaga tgagtagatg gaagacgtac  13920
gcgcaggagc acagggacgt gccaggcccg cgcccgccca cccgtcgtca aaggcacgac  13980
cgtcagcggg gtctggtgtg ggaggacgat gactcggcag acgacagcag cgtcctggat  14040
ttgggaggga gtggcaaccc gtttgcgcac cttcgcccca ggctggggag aatgttttaa  14100
aaaaaaaaaa gcatgatgca aaataaaaaa ctcaccaagg ccatggcacc gagcgttggt  14160
tttcttgtat tccccttagt atgcggcgcg cggcgatgta tgaggaaggt cctcctccct  14220
cctacgagag tgtggtgagc gcggcgccag tggcggcggc gctgggttct cccttcgatg  14280
ctcccctgga cccgccgttt gtgcctccgc ggtacctgcg gcctaccggg gggagaaaca  14340
gcatccgtta ctctgagttg gcacccctat tcgacaccac ccgtgtgtac ctggtggaca  14400
acaagtcaac ggatgtggca tccctgaact accagaacga ccacagcaac tttctgacca  14460
cggtcattca aaacaatgac tacagcccgg gggaggcaag cacacagacc atcaatcttg  14520
acgaccggtc gcactggggc ggcgacctga aaaccatcct gcataccaac atgccaaatg  14580
tgaacgagtt catgtttacc aataagttta aggcgcgggt gatggtgtcg cgcttgccta  14640
ctaaggacaa tcaggtggag ctgaaatacg agtgggtgga gttcacgctg cccgagggca  14700
actactccga gaccatgacc atagacctta tgaacaacgc gatcgtggag cactacttga  14760
aagtgggcag acagaacggg gttctggaaa gcgacatcgg ggtaaagttt gacacccgca  14820
acttcagact ggggtttgac cccgtcactg gtcttgtcat gcctggggta tatacaaacg  14880
aagccttcca tccagacatc attttgctgc caggatgcgg ggtggacttc acccacagcc  14940
gcctgagcaa cttgttgggc atccgcaagc ggcaaccctt ccaggagggc tttaggatca  15000
cctacgatga tctggagggt ggtaacattc ccgcactgtt ggatgtggac gcctaccagg  15060
cgagcttgaa agatgacacc gaacagggcg ggggtggcgc aggcggcagc aacagcagtg  15120
gcagcggcgc ggaagagaac tccaacgcgg cagccgcggc aatgcagccg gtggaggaca  15180
tgaacgatca tgccattcgc ggcgacacct ttgccacacg ggctgaggag aagcgcgctg  15240
aggccgaagc agcggccgaa gctgccgccc ccgctgcgca acccgaggtc gagaagcctc  15300
agaagaaacc ggtgatcaaa cccctgacag aggacagcaa gaaacgcagt tacaacctaa  15360
taagcaatga cagcaccttc acccagtacc gcagctggta ccttgcatac aactacggcg  15420
accctcagac cggaatccgc tcatggaccc tgctttgcac tcctgacgta acctgcggct  15480
cggagcaggt ctactggtcg ttgccagaca tgatgcaaga ccccgtgacc ttccgctcca  15540
cgcgccagat cagcaacttt ccggtggtgg gcgccgagct gttgcccgtg cactccaaga  15600
gcttctacaa cgaccaggcc gtctactccc aactcatccg ccagtttacc tctctgaccc  15660
acgtgttcaa tcgctttccc gagaaccaga ttttggcgcg cccgccagcc cccaccatca  15720
ccaccgtcag tgaaaacgtt cctgctctca cagatcacgg gacgctaccg ctgcgcaaca  15780
gcatcggagg agtccagcga gtgaccatta ctgacgccag acgccgcacc tgcccctacg  15840
tttacaaggc cctgggcata gtctcgccgc gcgtcctatc gagccgcact ttttgagcaa  15900
gcatgtccat ccttatatcg cccagcaata acacaggctg gggcctgcgc ttcccaagca  15960
agatgtttgg cggggccaag aagcgctccg accaacaccc agtgcgcgtg cgcgggcact  16020
accgcgcgcc ctggggcgcg cacaaacgcg gccgcactgg gcgcaccacc gtcgatgacg  16080
ccatcgacgc ggtggtggag gaggcgcgca actacacgcc cacgccgcca ccagtgtcca  16140
cagtggacgc ggccattcag accgtggtgc gcggagcccg gcgctatgct aaaatgaaga  16200
gacggcggag gcgcgtagca cgtcgccacc gccgccgacc cggcactgcc gcccaacgcg  16260
cggcggcggc cctgcttaac cgcgcacgtc gcaccggccg acgggcggcc atgcgggccg  16320
ctcgaaggct ggccgcgggt attgtcactg tgccccccag gtccaggcga cgagcggccg  16380
ccgcagcagc cgcggccatt agtgctatga ctcagggtcg caggggcaac gtgtattggg  16440
tgcgcgactc ggttagcggc ctgcgcgtgc ccgtgcgcac ccgccccccg cgcaactaga  16500
ttgcaagaaa aaactactta gactcgtact gttgtatgta tccagcggcg gcggcgcgca  16560
acgaagctat gtccaagcgc aaaatcaaag aagagatgct ccaggtcatc gcgccggaga  16620
tctatggccc cccgaagaag gaagagcagg attacaagcc ccgaaagcta aagcgggtca  16680
aaaagaaaaa gaaagatgat gatgatgaac ttgacgacga ggtggaactg ctgcacgcta  16740
ccgcgcccag gcgacgggta cagtggaaag gtcgacgcgt aaaacgtgtt ttgcgacccg  16800
gcaccaccgt agtctttacg cccggtgagc gctccacccg cacctacaag cgcgtgtatg  16860
atgaggtgta cggcgacgag gacctgcttg agcaggccaa cgagcgcctc ggggagtttg  16920
cctacggaaa gcggcataag gacatgctgg cgttgccgct ggacgagggc aacccaacac  16980
ctagcctaaa gcccgtaaca ctgcagcagg tgctgcccgc gcttgcaccg tccgaagaaa  17040
agcgcggcct aaagcgcgag tctggtgact tggcacccac cgtgcagctg atggtaccca  17100
agcgccagcg actggaagat gtcttggaaa aaatgaccgt ggaacctggg ctggagcccg  17160
aggtccgcgt gcggccaatc aagcaggtgg cgccgggact gggcgtgcag accgtggacg  17220
ttcagatacc cactaccagt agcaccagta ttgccaccgc cacagagggc atggagacac  17280
aaacgtcccc ggttgcctca gcggtggcgg atgccgcggt gcaggcggtc gctgcggccg  17340
cgtccaagac ctctacggag gtgcaaacgg acccgtggat gtttcgcgtt tcagcccccc  17400
ggcgcccgcg cggttcgagg aagtacggcg ccgccagcgc gctactgccc gaatatgccc  17460
tacatccttc cattgcgcct acccccggct atcgtggcta cacctaccgc cccagaagac  17520
gagcaactac ccgacgccga accaccactg gaacccgccg ccgccgtcgc cgtcgccagc  17580
ccgtgctggc cccgatttcc gtgcgcaggg tggctcgcga aggaggcagg accctggtgc  17640
tgccaacagc gcgctaccac cccagcatcg tttaaaagcc ggtctttgtg gttcttgcag  17700
atatggccct cacctgccgc ctccgtttcc cggtgccggg attccgagga agaatgcacc  17760
gtaggagggg catggccggc cacggcctga cgggcggcat gcgtcgtgcg caccaccggc  17820
ggcggcgcgc gtcgcaccgt cgcatgcgcg gcggtatcct gcccctcctt attccactga  17880
tcgccgcggc gattggcgcc gtgcccggaa ttgcatccgt ggccttgcag gcgcagagac  17940
```

```
actgattaaa aacaagttgc atgtggaaaa atcaaaataa aaagtctgga ctctcacgct  18000
cgcttggtcc tgtaactatt ttgtagaatg gaagacatca actttgcgtc tctggccccg  18060
cgacacggct cgcgcccgtt catgggaaac tggcaagata tcggcaccag caatatgagc  18120
ggtggcgcct tcagctgggg ctcgctgtgg agcggcatta aaaatttcgg ttccaccgtt  18180
aagaactatg gcagcaaggc ctggaacagc agcacaggcc agatgctgag ggataagttg  18240
aaagagcaaa atttccaaca aaaggtggta gatggcctgg cctctggcat tagcggggtg  18300
gtggacctgg ccaaccaggc agtgcaaaat aagattaaca gtaagcttga tccccgccct  18360
cccgtagagg agcctccacc ggccgtggag acagtgtctc cagaggggcg tggcgaaaag  18420
cgtccgcgcc ccgacaggga agaaactctg gtgacgcaaa tagacgagcc tccctcgtac  18480
gaggaggcac taaagcaagg cctgcccacc acccgtccca tcgcgcccat ggctaccgga  18540
gtgctgggcc agcacacacc cgtaacgctg gacctgcctc cccccgccga cacccagcag  18600
aaacctgtgc tgccaggccc gaccgccgtt gttgtaaccc gtcctagccg cgcgtccctg  18660
cgccgcgccg ccagcggtcc gcgatcgttg cggcccgtag ccagtggcaa ctggcaaagc  18720
acactgaaca gcatcgtggg tctgggggtg caatccctga agcgccgacg atgcttctga  18780
atagctaacg tgtcgtatgt gtgtcatgta tgcgtccatg tcgccgccag aggagctgct  18840
gagccgccgc gcgcccgctt tccaagatgg ctaccccttc gatgatgccg cagtggtctt  18900
acatgcacat ctcgggccag gacgcctcgg agtacctgag ccccgggctg gtgcagtttg  18960
cccgcgccac cgagacgtac ttcagcctga ataacaagtt tagaaacccc acggtggcgc  19020
ctacgcacga cgtgaccaca gaccggtccc agcgtttgac gctgcggttc atccctgtgg  19080
accgtgagga tactgcgtac tcgtacaagg cgcggttcac cctagctgtg ggtgataacc  19140
gtgtgctgga catggcttcc acgtactttg acatccgcgg cgtgctggac aggggcccta  19200
cttttaagcc ctactctggc actgcctaca acgccctggc tcccaagggt gccccaaatc  19260
cttgcgaatg ggatgaagct gctactgctc ttgaaataaa cctagaagaa gaggacgatg  19320
acaacgaaga cgaagtagac gagcaagctg agcagcaaaa aactcacgta tttgggcagg  19380
cgccttattc tggtataaat attacaaagg agggtattca aataggtgtc gaaggtcaaa  19440
cacctaaata tgccgataaa acatttcaac ctgaacctca aataggagaa tctcagtggt  19500
acgaaactga aattaatcat gcagctggga gagtccttaa aaagactacc ccaatgaaac  19560
catgttacgg ttcatatgca aaacccacaa atgaaaatgg agggcaaggc attcttgtaa  19620
agcaacaaaa tggaaagcta gaaagtcaag tggaaatgca atttttctca actactgagg  19680
cgaccgcagg caatggtgat aacttgactc ctaaagtggt attgtacagt gaagatgtag  19740
atatagaaac cccagacact catatttctt acatgcccac tattaaggaa ggtaactcac  19800
gagaactaat gggccaacaa tctatgccca acaggcctaa ttacattgct tttagggaca  19860
attttattgg tctaatgtat tacaacagca cgggtaatat gggtgttctg gcgggccaag  19920
catcgcagtt gaatgctgtt gtagatttgc aagacagaaa cacagagctt tcataccagc  19980
ttttgcttga ttccattggt gatagaacca ggtacttttc tatgtggaat caggctgttg  20040
acagctatga tccagatgtt agaattattg aaaatcatgg aactgaagat gaacttccaa  20100
attactgctt tccactggga ggtgtgatta atacagagac tcttaccaag gtaaaaccta  20160
aaacaggtca ggaaaatgga tggaaaaaag atgctacaga attttcagat aaaaatgaaa  20220
taagagttgg aaataatttt gccatggaaa tcaatctaaa tgccaacctg tggagaaatt  20280
tcctgtactc caacatagcg ctgtatttgc ccgacaagct aaagtacagt ccttccaacg  20340
taaaaatttc tgataaccca aacacctacg actacatgaa caagcgagtg gtggctcccg  20400
ggttagtgga ctgctacatt aaccttggag cacgctggtc ccttgactat atggacaacg  20460
tcaacccatt taaccaccac cgcaatgctg gcctgcgcta ccgctcaatg ttgctgggca  20520
atggtcgcta tgtgcccttc cacatccagg tgcctcagaa gttctttgcc attaaaaacc  20580
tccttctcct gccgggctca tacacctacg agtggaactt caggaaggat gttaacatgg  20640
ttctgcagag ctccctagga aatgacctaa gggttgacgg agccagcatt aagtttgata  20700
gcatttgcct ttacgccacc ttcttcccca tggcccacaa caccgcctcc acgcttgagg  20760
ccatgcttag aaacgacacc aacgaccagt cctttaacga ctatctctcc gccgccaaca  20820
tgctctaccc tatacccgcc aacgctacca acgtgcccat atccatcccc tcccgcaact  20880
gggcggcttt ccgcggctgg gccttcacgc gccttaagac taaggaaacc ccatcactgg  20940
gctcgggcta cgacccttat tacacctact ctggctctat accctaccta gatggaacct  21000
tttacctcaa ccacaccttt aagaaggtgg ccattacctt tgactcttct gtcagctggc  21060
ctggcaatga ccgcctgctt acccccaacg agtttgaaat taagcgctca gttgacgggg  21120
agggttacaa cgttgcccag tgtaacatga ccaaagactg gttcctggta caaatgctag  21180
ctaactataa cattggctac cagggcttct atatcccaga gagctacaag gaccgcatgt  21240
actccttctt tagaaacttc cagcccatga gccgtcaggt ggtggatgat actaaataca  21300
aggactacca acaggtgggc atcctacacc aacacaacaa ctctggattt gttggctacc  21360
ttgcccccac catgcgcgaa ggacaggcct accctgctaa cttcccctat ccgcttatag  21420
gcaagaccgc agttgacagc attacccaga aaaagtttct ttgcgatcgc accctttggc  21480
gcatcccatt ctccagtaac tttatgtcca tgggcgcact cacagacctg ggccaaaacc  21540
ttctctacgc caactccgcc cacgcgctag acatgacttt tgaggtggat cccatggacg  21600
agcccaccct tctttatgtt ttgtttgaag tctttgacgt ggtccgtgtg caccagccgc  21660
accgcggcgt catcgaaacc gtgtacctgc gcacgccctt ctcggccggc aacgccacaa  21720
cataaagaag caagcaacat caacaacagc tgccgccatg ggctccagtg agcaggaact  21780
gaaagccatt gtcaaagatc ttggttgtgg gccatatttt ttgggcacct atgacaagcg  21840
ctttccaggc tttgtttctc cacacaagct cgcctgcgcc atagtcaata cggccggtcg  21900
cgagactggg ggcgtacact ggatggcctt tgcctggaac ccgcactcaa aaacatgcta  21960
cctctttgag ccctttggct tttctgacca gcgactcaag caggtttacc agtttgagta  22020
cgagtcactc ctgcgccgta gcgccattgc ttcttccccc gaccgctgta taacgctgga  22080
aaagtccacc caaagcgtac aggggcccaa ctcggccgcc tgtggactat tctgctgcat  22140
gtttctccac gcctttgcca actggcccca aactcccatg gatcacaacc ccaccatgaa  22200
ccttattacc ggggtaccca actccatgct caacagtccc caggtacagc ccaccctgcg  22260
tcgcaaccag gaacagctct acagcttcct ggagcgccac tcgccctact tccgcagcca  22320
cagtgcgcag attaggagcg ccacttcttt ttgtcacttg aaaaacatgt aaaaataatg  22380
tactagagac actttcaata aaggcaaatg cttttatttg tacactctcg ggtgattatt  22440
taccccccacc cttgccgtct gcgccgtttc cttctcctat aggcagaaaa agatcatgga  22500
gtcagtcgag aagaaggaca gcctaaccgc cccctctgag ttcgccacca ccgcctccac  22560
cgatgccgcc aacgcgccta ccaccttccc cgtcgaggca cccccgcttg aggaggagga  22620
agtgattatc gagcaggacc caggttttgt aagcgaagac gacgaggacc gctcagtacc  22680
```

-continued

```
aacagaggat aaaaagcaag accaggacaa cgcagaggca aacgaggaac aagtcgggcg  22740
gggggacgaa aggcatggcg actacctaga tgtgggagac gacgtgctgt tgaagcatct  22800
gcagcgccag tgcgccatta tctgcgacgc gttgcaagag cgcagcgatg tgcccctcgc  22860
catagcggat gtcagccttg cctacgaacg ccacctattc tcaccgcgcg taccccccaa  22920
acgccaagaa aacggcacat gcgagcccaa cccgcgcctc aacttctacc ccgtatttgc  22980
cgtgccagag gtgcttgcca cctatcacat ctttttccaa aactgcaaga tacccctatc  23040
ctgccgtgcc aaccgcagcc gagcggacaa gcagctggcc ttgcggcagg gcgctgtcat  23100
acctgatatc gcctcgctca acgaagtgcc aaaaatcttt gagggtcttg gacgcgacga  23160
gaagcgcgcg gcaaacgctc tgcaacagga aaacagcgaa aatgaaagtc actctggagt  23220
gttggtggaa ctcgagggtg acaacgcgcg cctagccgta ctaaaacgca gcatcgaggt  23280
cacccacttt gcctacccgg cacttaacct acccccaag gtcatgagca cagtcatgag  23340
tgagctgatc gtgcgccgtg cgcagcccct ggagagggat gcaaatttgc aagaacaaac  23400
agaggagggc ctacccgcag ttggcgacga gcagctagcg cgctggcttc aaacgcgcga  23460
gcctgccgac ttggaggagc gacgcaaact aatgatggcc gcagtgctcg ttaccgtgga  23520
gcttgagtgc atgcagcggt tctttgctga cccggagatg cagcgcaagc tagaggaaac  23580
attgcactac acctttcgac agggctacgt acgccaggcc tgcaagatct ccaacgtgga  23640
gctctgcaac ctggtctcct accttggaat tttgcacgaa aaccgccttg ggcaaaacgt  23700
gcttcattcc acgctcaagg gcgaggcgcg ccgcgactac gtccgcgact gcgtttactt  23760
atttctatgc tacacctggc agacggccat gggcgtttgg cagcagtgct tggaggagtg  23820
caacctcaag gagctgcaga aactgctaaa gcaaaacttg aaggacctat ggacggcctt  23880
caacgagcgc tccgtggccg cgcacctggc ggacatcatt ttccccgaac gcctgcttaa  23940
aaccctgcaa cagggtctgc cagacttcac cagtcaaagc atgttgcaga actttaggaa  24000
ctttatccta gagcgctcag gaatcttgcc cgccacctgc tgtgcacttc ctagcgactt  24060
tgtgcccatt aagtaccgcg aatgccctcc gccgctttgg ggccactgct accttctgca  24120
gctagccaac taccttgcct accactctga cataatggaa gacgtgagcg gtgacggtct  24180
actggagtgt cactgtcgct gcaacctatg caccccgcac cgctccctgg tttgcaattc  24240
gcagctgctt aacgaaagtc aaattatcgg tacctttgag ctgcagggtc cctcgcctga  24300
cgaaaagtcc gcggctccgg ggttgaaact cactccgggg ctgtggacgt cggcttacct  24360
tcgcaaattt gtacctgagg actaccacgc ccacgagatt aggttctacg aagaccaatc  24420
ccgcccgcct aatgcggagc ttaccgcctg cgtcattacc cagggccaca ttcttggcca  24480
attgcaagcc atcaacaaag cccgccaaga gtttctgcta cgaaagggac gggggtttta  24540
cttggacccc cagtccggcg aggagctcaa cccaatcccc ccgccgccgc agccctatca  24600
gcagcagccg cgggcccttg cttcccagga tggcacccaa aaagaagctg cagctgccgc  24660
cgccacccac ggacgaggag gaatactggg acagtcaggc agaggaggtt ttggacgagg  24720
aggaggagga catgatggaa gactgggaga gcctagacga ggaagcttcc gaggtcgaag  24780
aggtgtcaga cgaaacaccg tcaccctcgg tcgcattccc ctcgccggcg ccccagaaat  24840
cggcaaccgg ttccagcatg gctacaacct ccgctcctca ggcgccgccg gcactgcccg  24900
ttcgccgacc caaccgtaga tgggacacca ctggaaccag ggccggtaag tccaagcagc  24960
cgccgccgtt agcccaagag caacaacagc gccaaggcta ccgctcatgg cgcgggcaca  25020
agaacgccat agttgcttgc ttgcaagact gtgggggcaa catctccttc gcccgccgct  25080
ttcttctcta ccatcacggc gtggccttcc cccgtaacat cctgcattac taccgtcatc  25140
tctacagccc atactgcacc ggcggcagcg gcagcaacag cagcggccac acagaagcaa  25200
aggcgaccgg atagcaagac tctgacaaag cccaagaaat ccacagcggc ggcagcagca  25260
ggaggaggag cgctgcgtct ggcgcccaac gaacccgtat cgacccgcga gcttagaaac  25320
aggatttttc ccactctgta tgctatattt caacagagca ggggccaaga acaagagctg  25380
aaaataaaaa acaggtctct gcgatccctc acccgcagct gcctgtatca caaaagcgaa  25440
gatcagcttc ggcgcacgct ggaagacgcg gaggctctct tcagtaaata ctgcgcgctg  25500
actcttaagg actagtttcg cgccctttct caaatttaag cgcgaaaact acgtcatctc  25560
cagcggccac acccggcgcc agcacctgtc gtcagcgcca tttcaacttt gtatacaaaa  25620
gttgtgatga gcaaggaaat tcccacgccc tacatgtgga gttaccagcc acaaatggga  25680
cttgcggctg gagctgccca agactactca acccgaataa actacatgag cgcgggaccc  25740
cacatgatat cccgggtcaa cggaatacgc gcccaccgaa accgaattct cctggaacag  25800
gcggctatta ccaccacacc tcgtaataac cttaatcccc gtagttggcc cgctgccctg  25860
gtgtaccagg aaagtcccgc tcccaccact gtggtacttc ccagagacgc ccaggccgaa  25920
gttcagatga ctaactcagg ggcgcagctt gcgggcggct ttcgtcacag ggtgcggtcg  25980
cccgggcagg gtataactca cctgacaatc agagggcgag gtattcagct caacgacgag  26040
tcggtgagct cctcgcttgg tctccgtccg gacgggacat ttcagatcgg cggcgccggc  26100
cgctcttcat tcacgcctcg tcaggcaatc ctaactctgc agacctcgtc ctctgagccg  26160
cgctctggag gcattggaac tctgcaattt attgaggagt ttgtgccatc ggtctacttt  26220
aaccccttct cgggacctcc cggccactat ccggatcaat ttattcctaa ctttgacgcg  26280
gtaaaggact cggcggacgg ctacgactga ctctatgtgg gatatgctcc agcgctacaa  26340
ccttgaagtc aggcttcctg gatgtcagca tctgactttg gccagcacct gtcccgcgga  26400
tttgttccag tccaactaca gcgacccacc ctaacagaga tggtgagcaa gggcgaggag  26460
gataacatgg ccatcatcaa ggagttcatg cgcttcaagg tgcacatgga gggctccgtg  26520
aacggccacg agttcgagat cgagggcgag ggcgagggcc gcccctacga gggcacccag  26580
accgccaagc tgaaggtgac caagggtggc cccctgccct tcgcctggga catcctgtcc  26640
cctcagttca tgtacggctc caaggcctac gtgaagcacc ccgccgacat ccccgactac  26700
ttgaagctgt ccttccccga gggcttcaag tgggagcgcg tgatgaactt cgaggacggc  26760
ggcgtggtga ccgtgaccca ggactcctcc ctgcaggacg gcgagttcat ctacaaggtg  26820
aagctgcgcg gcaccaactt cccctccgac ggccccgtaa tgcagaagaa gaccatgggc  26880
tgggaggcct cctccgagcg gatgtacccc gaggacggcg ccctgaaggg cgagatcaag  26940
cagaggctga agctgaagga cggcggccac tacgacgctg aggtcaagac cacctacaag  27000
gccaagaagc ccgtgcagct gcccggcgcc tacaacgtca acatcaagtt ggacatcacc  27060
tcccacaacg aggactacac catcgtggaa cagtacgaac gcgccgaggg ccgccactcc  27120
accggcggca tggacgagct gtacaaggga agcggagcta ctaacttcag cctgctgaag  27180
caggctggtg acgtcgagga gaatcctggc ccaatggtga tgaccaacac aaccaacgcg  27240
gccgccgcta ccggacttac atctaccaca aatacacccc aagtttctgc ctttgtcaat  27300
aactgggata acttgggcat gtggtggttc tccatagcgc ttatgtttgt atgccttatt  27360
attatgtggc tcatctgctg cctaaagcgc aaacgcgccc gaccacccat ctatagtccc  27420
```

-continued

```
atcattgtgc tacacccaaa caatgatgga atccatagat tggacggact gaaacacatg  27480
ttcttttctc ttacagtatg attaaatgag actaataaaa aaaaataata aagcatcact  27540
tacttaaaat cagttagcaa atttctgtcc agtttattca gcagcacctc cttgccctcc  27600
tcccagctct ggtattgcag cttcctcctg gctgcaaact ttctccacaa tctaaatgga  27660
atgtcagttt cctcctgttc ctgtccatcc gcacccacta tcttcatgtt gttgcagatg  27720
aagcgcgcaa gaccgtctga agataccttc aaccccgtgt atccatatga cacggaaacc  27780
ggtcctccaa ctgtgccttt tcttactcct ccctttgtat cccccaatgg gtttcaagag  27840
agtcccccctg gggtactctc tttgcgccta tccgaacctc tagttacctc caatggcatg  27900
cttgcgctca aaatgggcaa cggcctctct ctggacgagg ccggcaacct tacctcccaa  27960
aatgtaacca ctgtgagccc acctctcaaa aaaaccaagt caaacataaa cctggaaata  28020
tctgcacccc tcacagttac ctcagaagcc ctaactgtgg ctgccgccgc acctctaatg  28080
gtcgcgggca acacactcac catgcaatca caggccccgc taaccgtgca cgactccaaa  28140
cttagcattg ccacccaagg acccctcaca gtgtcagaag gaaagctagc cctgcaaaca  28200
tcaggccccc tcaccaccac cgatagcagt acccttacta tcactgcctc acccctcta  28260
actactgcca ctggtagctt gggcattgac ttgaaagagc ccatttatac acaaaatgga  28320
aaactaggac taaagtacgg ggctcctttg catgtaacag acgacctaaa cactttgacc  28380
gtagcaactg gtccaggtgt gactattaat aatacttcct tgcaaactaa agttactgga  28440
gccttgggtt ttgattcaca aggcaatatg caacttaatg tagcaggagg actaaggatt  28500
gattctcaaa acagacgcct tatacttgat gttagttatc cgtttgatgc tcaaaaccaa  28560
ctaaatctaa gactaggaca gggccctctt tttataaact cagcccacaa cttggatatt  28620
aactacaaca aaggccttta cttgtttaca gcttcaaaca attccaaaaa gcttgaggtt  28680
aacctaagca ctgccaaggg gttgatgttt gacgctacag ccatagccat taatgcagga  28740
gatgggcttg aatttggttc acctaatgca ccaaacacaa atcccctcaa aacaaaaatt  28800
ggccatggcc tagaatttga ttcaaacaag gctatggttc ctaaactagg aactggcctt  28860
agttttgaca gcacaggtgc cattacagta ggaaacaaaa ataatgataa gctaactttg  28920
tggaccacac cagctccatc tcctaactgt agactaaatg cagagaaaga tgctaaactc  28980
actttggtct taacaaaatg tggcagtcaa atacttgcta cagtttcagt tttggctgtt  29040
aaaggcagtt tggctccaat atctggaaca gttcaaagtg ctcatcttat tataagattt  29100
gacgaaaatg gagtgctact aaacaattcc ttcctggacc cagaatattg gaactttaga  29160
aatggagatc ttactgaagg cacagcctat acaaacgctg ttggatttat gcctaaccta  29220
tcagcttatc caaaatctca cggtaaaact gccaaaagta acattgtcag tcaagtttac  29280
ttaaacggag acaaaactaa acctgtaaca ctaaccatta cactaaacgg tacacaggaa  29340
acaggagaca caactccaag tgcatactct atgtcatttt catgggactg gtctggccac  29400
aactacatta atgaaatatt tgccacatcc tcttacactt tttcatacat tgcccaagaa  29460
taaagcaata gcatcacaaa tttcacaaat aaagcattat tttagttatt aatagtaatc  29520
aattacgggg tcattagttc atagcccata tatggagttc cgcgttacat aacttacggt  29580
aaatggcccg cctggctgac cgcccaacga cccccgccca ttgacgtcaa taatgacgta  29640
tgttcccata gtaacgccaa tagggacttt ccattgacgt caatgggtgg agtatttacg  29700
gtaaactgcc cacttggcag tacatcaagt gtatcatatg ccaagtacgc cccctattga  29760
cgtcaatgac ggtaaatggc ccgcctggca ttatgcccag tacatgacct tatgggactt  29820
tcctacttgg cagtacatct acgtattagt catcgctatt accatggtga tgcggttttg  29880
gcagtacatc aatgggcgtg gatagcggtt tgactcacgg ggatttccaa gtctccaccc  29940
cattgacgtc aatgggagtt tgttttggca ccaaaatcaa cgggactttc caaaatgtcg  30000
taacaactcc gccccattga cgcaaatggg cggtaggcgt gtacggtggg aggtctatat  30060
aagcatccct atcagtgata gagatcagat ctccctatca gtgatagaga gctgttttga  30120
cctccataga agacaccggg accgatccag cctccggact ctagcgttta aacttaagct  30180
tggtacccgg ggatcctcta gggcctctga gctattccag aagtagtgaa gaggcttttt  30240
tggaggccta ggcttttgca aaaagctccg gatcgatcct gagacaccat ggccagtcgg  30300
gaagaggagc agcgcgaaac cacccccgag cgcggacgcg gtgcggcgcg acgtccccca  30360
accatggagg acgtgtcgtc cccgtccccg tcgccgccgc ctccccgggc gcccccaaaa  30420
aagcggatga ggcggcgtat cgagtccgag gacgaggaag actcatcaca agacgcgctg  30480
gtgccgcgca cacccagccc gcggccatcg acctcggcgg cggatttggc cattgcgccc  30540
aagaagaaaa agaagcgccc ttctcccaag cccgagcgcc cgccatcacc agaggtaatc  30600
gtggacagcg aggaagaaag agaagatgtg gcgctacaaa tggtgggttt cagcaaccca  30660
ccggtgctaa tcaagcatgg caaaggaggt aagcgcacag tgcggcggct gaatgaagac  30720
gacccagtgg cgcgtggtat gcggacgcaa gaggaagagg aagagcccag cgaagcggaa  30780
agtgaaatta cggtgatgaa cccgctgagt gtgccgatcg tgtctgcgtg ggagaagggc  30840
atggaggctg cgcgcgcgct gatggacaag taccacgtgg ataacgatct aaaggcgaac  30900
ttcaaactac tgcctgacca agtggaagct ctggcggccg tatgcaagac ctggctgaac  30960
gaggagcacc gcgggttgca gctgaccttc accagcaaca agacctttgt gacgatgatg  31020
gggcgattcc tgcaggcgta cctgcagtcg tttgcagagg tgacctacaa gcatcacgag  31080
cccacgggct gcgcgttgtg gctgcaccgc tgcgctgaga tcgaaggcga gcttaagtgt  31140
ctacacggaa gcattatgat aaataaggag cacgtgattg aaatggatgt gacgagcgaa  31200
aacgggcagc gcgcgctgaa ggagcagtct agcaaggcca agatcgtgaa gaaccggtgg  31260
ggccgaaatg tggtgcagat ctccaacacc gacgcaaggt gctgcgtgca cgacgcggcc  31320
tgtccggcca atcagtttc cggcaagtct tgcggcatgt tcttctctga aggcgcaaag  31380
gctcaggtgg cttttaagca gatcaaggct tttatgcagg cgctgtatcc taacgcccag  31440
accgggcacg gtcacctttt gatgccacta cggtgcgagt gcaactcaaa gcctgggcac  31500
gcgccctttt tgggaaggca gctaccaaag ttgactccgt tcgccctgag caacgcggag  31560
gacctggacg cggatctgat ctccgacaag agcgtgctgg ccagcgtgca ccacccggcg  31620
ctgatagtgt tccagtgctg caaccctgtg tatcgcaact cgcgcgcgca gggcggaggc  31680
cccaactgcg acttcaagat atcggcgccc gacctgctaa acgcgttggt gatggtgcgc  31740
agcctgtgga gtgaaaactt caccgagctg ccgcggatgg ttgtgcctga gtttaagtgg  31800
agcactaaac accagtatcg caacgtgtcc ctgccagtgg cgcatagcga tgcgcggcag  31860
aacccctttg atttttaaaa taaacaagtt aacaacaaca caaaaataat gctttatttc  31920
tcgagagctt gatgccaggc aagtccaggc aggccaggca agtccaggca ggccaggcaa  31980
gtccaggcag gccaggcaag tccaggcagg ccaggcaagt ccaggcaggc caggcaagtc  32040
caggcaggcc aggcaagtcc aggcaggcca ggcaagtcca ggcaggccag gcaagtccag  32100
gcaggccagg caagtccagg cagggccagg caagtccagg caggccaggc aagtccaggc  32160
```

```
aggccaggca agtccaggca ggatcgaatt aagctttagg cgtgtacggt gggcgcctat  32220
aaaagcagag ctcgtttagt gaaccgtcag atcgcctgga gcaattccac aacacttttg  32280
tcttatacca actttccgta ccacttccta ccctcgtaaa cctggagacg ccatccacgc  32340
tgttttgacc tccatagaag acaccgggac cgatccagcc tccggtcgac cgatcctgat  32400
tcaccatgtc tagactggac aagagcaaag tcataaactc tgctctggaa ttactcaatg  32460
aagtcggtat cgaaggcctg acgacaagga aactcgctca aaagctggga gttgagcagc  32520
ctaccctgta ctggcacgtg aagaacaagc gggccctgct cgatgccctg gcaatcgaga  32580
tgctggacag gcatcatacc cacttctgcc ccctggaagg cgagtcatgg caagactttc  32640
tgcggaacaa cgccaagtca ttccgctgtg ctctcctctc acatcgcgac ggggctaaag  32700
tgcatctcgg cacccgccca acagagaaac agtacgaaac cctggaaaat cagctcgcgt  32760
tcctgtgtca gcaaggcttc tccctggaga acgcactgta cgctctgtcc gccgtgggcc  32820
actttacact gggctgcgta ttggaggatc aggagcatca agtagcaaaa gaggaaagag  32880
agacacctac caccgattct atgcccccac ttctgagaca agcaattgag ctgttcgacc  32940
atcagggagc cgaacctgcc ttccttttcg gcctggaact aatcatatgt ggcctggaga  33000
aacagctaaa gtgcgaaagc ggctccgcgt acagcggatc ccgggaattc agatcttatt  33060
aataaacaag ttaacaacaa cacaaaaata atgctttatt taatcgtggc aaatccacta  33120
taataaaaga atcgtttgtg ttatgtttca acgtgtttat ttttcaattg cagaaaattt  33180
cgaatcattt ttcattcagt agtatagccc caccaccaca tagcttatac agatcaccgt  33240
acctcaactt tgtataataa agttgtaatc aaactcacag aaccctagta ttcaacctgc  33300
cacctccctc ccaacacaca gagtacacag tcctttctcc ccggctggcc ttaaaaagca  33360
tcatatcatg ggtaacagac atattcttag gtgttatatt ccacacggtt tcctgtcgag  33420
ccaaacgctc atcagtgata ttaataaact ccccgggcag ctcacttaag ttcatgtcgc  33480
tgtccagctg ctgagccaca ggctgctgtc caacttgcgg ttgcttaacg ggcggcgaag  33540
gagaagtcca cgcctacatg gggtagagt cataatcgtg catcaggata gggcggtggt  33600
gctgcagcag cgcgcgaata aactgctgcc gccgccgctc cgtcctgcag gaatacaaca  33660
tggcagtggt ctcctcagcg atgattcgca ccgcccgcag cataaggcgc cttgtcctcc  33720
gggcacagca gcgcaccctg atctcactta aatcagcaca gtaactgcag cacagcacca  33780
caatattgtt caaaatccca cagtgcaagg cgctgtatcc aaagctcatg gcggggacca  33840
cagaacccac gtggccatca taccacaagc gcaggtagat taagtggcga cccctcataa  33900
acacgctgga cataaacatt acctcttttg gcatgttgta attcaccacc tcccggtacc  33960
atataaacct ctgattaaac atggcgccat ccaccaccat cctaaaccag ctggccaaaa  34020
cctgcccgcc ggctatacac tgcagggaac cgggactgga acaatgacag tggagagccc  34080
aggactcgta accatggatc atcatgctcg tcatgatatc aatgttggca caacacaggc  34140
acacgtgcat acacttcctc aggattacaa gctcctcccg cgttagaacc atatcccagg  34200
gaacaaccca ttcctgaatc agcgtaaatc ccacactgca gggaagacct cgcacgtaac  34260
tcacgttgtg cattgtcaaa gtgttacatt cgggcagcag cggatgatcc tccagtatgg  34320
tagcgcgggt ttctgtctca aaaggaggta gacgatccct actgtacgga gtgcgccgag  34380
acaaccgaga tcgtgttggt cgtagtgtca tgccaaatgg aacgccggac gtagtcatat  34440
ttcctgaagc aaaaccaggt gcgggcgtga caaacagatc tgcgtctccg gtctcgccgc  34500
ttagatcgct ctgtgtagta gttgtagtat atccactctc tcaaagcatc caggcgcccc  34560
ctggcttcgg gttctatgta aactccttca tgcgccgctg ccctgataac atccaccacc  34620
gcagaataag ccacacccag ccaacctaca cattcgttct gcgagtcaca cacgggagga  34680
gcgggaagag ctggaagaac catgtttttt tttttattcc aaaagattat ccaaaacctc  34740
aaaatgaaga tctattaagt gaacgcgctc ccctccggtg gcgtggtcaa actctacagc  34800
caaagaacag ataatggcat ttgtaagatg ttgcacaatg gcttccaaaa ggcaaacggc  34860
cctcacgtcc aagtggacgt aaaggctaaa cccttcaggg tgaatctcct ctataaacat  34920
tccagcacct tcaaccatgc ccaaataatt ctcatctcgc caccttctca atatatctct  34980
aagcaaatcc cgaatattaa gtccggccat tgtaaaaatc tgctccagag cgccctccac  35040
cttcagcctc aagcagcgaa tcatgattgc aaaaattcag gttcctcaca gacctgtata  35100
agattcaaaa gcggaacatt aacaaaaata ccgcgatccc gtaggtccct tcgcagggcc  35160
agctgaacat aatcgtgcag gtctgcacgg accagcgcgg ccacttcccc gccaggaacc  35220
atgacaaaag aacccacact gattatgaca cgcatactcg gagctatgct aaccagcgta  35280
gccccgatgt aagcttgttg catgggcggc gatataaaat gcaaggtgct gctcaaaaaa  35340
tcaggcaaag cctcgcgcaa aaaagaaagc acatcgtagt catgctcatg cagataaagg  35400
caggtaagct ccggaaccac cacagaaaaa gacaccattt ttctctcaaa catgtctgcg  35460
ggtttctgca taaacacaaa ataaaataac aaaaaaacat ttaaacatta gaagcctgtc  35520
ttacaacagg aaaaacaacc cttataagca taagacggac tacggccatg ccggcgtgac  35580
cgtaaaaaaa ctggtcaccg tgattaaaaa gcaccaccga cagctcctcg gtcatgtccg  35640
gagtcataat gtaagactcg gtaaacacat caggttgatt cacatcggtc agtgctaaaa  35700
agcgaccgaa atagcccggg ggaatacata cccgcaggcg tagagacaac attacagccc  35760
ccataggagg tataacaaaa ttaataggag agaaaaacac ataaacacct gaaaaaccct  35820
cctgcctagg caaaatagca ccctcccgct ccagaacaac atacagcgct tccacagcgg  35880
cagccataac agtcagcctt accagtaaaa aagaaaacct attaaaaaaa caccactcga  35940
cacggcacca gctcaatcag tcacagtgta aaaaagggcc aagtgcagag cgagtatata  36000
taggactaaa aaatgacgta acggttaaag tccacaaaaa acacccagaa aaccgcacgc  36060
gaacctacgc ccagaaacga aagccaaaaa acccacaact tcctcaaatc gtcacttccg  36120
ttttcccacg ttacgtcact tcccatttta agaaaactac aattcccaac acatacaagt  36180
tactccgccc taaaacctac gtcacccgcc ccgttcccac gccccgcgcc acgtcacaaa  36240
ctccaccccc tcattatcat attggcttca atccaaaata aggtatatta ttgatgatg   36299
```

```
SEQ ID NO: 4            moltype = DNA  length = 36299
FEATURE                 Location/Qualifiers
misc_feature            1..36299
                        note = Synthetic adenovirus genome (CMBT-1094)
source                  1..36299
                        mol_type = other DNA
                        organism = synthetic construct
SEQUENCE: 4
catcatcaat aatatacctt attttggatt gaagccaata tgataatgag gggtggagt  60
```

-continued ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatat tatctgccac ggaggtgtta ttaccgaaga 600
aatggccgcc agtcttttgg accagctgat cgaagaggta ctggctgata atcttccacc 660
tcctagccat tttgaaccac ctacccttca cgaactgtat gatttagacg tgacggcccc 720
cgaagatccc aacgaggagg cggtttcgca gatttttccc gactctgtaa tgttggcggt 780
gcaggaaggg attgacttac tcacttttcc gccggcgccc ggttctccgg agccgcctca 840
cctttcccgg cagcccgagc agccggagca gagagccttg ggtccggttt ctatgccaaa 900
ccttgtaccg gaggtgatcg atcttacctg ccacgaggct ggctttccac ccagtgacga 960
cgaggatgaa gagggtgagg agtttgtgtt agattatgtg gagcaccccg ggcacggttg 1020
caggtcttgt cattatcacc ggaggaatac gggggaccca gatattatgt gttcgctttg 1080
ctatatgagg acctgtggca tgtttgtcta cagtaagtga aaattatggg cagtgggtga 1140
tagagtggtg ggtttggtgt ggtaattttt tttttaattt ttacagtttt gtggtttaaa 1200
gaattttgta ttgtgatttt tttaaaaggt cctgtgtctg aacctgagcc tgagcccgag 1260
ccagaaccgg agcctgcaag acctacccgc cgtcctaaaa tggcgcctgc tatcctgaga 1320
cgcccgacat cacctgtgtc tagagaatgc aatagtagta cggatagctg tgactccggt 1380
ccttctaaca cacctcctga gatacacccg gtggtcccgc tgtgccccat taaaccagtt 1440
gccgtgagag ttggtgggcg tcgccaggct gtggaatgta tcgaggactt gcttaacgag 1500
cctgggcaac ctttggactt gagctgtaaa cgccccaggc cataaggtgt aaacctgtga 1560
ttgcgtgtgt ggttaacgcc tttgtttgct gaatgagttg atgtaagttt aataaagggt 1620
gagataatgt ttaacttgca tggcgtgtta aatggggcgg ggcttaaagg gtatataatg 1680
cgccgtgggc taatcttggt tacatctgac ctcatggagg cttgggagtg tttggaagat 1740
ttttctgctg tgcgtaactt gctggaacag agctctaaca gtacctcttg gttttggagg 1800
tttctgtggg gctcatccca ggcaaagtta gtctgcagaa ttaaggagga ttacaagtgg 1860
gaatttgaag agcttttgaa atcctgtggt gagctgtttg attctttgaa tctgggtcac 1920
caggcgcttt tccaagagaa ggtcatcaag actttggatt tttccacacc ggggcgcgct 1980
gcggctgctg ttgctttttt gagttttata aaggataaat ggagcgaaga aacccatctg 2040
agcggggggt acctgctgga ttttctggcc atgcatctgt ggagagcggt tgtgagacac 2100
aagaatcgcc tgctactgtt gtcttccgtc cgcccggcga taataccgac ggaggagcag 2160
cagcagcagc aggaggaagc caggcggcgg cggcaggagc agagcccatg gaacccgaga 2220
gccggcctgg accctcggga atgaatgttg tacaggtggc tgaactgtat ccagaactga 2280
gacgcatttt gacaattaca gaggatgggc aggggctaaa gggggtaaag agggagcggg 2340
gggcttgtga ggctacagag gaggctagga atctagcttt tagcttaatg accagacacc 2400
gtcctgagtg tattactttt caacagatca aggataattg cgctaatgag cttgatctgc 2460
tggcgcagaa gtattccata gagcagctga ccacttactg gctgcagcca ggggatgatt 2520
ttgaggaggc tattagggta tatgcaaagg tggcacttag gccagattgc aagtacaaga 2580
tcagcaaact tgtaaatatc aggaattgtt gctacatttc tgggaacggg gccgaggtgg 2640
agatagatac ggaggatagg gtggccttta gatgtagcat gataaatatg tggccggggg 2700
tgcttggcat ggacggggtg gttattatga atgtagcgtt tactggcccc aattttagcg 2760
gtacggtttt cctggccaat accaacctta tcctacacgg tgtaagcttc tatgggttta 2820
acaatacctg tgtggaagcc tggaccgatg taagggttcg ggctgtgcc ttttactgct 2880
gctggaaggg ggtggtgtgt cgccccaaaa gcagggcttc aattaagaaa tgcctctttg 2940
aaaggtgtac cttgggtatc ctgtctgagg gtaactccag ggtgcgccac aatgtggcct 3000
ccgactgtgg ttgcttcatg ctagtgaaaa gcgtggctgt gattaagcat aacatggtat 3060
gtggcaactg cgaggacagg gcctctcaga tgctgacctg ctcggacggc aactgtcacc 3120
tgctgaagac cattcacgta gccagccact ctcgcaaggc ctggccagtg tttgagcata 3180
acatactgac ccgctgttcc ttgcatttgg gtaacaggag gggggtgttc ctaccttacc 3240
aatgcaattt gagtcacact aagatattgc ttgagcccga gagcatgtcc aaggtgaacc 3300
tgaacggggt gtttgacatg accatgaaga tctggaaggt gctgaggtac gatgagaccc 3360
gcaccaggtg cagaccctgc gagtgtggcg gtaaacatat taggaaccag cctgtgatgc 3420
tggatgtgac cgaggagctg aggcccgatc acttggtgct ggcctgcacc cgcgctgagt 3480
ttggctctag cgatgaagat acagattgag gtactgaaat gtgtgggcgt ggcttaaggg 3540
tgggaaagaa tatataaggt gggggtctta tgtagttttg tatctgtttt gcagcagccg 3600
ccgccgccca acttttctat acaaagttgt aatgagcacc aactcgtttg atggaagcat 3660
tgtgagctca tatttgacaa cgcgcatgcc cccatgggcc ggggtgcgtc agaatgtgat 3720
gggctccagc attgatggtc gccccgtcct gcccgcaaac tctactacct tgacctacga 3780
gaccgtgtct ggaacgccgt tggagactgc agcctccgcc gccgcttcag ccgctgcagc 3840
caccgcccgc gggattgtga ctgactttgc tttcctgagc ccgcttgcaa gcagtgcagc 3900
ttcccgttca tccgcccgcg atgacaagtt gacggctctt ttggcacaat tggattcttt 3960
gacccgggaa cttaatgtcg tttctcagca gctgttggat ctgcgccagc aggtttctgc 4020
cctgaaggct tcctcccctc ccaatgcggt ttaaaacata aataaaaaac cagactctgt 4080
ttggatttgg atcaagcata agtgtcttgc tgtctttatt taggggtttt gcgcgcgcgg 4140
taggcccggg accagcggtc tcggtcgttg agggtcctgt gtattttttc caggacgtgg 4200
taaaggtgac tctggatgtt cagatacatg ggcataagcc cgtctctggg gtggaggtag 4260
caccactgca gagcttcatg ctgcggggtg gtgttgtaga tgatccagtc gtagcaggag 4320
cgctgggcgt ggtgcctaaa aatgtctttc agtagcaagc tgattgccag gggcaggccc 4380
ttggtgtaag tgtttacaaa gcggttaagc tgggatgggt gcatacgtgg ggatatgaga 4440
tgcatcttgg actgtatttt taggttggct atgttcccag ccatatccct ccggggattc 4500
atgttgtgca gaaccaccag cacagtgtat ccggtgcact tgggaaattt gtcatgtagc 4560
ttagaaggaa atgcgtggaa gaacttggag acgcccttgt gacctccaag attttccatg 4620
cattcgtcca taatgatggc aatgggccca cgggcggcgg cctgggcgaa gatatttctg 4680
ggatcactaa cgtcatagtt gtgttccagg atgagatcgt cataggccat ttttacaaag 4740
cgcgggcgga gggtgccaga ctgcggtata atggttccat ccggcccagg ggcgtagtta 4800

```
ccctcacaga tttgcatttc ccacgctttg agttcagatg gggggatcat gtctacctgc  4860
ggggcgatga agaaaacggt ttccggggta ggggagatca gctgggaaga aagcaggttc  4920
ctgagcagct gcgacttacc gcagccggtg ggcccgtaaa tcacacctat taccgggtgc  4980
aactggtagt taagagagct gcagctgccg tcatccctga gcaggggggc cacttcgtta  5040
agcatgtccc tgactcgcat gttttccctg accaaatccg ccagaaggcg ctcgccgccc  5100
agcgatagca gttcttgcaa ggaagcaaag tttttcaacg gtttgagacc gtccgccgta  5160
ggcatgcttt tgagcgtttg accaagcagt tccaggcggt cccacagctc ggtcacctgc  5220
tctacggcat ctcgatccag catatctcct cgtttcgcgg gttggggcgg ctttcgctgt  5280
acggcagtag tcggtgctcg tccagacggg ccagggtcat gtctttccac gggcgcaggg  5340
tcctcgtcag cgtagtctgg gtcacggtga aggggtgcgc tccgggctgc gcgctggcca  5400
gggtgcgctt gaggctggtc ctgctggtgc tgaagcgctg ccggtcttcg ccctgcgcgt  5460
cggccaggta gcatttgacc atggtgtcat agtccagccc ctccgcggcg tggcccttgg  5520
cgcgcagctt gcccttggag gaggcgccgc acgaggggca gtgcagactt ttgagggcgt  5580
agagcttggg cgcgagaaat accgattccg gggagtaggc atccgcgccg caggccccgc  5640
agacggtctc gcattccacg agccaggtga gctctggccg ttcggggtca aaaaccaggt  5700
ttcccccatg ctttttgatg cgtttcttac ctctggtttc catgagccgg tgtccacgct  5760
cggtgacgaa aaggctgtcc gtgtccccgt atacagactt gagaggcctg tcctcgagcg  5820
gtgttccgcg gtcctcctcg tatagaaact cggaccactc tgagacaaag gctcgcgtcc  5880
aggccagcac gaaggaggct aagtgggagg ggtagcggtc gttgtccact agggggtcca  5940
ctcgctccag ggtgtgaaga cacatgtcgc cctcttcggc atcaaggaag gtgattggtt  6000
tgtaggtgta ggccacgtga ccgggtgttc ctgaaggggg gctataaaag gggtgggggg  6060
cgcgttcgtc ctcactctct tccgcatcgc tgtctgcgag ggccagctgt tggggtgagt  6120
actccctctg aaaagcgggc atgacttctg cgctaagatt gtcagtttcc aaaaacgagg  6180
aggatttgat attcacctgg cccgcggtga tgcctttgag ggtggccgca tccatctggt  6240
cagaaaagac aatctttttg ttgtcaagct tggtggcaaa cgacccgtag agggcgttgg  6300
acagcaactt ggcgatggag cgcagggttt ggtttttgtc gcgatcggcg cgctccttgg  6360
ccgcgatgtt tagctgcacg tattcgcgcg caacgcaccg ccattcggga aagacggtgg  6420
tgcgctcgtc gggcaccagg tgcacgcgcc aaccgcggtt gtgcagggtg acaaggtcaa  6480
cgctggtggc tacctctccg cgtaggcgct cgttggtcca gcagaggcgg ccgcccttgc  6540
gcgagcagaa tggcggtagg gggtctagct gcgtctcgtc cggggggtct gcgtccacgg  6600
taaagacccc gggcagcagg cgcgcgtcga agtagtctat cttgcatcct tgcaagtcta  6660
gcgcctgctg ccatgcgcgg gcggcaagcg cgcgctcgta tgggttgagt gggggacccc  6720
atggcatggg gtgggtgagc gcggaggcgt acatgccgca aatgtcgtaa acgtagaggg  6780
gctctctgag tattccaaga tatgtagggt agcatcttcc accgcggatg ctggcgcgca  6840
cgtaatcgta tagttcgtgc gagggagcga ggaggtcggg accgaggttg ctacgggcgg  6900
gctgctctgc tcggaagact atctgcctga agatggcatg tgagttggat gatatggttg  6960
gacgctggaa gacgttgaag ctggcgtctg tgagacctac cgcgtcacgc acgaaggagg  7020
cgtaggagtc gcgcagcttg ttgaccagct cggcggtgac ctgcacgtct agggcgcagt  7080
agtccagggt ttccttgatg atgtcatact tatcctgtcc cttttttttc cacagctcgc  7140
ggttgaggac aaactcttcg cggtctttcc agtactcttg gatcggaaac ccgtcggcct  7200
ccgaacggta agagcctagc atgtagaact ggttgacggc ctggtaggcg cagcatccct  7260
tttctacggg tagcgcgtat gcctgcgcgg ccttccggag cgaggtgtgg gtgagcgcaa  7320
aggtgtccct gaccatgact ttgaggtact ggtatttgaa gtcagtgtcg tcgcatccgc  7380
cctgctccca gagcaaaaag tccgtgcgct ttttggaacg cggatttggc agggcgaagg  7440
tgacatcgtt gaagagtatc tttcccgcgc gaggcataaa gttgcgtgtg atgcggaagg  7500
gtcccggcac ctcggaacgg ttgttaatta cctgggcggc gagcacgatc tcgtcaaagc  7560
cgttgatgtt gtggcccaca atgtaaagtt ccaagaagcg cgggatgccc ttgatggaag  7620
gcaatttttt aagttcctcg taggtgagct cttcagggga gctgagcccg tgctctgaaa  7680
gggcccagtc tgcaagatga gggttggaag cgacgaatga gctccacagg tcacgggcca  7740
ttagcatttg caggtggtcg cgaaaggtcc taaactggcg acctatggcc atttttctg  7800
gggtgatgca gtagaaggta agcgggtctt gttcccagcg gtcccatcca aggttcgcgg  7860
ctaggtctcg cgcggcagtc actagaggct catctccgcc gaacttcatg accagcatga  7920
agggcacgag ctgcttccca aaggccccca tccaagtata ggtctctaca tcgtaggtga  7980
caaagagacg ctcggtgcga ggatgcgagc cgatcgggaa gaactggatc tcccgccacc  8040
aattggagga gtggctattg atgtggtgaa agtagaagtc cctgcgacgg gccgaacact  8100
cgtgctggct tttgtaaaaa cgtgcgcagt actggcagcg gtgcacgggc tgtacatcct  8160
gcacgaggtt gacctgacga ccgcgcacaa ggaagcagag tgggaatttg agcccctcgc  8220
ctggcgggtt tggctggtgg tcttctactt cggctgcttg tccttgaccg tctggctgct  8280
cgaggggagt tacggtggat cggaccacca cgccgcgcga gcccaaagtc cagatgtccg  8340
cgcgcggcgg tcggagcttg atgacaacat cgcgcagatg ggagctgtcc atggtctgga  8400
gctcccgcgg cgtcaggtca ggcgggagct cctgcaggtt tacctcgcat agacgggtca  8460
gggcgcgggc tagatccagg tgatacctaa tttccagggg ctggttggtg gcggcgtcga  8520
tggcttgcaa gaggccgcat ccccgcggcg cgactacggt accgcgcggc gggcggtggg  8580
ccgcgggggt gtccttggat gatgcatcta aaagcggtga cgcgggcgag cccccggagg  8640
taggggggc tccggacccg ccgggagagg gggcaggggc acgtcggcgc cgcgcgcggg  8700
caggagctgg tgctgcgcgc gtaggttgct ggcgaacgcg acgacgcggc ggttgatctc  8760
ctgaatctgg cgcctctgcg tgaagacgac gggcccggtg agcttgagcc tgaaagagag  8820
ttcgacagaa tcaatttcgg tgtcgttgac ggcggcctgg cgcaaaatct cctgcacgtc  8880
tcctgagttg tcttgatagg cgatctcggc catgaactgc tcgatctctt cctcctggag  8940
atctccgcgt ccggctcgct ccacggtggc ggcgaggtcg ttggaaatgc gggccatgag  9000
ctgcgagaag gcgttgaggc ctccctcgtt ccagacgcgg ctgtagacca cgccccccttc  9060
ggcatcgcgg gcgcgcatga ccacctgcgc gagattgagc tccacgtgcc gggcgaagac  9120
ggcgtagttt cgcaggcgct gaaagaggta gttgagggtg gtggcggtgt gttctgccac  9180
gaagaagtac ataacccagc gtcgcaacgt ggattcgttg atatccccca aggcctcaag  9240
gcgctccatg gcctcgtaga agtccacggc gaagttgaaa aactgggagt tgcgcgccga  9300
cacggttaac tcctcctcca gaagacggat gagctcggcg acagtgtcgc gcacctcgcg  9360
ctcaaaggct acaggggcct cttcttcttc ttcaatctcc tcttccataa gggcctcccc  9420
ttcttcttct tctggcggcg gtgggggagg ggggacacgg cggcgacgac ggcgcaccgg  9480
gaggcggtcg acaaagcgct cgatcatctc cccgcggcga cggcgcatgg tctcggtgac  9540
```

```
ggcgcggccg ttctcgcggg ggcgcagttg gaagacgccg cccgtcatgt cccggttatg  9600
ggttggcggg gggctgccat gcggcaggga tacggcgcta acgatgcatc tcaacaattg  9660
ttgtgtaggt actccgccgc cgagggacct gagcgagtcc gcatcgaccg gatcggaaaa  9720
cctctcgaga aaggcgtcta accagtcaca gtcgcaaggt aggctgagca ccgtggcggg  9780
cggcagcggg cggcggtcgg ggttgtttct ggcggaggtg ctgctgatga tgtaattaaa  9840
gtaggcggtc ttgagacggc ggatggtcga cagaagcacc atgtccttgg gtccggcctg  9900
ctgaatgcgc aggcggtcgg ccatgcccca ggcttcgttt tgacatcggc gcaggtcttt  9960
gtagtagtct tgcatgagcc tttctaccgg cacttcttct tctccttcct cttgtcctgc  10020
atctcttgca tctatcgctg cggcggcggc ggagtttggc cgtaggtggc gccctcttcc  10080
tcccatgcgt gtgaccccga agcccctcat cggctgaagc agggctaggt cggcgacaac  10140
gcgctcggct aatatggcct gctgcacctg cgtgagggta gactggaagt catccatgtc  10200
cacaaagcgg tggtatgcgc ccgtgttgat ggtgtaagtg cagttggcca taacggacca  10260
gttaacggtc tggtgacccg gctgcgagag ctcggtgtac ctgagacgcg agtaagccct  10320
cgagtcaaat acgtagtcgt tgcaagtccg caccaggtac tggtatccca ccaaaaagtg  10380
cggcggcggc tggcggtaga ggggccagcg tagggtggcc ggggctccgg gggcgagatc  10440
ttccaacata aggcgatgat atccgtagat gtacctggac atccaggtga tgccggcggc  10500
ggtggtggag gcgcgcggaa agtcgcggac gcggttccag atgttgcgca gcggcaaaaa  10560
gtgctccatg gtcgggacgc tctggccggt caggcgcgcg caatcgttga cgctctagac  10620
cgtgcaaaag gagagcctgt aagcgggcac tcttccgtgg tctggtggat aaattcgcaa  10680
gggtatcatg gcggacgacc ggggttcgag ccccgtatcc ggccgtccgc cgtgatccat  10740
gcggttaccg cccgcgtgtc gaacccaggt gtgcgacgtc agacaacggg ggagtgctcc  10800
ttttggcttc cttccaggcg cggcggctgc tgcgctagct tttttggcca ctggccgcgc  10860
gcagcgtaag cggttaggct ggaaagcgaa agcattaagt ggctcgctcc ctgtagccgg  10920
agggttattt tccaagggtt gagtcgcggg acccccggtt cgagtctcgg accggccgga  10980
ctgcggcgaa cgggggtttg cctccccgtc atgcaagacc ccgcttgcaa attcctccgg  11040
aaacagggac gagccccttt tttgcttttc ccagatgcat ccggtgctgc ggcagatgcg  11100
ccccccctcct cagcagcggc aagagcaaga gcagcggcag acatgcaggg caccctcccc  11160
tcctcctacc gcgtcaggag gggcgacatc cgcggttgac gcggcagcag atggtgatta  11220
cgaacccccg cggcgccggg cccggcacta cctggacttg gaggagggcg agggcctggc  11280
gcggctagga gcgccctctc ctgagcggta cccaagggtg cagctgaagc gtgatacgcg  11340
tgaggcgtac gtgccgcggc agaacctgtt tcgcgaccgc gagggagagg agcccgagga  11400
gatgcgggat cgaaagttcc acgcagggcg cgagctgcgg catggcctga atcgcgagcg  11460
gttgctgcgc gaggaggact ttgagcccga cgcgcgaacc gggattagtc ccgcgcgcgc  11520
acacgtggcg gccgccgacc tggtaaccgc atacgagcag acggtgaacc aggagattaa  11580
ctttcaaaaa agctttaaca accacgtgcg tacgcttgtg gcgcgcgagg aggtggctat  11640
aggactgatg catctgtggg actttgtaag cgcgctggag caaaacccaa atagcaagcc  11700
gctcatggcg cagctgttcc ttatagtgca gcacagcagg gacaacgagg cattcaggga  11760
tgcgctgcta aacatagtag agcccgaggg ccgctggctg ctcgatttga taaacatcct  11820
gcagagcata gtggtgcagg agcgcagctt gagcctggct gacaaggtgg ccgccatcaa  11880
ctattccatg cttagcctgg gcaagtttta cgcccgcaag atataccata ccccttacgt  11940
tcccatagac aaggaggtaa agatcgaggg gttctacatg cgcatggcgc tgaaggtgct  12000
taccttgagc gacgacctgg gcgtttatcg caacgagcgc atccacaagg ccgtgagcgt  12060
gagccggcgg cgcgagctca gcgaccgcga gctgatgcac agcctgcaaa gggccctggc  12120
tggcacgggc agcggcgata gagaggccga gtcctacttt gacgcgggcg ctgacctgcg  12180
ctgggcccca agccgacgcg ccctggaggc agctggggcc ggacctgggc tggcggtggc  12240
acccgcgcgc gctggcaacg tcggcggcgt ggaggaatat gacgaggacg atgagtacga  12300
gccagaggac ggcgagtact aagcggtgat gtttctgatc agatgatgca agacgcaacg  12360
gacccggcgg tgcgggcggc gctgcagagc cagccgtccg gccttaactc cacggacgac  12420
tggcgccagg tcatggaccg catcatgtcg ctgactgcgc gcaatcctga cgcgttccgg  12480
cagcagccgc aggccaaccg gctctccgca attctggaag cggtggtccc ggcgcgcgca  12540
aaccccacgc acgagaaggt gctggcgatc gtaaacgcgc tggccgaaaa cagggccatc  12600
cggcccgacg aggccggcct ggtctacgac gcgctgcttc agcgcgtggc tcgttacaac  12660
agcggcaacg tgcagaccaa cctggaccgg ctggtggggg atgtgcgcga ggccgtggcg  12720
cagcgtgagc gcgcgcagca gcagggcaac ctgggctcca tggttgcact aaacgccttc  12780
ctgagtacac agcccgccaa cgtgccgcgg ggacaggagg actacaccaa ctttgtgagc  12840
gcactgcggc taatggtgac tgagacaccg caaagtgagg tgtaccagtc tgggccagac  12900
tattttttcc agaccagtag acaaggcctg cagaccgtaa acctgagcca ggctttcaaa  12960
aacttgcagg ggctgtgggg ggtgcgggct cccacaggcg accgcgcgac cgtgtctagc  13020
ttgctgacgc ccaactcgcg cctgttgctg ctgctaatag cgcccttcac ggacagtggc  13080
agcgtgtccc gggacacata cctaggtcac ttgctgacac tgtaccgcga ggccataggt  13140
caggcgcatg tggacgagca tactttccag gagattacaa gtgtcagccg cgcgctgggg  13200
caggaggaca cgggcagcct ggaggcaacc ctaaactacc tgctgaccaa ccggcggcag  13260
aagatcccct cgttgcacag tttaaacagc gaggaggagc gcattttgcg ctacgtgcag  13320
cagagcgtga gccttaacct gatgcgcgac ggggtaacgc ccagcgtggc gctggacatg  13380
accgcgcgca acatggaacc gggcatgtat gcctcaaacc ggccgtttat caaccgccta  13440
atggactact tgcatcgcgc ggccgccgtg aaccccgagt atttcaccaa tgccatcttg  13500
aacccgcact ggctaccgcc ccctggtttc tacaccgggg gattcgaggt gcccgagggt  13560
aacgatggat tcctctggga cgacatagac gacagcgtgt tttccccgca accgcagacc  13620
ctgctagagt tgcaacagcg cgagcaggca gaggcggcgc tgcgaaagga aagcttccgc  13680
aggccaagca gcttgtccga tctaggcgct gcggccccgc ggtcagatgc tagtagccca  13740
tttccaagct tgatagggtc tcttaccagc actcgcacca cccgcccgcg cctgctgggc  13800
gaggaggagt acctaaacaa ctcgctgctg cagccgcagc gcgaaaaaaa cctgcctccg  13860
gcatttccca acaacgggat agagagccta gtggacaaga tgagtagatg gaagacgtac  13920
gcgcaggagc acagggacgt gccaggcccg cgcccgccca cccgtcgtca aaggcacgac  13980
cgtcagcggg gtctggtgtg ggaggacgat gactcggcag acgacagcag cgtcctggat  14040
ttgggaggga gtggcaaccc gtttgcgcac cttcgcccca ggctggggag aatgttttaa  14100
aaaaaaaaaa gcatgatgca aaataaaaaa ctcaccaagg ccatggcacc gagcgttggt  14160
tttcttgtat tcccttagt atgcggcgcg cggcgatgta tgaggaaggt cctcctccct  14220
cctacgagag tgtggtgagc gcggcgccag tggcggcggc gctgggttct cccttcgatg  14280
```

-continued

```
ctcccctgga cccgccgttt gtgcctccgc ggtacctgcg gcctaccggg gggagaaaca  14340
gcatccgtta ctctgagttg gcacccctat tcgacaccac ccgtgtgtac ctggtggaca  14400
acaagtcaac ggatgtggca tccctgaact accagaacga ccacagcaac tttctgacca  14460
cggtcattca aaacaatgac tacagcccgg gggaggcaag cacacagacc atcaatcttg  14520
acgaccggtc gcactggggc ggcgacctga aaaccatcct gcataccaac atgccaaatg  14580
tgaacgagtt catgtttacc aataagttta aggcgcgggt gatggtgtcg cgcttgccta  14640
ctaaggacaa tcaggtggag ctgaaatacg agtgggtgga gttcacgctg cccgagggca  14700
actactccga gaccatgacc atagacctta tgaacaacgc gatcgtggag cactacttga  14760
aagtgggcag acagaacggg gttctggaaa gcgacatcgg ggtaaagttt gacacccgca  14820
acttcagact ggggtttgac cccgtcactg gtcttgtcat gcctggggta tatacaaacg  14880
aagccttcca tccagacatc attttgctgc caggatgcgg ggtggacttc acccacagcc  14940
gcctgagcaa cttgttgggc atccgcaagc ggcaaccctt ccaggagggc tttaggatca  15000
cctacgatga tctggagggt ggtaacattc ccgcactgtt ggatgtggac gcctaccagg  15060
cgagcttgaa agatgacacc gaacagggcg gggtggcgc aggcggcagc aacagcagtg  15120
gcagcggcgc ggaagagaac tccaacgcgg cagccgcggc aatgcagccg gtggaggaca  15180
tgaacgatca tgccattcgc ggcgacacct ttgccacacg ggctgaggag aagcgcgctg  15240
aggccgaagc agcggccgaa gctgccgccc ccgctgcgca acccgaggtc gagaagcctc  15300
agaagaaacc ggtgatcaaa cccctgacag aggacagcaa gaaacgcagt tacaacctaa  15360
taagcaatga cagcaccttc acccagtacc gcagctggta ccttgcatac aactacggcg  15420
accctcagac cggaatccgc tcatggaccc tgctttgcac tcctgacgta acctgcggct  15480
cggagcaggt ctactggtcg ttgccagaca tgatgcaaga ccccgtgacc ttccgctcca  15540
cgcgccagat cagcaacttt ccggtggtgg gcgccgagct gttgcccgtg cactccaaga  15600
gcttctacaa cgaccaggcc gtctactccc aactcatccg ccagtttacc tctctgaccc  15660
acgtgttcaa tcgctttccc gagaaccaga ttttggcgcg cccgccagcc cccaccatca  15720
ccaccgtcag tgaaaacgtt cctgctctca cagatcacgg gacgctaccg ctgcgcaaca  15780
gcatcggagg agtccagcga gtgaccatta ctgacgccag acgccgcacc tgcccctacg  15840
tttacaaggc cctgggcata gtctcgccgc gcgtcctatc gagccgcact ttttgagcaa  15900
gcatgtccat ccttatatcg cccagcaata acacaggctg ggcctgcgc ttcccaagca  15960
agatgtttgg cggggccaag aagcgctccg accaacaccc agtgcgcgtg cgcgggcact  16020
accgcgcgcc ctggggcgcg cacaaacgcg gccgcactgg gcgcaccacc gtcgatgacg  16080
ccatcgacgc ggtggtggag gaggcgcgca actacacgcc cacgccgcca ccagtgtcca  16140
cagtggacgc ggccattcag accgtggtgc gcggagcccg gcgctatgct aaaatgaaga  16200
gacggcggag gcgcgtagca cgtcgccacc gccgccgacc cggcactgcc gcccaacgcg  16260
cggcggcggc cctgcttaac cgcgcacgtc gcaccggccg acgggcggcc atgcgggccg  16320
ctcgaaggct ggccgcgggt attgtcactg tgccccccag gtccaggcga cgagcggccg  16380
ccgcagcagc cgcggccatt agtgctatga ctcagggtcg caggggcaac gtgtattggg  16440
tgcgcgactc ggttagcggc ctgcgcgtgc ccgtgcgcac ccgcccccg cgcaactaga  16500
ttgcaagaaa aaactactta gactcgtact gttgtatgta tccagcggcg gcggcgcgca  16560
acgaagctat gtccaagcgc aaaatcaaag aagagatgct ccaggtcatc gcgccggaga  16620
tctatggccc cccgaagaag gaagagcagg attacaagcc ccgaaagcta aagcgggtca  16680
aaaagaaaaa gaaagatgat gatgatgaac ttgacgacga ggtggaactg ctgcacgcta  16740
ccgcgcccag gcgacgggta cagtggaaag gtcgacgcgt aaaacgtgtt ttgcgacccg  16800
gcaccaccgt agtctttacg cccggtgagc gctccacccg cacctacaag cgcgtgtatg  16860
atgaggtgta cggcgacgag gacctgcttg agcaggccaa cgagcgcctc ggggagtttg  16920
cctacggaaa gcggcataag gacatgctgg cgttgccgct ggacgagggc aacccaacac  16980
ctagcctaaa gcccgtaaca ctgcagcagg tgctgcccgc gcttgcaccg tccgaagaaa  17040
agcgcggcct aaagcgcgag tctggtgact tggcacccac cgtgcagctg atggtaccca  17100
agcgccagcg actggaagat gtcttggaaa aaatgaccgt ggaacctggg ctggagcccg  17160
aggtccgcgt gcggccaatc aagcaggtgg cgccgggact gggcgtgcag accgtggacg  17220
ttcagatacc cactaccagt agcaccagta ttgccaccgc cacagagggc atggagacac  17280
aaacgtcccc ggttgcctca gcggtggcgg atgccgcggt gcaggcggtc gctgcggccg  17340
cgtccaagac ctctacggag gtgcaaacgg acccgtggat gtttcgcgtt tcagcccccc  17400
ggcgcccgcg cggttcgagg aagtacggcg ccgccagcgc gctactgccc gaatatgccc  17460
tacatccttc cattgcgcct acccccggct atcgtggcta cacctaccgc cccagaagac  17520
gagcaactac ccgacgccga accaccactg gaacccgccg ccgccgtcgc cgtcgccagc  17580
ccgtgctggc cccgatttcc gtgcgcaggg tggctcgcga aggaggcagg accctggtgc  17640
tgccaacagc gcgctaccac cccagcatcg tttaaaagcc ggtctttgtg gttcttgcag  17700
atatggccct cacctgccgc ctccgtttcc cggtgccggg attccgagga agaatgcacc  17760
gtaggagggg catggccggc cacggcctga cgggcggcat gcgtcgtgcg caccaccggc  17820
ggcggcgcgc gtcgcaccgt cgcatgcgcg gcggtatcct gcccctcctt attccactga  17880
tcgccgcggc gattggcgcc gtgcccggaa ttgcatccgt ggccttgcag gcgcagagac  17940
actgattaaa aacaagttgc atgtggaaaa atcaaaataa aaagtctgga ctctcacgct  18000
cgcttggtcc tgtaactatt ttgtagaatg gaagacatca actttgcgtc tctggccccg  18060
cgacacggct cgcgcccgtt catgggaaac tggcaagata tcggcaccag caatatgagc  18120
ggtggcgcct tcagctgggg ctcgctgtgg agcggcatta aaaatttcgg ttccaccgtt  18180
aagaactatg gcagcaaggc ctggaacagc agcacaggcc agatgctgag ggataagttg  18240
aaagagcaaa atttccaaca aaaggtggta gatggcctgg cctctggcat tagcggggtg  18300
gtggacctgg ccaaccaggc agtgcaaaat aagattaaca gtaagcttga tccccgccct  18360
cccgtagagg agcctccacc ggccgtggag acagtgtctc cagaggggcg tggcgaaaag  18420
cgtccgcgcc ccgacaggga agaaactctg gtgacgcaaa tagacgagcc tccctcgtac  18480
gaggaggcac taaagcaagg cctgcccacc acccgtccca tcgcgcccat ggctaccgga  18540
gtgctgggcc agcacacacc cgtaacgctg gacctgcctc cccccgccga cacccagcag  18600
aaacctgtgc tgccaggccc gaccgccgtt gttgtaaccc gtcctagccg cgcgtccctg  18660
cgccgcgccg ccagcggtcc gcgatcgttg cggcccgtag ccagtggcaa ctggcaaagc  18720
acactgaaca gcatcgtggg tctgggggtg caatccctga agcgccgacg atgcttctga  18780
atagctaacg tgtcgtatgt gtgtcatgta tgcgtccatg tcgccgccag aggagctgct  18840
gagccgccgc gcgcccgctt tccaagatgg ctaccccttc gatgatgccg cagtggtctt  18900
acatgcacat ctcgggccag gacgcctcgg agtacctgag ccccgggctg gtgcagtttg  18960
cccgcgccac cgagacgtac ttcagcctga ataacaagtt tagaaacccc acggtggcgc  19020
```

```
ctacgcacga cgtgaccaca gaccggtccc agcgtttgac gctgcggttc atccctgtgg  19080
accgtgagga tactgcgtac tcgtacaagg cgcggttcac cctagctgtg ggtgataacc  19140
gtgtgctgga catggcttcc acgtactttg acatccgcgg cgtgctggac aggggcccta  19200
cttttaagcc ctactctggc actgcctaca acgccctggc tcccaagggt gccccaaatc  19260
cttgcgaatg ggatgaagct gctactgctc ttgaaataaa cctagaagaa gaggacgatg  19320
acaacgaaga cgaagtagac gagcaagctg agcagcaaaa aactcacgta tttgggcagg  19380
cgccttattc tggtataaat attacaaagg agggtattca aataggtgtc gaaggtcaaa  19440
cacctaaata tgccgataaa acatttcaac ctgaacctca aataggagaa tctcagtggt  19500
acgaaactga aattaatcat gcagctggga gagtccttaa aaagactacc ccaatgaaac  19560
catgttacgg ttcatatgca aaacccacaa atgaaaatgg agggcaaggc attcttgtaa  19620
agcaacaaaa tggaaagcta gaaagtcaag tggaaatgca atttttctca actactgagg  19680
cgaccgcagg caatggtgat aacttgactc ctaaagtggt attgtacagt gaagatgtag  19740
atatagaaac cccagacact catatttctt acatgcccac tattaaggaa ggtaactcac  19800
gagaactaat gggccaacaa tctatgccca acaggcctaa ttacattgct tttagggaca  19860
attttattgg tctaatgtat tacaacagca cgggtaatat gggtgttctg gcgggccaag  19920
catcgcagtt gaatgctgtt gtagatttgc aagacagaaa cacagagctt tcataccagc  19980
ttttgcttga ttccattggt gatagaacca ggtacttttc tatgtggaat caggctgttg  20040
acagctatga tccagatgtt agaattattg aaaatcatgg aactgaagat gaacttccaa  20100
attactgctt tccactggga ggtgtgatta atacagagac tcttaccaag gtaaaaccta  20160
aaacaggtca ggaaaatgga tgggaaaaag atgctacaga attttcagat aaaaatgaaa  20220
taagagttgg aaataatttt gccatggaaa tcaatctaaa tgccaacctg tggagaaatt  20280
tcctgtactc caacatagcg ctgtatttgc ccgacaagct aaagtacagt ccttccaacg  20340
taaaaatttc tgataaccca aacacctacg actacatgaa caagcgagtg gtggctcccg  20400
ggttagtgga ctgctacatt aaccttggag cacgctggtc ccttgactat atggacaacg  20460
tcaacccatt taaccaccac cgcaatgctg gcctgcgcta ccgctcaatg ttgctgggca  20520
atggtcgcta tgtgcccttc cacatccagg tgcctcagaa gttctttgcc attaaaaacc  20580
tccttctcct gccgggctca tacacctacg agtggaactt caggaaggat gttaacatgg  20640
ttctgcagag ctccctagga aatgacctaa gggttgacgg agccagcatt aagtttgata  20700
gcatttgcct ttacgccacc ttcttcccca tggcccacaa caccgcctcc acgcttgagg  20760
ccatgcttag aaacgacacc aacgaccagt cctttaacga ctatctctcc gccgccaaca  20820
tgctctaccc tatacccgcc aacgctacca acgtgcccat atccatcccc tcccgcaact  20880
gggcggcttt ccgcggctgg gccttcacgc gccttaagac taaggaaacc ccatcactgg  20940
gctcgggcta cgacccttat tacacctact ctggctctat accctaccta gatggaacct  21000
tttacctcaa ccacaccttt aagaaggtgg ccattacctt tgactcttct gtcagctggc  21060
ctggcaatga ccgcctgctt acccccaacg agtttgaaat taagcgctca gttgacgggg  21120
agggttacaa cgttgcccag tgtaacatga ccaaagactg gttcctggta caaatgctag  21180
ctaactataa cattggctac cagggcttct atatcccaga gagctacaag gaccgcatgt  21240
actccttctt tagaaacttc cagcccatga gccgtcaggt ggtggatgat actaaataca  21300
aggactacca acaggtgggc atcctacacc aacacaacaa ctctggattt gttggctacc  21360
ttgcccccac catgcgcgaa ggacaggcct accctgctaa cttcccctat ccgcttatag  21420
gcaagaccgc agttgacagc attacccaga aaaagtttct ttgcgatcgc accctttggc  21480
gcatcccatt ctccagtaac tttatgtcca tgggcgcact cacagacctg ggccaaaacc  21540
ttctctacgc caactccgcc cacgcgctag acatgacttt tgaggtggat cccatggacg  21600
agcccaccct tctttatgtt ttgtttgaag tctttgacgt ggtccgtgtg caccagccgc  21660
accgcggcgt catcgaaacc gtgtacctgc gcacgccctt ctcggccggc aacgccacaa  21720
cataaagaag caagcaacat caacaacagc tgccgccatg ggctccagtg agcaggaact  21780
gaaagccatt gtcaaagatc ttggttgtgg gccatatttt ttgggcacct atgacaagcg  21840
ctttccaggc tttgtttctc cacacaagct cgcctgcgcc atagtcaata cggccggtcg  21900
cgagactggg ggcgtacact ggatggcctt tgcctggaac ccgcactcaa aaacatgcta  21960
cctctttgag ccctttggct tttctgacca gcgactcaag caggtttacc agtttgagta  22020
cgagtcactc ctgcgccgta gcgccattgc ttcttccccc gaccgctgta taacgctgga  22080
aaagtccacc caaagcgtac aggggcccaa ctcggccgcc tgtggactat tctgctgcat  22140
gtttctccac gcctttgcca actggcccca aactcccatg gatcacaacc ccaccatgaa  22200
ccttattacc ggggtaccca actccatgct caacagtccc caggtacagc ccaccctgcg  22260
tcgcaaccag gaacagctct acagcttcct ggagcgccac tcgccctact tccgcagcca  22320
cagtgcgcag attaggagcg ccacttcttt ttgtcacttg aaaaacatgt aaaaataatg  22380
tactagagac actttcaata aaggcaaatg cttttatttg tacactctcg ggtgattatt  22440
tacccccacc cttgccgtct gcgccgtttc cttctcctat aggcagaaaa agatcatgga  22500
gtcagtcgag aagaaggaca gcctaaccgc cccctctgag ttcgccacca ccgcctccac  22560
cgatgccgcc aacgcgccta ccaccttccc cgtcgaggca cccccgcttg aggaggagga  22620
agtgattatc gagcaggacc caggttttgt aagcgaagac gacgaggacc gctcagtacc  22680
aacagaggat aaaaagcaag accaggacaa cgcagaggca aacgaggaac aagtcgggcg  22740
gggggacgaa aggcatggcg actacctaga tgtgggagac gacgtgctgt tgaagcatct  22800
gcagcgccag tcgcgcatta tctgcgacgc gttgcaagag cgcagcgatg tgcccctcgc  22860
catagcggat gtcagccttg cctacgaacg ccacctattc tcaccgcgcg taccccccaa  22920
acgccaagaa aacggcacat gcgagcccaa cccgcgcctc aacttctacc ccgtatttgc  22980
cgtgccagag gtgcttgcca cctatcacat ctttttccaa aactgcaaga taccccctatc  23040
ctgccgtgcc aaccgcagcc gagcggacaa gcagctggcc ttgcggcagg gcgctgtcat  23100
acctgatatc gcctcgctca acgaagtgcc aaaaatcttt gagggtcttg gacgcgacga  23160
gaagcgcgcg gcaaacgctc tgcaacagga aaacagcgaa aatgaaagtc actctggagt  23220
gttggtggaa ctcgagggtg acaacgcgcg cctagccgta ctaaaacgca gcatcgaggt  23280
cacccacttt gcctacccgg cacttaacct accccccaag gtcatgagca cagtcatgag  23340
tgagctgatc gtgcgccgtg cgcagcccct ggagagggat gcaaatttgc aagaacaaac  23400
agaggagggc ctacccgcag ttggcgacga gcagctagcg cgctggcttc aaacgcgcga  23460
gcctgccgac ttggaggagc gacgcaaact aatgatggcc gcagtgctcg ttaccgtgga  23520
gcttgagtgc atgcagcggt tctttgctga cccggagatg cagcgcaagc tagaggaaac  23580
attgcactac acctttcgac agggctacgt acgccaggcc tgcaagatct ccaacgtgga  23640
gctctgcaac ctggtctcct accttggaat tttgcacgaa aaccgccttg ggcaaaacgt  23700
gcttcattcc acgctcaagg gcgaggcgcg ccgcgactac gtccgcgact gcgtttactt  23760
```

```
atttctatgc tacacctggc agacggccat gggcgtttgg cagcagtgct tggaggagtg  23820
caacctcaag gagctgcaga aactgctaaa gcaaaacttg aaggacctat ggacggcctt  23880
caacgagcgc tccgtggccg cgcacctggc ggacatcatt ttccccgaac gcctgcttaa  23940
aaccctgcaa cagggtctgc cagacttcac cagtcaaagc atgttgcaga actttaggaa  24000
ctttatccta gagcgctcag gaatcttgcc cgccacctgc tgtgcacttc ctagcgactt  24060
tgtgcccatt aagtaccgcg aatgccctcc gccgctttgg ggccactgct accttctgca  24120
gctagccaac taccttgcct accactctga cataatggaa gacgtgagcg gtgacggtct  24180
actggagtgt cactgtcgct gcaacctatg caccccgcac cgctccctgg tttgcaattc  24240
gcagctgctt aacgaaagtc aaattatcgg tacctttgag ctgcagggtc cctcgcctga  24300
cgaaaagtcc gcggctccgg ggttgaaact cactccgggg ctgtggacgt cggcttacct  24360
tcgcaaattt gtacctgagg actaccacgc ccacgagatt aggttctacg aagaccaatc  24420
ccgcccgcct aatgcggagc ttaccgcctg cgtcattacc cagggccaca ttcttggcca  24480
attgcaagcc atcaacaaag cccgccaaga gtttctgcta cgaaagggac gggggggtta  24540
cttggacccc cagtccggcg aggagctcaa cccaatcccc ccgccgccgc agccctatca  24600
gcagcagccg cgggcccttg cttcccagga tggcacccaa aaagaagctg cagctgccgc  24660
cgccacccac ggacgaggag gaatactggg acagtcaggc agaggaggtt ttggacgagg  24720
aggaggagga catgatggaa gactgggaga gcctagacga ggaagcttcc gaggtcgaag  24780
aggtgtcaga cgaaacaccg tcaccctcgg tcgcattccc ctcgccggcg ccccagaaat  24840
cggcaaccgg ttccagcatg gctacaacct ccgctcctca ggcgccgccg gcactgcccg  24900
ttcgccgacc caaccgtaga tgggacacca ctggaaccag ggccggtaag tccaagcagc  24960
cgccgccgtt agcccaagag caacaacagc gccaaggcta ccgctcatgg cgcgggcaca  25020
agaacgccat agttgcttgc ttgcaagact gtgggggcaa catctccttc gcccgccgct  25080
ttcttctcta ccatcacggc gtggccttcc cccgtaacat cctgcattac taccgtcatc  25140
tctacagccc atactgcacc ggcggcagcg gcagcaacag cagcggccac acagaagcaa  25200
aggcgaccgg atagcaagac tctgacaaag cccaagaaat ccacagcggc ggcagcagca  25260
ggaggaggag cgctgcgtct ggcgcccaac gaacccgtat cgacccgcga gcttagaaac  25320
aggatttttc ccactctgta tgctatattt caacagagca ggggccaaga acaagagctg  25380
aaaataaaaa acaggtctct gcgatccctc acccgcagct gcctgtatca caaaagcgaa  25440
gatcagcttc ggcgcacgct ggaagacgcg gaggctctct tcagtaaata ctgcgcgctg  25500
actcttaagg actagtttcg cgccctttct caaatttaag cgcgaaaact acgtcatctc  25560
cagcggccac acccggcgcc agcacctgtc gtcagcgcca tttcaacttt gtatacaaaa  25620
gttgtgatga gcaaggaaat tcccacgccc tacatgtgga gttaccagcc acaaatggga  25680
cttgcggctg gagctgccca agactactca acccgaataa actacatgag cgcgggaccc  25740
cacatgatat cccgggtcaa cggaatacgc gcccaccgaa accgaattct cctggaacag  25800
gcggctatta ccaccacacc tcgtaataac cttaatcccc gtagttggcc cgctgccctg  25860
gtgtaccagg aaagtcccgc tcccaccact gtggtacttc ccagagacgc ccaggccgaa  25920
gttcagatga ctaactcagg ggcgcagctt gcgggcggct ttcgtcacag ggtgcggtcg  25980
cccgggcagg gtataactca cctgacaatc agagggcgag gtattcagct caacgacgag  26040
tcggtgagct cctcgcttgg tctccgtccg gacgggacat ttcagatcgg cggcgccggc  26100
cgctcttcat tcacgcctcg tcaggcaatc ctaactctgc agacctcgtc ctctgagccg  26160
cgctctggag gcattggaac tctgcaattt attgaggagt ttgtgccatc ggtctacttt  26220
aaccccttct cgggacctcc cggccactat ccggatcaat ttattcctaa ctttgacgcg  26280
gtaaaggact cggcggacgg ctacgactga ctctatgtgg gatatgctcc agcgctacaa  26340
ccttgaagtc aggcttcctg gatgtcagca tctgactttg gccagcacct gtcccgcgga  26400
tttgttccag tccaactaca gcgacccacc ctaacagaga tggtgagcaa gggcgaggag  26460
gataacatgg ccatcatcaa ggagttcatg cgcttcaagg tgcacatgga gggctccgtg  26520
aacggccacg agttcgagat cgagggcgag ggcgagggcc gcccctacga gggcacccag  26580
accgccaagc tgaaggtgac caagggtggc cccctgccct tcgcctggga catcctgtcc  26640
cctcagttca tgtacggctc caaggcctac gtgaagcacc ccgccgacat ccccgactac  26700
ttgaagctgt ccttccccga gggcttcaag tgggagcgcg tgatgaactt cgaggacggc  26760
ggcgtggtga ccgtgaccca ggactcctcc ctgcaggacg gcgagttcat ctacaaggtg  26820
aagctgcgcg gcaccaactt cccctccgac ggccccgtaa tgcagaagaa gaccatgggc  26880
tgggaggcct cctccgagcg gatgtacccc gaggacggcg ccctgaaggg cgagatcaag  26940
cagaggctga agctgaagga cggcggccac tacgacgctg aggtcaagac cacctacaag  27000
gccaagaagc ccgtgcagct gcccggcgcc tacaacgtca acatcaagtt ggacatcacc  27060
tcccacaacg aggactacac catcgtggaa cagtacgaac gcgccgaggg ccgccactcc  27120
accggcggca tggacgagct gtacaaggga agcggagcta ctaacttcag cctgctgaag  27180
caggctggtg acgtcgagga gaatcctggc ccaatggtga tgaccaacac aaccaacgcg  27240
gccgccgcta ccggacttac atctaccaca aatacacccc aagtttctgc ctttgtcaat  27300
aactgggata acttgggcat gtggtggttc tccatagcgc ttatgtttgt atgccttatt  27360
attatgtggc tcatctgctg cctaaagcgc aaacgcgccc gaccacccat ctatagtccc  27420
atcattgtgc tacacccaaa caatgatgga atccatagat tggacggact gaaacacatg  27480
ttcttttctc ttacagtatg attaaatgag actaataaaa aaaaataata aagcatcact  27540
tacttaaaat cagttagcaa atttctgtcc agtttattca gcagcacctc cttgccctcc  27600
tcccagctct ggtattgcag cttcctcctg gctgcaaact ttctccacaa tctaaatgga  27660
atgtcagttt cctcctgttc ctgtccatcc gcacccacta tcttcatgtt gttgcagatg  27720
aagcgcgcaa gaccgtctga agataccttc aaccccgtgt atccatatga cacggaaacc  27780
ggtcctccaa ctgtgccttt tcttactcct ccctttgtat cccccaatgg gtttcaagag  27840
agtcccccctg gggtactctc tttgcgccta tccgaacctc tagttacctc caatggcatg  27900
cttgcgctca aaatgggcaa cggcctctct ctggacgagg ccggcaacct tacctcccaa  27960
aatgtaacca ctgtgagccc acctctcaaa aaaaccaagt caaacataaa cctggaaata  28020
tctgcacccc tcacagttac ctcagaagcc ctaactgtgg ctgccgccgc acctctaatg  28080
gtcgcgggca acacactcac catgcaatca caggccccgc taaccgtgca cgactccaaa  28140
cttagcattg ccacccaagg acccctcaca gtgtcagaag gaaagctagc cctgcaaaca  28200
tcaggccccc tcaccaccac cgatagcagt acccttacta tcactgcctc acccccctcta  28260
actactgcca ctggtagctt gggcattgac ttgaaagagc ccatttatac acaaaatgga  28320
aaactaggac taaagtacgg ggctcctttg catgtaacag acgacctaaa cactttgacc  28380
gtagcaactg gtccaggtgt gactattaat aatacttcct tgcaaactaa agttactgga  28440
gccttgggtt ttgattcaca aggcaatatg caacttaatg tagcaggagg actaaggatt  28500
```

```
gattctcaaa acagacgcct tatacttgat gttagttatc cgtttgatgc tcaaaaccaa  28560
ctaaatctaa gactaggaca gggccctctt tttataaact cagcccacaa cttggatatt  28620
aactacaaca aaggccttta cttgtttaca gcttcaaaca attccaaaaa gcttgaggtt  28680
aacctaagca ctgccaaggg gttgatgttt gacgctacag ccatagccat taatgcagga  28740
gatgggcttg aatttggttc acctaatgca ccaaacacaa atcccctcaa aacaaaaatt  28800
ggccatggcc tagaatttga ttcaaacaag gctatggttc ctaaactagg aactggcctt  28860
agttttgaca gcacaggtgc cattacagta ggaaacaaaa ataatgataa gctaactttg  28920
tggaccacac cagctccatc tcctaactgt agactaaatg cagagaaaga tgctaaactc  28980
actttggtct taacaaaatg tggcagtcaa atacttgcta cagtttcagt tttggctgtt  29040
aaaggcagtt tggctccaat atctggaaca gttcaaagtg ctcatcttat tataagattt  29100
gacgaaaatg gagtgctact aaacaattcc ttcctggacc cagaatattg gaactttaga  29160
aatggagatc ttactgaagg cacagcctat acaaacgctg ttggatttat gcctaaccta  29220
tcagcttatc caaaatctca cggtaaaact gccaaaagta acattgtcag tcaagtttac  29280
ttaaacggag acaaaactaa acctgtaaca ctaaccatta cactaaacgg tacacaggaa  29340
acaggagaca caactccaag tgcatactct atgtcatttt catgggactg gtctggccac  29400
aactacatta atgaaatatt tgccacatcc tcttacactt tttcatacat tgcccaagaa  29460
taaagcaata gcatcacaaa tttcacaaat aaagcattat tttagttatt aatagtaatc  29520
aattacgggg tcattagttc atagcccata tatggagttc cgcgttacat aacttacggt  29580
aaatggcccg cctggctgac cgcccaacga cccccgccca ttgacgtcaa taatgacgta  29640
tgttcccata gtaacgccaa tagggacttt ccattgacgt caatgggtgg agtatttacg  29700
gtaaactgcc cacttggcag tacatcaagt gtatcatatg ccaagtacgc cccctattga  29760
cgtcaatgac ggtaaatggc ccgcctggca ttatgcccag tacatgacct tatgggactt  29820
tcctacttgg cagtacatct acgtattagt catcgctatt accatggtga tgcggttttg  29880
gcagtacatc aatgggcgtg gatagcggtt tgactcacgg ggatttccaa gtctccaccc  29940
cattgacgtc aatgggagtt tgttttggca ccaaaatcaa cgggactttc caaaatgtcg  30000
taacaactcc gccccattga cgcaaatggg cggtaggcgt gtacggtggg aggtctatat  30060
aagcatccct atcagtgata gagatcagat ctccctatca gtgatagaga gctgttttga  30120
cctccataga agacaccggg accgatccag cctccggact ctagcgttta aacttaagct  30180
tggtacccgg ggatcctcta gggcctctga gctattccag aagtagtgaa gaggcttttt  30240
tggaggccta ggcttttgca aaaagctccg gatcgatcct gagacaccat ggccagtcgg  30300
gaagaggagc agcgcgaaac cacccccgag cgcggacgcg gtgcggcgcg acgtccccca  30360
accatggagg acgtgtcgtc cccgtccccg tcgccgccgc ctccccgggc gcccccaaaa  30420
aagcggatga ggcggcgtat cgagtccgag gacgaggaag actcatcaca agacgcgctg  30480
gtgccgcgca cacccagccc gcggccatcg acctcggcgg cggatttggc cattgcgccc  30540
aagaagaaaa agaagcgccc ttctcccaag cccgagcgcc cgccatcacc agaggtaatc  30600
gtggacagcg aggaagaaag agaagatgtg gcgctacaaa tggtgggttt cagcaaccca  30660
ccggtgctaa tcaagcatgg caaaggaggt aagcgcacag tgcggcggct gaatgaagac  30720
gacccagtgg cgcgtggtat gcggacgcaa gaggaagagg aagagcccag cgaagcggaa  30780
agtgaaatta cggtgatgaa cccgctgagt gtgccgatcg tgtctgcgtg ggagaagggc  30840
atggaggctg cgcgcgcgct gatggacaag taccacgtgg ataacgatct aaaggcgaac  30900
ttcaaactac tgcctgacca agtggaagct ctggcggccg tatgcaagac ctggctgaac  30960
gaggagcacc gcgggttgca gctgaccttc accagcaaca agacctttgt gacgatgatg  31020
gggcgattcc tgcaggcgta cctgcagtcg tttgcagagg tgacctacaa gcatcacgag  31080
cccacgggct gcgcgttgtg gctgcaccgc tgcgctgaga tcgaaggcga gcttaagtgt  31140
ctacacggaa gcattatgat aaataaggag cacgtgattg aaatggatgt gacgagcgaa  31200
aacgggcagc gcgcgctgaa ggagcagtct agcaaggcca agatcgtgaa gaaccggtgg  31260
ggccgaaatg tggtgcagat ctccaacacc gacgcaaggt gctgcgtgca cgacgcggcc  31320
tgtccggcca atcagttttc cggcaagtct tgcggcatgt tcttctctga aggcgcaaag  31380
gctcaggtgg cttttaagca gatcaaggct tttatgcagg cgctgtatcc taacgcccag  31440
accgggcacg gtcacctttt gatgccacta cggtgcgagt gcaactcaaa gcctgggcac  31500
gcgccctttt tgggaaggca gctaccaaag ttgactccgt tcgccctgag caacgcggag  31560
gacctggacg cggatctgat ctccgacaag agcgtgctgg ccagcgtgca ccacccggcg  31620
ctgatagtgt tccagtgctg caaccctgtg tatcgcaact cgcgcgcgca gggcggaggc  31680
cccaactgcg acttcaagat atcggcgccc gacctgctaa acgcgttggt gatggtgcgc  31740
agcctgtgga gtgaaaactt caccgagctg ccgcggatgg ttgtgcctga gtttaagtgg  31800
agcactaaac accagtatcg caacgtgtcc ctgccagtgg cgcatagcga tgcgcggcag  31860
aacccctttg atttttaaaa taaacaagtt aacaacaaca caaaaataat gctttatttc  31920
tcgagagctt gatgccaggc aagtccaggc aggccaggca agtccaggca ggccaggcaa  31980
gtccaggcag gccaggcaag tccaggcagg ccaggcaagt ccaggcaggc caggcaagtc  32040
caggcaggcc aggcaagtcc aggcaggcca ggcaagtcca ggcaggccag gcaagtccag  32100
gcaggccagg caagtccagg cagggccagg caagtccagg caggccaggc aagtccaggc  32160
aggccaggca agtccaggca ggatcgaatt aagctttagg cgtgtacggt gggcgcctat  32220
aaaagcagag ctcgtttagt gaaccgtcag atcgcctgga gcaattccac aacacttttg  32280
tcttatacca actttccgta ccacttccta ccctcgtaaa cctggagacg ccatccacgc  32340
tgttttgacc tccatagaag acaccgggac cgatccagcc tccggtcgac cgatcctgat  32400
tcaccatgtc tagactggac aagagcaaag tcataaactc tgctctggaa ttactcaatg  32460
aagtcggtat cgaaggcctg acgacaagga aactcgctca aaagctggga gttgagcagc  32520
ctaccctgta ctggcacgtg aagaacaagc gggccctgct cgatgccctg gcaatcgaga  32580
tgctggacag gcatcatacc cacttctgcc ccctggaagg cgagtcatgg caagactttc  32640
tgcggaacaa cgccaagtca ttccgctgtg ctctcctctc acatcgcgac ggggctaaag  32700
tgcatctcgg cacccgccca acagagaaac agtacgaaac cctggaaaat cagctcgcgt  32760
tcctgtgtca gcaaggcttc tccctggaga acgcactgta cgctctgtcc gccgtgggcc  32820
actttacact gggctgcgta ttggaggatc aggagcatca agtagcaaaa gaggaaagag  32880
agacacctac caccgattct atgcccccac ttctgagaca agcaattgag ctgttcgacc  32940
atcagggagc cgaacctgcc ttccttttcg gcctggaact aatcatatgt ggcctggaga  33000
aacagctaaa gtgcgaaagc ggctccgcgt acagcggatc ccgggaattc agatcttatt  33060
aataaacaag ttaacaacaa cacaaaaata atgctttatt taatcgtggc aaatccacta  33120
taataaaaga atcgtttgtg ttatgtttca acgtgtttat ttttcaattg cagaaaattt  33180
cgaatcattt ttcattcagt agtatagccc caccaccaca tagcttatac agatcaccgt  33240
```

```
acctcaactt tgtataataa agttgtaatc aaactcacag aaccctagta ttcaacctgc  33300
cacctccctc ccaacacaca gagtacacag tcctttctcc ccggctggcc ttaaaaagca  33360
tcatatcatg ggtaacagac atattcttag gtgttatatt ccacacggtt tcctgtcgag  33420
ccaaacgctc atcagtgata ttaataaact ccccgggcag ctcacttaag ttcatgtcgc  33480
tgtccagctg ctgagccaca ggctgctgtc caacttgcgg ttgcttaacg ggcggcgaag  33540
gagaagtcca cgcctacatg ggggtagagt cataatcgtg catcaggata gggcggtggt  33600
gctgcagcag cgcgcgaata aactgctgcc gccgccgctc cgtcctgcag gaatacaaca  33660
tggcagtggt ctcctcagcg atgattcgca ccgcccgcag cataaggcgc cttgtcctcc  33720
gggcacagca gcgcaccctg atctcactta aatcagcaca gtaactgcag cacagcacca  33780
caatattgtt caaaatccca cagtgcaagg cgctgtatcc aaagctcatg gcggggacca  33840
cagaacccac gtggccatca taccacaagc gcaggtagat taagtggcga cccctcataa  33900
acacgctgga cataaacatt acctctttgg gcatgttgta attcaccacc tcccggtacc  33960
atataaacct ctgattaaac atggcgccat ccaccaccat cctaaaccag ctggccaaaa  34020
cctgcccgcc ggctatacac tgcagggaac cgggactgga acaatgacag tggagagccc  34080
aggactcgta accatggatc atcatgctcg tcatgatatc aatgttggca caacacaggc  34140
acacgtgcat acacttcctc aggattacaa gctcctcccg cgttagaacc atatcccagg  34200
gaacaaccca ttcctgaatc agcgtaaatc ccacactgca gggaagacct cgcacgtaac  34260
tcacgttgtg cattgtcaaa gtgttacatt cgggcagcag cggatgatcc tccagtatgg  34320
tagcgcgggt ttctgtctca aaaggaggta gacgatccct actgtacgga gtgcgccgag  34380
acaaccgaga tcgtgttggt cgtagtgtca tgccaaatgg aacgccggac gtagtcatat  34440
ttcctgaagc aaaaccaggt gcgggcgtga caaacagatc tgcgtctccg gtctcgccgc  34500
ttagatcgct ctgtgtagta gttgtagtat atccactctc tcaaagcatc caggcgcccc  34560
ctggcttcgg gttctatgta aactccttca tgcgccgctg ccctgataac atccaccacc  34620
gcagaataag ccacacccag ccaacctaca cattcgttct gcgagtcaca cacgggagga  34680
gcgggaagag ctggaagaac catgtttttt tttttattcc aaaagattat ccaaaacctc  34740
aaaatgaaga tctattaagt gaacgcgctc ccctccggtg gcgtggtcaa actctacagc  34800
caaagaacag ataatggcat ttgtaagatg ttgcacaatg gcttccaaaa ggcaaacggc  34860
cctcacgtcc aagtggacgt aaaggctaaa cccttcaggg tgaatctcct ctataaacat  34920
tccagcacct tcaaccatgc ccaaataatt ctcatctcgc caccttctca atatatctct  34980
aagcaaatcc cgaatattaa gtccggccat tgtaaaaatc tgctccagag cgccctccac  35040
cttcagcctc aagcagcgaa tcatgattgc aaaaattcag gttcctcaca gacctgtata  35100
agattcaaaa gcggaacatt aacaaaaata ccgcgatccc gtaggtccct tcgcagggcc  35160
agctgaacat aatcgtgcag gtctgcacgg accagcgcgg ccacttcccc gccaggaacc  35220
atgacaaaag aacccacact gattatgaca cgcatactcg gagctatgct aaccagcgta  35280
gccccgatgt aagcttgttg catgggcggc gatataaaat gcaaggtgct gctcaaaaaa  35340
tcaggcaaag cctcgcgcaa aaaagaaagc acatcgtagt catgctcatg cagataaagg  35400
caggtaagct ccggaaccac cacagaaaaa gacaccattt ttctctcaaa catgtctgcg  35460
ggtttctgca taaacacaaa ataaaataac aaaaaaacat ttaaacatta gaagcctgtc  35520
ttacaacagg aaaaacaacc cttataagca taagacggac tacggccatg ccggcgtgac  35580
cgtaaaaaaa ctggtcaccg tgattaaaaa gcaccaccga cagctcctcg gtcatgtccg  35640
gagtcataat gtaagactcg gtaaacacat caggttgatt cacatcggtc agtgctaaaa  35700
agcgaccgaa atagcccggg ggaatacata cccgcaggcg tagagacaac attacagccc  35760
ccataggagg tataacaaaa ttaataggag agaaaaacac ataaacacct gaaaaaccct  35820
cctgcctagg caaaatagca ccctcccgct ccagaacaac atacagcgct tccacagcgg  35880
cagccataac agtcagcctt accagtaaaa aagaaaacct attaaaaaaa caccactcga  35940
cacggcacca gctcaatcag tcacagtgta aaaaagggcc aagtgcagag cgagtatata  36000
taggactaaa aaatgacgta acggttaaag tccacaaaaa acacccagaa aaccgcacgc  36060
gaacctacgc ccagaaacga aagccaaaaa acccacaact tcctcaaatc gtcacttccg  36120
ttttcccacg ttacgtcact tcccatttta agaaaactac aattcccaac acatacaagt  36180
tactccgccc taaaacctac gtcacccgcc ccgttcccac gccccgcgcc acgtcacaaa  36240
ctccaccccc tcattatcat attggcttca atccaaaata aggtatatta ttgatgatg   36299

SEQ ID NO: 5            moltype = DNA  length = 36299
FEATURE                 Location/Qualifiers
misc_feature            1..36299
                        note = Synthetic adenovirus genome (CMBT-1254)
source                  1..36299
                        mol_type = other DNA
                        organism = synthetic construct
SEQUENCE: 5
catcatcaat aatatacctt attttggatt gaagccaata tgataatgag gggtggagt  60
ttgtgacgtg gcgcggggcg tgggaacggg gcgggtgacg tagtagtgtg gcggaagtgt  120
gatgttgcaa gtgtggcgga acacatgtaa gcgacggatg tggcaaaagt gacgtttttg  180
gtgtgcgccg gtgtacacag gaagtgacaa ttttcgcgcg gttttaggcg gatgttgtag  240
taaatttggg cgtaaccgag taagatttgg ccattttcgc gggaaaactg aataagagga  300
agtgaaatct gaataatttt gtgttactca tagcgcgtaa tatttgtcta gggccgcggg  360
gactttgacc gtttacgtgg agactcgccc aggtgttttt ctcaggtgtt ttccgcgttc  420
cgggtcaaag ttggcgtttt attattatag tcagctgacg tgtagtgtat ttatacccgg  480
tgagttcctc aagaggccac tcttgagtgc cagcgagtag agttttctcc tccgagccgc  540
tccgacaccg ggactgaaaa tgagacatat tatctgccac ggaggtgtta ttaccgaaga  600
aatggccgcc agtcttttgg accagctgat cgaagaggta ctggctgata atcttccacc  660
tcctagccat tttgaaccac ctacccttca cgaactgtat gatttagacg tgacggcccc  720
cgaagatccc aacgaggagg cggtttcgca gatttttccc gactctgtaa tgttggcggt  780
gcaggaaggg attgacttac tcacttttcc gccggcgccc ggttctccgg agccgcctca  840
cctttcccgg cagcccgagc agccggagca gagagccttg ggtccggttt ctatgccaaa  900
ccttgtaccg gaggtgatcg atcttacctg ccacgaggct ggctttccac ccagtgacga  960
cgaggatgaa gagggtgagg agtttgtgtt agattatgtg gagcaccccg ggcacggttg  1020
caggtcttgt cattatcacc ggaggaatac gggggaccca gatattatgt gttcgctttg  1080
ctatatgagg acctgtggca tgtttgtcta cagtaagtga aaattatggg cagtgggtga  1140
```

-continued

```
tagagtggtg ggtttggtgt ggtaattttt tttttaattt ttacagtttt gtggtttaaa  1200
gaattttgta ttgtgatttt tttaaaaggt cctgtgtctg aacctgagcc tgagcccgag  1260
ccagaaccgg agcctgcaag acctacccgc cgtcctaaaa tggcgcctgc tatcctgaga  1320
cgcccgacat cacctgtgtc tagagaatgc aatagtagta cggatagctg tgactccggt  1380
ccttctaaca cacctcctga gatacacccg gtggtcccgc tgtgccccat taaaccagtt  1440
gccgtgagag ttggtgggcg tcgccaggct gtggaatgta tcgaggactt gcttaacgag  1500
cctgggcaac ctttggactt gagctgtaaa cgccccaggc cataaggtgt aaacctgtga  1560
ttgcgtgtgt ggttaacgcc tttgtttgct gaatgagttg atgtaagttt aataaagggt  1620
gagataatgt ttaacttgca tggcgtgtta aatggggcgg ggcttaaagg gtatataatg  1680
cgccgtgggc taatcttggt tacatctgac ctcatggagg cttgggagtg tttggaagat  1740
ttttctgctg tgcgtaactt gctggaacag agctctaaca gtacctcttg gttttggagg  1800
tttctgtggg gctcatccca ggcaaagtta gtctgcagaa ttaaggagga ttacaagtgg  1860
gaatttgaag agcttttgaa atcctgtggt gagctgtttg attctttgaa tctgggtcac  1920
caggcgcttt tccaagagaa ggtcatcaag actttggatt tttccacacc ggggcgcgct  1980
gcggctgctg ttgctttttt gagttttata aaggataaat ggagcgaaga aacccatctg  2040
agcggggggt acctgctgga ttttctggcc atgcatctgt ggagagcggt tgtgagacac  2100
aagaatcgcc tgctactgtt gtcttccgtc cgcccggcga taataccgac ggaggagcag  2160
cagcagcagc aggaggaagc caggcggcgg cggcaggagc agagcccatg gaacccgaga  2220
gccggcctgg accctcggga atgaatgttg tacaggtggc tgaactgtat ccagaactga  2280
gacgcatttt gacaattaca gaggatgggc aggggctaaa gggggtaaag agggagcggg  2340
gggcttgtga ggctacagag gaggctagga atctagcttt tagcttaatg accagacacc  2400
gtcctgagtg tattactttt caacagatca aggataattg cgctaatgag cttgatctgc  2460
tggcgcagaa gtattccata gagcagctga ccacttactg gctgcagcca ggggatgatt  2520
ttgaggaggc tattagggta tatgcaaagg tggcacttag gccagattgc aagtacaaga  2580
tcagcaaact tgtaaatatc aggaattgtt gctacatttc tgggaacggg gccgaggtgg  2640
agatagatac ggaggatagg gtggccttta gatgtagcat gataaatatg tggccggggg  2700
tgcttggcat ggacggggtg gttattatga atgtaaggtt tactggcccc aattttagcg  2760
gtacggtttt cctggccaat accaacctta tcctaagggg tgtaagcttc tatgggttta  2820
acaatacctg tgtggaagcc tggaccgatg taagggttcg ggctgtgcc ttttactgct  2880
gctggaaggg ggtggtgtgt cgccccaaaa gcagggcttc aattaagaaa tgcctctttg  2940
aaaggtgtac cttgggtatc ctgtctgagg gtaactccag ggtgcgccac aatgtggcct  3000
ccgactgtgg ttgcttcatg ctagtgaaaa gcgtggctgt gattaagcat aacatggtat  3060
gtggcaactg cgaggacagg gcctctcaga tgctgacctg ctcggacggc aactgtcacc  3120
tgctgaagac cattcacgta gccagccact ctcgcaaggc ctggccagtg tttgagcata  3180
acatactgac ccgctgttcc ttgcatttgg gtaacaggag gggggtgttc ctaccttacc  3240
aatgcaattt gagtcacact aagatattgc ttgagcccga gagcatgtcc aaggtgaacc  3300
tgaacggggt gtttgacatg accatgaaga tctggaaggt gctgaggtac gatgagaccc  3360
gcaccaggtg cagaccctgc gagtgtggcg gtaaacatat taggaaccag cctgtgatgc  3420
tggatgtgac cgaggagctg aggcccgatc acttggtgct ggcctgcacc cgcgctgagt  3480
ttggctctag cgatgaagat acagattgag gtactgaaat gtgtgggcgt ggcttaaggg  3540
tgggaaagaa tatataaggt gggggtctta tgtagttttg tatctgtttt gcagcagccg  3600
ccgccgccca acttttctat acaaagttgt aatgagcacc aactcgtttg atggaagcat  3660
tgtgagctca tatttgacaa cgcgcatgcc cccatgggcc ggggtgcgtc agaatgtgat  3720
gggctccagc attgatggtc gccccgtcct gcccgcaaac tctactacct tgacctacga  3780
gaccgtgtct ggaacgccgt tggagactgc agcctccgcc gccgcttcag ccgctgcagc  3840
caccgcccgc gggattgtga ctgactttgc tttcctgagc ccgcttgcaa gcagtgcagc  3900
ttcccgttca tccgcccgcg atgacaagtt gacggctctt ttggcacaat tggattcttt  3960
gacccgggaa cttaatgtcg tttctcagca gctgttggat ctgcgccagc aggtttctgc  4020
cctgaaggct tcctcccctc ccaatgcggt ttaaaacata aataaaaaac cagactctgt  4080
ttggatttgg atcaagcata agtgtcttgc tgtctttatt taggggtttt gcgcgcgcgg  4140
taggcccggg accagcggtc tcggtcgttg agggtcctgt gtattttttc caggacgtgg  4200
taaaggtgac tctggatgtt cagatacatg ggcataagcc cgtctctggg gtggaggtag  4260
caccactgca gagcttcatg ctgcggggtg gtgttgtaga tgatccagtc gtagcaggag  4320
cgctgggcgt ggtgcctaaa aatgtctttc agtagcaagc tgattgccag gggcaggccc  4380
ttggtgtaag tgtttacaaa gcggttaagc tgggatgggt gcatacgtgg ggatatgaga  4440
tgcatcttgg actgtatttt taggttggct atgttcccag ccatatccct ccggggattc  4500
atgttgtgca gaaccaccag cacagtgtat ccggtgcact tgggaaattt gtcatgtagc  4560
ttagaaggaa atgcgtggaa gaacttggag acgcccttgt gacctccaag attttccatg  4620
cattcgtcca taatgatggc aatgggccca cgggcggcgg cctgggcgaa gatatttctg  4680
ggatcactaa cgtcatagtt gtgttccagg atgagatcgt cataggccat ttttacaaag  4740
cgcgggcgga gggtgccaga ctgcggtata atggttccat ccggcccagg ggcgtagtta  4800
ccctcacaga tttgcatttc ccacgctttg agttcagatg gggggatcat gtctacctgc  4860
ggggcgatga agaaaacggt ttccggggta ggggagatca gctgggaaga aagcaggttc  4920
ctgagcagct gcgacttacc gcagccggtg ggcccgtaaa tcacacctat taccgggtgc  4980
aactggtagt taagagagct gcagctgccg tcatccctga gcaggggggc cacttcgtta  5040
agcatgtccc tgactcgcat gttttccctg accaaatccg ccagaaggcg ctcgccgccc  5100
agcgatagca gttcttgcaa ggaagcaaag tttttcaacg gtttgagacc gtccgccgta  5160
ggcatgcttt tgagcgtttg accaagcagt tccaggcggt cccacagctc ggtcacctgc  5220
tctacggcat ctcgatccag catatctcct cgtttcgcgg gttggggcgg ctttcgctgt  5280
acggcagtag tcggtgctcg tccagacggg ccagggtcat gtctttccac gggcgcaggg  5340
tcctcgtcag cgtagtctgg gtcacggtga aggggtgcgc tccgggctgc gcgctggcca  5400
gggtgcgctt gaggctggtc ctgctggtgc tgaagcgctg ccggtcttcg ccctgcgcgt  5460
cggccaggta gcatttgacc atggtgtcat agtccagccc ctccgcggcg tggcccttgg  5520
cgcgcagctt gcccttggag gaggcgccgc acgaggggca gtgcagactt ttgagggcgt  5580
agagcttggg cgcgagaaat accgattccg gggagtaggc atccgcgccg caggccccgc  5640
agacggtctc gcattccacg agccaggtga gctctggccg ttcggggtca aaaaccaggt  5700
ttcccccatg ctttttgatg cgtttcttac ctctggtttc catgagccgg tgtccacgct  5760
cggtgacgaa aaggctgtcc gtgtccccgt atacagactt gagaggcctg tcctcgagcg  5820
gtgttccgcg gtcctcctcg tatagaaact cggaccactc tgagacaaag gctcgcgtcc  5880
```

```
aggccagcac gaaggaggct aagtgggagg ggtagcggtc gttgtccact agggggtcca  5940
ctcgctccag ggtgtgaaga cacatgtcgc cctcttcggc atcaaggaag gtgattggtt  6000
tgtaggtgta ggccacgtga ccgggtgttc ctgaaggggg gctataaaag ggggtggggg  6060
cgcgttcgtc ctcactctct tccgcatcgc tgtctgcgag ggccagctgt tggggtgagt  6120
actccctctg aaaagcgggc atgacttctg cgctaagatt gtcagtttcc aaaaacgagg  6180
aggatttgat attcacctgg cccgcggtga tgcctttgag ggtggccgca tccatctggt  6240
cagaaaagac aatctttttg ttgtcaagct tggtggcaaa cgacccgtag agggcgttgg  6300
acagcaactt ggcgatggag cgcagggttt ggtttttgtc gcgatcggcg cgctccttgg  6360
ccgcgatgtt tagctgcacg tattcgcgcg caacgcaccg ccattcggga aagacggtgg  6420
tgcgctcgtc gggcaccagg tgcacgcgcc aaccgcggtt gtgcagggtg acaaggtcaa  6480
cgctggtggc tacctctccg cgtaggcgct cgttggtcca gcagaggcgg ccgcccttgc  6540
gcgagcagaa tggcggtagg gggtctagct gcgtctcgtc cggggggtct gcgtccacgg  6600
taaagacccc gggcagcagg cgcgcgtcga agtagtctat cttgcatcct tgcaagtcta  6660
gcgcctgctg ccatgcgcgg gcggcaagcg cgcgctcgta tgggttgagt gggggacccc  6720
atggcatggg gtgggtgagc gcggaggcgt acatgccgca aatgtcgtaa acgtagaggg  6780
gctctctgag tattccaaga tatgtagggt agcatcttcc accgcggatg ctggcgcgca  6840
cgtaatcgta tagttcgtgc gagggagcga ggaggtcggg accgaggttg ctacgggcgg  6900
gctgctctgc tcggaagact atctgcctga agatggcatg tgagttggat gatatggttg  6960
gacgctggaa gacgttgaag ctggcgtctg tgagacctac cgcgtcacgc acgaaggagg  7020
cgtaggagtc gcgcagcttg ttgaccagct cggcggtgac ctgcacgtct agggcgcagt  7080
agtccagggt ttccttgatg atgtcatact tatcctgtcc cttttttttc cacagctcgc  7140
ggttgaggac aaactcttcg cggtctttcc agtactcttg gatcggaaac ccgtcggcct  7200
ccgaacggta agagcctagc atgtagaact ggttgacggc ctggtaggcg cagcatccct  7260
tttctacggg tagcgcgtat gcctgcgcgg ccttccggag cgaggtgtgg gtgagcgcaa  7320
aggtgtccct gaccatgact ttgaggtact ggtatttgaa gtcagtgtcg tcgcatccgc  7380
cctgctccca gagcaaaaag tccgtgcgct ttttggaacg cggatttggc agggcgaagg  7440
tgacatcgtt gaagagtatc tttcccgcgc gaggcataaa gttgcgtgtg atgcggaagg  7500
gtcccggcac ctcggaacgg ttgttaatta cctgggcggc gagcacgatc tcgtcaaagc  7560
cgttgatgtt gtggcccaca atgtaaagtt ccaagaagcg cgggatgccc ttgatggaag  7620
gcaatttttt aagttcctcg taggtgagct cttcagggga gctgagcccg tgctctgaaa  7680
gggcccagtc tgcaagatga gggttggaag cgacgaatga gctccacagg tcacgggcca  7740
ttagcatttg caggtggtcg cgaaaggtcc taaactggcg acctatggcc atttttttctg  7800
gggtgatgca gtagaaggta agcgggtctt gttcccagcg gtcccatcca aggttcgcgg  7860
ctaggtctcg cgcggcagtc actagaggct catctccgcc gaacttcatg accagcatga  7920
agggcacgag ctgcttccca aaggccccca tccaagtata ggtctctaca tcgtaggtga  7980
caaagagacg ctcggtgcga ggatgcgagc cgatcgggaa gaactggatc tcccgccacc  8040
aattggagga gtggctattg atgtggtgaa agtagaagtc cctgcgacgg gccgaacact  8100
cgtgctggct tttgtaaaaa cgtgcgcagt actggcagcg gtgcacgggc tgtacatcct  8160
gcacgaggtt gacctgacga ccgcgcacaa ggaagcagag tgggaatttg agcccctcgc  8220
ctggcgggtt tggctggtgg tcttctactt cggctgcttg tccttgaccg tctggctgct  8280
cgaggggagt tacggtggat cggaccacca cgccgcgcga gcccaaagtc cagatgtccg  8340
cgcgcggcgg tcggagcttg atgacaacat cgcgcagatg ggagctgtcc atggtctgga  8400
gctcccgcgg cgtcaggtca ggcgggagct cctgcaggtt tacctcgcat agacgggtca  8460
gggcgcgggc tagatccagg tgatacctaa tttccagggg ctggttggtg gcggcgtcga  8520
tggcttgcaa gaggccgcat ccccgcggcg cgactacggt accgcgcggc gggcggtggg  8580
ccgcgggggt gtccttggat gatgcatcta aaagcggtga cgcgggcgag cccccggagg  8640
taggggggc tccggacccg ccgggagagg gggcaggggc acgtcggcgc cgcgcgcggg  8700
caggagctgg tgctgcgcgc gtaggttgct ggcgaacgcg acgacgcggc ggttgatctc  8760
ctgaatctgg cgcctctgcg tgaagacgac gggcccggtg agcttgagcc tgaaagagag  8820
ttcgacagaa tcaatttcgg tgtcgttgac ggcggcctgg cgcaaaatct cctgcacgtc  8880
tcctgagttg tcttgatagg cgatctcggc catgaactgc tcgatctctt cctcctggag  8940
atctccgcgt ccggctcgct ccacggtggc ggcgaggtcg ttggaaatgc gggccatgag  9000
ctgcgagaag gcgttgaggc ctccctcgtt ccagacgcgg ctgtagacca cgccccccttc  9060
ggcatcgcgg gcgcgcatga ccacctgcgc gagattgagc tccacgtgcc gggcgaagac  9120
ggcgtagttt cgcaggcgct gaaagaggta gttgagggtg gtggcggtgt gttctgccac  9180
gaagaagtac ataacccagc gtcgcaacgt ggattcgttg atatccccca aggcctcaag  9240
gcgctccatg gcctcgtaga agtccacggc gaagttgaaa aactgggagt tgcgcgccga  9300
cacggttaac tcctcctcca gaagacggat gagctcggcg acagtgtcgc gcacctcgcg  9360
ctcaaaggct acaggggcct cttcttcttc ttcaatctcc tcttccataa gggcctcccc  9420
ttcttcttct tctggcggcg gtgggggagg ggggacacgg cggcgacgac ggcgcaccgg  9480
gaggcggtcg acaaagcgct cgatcatctc cccgcggcga cggcgcatgg tctcggtgac  9540
ggcgcggccg ttctcgcggg ggcgcagttg gaagacgccg cccgtcatgt cccggttatg  9600
ggttggcggg gggctgccat gcggcaggga tacggcgcta acgatgcatc tcaacaattg  9660
ttgtgtaggt actccgccgc cgagggacct gagcgagtcc gcatcgaccg gatcggaaaa  9720
cctctcgaga aaggcgtcta accagtcaca gtcgcaaggt aggctgagca ccgtggcggg  9780
cggcagcggg cggcggtcgg ggttgtttct ggcggaggtg ctgctgatga tgtaattaaa  9840
gtaggcggtc ttgagacggc ggatggtcga cagaagcacc atgtccttgg gtccggcctg  9900
ctgaatgcgc aggcggtcgg ccatgcccca ggcttcgttt tgacatcggc gcaggtcttt  9960
gtagtagtct tgcatgagcc tttctaccgg cacttcttct tctccttcct cttgtcctgc  10020
atctcttgca tctatcgctg cggcggcggc ggagtttggc cgtaggtggc gccctcttcc  10080
tcccatgcgt gtgaccccga agcccctcat cggctgaagc agggctaggt cggcgacaac  10140
gcgctcggct aatatggcct gctgcacctg cgtgagggta gactggaagt catccatgtc  10200
cacaaagcgg tggtatgcgc ccgtgttgat ggtgtaagtg cagttggcca taacggacca  10260
gttaacggtc tggtgacccg gctgcgagag ctcggtgtac ctgagacgcg agtaagccct  10320
cgagtcaaat acgtagtcgt tgcaagtccg caccaggtac tggtatccca ccaaaaagtg  10380
cggcggcggc tggcggtaga ggggccagcg tagggtggcc ggggctccgg gggcgagatc  10440
ttccaacata aggcgatgat atccgtagat gtacctggac atccaggtga tgccggcggc  10500
ggtggtggag gcgcgcggaa agtcgcggac gcggttccag atgttgcgca gcggcaaaaa  10560
gtgctccatg gtcgggacgc tctggccggt caggcgcgcg caatcgttga cgctctagac  10620
```

-continued

```
cgtgcaaaag gagagcctgt aagcgggcac tcttccgtgg tctggtggat aaattcgcaa  10680
gggtatcatg gcggacgacc ggggttcgag ccccgtatcc ggccgtccgc cgtgatccat  10740
gcggttaccg cccgcgtgtc gaacccaggt gtgcgacgtc agacaacggg ggagtgctcc  10800
ttttggcttc cttccaggcg cggcggctgc tgcgctagct tttttggcca ctggccgcgc  10860
gcagcgtaag cggttaggct ggaaagcgaa agcattaagt ggctcgctcc ctgtagccgg  10920
agggttattt tccaagggtt gagtcgcggg acccccggtt cgagtctcgg accggccgga  10980
ctgcggcgaa cgggggtttg cctccccgtc atgcaagacc ccgcttgcaa attcctccgg  11040
aaacagggac gagcccctt tttgcttttc ccagatgcat ccggtgctgc ggcagatgcg  11100
ccccctcct cagcagcggc aagagcaaga gcagcggcag acatgcaggg caccctcccc  11160
tcctcctacc gcgtcaggag gggcgacatc cgcggttgac gcggcagcag atggtgatta  11220
cgaacccccg cggcgccggg cccggcacta cctggacttg gaggagggcg agggcctggc  11280
gcggctagga gcgccctctc ctgagcggta cccaagggtg cagctgaagc gtgatacgcg  11340
tgaggcgtac gtgccgcggc agaacctgtt tcgcgaccgc gagggagagg agcccgagga  11400
gatgcgggat cgaaagttcc acgcagggcg cgagctgcgg catggcctga atcgcgagcg  11460
gttgctgcgc gaggaggact ttgagcccga cgcgcgaacc gggattagtc ccgcgcgcgc  11520
acacgtggcg gccgccgacc tggtaaccgc atacgagcag acggtgaacc aggagattaa  11580
ctttcaaaaa agctttaaca accacgtgcg tacgcttgtg gcgcgcgagg aggtggctat  11640
aggactgatg catctgtggg actttgtaag cgcgctggag caaaacccaa atagcaagcc  11700
gctcatggcg cagctgttcc ttatagtgca gcacagcagg gacaacgagg cattcaggga  11760
tgcgctgcta aacatagtag agcccgaggg ccgctggctg ctcgatttga taaacatcct  11820
gcagagcata gtggtgcagg agcgcagctt gagcctggct gacaaggtgg ccgccatcaa  11880
ctattccatg cttagcctgg gcaagtttta cgcccgcaag atataccata ccccttacgt  11940
tcccatagac aaggaggtaa agatcgaggg gttctacatg cgcatggcgc tgaaggtgct  12000
taccttgagc gacgacctgg gcgtttatcg caacgagcgc atccacaagg ccgtgagcgt  12060
gagccggcgg cgcgagctca gcgaccgcga gctgatgcac agcctgcaaa gggccctggc  12120
tggcacgggc agcggcgata gagaggccga gtcctacttt gacgcgggcg ctgacctgcg  12180
ctgggcccca agccgacgcg ccctggaggc agctggggcc ggacctgggc tggcggtggc  12240
acccgcgcgc gctggcaacg tcggcggcgt ggaggaatat gacgaggacg atgagtacga  12300
gccagaggac ggcgagtact aagcggtgat gtttctgatc agatgatgca agacgcaacg  12360
gacccggcgg tgcgggcggc gctgcagagc cagccgtccg gccttaactc cacggacgac  12420
tggcgccagg tcatggaccg catcatgtcg ctgactgcgc gcaatcctga cgcgttccgg  12480
cagcagccgc aggccaaccg gctctccgca attctggaag cggtggtccc ggcgcgcgca  12540
aaccccacgc acgagaaggt gctggcgatc gtaaacgcgc tggccgaaaa cagggccatc  12600
cggcccgacg aggccggcct ggtctacgac gcgctgcttc agcgcgtggc tcgttacaac  12660
agcggcaacg tgcagaccaa cctggaccgg ctggtggggg atgtgcgcga ggccgtggcg  12720
cagcgtgagc gcgcgcagca gcagggcaac ctgggctcca tggttgcact aaacgccttc  12780
ctgagtacac agcccgccaa cgtgccgcgg ggacaggagg actacaccaa ctttgtgagc  12840
gcactgcggc taatggtgac tgagacaccg caaagtgagg tgtaccagtc tgggccagac  12900
tattttttcc agaccagtag acaaggcctg cagaccgtaa acctgagcca ggctttcaaa  12960
aacttgcagg ggctgtgggg ggtgcgggct cccacaggcg accgcgcgac cgtgtctagc  13020
ttgctgacgc ccaactcgcg cctgttgctg ctgctaatag cgcccttcac ggacagtggc  13080
agcgtgtccc gggacacata cctaggtcac ttgctgacac tgtaccgcga ggccataggt  13140
caggcgcatg tggacgagca tactttccag gagattacaa gtgtcagccg cgcgctgggg  13200
caggaggaca cgggcagcct ggaggcaacc ctaaactacc tgctgaccaa ccggcggcag  13260
aagatcccct cgttgcacag tttaaacagc gaggaggagc gcattttgcg ctacgtgcag  13320
cagagcgtga gccttaacct gatgcgcgac ggggtaacgc ccagcgtggc gctggacatg  13380
accgcgcgca acatggaacc gggcatgtat gcctcaaacc ggccgtttat caaccgccta  13440
atggactact tgcatcgcgc ggccgccgtg aaccccgagt atttcaccaa tgccatcttg  13500
aacccgcact ggctaccgcc ccctggtttc tacaccgggg gattcgaggt gcccgagggt  13560
aacgatggat tcctctggga cgacatagac gacagcgtgt tttccccgca accgcagacc  13620
ctgctagagt tgcaacagcg cgagcaggca gaggcggcgc tgcgaaagga aagcttccgc  13680
aggccaagca gcttgtccga tctaggcgct gcggccccgc ggtcagatgc tagtagccca  13740
tttccaagct tgatagggtc tcttaccagc actcgcacca cccgcccgcg cctgctgggc  13800
gaggaggagt acctaaacaa ctcgctgctg cagccgcagc gcgaaaaaaa cctgcctccg  13860
gcatttccca acaacgggat agagagccta gtggacaaga tgagtagatg gaagacgtac  13920
gcgcaggagc acagggacgt gccaggcccg cgcccgccca cccgtcgtca aaggcacgac  13980
cgtcagcggg gtctggtgtg ggaggacgat gactcggcag acgacagcag cgtcctggat  14040
ttgggaggga gtggcaaccc gtttgcgcac cttcgcccca ggctggggag aatgttttaa  14100
aaaaaaaaaa gcatgatgca aaataaaaaa ctcaccaagg ccatggcacc gagcgttggt  14160
tttcttgtat tccccttagt atgcggcgcg cggcgatgta tgaggaaggt cctcctccct  14220
cctacgagag tgtggtgagc gcggcgccag tggcggcggc gctgggttct cccttcgatg  14280
ctcccctgga cccgccgttt gtgcctccgc ggtacctgcg gcctaccggg gggagaaaca  14340
gcatccgtta ctctgagttg gcacccctat tcgacaccac ccgtgtgtac ctggtggaca  14400
acaagtcaac ggatgtggca tccctgaact accagaacga ccacagcaac tttctgacca  14460
cggtcattca aaacaatgac tacagcccgg gggaggcaag cacacagacc atcaatcttg  14520
acgaccggtc gcactggggc ggcgacctga aaaccatcct gcataccaac atgccaaatg  14580
tgaacgagtt catgtttacc aataagttta aggcgcgggt gatggtgtcg cgcttgccta  14640
ctaaggacaa tcaggtggag ctgaaatacg agtgggtgga gttcacgctg cccgagggca  14700
actactccga gaccatgacc atagacctta tgaacaacgc gatcgtggag cactacttga  14760
aagtgggcag acagaacggg gttctggaaa gcgacatcgg ggtaaagttt gacacccgca  14820
acttcagact ggggtttgac cccgtcactg gtcttgtcat gcctggggta tatacaaacg  14880
aagccttcca tccagacatc attttgctgc caggatgcgg ggtggacttc acccacagcc  14940
gcctgagcaa cttgttgggc atccgcaagc ggcaaccctt ccaggagggc tttaggatca  15000
cctacgatga tctggagggt ggtaacattc ccgcactgtt ggatgtggac gcctaccagg  15060
cgagcttgaa agatgacacc gaacagggcg ggggtggcgc aggcggcagc aacagcagtg  15120
gcagcggcgc ggaagagaac tccaacgcgg cagccgcggc aatgcagccg gtggaggaca  15180
tgaacgatca tgccattcgc ggcgacacct ttgccacacg ggctgaggag aagcgcgctg  15240
aggccgaagc agcggccgaa gctgccgccc ccgctgcgca acccgaggtc gagaagcctc  15300
agaagaaacc ggtgatcaaa cccctgacag aggacagcaa gaaacgcagt tacaacctaa  15360
```

```
taagcaatga cagcaccttc acccagtacc gcagctggta ccttgcatac aactacggcg  15420
accctcagac cggaatccgc tcatggaccc tgctttgcac tcctgacgta acctgcggct  15480
cggagcaggt ctactggtcg ttgccagaca tgatgcaaga ccccgtgacc ttccgctcca  15540
cgcgccagat cagcaacttt ccggtggtgg gcgccgagct gttgcccgtg cactccaaga  15600
gcttctacaa cgaccaggcc gtctactccc aactcatccg ccagtttacc tctctgaccc  15660
acgtgttcaa tcgctttccc gagaaccaga ttttggcgcg cccgccagcc cccaccatca  15720
ccaccgtcag tgaaaacgtt cctgctctca cagatcacgg gacgctaccg ctgcgcaaca  15780
gcatcggagg agtccagcga gtgaccatta ctgacgccag acgccgcacc tgcccctacg  15840
tttacaaggc cctgggcata gtctcgccgc gcgtcctatc gagccgcact ttttgagcaa  15900
gcatgtccat ccttatatcg cccagcaata acacaggctg gggcctgcgc ttcccaagca  15960
agatgtttgg cggggccaag aagcgctccg accaacaccc agtgcgcgtg cgcgggcact  16020
accgcgcgcc ctggggcgcg cacaaacgcg gccgcactgg gcgcaccacc gtcgatgacg  16080
ccatcgacgc ggtggtggag gaggcgcgca actacacgcc cacgccgcca ccagtgtcca  16140
cagtggacgc ggccattcag accgtggtgc gcggagcccg gcgctatgct aaaatgaaga  16200
gacggcggag gcgcgtagca cgtcgccacc gccgccgacc cggcactgcc gcccaacgcg  16260
cggcggcggc cctgcttaac cgcgcacgtc gcaccggccg acgggcggcc atgcgggccg  16320
ctcgaaggct ggccgcgggt attgtcactg tgccccccag gtccaggcga cgagcggccg  16380
ccgcagcagc cgcggccatt agtgctatga ctcagggtcg caggggcaac gtgtattggg  16440
tgcgcgactc ggttagcggc ctgcgcgtgc ccgtgcgcac ccgcccccccg cgcaactaga  16500
ttgcaagaaa aaactactta gactcgtact gttgtatgta tccagcggcg gcggcgcgca  16560
acgaagctat gtccaagcgc aaaatcaaag aagagatgct ccaggtcatc gcgccggaga  16620
tctatggccc cccgaagaag gaagagcagg attacaagcc ccgaaagcta aagcgggtca  16680
aaaagaaaaa gaaagatgat gatgatgaac ttgacgacga ggtggaactg ctgcacgcta  16740
ccgcgcccag gcgacgggta cagtggaaag gtcgacgcgt aaaacgtgtt ttgcgacccg  16800
gcaccaccgt agtctttacg cccggtgagc gctccacccg cacctacaag cgcgtgtatg  16860
atgaggtgta cggcgacgag gacctgcttg agcaggccaa cgagcgcctc ggggagtttg  16920
cctacggaaa gcggcataag gacatgctgg cgttgccgct ggacgagggc aacccaacac  16980
ctagcctaaa gcccgtaaca ctgcagcagg tgctgcccgc gcttgcaccg tccgaagaaa  17040
agcgcggcct aaagcgcgag tctggtgact tggcacccac cgtgcagctg atggtaccca  17100
agcgccagcg actggaagat gtcttggaaa aaatgaccgt ggaacctggg ctggagcccg  17160
aggtccgcgt gcggccaatc aagcaggtgg cgccgggact gggcgtgcag accgtggacg  17220
ttcagatacc cactaccagt agcaccagta ttgccaccgc cacagagggc atggagacac  17280
aaacgtcccc ggttgcctca gcggtggcgg atgccgcggt gcaggcggtc gctgcggccg  17340
cgtccaagac ctctacggag gtgcaaacgg acccgtggat gtttcgcgtt tcagcccccc  17400
ggcgcccgcg cggttcgagg aagtacggcg ccgccagcgc gctactgccc gaatatgccc  17460
tacatccttc cattgcgcct acccccggct atcgtggcta cacctaccgc cccagaagac  17520
gagcaactac ccgacgccga accaccactg gaacccgccg ccgccgtcgc cgtcgccagc  17580
ccgtgctggc cccgatttcc gtgcgcaggg tggctcgcga aggaggcagg accctggtgc  17640
tgccaacagc gcgctaccac cccagcatcg tttaaaagcc ggtctttgtg gttcttgcag  17700
atatggccct cacctgccgc ctccgtttcc cggtgccggg attccgagga agaatgcacc  17760
gtaggagggg catggccggc cacggcctga cgggcggcat gcgtcgtgcg caccaccggc  17820
ggcggcgcgc gtcgcaccgt cgcatgcgcg gcggtatcct gcccctcctt attccactga  17880
tcgccgcggc gattggcgcc gtgcccggaa ttgcatccgt ggccttgcag gcgcagagac  17940
actgattaaa aacaagttgc atgtggaaaa atcaaaataa aaagtctgga ctctcacgct  18000
cgcttggtcc tgtaactatt ttgtagaatg gaagacatca actttgcgtc tctggccccg  18060
cgacacggct cgcgcccgtt catgggaaac tggcaagata tcggcaccag caatatgagc  18120
ggtggcgcct tcagctgggg ctcgctgtgg agcggcatta aaaatttcgg ttccaccgtt  18180
aagaactatg gcagcaaggc ctggaacagc agcacaggcc agatgctgag ggataagttg  18240
aaagagcaaa atttccaaca aaaggtggta gatggcctgg cctctggcat tagcggggtg  18300
gtggacctgg ccaaccaggc agtgcaaaat aagattaaca gtaagcttga tccccgccct  18360
cccgtagagg agcctccacc ggccgtggag acagtgtctc cagaggggcg tggcgaaaag  18420
cgtccgcgcc ccgacaggga agaaactctg gtgacgcaaa tagacgagcc tccctcgtac  18480
gaggaggcac taaagcaagg cctgcccacc acccgtccca tcgcgcccat ggctaccgga  18540
gtgctgggcc agcacacacc cgtaacgctg gacctgcctc cccccgccga cacccagcag  18600
aaacctgtgc tgccaggccc gaccgccgtt gttgtaaccc gtcctagccg cgcgtccctg  18660
cgccgcgccg ccagcggtcc gcgatcgttg cggcccgtag ccagtggcaa ctggcaaagc  18720
acactgaaca gcatcgtggg tctgggggtg caatccctga agcgccgacg atgcttctga  18780
atagctaacg tgtcgtatgt gtgtcatgta tgcgtccatg tcgccgccag aggagctgct  18840
gagccgccgc gcgcccgctt tccaagatgg ctaccccttc gatgatgccg cagtggtctt  18900
acatgcacat ctcgggccag gacgcctcgg agtacctgag ccccgggctg gtgcagtttg  18960
cccgcgccac cgagacgtac ttcagcctga ataacaagtt tagaaacccc acggtggcgc  19020
ctacgcacga cgtgaccaca gaccggtccc agcgtttgac gctgcggttc atccctgtgg  19080
accgtgagga tactgcgtac tcgtacaagg cgcggttcac cctagctgtg ggtgataacc  19140
gtgtgctgga catggcttcc acgtactttg acatccgcgg cgtgctggac aggggcccta  19200
cttttaagcc ctactctggc actgcctaca acgccctggc tcccaagggt gccccaaatc  19260
cttgcgaatg ggatgaagct gctactgctc ttgaaataaa cctagaagaa gaggacgatg  19320
acaacgaaga cgaagtagac gagcaagctg agcagcaaaa aactcacgta tttgggcagg  19380
cgccttattc tggtataaat attacaaagg agggtattca aataggtgtc gaaggtcaaa  19440
cacctaaata tgccgataaa acatttcaac ctgaacctca aataggagaa tctcagtggt  19500
acgaaactga aattaatcat gcagctggga gagtccttaa aaagactacc ccaatgaaac  19560
catgttacgg ttcatatgca aaacccacaa atgaaaatgg agggcaaggc attcttgtaa  19620
agcaacaaaa tggaaagcta gaaagtcaag tggaaatgca atttttctca actactgagg  19680
cgaccgcagg caatggtgat aacttgactc ctaaagtggt attgtacagt gaagatgtag  19740
atatagaaac cccagacact catatttctt acatgcccac tattaaggaa ggtaactcac  19800
gagaactaat gggccaacaa tctatgccca acaggcctaa ttacattgct tttagggaca  19860
attttattgg tctaatgtat tacaacagca cgggtaatat gggtgttctg gcgggccaag  19920
catcgcagtt gaatgctgtt gtagatttgc aagacagaaa cacagagctt tcataccagc  19980
ttttgcttga ttccattggt gatagaacca ggtacttttc tatgtggaat caggctgttg  20040
acagctatga tccagatgtt agaattattg aaaatcatgg aactgaagat gaacttccaa  20100
```

```
attactgctt tccactggga ggtgtgatta atacagagac tcttaccaag gtaaaaccta  20160
aaacaggtca ggaaaatgga tgggaaaaag atgctacaga attttcagat aaaaatgaaa  20220
taagagttgg aaataatttt gccatggaaa tcaatctaaa tgccaacctg tggagaaatt  20280
tcctgtactc caacatagcg ctgtatttgc ccgacaagct aaagtacagt ccttccaacg  20340
taaaaatttc tgataaccca aacacctacg actacatgaa caagcgagtg gtggctcccg  20400
ggttagtgga ctgctacatt aaccttggag cacgctggtc ccttgactat atggacaacg  20460
tcaacccatt taaccaccac cgcaatgctg gcctgcgcta ccgctcaatg ttgctgggca  20520
atggtcgcta tgtgcccttc cacatccagg tgcctcagaa gttctttgcc attaaaaacc  20580
tccttctcct gccgggctca tacacctacg agtggaactt caggaaggat gttaacatgg  20640
ttctgcagag ctccctagga aatgacctaa gggttgacgg agccagcatt aagtttgata  20700
gcatttgcct ttacgccacc ttcttcccca tggcccacaa caccgcctcc acgcttgagg  20760
ccatgcttag aaacgacacc aacgaccagt cctttaacga ctatctctcc gccgccaaca  20820
tgctctaccc tatacccgcc aacgctacca acgtgcccat atccatcccc tcccgcaact  20880
gggcggcttt ccgcggctgg gccttcacgc gccttaagac taaggaaacc ccatcactgg  20940
gctcgggcta cgacccttat tacacctact ctggctctat accctaccta gatggaacct  21000
tttacctcaa ccacaccttt aagaaggtgg ccattacctt tgactcttct gtcagctggc  21060
ctggcaatga ccgcctgctt acccccaacg agtttgaaat taagcgctca gttgacgggg  21120
agggttacaa cgttgcccag tgtaacatga ccaaagactg gttcctggta caaatgctag  21180
ctaactataa cattggctac cagggcttct atatcccaga gagctacaag gaccgcatgt  21240
actccttctt tagaaacttc cagcccatga gccgtcaggt ggtggatgat actaaataca  21300
aggactacca acaggtgggc atcctacacc aacacaacaa ctctggattt gttggctacc  21360
ttgcccccac catgcgcgaa ggacaggcct accctgctaa cttcccctat ccgcttatag  21420
gcaagaccgc agttgacagc attacccaga aaaagtttct ttgcgatcgc accctttggc  21480
gcatcccatt ctccagtaac tttatgtcca tgggcgcact cacagacctg ggccaaaacc  21540
ttctctacgc caactccgcc cacgcgctag acatgacttt tgaggtggat cccatggacg  21600
agcccaccct tctttatgtt ttgtttgaag tctttgacgt ggtccgtgtg caccagccgc  21660
accgcggcgt catcgaaacc gtgtacctgc gcacgccctt ctcggccggc aacgccacaa  21720
cataaagaag caagcaacat caacaacagc tgccgccatg ggctccagtg agcaggaact  21780
gaaagccatt gtcaaagatc ttggttgtgg gccatatttt ttgggcacct atgacaagcg  21840
ctttccaggc tttgtttctc cacacaagct cgcctgcgcc atagtcaata cggccggtcg  21900
cgagactggg ggcgtacact ggatggcctt tgcctggaac ccgcactcaa aaacatgcta  21960
cctctttgag ccctttggct tttctgacca gcgactcaag caggtttacc agtttgagta  22020
cgagtcactc ctgcgccgta gcgccattgc ttcttccccc gaccgctgta taacgctgga  22080
aaagtccacc caaagcgtac aggggcccaa ctcggccgcc tgtggactat tctgctgcat  22140
gtttctccac gcctttgcca actggcccca aactcccatg gatcacaacc ccaccatgaa  22200
ccttattacc ggggtaccca actccatgct caacagtccc caggtacagc ccaccctgcg  22260
tcgcaaccag gaacagctct acagcttcct ggagcgccac tcgccctact tccgcagcca  22320
cagtgcgcag attaggagcg ccacttcttt ttgtcacttg aaaaacatgt aaaaataatg  22380
tactagagac actttcaata aaggcaaatg cttttatttg tacactctcg ggtgattatt  22440
taccccccacc cttgccgtct gcgccgtttc cttctcctat aggcagaaaa agatcatgga  22500
gtcagtcgag aagaaggaca gcctaaccgc cccctctgag ttcgccacca ccgcctccac  22560
cgatgccgcc aacgcgccta ccaccttccc cgtcgaggca cccccgcttg aggaggagga  22620
agtgattatc gagcaggacc caggttttgt aagcgaagac gacgaggacc gctcagtacc  22680
aacagaggat aaaaagcaag accaggacaa cgcagaggca aacgaggaac aagtcgggcg  22740
gggggacgaa aggcatggcg actacctaga tgtgggagac gacgtgctgt tgaagcatct  22800
gcagcgccag tgcgccatta tctgcgacgc gttgcaagag cgcagcgatg tgcccctcgc  22860
catagcggat gtcagccttg cctacgaacg ccacctattc tcaccgcgcg taccccccaa  22920
acgccaagaa aacggcacat gcgagcccaa cccgcgcctc aacttctacc ccgtatttgc  22980
cgtgccagag gtgcttgcca cctatcacat ctttttccaa aactgcaaga taccccctatc  23040
ctgccgtgcc aaccgcagcc gagcggacaa gcagctggcc ttgcggcagg gcgctgtcat  23100
acctgatatc gcctcgctca acgaagtgcc aaaaatcttt gagggtcttg gacgcgacga  23160
gaagcgcgcg gcaaacgctc tgcaacagga aaacagcgaa aatgaaagtc actctggagt  23220
gttggtggaa ctcgagggtg acaacgcgcg cctagccgta ctaaaacgca gcatcgaggt  23280
cacccacttt gcctacccgg cacttaacct accccccaag gtcatgagca cagtcatgag  23340
tgagctgatc gtgcgccgtg cgcagcccct ggagagggat gcaaatttgc aagaacaaac  23400
agaggagggc ctacccgcag ttggcgacga gcagctagcg cgctggcttc aaacgcgcga  23460
gcctgccgac ttggaggagc gacgcaaact aatgatggcc gcagtgctcg ttaccgtgga  23520
gcttgagtgc atgcagcggt tctttgctga cccggagatg cagcgcaagc tagaggaaac  23580
attgcactac acctttcgac agggctacgt acgccaggcc tgcaagatct ccaacgtgga  23640
gctctgcaac ctggtctcct accttggaat tttgcacgaa aaccgccttg ggcaaaacgt  23700
gcttcattcc acgctcaagg gcgaggcgcg ccgcgactac gtccgcgact gcgtttactt  23760
atttctatgc tacacctggc agacggccat gggcgtttgg cagcagtgct tggaggagtg  23820
caacctcaag gagctgcaga aactgctaaa gcaaaacttg aaggacctat ggacggcctt  23880
caacgagcgc tccgtggccg cgcacctggc ggacatcatt ttccccgaac gcctgcttaa  23940
aaccctgcaa cagggtctgc cagacttcac cagtcaaagc atgttgcaga actttaggaa  24000
ctttatccta gagcgctcag gaatcttgcc cgccacctgc tgtgcacttc ctagcgactt  24060
tgtgcccatt aagtaccgcg aatgccctcc gccgctttgg ggccactgct accttctgca  24120
gctagccaac taccttgcct accactctga cataatggaa gacgtgagcg gtgacggtct  24180
actggagtgt cactgtcgct gcaacctatg caccccgcac cgctccctgg tttgcaattc  24240
gcagctgctt aacgaaagtc aaattatcgg tacctttgag ctgcagggtc cctcgcctga  24300
cgaaaagtcc gcggctccgg ggttgaaact cactccgggg ctgtggacgt cggcttacct  24360
tcgcaaattt gtacctgagg actaccacgc ccacgagatt aggttctacg aagaccaatc  24420
ccgcccgcct aatgcggagc ttaccgcctg cgtcattacc cagggccaca ttcttggcca  24480
attgcaagcc atcaacaaag cccgccaaga gtttctgcta cgaaagggac ggggggttta  24540
cttggacccc cagtccggcg aggagctcaa cccaatcccc ccgccgccgc agccctatca  24600
gcagcagccg cgggcccttg cttcccagga tggcacccaa aaagaagctg cagctgccgc  24660
cgccacccac ggacgaggag gaatactggg acagtcaggc agaggaggtt ttggacgagg  24720
aggaggagga catgatggaa gactgggaga gcctagacga ggaagcttcc gaggtcgaag  24780
aggtgtcaga cgaaacaccg tcaccctcgg tcgcattccc ctcgccggcg ccccagaaat  24840
```

```
cggcaaccgg ttccagcatg gctacaacct ccgctcctca ggcgccgccg gcactgcccg  24900
ttcgccgacc caaccgtaga tgggacacca ctggaaccag ggccggtaag tccaagcagc  24960
cgccgccgtt agcccaagag caacaacagc gccaaggcta ccgctcatgg cgcgggcaca  25020
agaacgccat agttgcttgc ttgcaagact gtgggggcaa catctccttc gcccgccgct  25080
ttcttctcta ccatcacggc gtggccttcc cccgtaacat cctgcattac taccgtcatc  25140
tctacagccc atactgcacc ggcggcagcg gcagcaacag cagcggccac acagaagcaa  25200
aggcgaccgg atagcaagac tctgacaaag cccaagaaat ccacagcggc ggcagcagca  25260
ggaggaggag cgctgcgtct ggcgcccaac gaacccgtat cgacccgcga gcttagaaac  25320
aggatttttc ccactctgta tgctatattt caacagagca ggggccaaga acaagagctg  25380
aaaataaaaa acaggtctct gcgatccctc acccgcagct gcctgtatca caaaagcgaa  25440
gatcagcttc ggcgcacgct ggaagacgcg gaggctctct tcagtaaata ctgcgcgctg  25500
actcttaagg actagtttcg cgccctttct caaatttaag cgcgaaaact acgtcatctc  25560
cagcggccac acccggcgcc agcacctgtc gtcagcgcca tttcaacttt gtatacaaaa  25620
gttgtgatga gcaaggaaat tcccacgccc tacatgtgga gttaccagcc acaaatggga  25680
cttgcggctg gagctgccca agactactca acccgaataa actacatgag cgcgggaccc  25740
cacatgatat cccgggtcaa cggaatacgc gcccaccgaa accgaattct cctggaacag  25800
gcggctatta ccaccacacc tcgtaataac cttaatcccc gtagttggcc cgctgccctg  25860
gtgtaccagg aaagtcccgc tcccaccact gtggtacttc ccagagacgc ccaggccgaa  25920
gttcagatga ctaactcagg ggcgcagctt gcgggcggct ttcgtcacag ggtgcggtcg  25980
cccgggcagg gtataactca cctgacaatc agagggcgag gtattcagct caacgacgag  26040
tcggtgagct cctcgcttgg tctccgtccg gacgggacat ttcagatcgg cggcgccggc  26100
cgctcttcat tcacgcctcg tcaggcaatc ctaactctgc agacctcgtc ctctgagccg  26160
cgctctggag gcattggaac tctgcaattt attgaggagt ttgtgccatc ggtctacttt  26220
aaccccttct cgggacctcc cggccactat ccggatcaat ttattcctaa ctttgacgcg  26280
gtaaaggact cggcggacgg ctacgactga ctctatgtgg gatatgctcc agcgctacaa  26340
ccttgaagtc aggcttcctg gatgtcagca tctgactttg gccagcacct gtcccgcgga  26400
tttgttccag tccaactaca gcgacccacc ctaacagaga tggtgagcaa gggcgaggag  26460
gataacatgg ccatcatcaa ggagttcatg cgcttcaagg tgcacatgga gggctccgtg  26520
aacggccacg agttcgagat cgagggcgag ggcgagggcc gcccctacga gggcacccag  26580
accgccaagc tgaaggtgac caagggtggc cccctgccct tcgcctggga catcctgtcc  26640
cctcagttca tgtacggctc caaggcctac gtgaagcacc ccgccgacat ccccgactac  26700
ttgaagctgt ccttccccga gggcttcaag tgggagcgcg tgatgaactt cgaggacggc  26760
ggcgtggtga ccgtgaccca ggactcctcc ctgcaggacg gcgagttcat ctacaaggtg  26820
aagctgcgcg gcaccaactt cccctccgac ggccccgtaa tgcagaagaa gaccatgggc  26880
tgggaggcct cctccgagcg gatgtacccc gaggacggcg ccctgaaggg cgagatcaag  26940
cagaggctga agctgaagga cggcggccac tacgacgctg aggtcaagac cacctacaag  27000
gccaagaagc ccgtgcagct gcccggcgcc tacaacgtca acatcaagtt ggacatcacc  27060
tcccacaacg aggactacac catcgtggaa cagtacgaac gcgccgaggg ccgccactcc  27120
accggcggca tggacgagct gtacaaggga agcggagcta ctaacttcag cctgctgaag  27180
caggctggtg acgtcgagga gaatcctggc ccaatggtga tgaccaacac aaccaacgcg  27240
gccgccgcta ccggacttac atctaccaca aatacacccc aagtttctgc ctttgtcaat  27300
aactgggata acttgggcat gtggtggttc tccatagcgc ttatgtttgt atgccttatt  27360
attatgtggc tcatctgctg cctaaagcgc aaacgcgccc gaccacccat ctatagtccc  27420
atcattgtgc tacacccaaa caatgatgga atccatagat tggacggact gaaacacatg  27480
ttcttttctc ttacagtatg attaaatgag actaataaaa aaaaataata aagcatcact  27540
tacttaaaat cagttagcaa atttctgtcc agtttattca gcagcacctc cttgccctcc  27600
tcccagctct ggtattgcag cttcctcctg gctgcaaact ttctccacaa tctaaatgga  27660
atgtcagttt cctcctgttc ctgtccatcc gcacccacta tcttcatgtt gttgcagatg  27720
aagcgcgcaa gaccgtctga agatacctte aaccccgtgt atccatatga cacggaaacc  27780
ggtcctccaa ctgtgccttt tcttactcct ccctttgtat cccccaatgg gtttcaagag  27840
agtcccccctg gggtactctc tttgcgccta tccgaacctc tagttacctc caatggcatg  27900
cttgcgctca aaatgggcaa cggcctctct ctggacgagg ccggcaacct tacctcccaa  27960
aatgtaacca ctgtgagccc acctctcaaa aaaaccaagt caaacataaa cctggaaata  28020
tctgcacccc tcacagttac ctcagaagcc ctaactgtgg ctgccgccgc acctctaatg  28080
gtcgcgggca acacactcac catgcaatca caggccccgc taaccgtgca cgactccaaa  28140
cttagcattg ccacccaagg acccctcaca gtgtcagaag gaaagctagc cctgcaaaca  28200
tcaggccccc tcaccaccac cgatagcagt accccttacta tcactgcctc acccccctcta  28260
actactgcca ctggtagctt gggcattgac ttgaaagagc ccatttatac acaaaatgga  28320
aaactaggac taaagtacgg ggctcctttg catgtaacag acgacctaaa cactttgacc  28380
gtagcaactg gtccaggtgt gactattaat aatacttcct tgcaaactaa agttactgga  28440
gccttgggtt ttgattcaca aggcaatatg caacttaatg tagcaggagg actaaggatt  28500
gattctcaaa acagacgcct tatacttgat gttagttatc cgtttgatgc tcaaaaccaa  28560
ctaaatctaa gactaggaca gggccctctt tttataaact cagcccacaa cttggatatt  28620
aactacaaca aaggccttta cttgtttaca gcttcaaaca attccaaaaa gcttgaggtt  28680
aacctaagca ctgccaaggg gttgatgttt gacgctacag ccatagccat taatgcagga  28740
gatgggcttg aatttggttc acctaatgca ccaaacacaa atcccctcaa aacaaaaatt  28800
ggccatggcc tagaatttga ttcaaacaag gctatggttc ctaaactagg aactggcctt  28860
agttttgaca gcacaggtgc cattacagta ggaaacaaaa ataatgataa gctaactttg  28920
tggaccacac cagctccatc tcctaactgt agactaaatg cagagaaaga tgctaaactc  28980
actttggtct taacaaaatg tggcagtcaa atacttgcta cagtttcagt tttggctgtt  29040
aaaggcagtt tggctccaat atctggaaca gttcaaagtg ctcatcttat tataagattt  29100
gacgaaaatg gagtgctact aaacaattcc ttcctggacc cagaatattg gaactttaga  29160
aatggagatc ttactgaagg cacagcctat acaaacgctg ttggatttat gcctaaccta  29220
tcagcttatc caaaatctca cggtaaaact gccaaaagta acattgtcag tcaagtttac  29280
ttaaacggag acaaaactaa acctgtaaca ctaaccatta cactaaacgg tacacaggaa  29340
acaggagaca caactccaag tgcatactct atgtcatttt catgggactg gtctggccac  29400
aactacatta atgaaatatt tgccacatcc tcttacactt tttcatacat tgcccaagaa  29460
taaagcaata gcatcacaaa tttcacaaat aaagcattat tttagttatt aatagtaatc  29520
aattacgggg tcattagttc atagcccata tatggagttc cgcgttacat aacttacggt  29580
```

```
aaatggcccg cctggctgac cgcccaacga cccccgccca ttgacgtcaa taatgacgta  29640
tgttcccata gtaacgccaa tagggacttt ccattgacgt caatgggtgg agtatttacg  29700
gtaaactgcc cacttggcag tacatcaagt gtatcatatg ccaagtacgc cccctattga  29760
cgtcaatgac ggtaaatggc ccgcctggca ttatgcccag tacatgacct tatgggactt  29820
tcctacttgg cagtacatct acgtattagt catcgctatt accatggtga tgcggttttg  29880
gcagtacatc aatgggcgtg gatagcggtt tgactcacgg ggatttccaa gtctccaccc  29940
cattgacgtc aatgggagtt tgttttggca ccaaaatcaa cgggactttc caaaatgtcg  30000
taacaactcc gccccattga cgcaaatggg cggtaggcgt gtacggtggg aggtctatat  30060
aagcatccct atcagtgata gagatcagat ctccctatca gtgatagaga gctgttttga  30120
cctccataga agacaccggg accgatccag cctccggact ctagcgttta aacttaagct  30180
tggtacccgg ggatcctcta gggcctctga gctattccag aagtagtgaa gaggcttttt  30240
tggaggccta ggcttttgca aaaagctccg gatcgatcct gagacaccat ggccagtcgg  30300
gaagaggagc agcgcgaaac cacccccgag cgcggacgcg gtgcggcgcg acgtccccca  30360
accatggagg acgtgtcgtc cccgtccccg tcgccgccgc ctccccgggc gcccccaaaa  30420
aagcggatga ggcggcgtat cgagtccgag gacgaggaag actcatcaca agacgcgctg  30480
gtgccgcgca cacccagccc gcggccatcg acctcggcgg cggatttggc cattgcgccc  30540
aagaagaaaa agaagcgccc ttctcccaag cccgagcgcc cgccatcacc agaggtaatc  30600
gtggacagcg aggaagaaag agaagatgtg gcgctacaaa tggtgggttt cagcaaccca  30660
ccggtgctaa tcaagcatgg caaaggaggt aagcgcacag tgcggcggct gaatgaagac  30720
gacccagtgg cgcgtggtat gcggacgcaa gaggaagagg aagagcccag cgaagcggaa  30780
agtgaaatta cggtgatgaa cccgctgagt gtgccgatcg tgtctgcgtg ggagaagggc  30840
atggaggctg cgcgcgcgct gatggacaag taccacgtgg ataacgatct aaaggcgaac  30900
ttcaaactac tgcctgacca agtggaagct ctggcggccg tatgcaagac ctggctgaac  30960
gaggagcacc gcgggttgca gctgaccttc accagcaaca agacctttgt gacgatgatg  31020
gggcgattcc tgcaggcgta cctgcagtcg tttgcagagg tgacctacaa gcatcacgag  31080
cccacgggct gcgcgttgtg gctgcaccgc tgcgctgaga tcgaaggcga gcttaagtgt  31140
ctacacggaa gcattatgat aaataaggag cacgtgattg aaatggatgt gacgagcgaa  31200
aacgggcagc gcgcgctgaa ggagcagtct agcaaggcca agatcgtgaa gaaccggtgg  31260
ggccgaaatg tggtgcagat ctccaacacc gacgcaaggt gctgcgtgca cgacgcggcc  31320
tgtccggcca atcagttttc cggcaagtct tgcggcatgt tcttctctga aggcgcaaag  31380
gctcaggtgg cttttaagca gatcaaggct tttatgcagg cgctgtatcc taacgcccag  31440
accgggcacg gtcacctttt gatgccacta cggtgcgagt gcaactcaaa gcctgggcac  31500
gcgccctttt tgggaaggca gctaccaaag ttgactccgt tcgccctgag caacgcggag  31560
gacctggacg cggatctgat ctccgacaag agcgtgctgg ccagcgtgca ccacccggcg  31620
ctgatagtgt tccagtgctg caaccctgtg tatcgcaact cgcgcgcgca gggcggaggc  31680
cccaactgcg acttcaagat atcggcgccc gacctgctaa acgcgttggt gatggtgcgc  31740
agcctgtgga gtgaaaactt caccgagctg ccgcggatgg ttgtgcctga gtttaagtgg  31800
agcactaaac accagtatcg caacgtgtcc ctgccagtgg cgcatagcga tgcgcggcag  31860
aacccctttg atttttaaaa taaacaagtt aacaacaaca caaaaataat gctttatttc  31920
tcgagagctt gatgccaggc aagtccaggc aggccaggca agtccaggca ggccaggcaa  31980
gtccaggcag gccaggcaag tccaggcagg ccaggcaagt ccaggcaggc caggcaagtc  32040
caggcaggcc aggcaagtcc aggcaggcca ggcaagtcca ggcaggccag gcaagtccag  32100
gcaggccagg caagtccagg cagggccagg caagtccagg caggccaggc aagtccaggc  32160
aggccaggca agtccaggca ggatcgaatt aagctttagg cgtgtacggt gggcgcctat  32220
aaaagcagag ctcgtttagt gaaccgtcag atcgcctgga gcaattccac aacacttttg  32280
tcttatacca actttccgta ccacttccta ccctcgtaaa cctggagacg ccatccacgc  32340
tgttttgacc tccatagaag acaccgggac cgatccagcc tccggtcgac cgatcctgat  32400
tcaccatgtc tagactggac aagagcaaag tcataaactc tgctctggaa ttactcaatg  32460
aagtcggtat cgaaggcctg acgacaagga aactcgctca aaagctggga gttgagcagc  32520
ctaccctgta ctggcacgtg aagaacaagc gggccctgct cgatgccctg gcaatcgaga  32580
tgctggacag gcatcatacc cacttctgcc ccctggaagg cgagtcatgg caagactttc  32640
tgcggaacaa cgccaagtca ttccgctgtg ctctcctctc acatcgcgac ggggctaaag  32700
tgcatctcgg cacccgccca acagagaaac agtacgaaac cctggaaaat cagctcgcgt  32760
tcctgtgtca gcaaggcttc tccctggaga acgcactgta cgctctgtcc gccgtgggcc  32820
actttacact gggctgcgta ttggaggatc aggagcatca agtagcaaaa gaggaaagag  32880
agacacctac caccgattct atgcccccac ttctgagaca agcaattgag ctgttcgacc  32940
atcagggagc cgaacctgcc ttccttttcg gcctggaact aatcatatgt ggcctggaga  33000
aacagctaaa gtgcgaaagc ggctccgcgt acagcggatc ccgggaattc agatcttatt  33060
aataaacaag ttaacaacaa cacaaaaata atgctttatt taatcgtggc aaatccacta  33120
taataaaaga atcgtttgtg ttatgtttca acgtgtttat ttttcaattg cagaaaattt  33180
cgaatcattt ttcattcagt agtatagccc caccaccaca tagcttatac agatcaccgt  33240
acctcaactt tgtataataa agttgtaatc aaactcacag aaccctagta ttcaacctgc  33300
cacctccctc ccaacacaca gagtacacag tcctttctcc ccggctggcc ttaaaaagca  33360
tcatatcatg ggtaacagac atattcttag gtgttatatt ccacacggtt tcctgtcgag  33420
ccaaacgctc atcagtgata ttaataaact ccccgggcag ctcacttaag ttcatgtcgc  33480
tgtccagctg ctgagccaca ggctgctgtc caacttgcgg ttgcttaacg ggcggcgaag  33540
gagaagtcca cgcctacatg ggggtagagt cataatcgtg catcaggata gggcggtggt  33600
gctgcagcag cgcgcgaata aactgctgcc gccgccgctc cgtcctgcag gaatacaaca  33660
tggcagtggt ctcctcagcg atgattcgca ccgcccgcag cataaggcgc cttgtcctcc  33720
gggcacagca gcgcaccctg atctcactta aatcagcaca gtaactgcag cacagcacca  33780
caatattgtt caaaatccca cagtgcaagg cgctgtatcc aaagctcatg gcggggacca  33840
cagaacccac gtggccatca taccacaagc gcaggtagat taagtggcga cccctcataa  33900
acacgctgga cataaacatt acctcttttg gcatgttgta attcaccacc tcccggtacc  33960
atataaacct ctgattaaac atggcgccat ccaccaccat cctaaaccag ctggccaaaa  34020
cctgcccgcc ggctatacac tgcagggaac cgggactgga acaatgacag tggagagccc  34080
aggactcgta accatggatc atcatgctcg tcatgatatc aatgttggca caacacaggc  34140
acacgtgcat acacttcctc aggattacaa gctcctcccg cgttagaacc atatcccagg  34200
gaacaaccca ttcctgaatc agcgtaaatc ccacactgca gggaagacct cgcacgtaac  34260
tcacgttgtg cattgtcaaa gtgttacatt cgggcagcag cggatgatcc tccagtatgg  34320
```

```
tagcgcgggt ttctgtctca aaaggaggta gacgatccct actgtacgga gtgcgccgag  34380
acaaccgaga tcgtgttggt cgtagtgtca tgccaaatgg aacgccggac gtagtcatat  34440
ttcctgaagc aaaaccaggt gcgggcgtga caaacagatc tgcgtctccg gtctcgccgc  34500
ttagatcgct ctgtgtagta gttgtagtat atccactctc tcaaagcatc caggcgcccc  34560
ctggcttcgg gttctatgta aactccttca tgcgccgctg ccctgataac atccaccacc  34620
gcagaataag ccacacccag ccaacctaca cattcgttct gcgagtcaca cacgggagga  34680
gcgggaagag ctggaagaac catgtttttt tttttattcc aaaagattat ccaaaacctc  34740
aaaatgaaga tctattaagt gaacgcgctc ccctccggtg gcgtggtcaa actctacagc  34800
caaagaacag ataatggcat ttgtaagatg ttgcacaatg gcttccaaaa ggcaaacggc  34860
cctcacgtcc aagtggacgt aaaggctaaa cccttcaggg tgaatctcct ctataaacat  34920
tccagcacct tcaaccatgc ccaaataatt ctcatctcgc caccttctca atatatctct  34980
aagcaaatcc cgaatattaa gtccggccat tgtaaaaatc tgctccagag cgccctccac  35040
cttcagcctc aagcagcgaa tcatgattgc aaaaattcag gttcctcaca gacctgtata  35100
agattcaaaa gcggaacatt aacaaaaata ccgcgatccc gtaggtccct tcgcagggcc  35160
agctgaacat aatcgtgcag gtctgcacgg accagcgcgg ccacttcccc gccaggaacc  35220
atgacaaaag aacccacact gattatgaca cgcatactcg gagctatgct aaccagcgta  35280
gccccgatgt aagcttgttg catgggcggc gatataaaat gcaaggtgct gctcaaaaaa  35340
tcaggcaaag cctcgcgcaa aaaagaaagc acatcgtagt catgctcatg cagataaagg  35400
caggtaagct ccggaaccac cacagaaaaa gacaccattt ttctctcaaa catgtctgcg  35460
ggtttctgca taaacacaaa ataaaataac aaaaaaacat ttaaacatta gaagcctgtc  35520
ttacaacagg aaaaacaacc cttataagca taagacggac tacggccatg ccggcgtgac  35580
cgtaaaaaaa ctggtcaccg tgattaaaaa gcaccaccga cagctcctcg gtcatgtccg  35640
gagtcataat gtaagactcg gtaaacacat caggttgatt cacatcggtc agtgctaaaa  35700
agcgaccgaa atagcccggg ggaatacata cccgcaggcg tagagacaac attacagccc  35760
ccataggagg tataacaaaa ttaataggag agaaaaacac ataaacacct gaaaaaccct  35820
cctgcctagg caaaatagca ccctcccgct ccagaacaac atacagcgct tccacagcgg  35880
cagccataac agtcagcctt accagtaaaa aagaaaacct attaaaaaaa caccactcga  35940
cacggcacca gctcaatcag tcacagtgta aaaaagggcc aagtgcagag cgagtatata  36000
taggactaaa aaatgacgta acggttaaag tccacaaaaa acacccagaa aaccgcacgc  36060
gaacctacgc ccagaaacga aagccaaaaa acccacaact tcctcaaatc gtcacttccg  36120
ttttcccacg ttacgtcact tcccatttta agaaaactac aattcccaac acatacaagt  36180
tactccgccc taaaacctac gtcacccgcc ccgttcccac gccccgcgcc acgtcacaaa  36240
ctccaccccc tcattatcat attggcttca atccaaaata aggtatatta ttgatgatg   36299

SEQ ID NO: 6            moltype = AA  length = 496
FEATURE                 Location/Qualifiers
source                  1..496
                        mol_type = protein
                        organism = Human adenovirus type 5
SEQUENCE: 6
MERRNPSERG VPAGFSGHAS VESGCETQES PATVVFRPPG DNTDGGAAAA AGGSQAAAAG  60
AEPMEPESRP GPSGMNVVQV AELYPELRRI LTITEDGQGL KGVKRERGAC EATEEARNLA  120
FSLMTRHRPE CITFQQIKDN CANELDLLAQ KYSIEQLTTY WLQPGDDFEE AIRVYAKVAL  180
RPDCKYKISK LVNIRNCCYI SGNGAEVEID TEDRVAFRCS MINMWPGVLG MDGVVIMNVR  240
FTGPNFSGTV FLANTNLILH GVSFYGFNNT CVEAWTDVRV RGCAFYCCWK GVVCRPKSRA  300
SIKKCLFERC TLGILSEGNS RVRHNVASDC GCFMLVKSVA VIKHNMVCGN CEDRASQMLT  360
CSDGNCHLLK TIHVASHSRK AWPVFEHNIL TRCSLHLGNR RGVFLPYQCN LSHTKILLEP  420
ESMSKVNLNG VFDMTMKIWK VLRYDETRTR CRPCECGGKH IRNQPVMLDV TEELRPDHLV  480
LACTRAEFGS SDEDTD                                                 496

SEQ ID NO: 7            moltype = AA  length = 19
FEATURE                 Location/Qualifiers
REGION                  1..19
                        note = Synthetic peptide
source                  1..19
                        mol_type = protein
                        organism = synthetic construct
SEQUENCE: 7
ATNFSLLKQA GDVEENPGP                                              19

SEQ ID NO: 8            moltype = AA  length = 22
FEATURE                 Location/Qualifiers
REGION                  1..22
                        note = Synthetic peptide
source                  1..22
                        mol_type = protein
                        organism = synthetic construct
SEQUENCE: 8
VKQTLNFDLL KLAGDVESNP GP                                          22

SEQ ID NO: 9            moltype = AA  length = 20
FEATURE                 Location/Qualifiers
REGION                  1..20
                        note = Synthetic peptide
source                  1..20
                        mol_type = protein
                        organism = synthetic construct
SEQUENCE: 9
QCTNYALLKL AGDVESNPGP                                             20
```

```
SEQ ID NO: 10           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 10
EGRGSLLTCG DVEENPGP                                                18

SEQ ID NO: 11           moltype = AA  length = 22
FEATURE                 Location/Qualifiers
REGION                  1..22
                        note = Synthetic peptide
source                  1..22
                        mol_type = protein
                        organism = synthetic construct
SEQUENCE: 11
GSGATNFSLL KQAGDVEENP GP                                           22

SEQ ID NO: 12           moltype = AA  length = 25
FEATURE                 Location/Qualifiers
REGION                  1..25
                        note = Synthetic peptide
source                  1..25
                        mol_type = protein
                        organism = synthetic construct
SEQUENCE: 12
GSGVKQTLNF DLLKLAGDVE SNPGP                                        25

SEQ ID NO: 13           moltype = AA  length = 23
FEATURE                 Location/Qualifiers
REGION                  1..23
                        note = Synthetic peptide
source                  1..23
                        mol_type = protein
                        organism = synthetic construct
SEQUENCE: 13
GSGQCTNYAL LKLAGDVESN PGP                                          23

SEQ ID NO: 14           moltype = AA  length = 21
FEATURE                 Location/Qualifiers
REGION                  1..21
                        note = Synthetic peptide
source                  1..21
                        mol_type = protein
                        organism = synthetic construct
SEQUENCE: 14
GSGEGRGSLL TCGDVEENPG P                                            21

SEQ ID NO: 15           moltype = AA  length = 952
FEATURE                 Location/Qualifiers
source                  1..952
                        mol_type = protein
                        organism = Human adenovirus type 5
SEQUENCE: 15
MATPSMMPQW SYMHISGQDA SEYLSPGLVQ FARATETYFS LNNKFRNPTV APTHDVTTDR  60
SQRLTLRFIP VDREDTAYSY KARFTLAVGD NRVLDMASTY FDIRGVLDRG PTFKPYSGTA  120
YNALAPKGAP NPCEWDEAAT ALEINLEEED DDNEDEVDEQ AEQQKTHVFG QAPYSGINIT  180
KEGIQIGVEG QTPKYADKTF QPEPQIGESQ WYETEINHAA GRVLKKTTPM KPCYGSYAKP  240
TNENGGQGIL VKQQNGKLES QVEMQFFSTT EATAGNGDNL TPKVVLYSED VDIETPDTHI  300
SYMPTIKEGN SRELMGQQSM PNRPNYIAFR DNFIGLMYYN STGNMGVLAG QASQLNAVVD  360
LQDRNTELSY QLLLDSIGDR TRYFSMWNQA VDSYDPDVRI IENHGTEDEL PNYCFPLGGV  420
INTETLTKVK PKTGQENGWE KDATEFSDKN EIRVGNNFAM EINLNANLWR NFLYSNIALY  480
LPDKLKYSPS NVKISDNPNT YDYMNKRVVA PGLVDCYINL GARWSLDYMD NVNPFNHHRN  540
AGLRYRSMLL GNGRYVPFHI QVPQKFFAIK NLLLLPGSYT YEWNFRKDVN MVLQSSLGND  600
LRVDGASIKF DSICLYATFF PMAHNTASTL EAMLRNDTND QSFNDYLSAA NMLYPIPANA  660
TNVPISIPSR NWAAFRGWAF TRLKTKETPS LGSGYDPYYT YSGSIPYLDG TFYLNHTFKK  720
VAITFDSSVS WPGNDRLLTP NEFEIKRSVD GEGYNVAQCN MTKDWFLVQM LANYNIGYQG  780
FYIPESYKDR MYSFFRNFQP MSRQVVDDTK YKDYQQVGIL HQHNNSGFVG YLAPTMREGQ  840
AYPANFPYPL IGKTAVDSIT QKKFLCDRTL WRIPFSSNFM SMGALTDLGQ NLLYANSAHA  900
LDMTFEVDPM DEPTLLYVLF EVFDVVRVHR PHRGVIETVY LRTPFSAGNA TT          952

SEQ ID NO: 16           moltype = DNA  length = 41
FEATURE                 Location/Qualifiers
misc_feature            1..41
                        note = Synthetic polynucleotide
source                  1..41
```

-continued

```
                  mol_type = other DNA
                  organism = synthetic construct
SEQUENCE: 16
aataaacaag ttaacaacaa cacaaaaata atgctttatt t                        41
```

ONCOLYTIC ADENOVIRUS WITH REPLICATION SELECTIVITY BASED ON STATUS OF P53 TRANSCRIPTIONAL ACTIVITY

CROSS REFERENCE TO RELATED APPLICATIONS

This application is a continuation of International Application No. PCT/US2021/040580, filed Jul. 6, 2021, which claims the benefit of U.S. Provisional Application No. 63/048,499, filed Jul. 6, 2020. The above-listed applications are herein incorporated by reference in their entireties.

FIELD

This disclosure concerns synthetic adenoviruses that specifically replicate in cells that lack p53 transcriptional activity, such as tumor cells with p53 mutations. This disclosure further concerns use of the synthetic adenoviruses for the treatment of cancer.

INCORPORATION OF ELECTRONIC SEQUENCE LISTING

The electronic sequence listing, submitted herewith as an XML file named 7158-100816-08.xml (203,238 bytes), created on Jan. 4, 2023, is herein incorporated by reference in its entirety.

BACKGROUND

Cancer is a complex, debilitating disease that accounts for more than half a million deaths each year. There is a profound need for more effective, selective and safe treatments for cancer. Existing treatments, such as chemotherapy and surgery, rarely eliminate all malignant cells, and often exhibit deleterious side-effects that can outweigh therapeutic benefit.

One approach that has the potential to address many of the shortcomings of current cancer treatments is oncolytic adenoviral therapy (Pesonen et al., *Molecular Pharmaceutics* 8(1):12-28, 2010). Adenovirus (Ad) is a self-replicating biological machine. It consists of a linear double-stranded 36 kb DNA genome sheathed in a protein coat. Adenoviruses invade and hijack the cellular replicative machinery to reproduce, and upon assembly, induce lytic cell death to spread to surrounding cells. These very same cellular controls are targeted by mutations in cancer. This knowledge can be exploited to create synthetic viruses that act like guided missiles, specifically infecting and replicating in tumor cells, and lysing the cells to release thousands of virus progeny that can seek out and destroy distant metastases, while overcoming possible resistance. Thus, the goal of oncolytic virus design is to generate a virus that specifically replicates in cancer cells, but leaves normal cells unharmed. However, there have been challenges in designing a virus that can selectively replicate in cancer cells. Thus, there remains a need for viruses that selectively replicate in cancer cells with high efficiency. In addition, many oncolytic viruses have proven safe in human cancer patients in clinical trials, but most have fallen short on efficacy in treating advanced cancer. As such, there remains a need for viruses with enhanced potency as compared to those currently available.

SUMMARY

Disclosed herein are synthetic adenoviruses that selectively replicate in cells, such as tumor cells, lacking p53 transcriptional activity. The synthetic p53-selective adenoviruses described herein contain a synthetic p53-responsive two step transcriptional activation (TSTA) circuit. In some embodiments, the TSTA module is inserted into the adenoviral genome between the L5 and E4 transcript units. An essential viral protein, such as E2A DNA binding protein (DBP), is deleted from the viral genome and placed under the control of the TSTA circuit. A transcriptional activator or repressor, such as Tet, is expressed in the TSTA circuit under the control of a p53-regulated promoter. The transcription factor repressor or activator regulates the promoter and expression of the essential viral protein. In one embodiment, the TSTA transcriptional circuit includes a doxycycline regulated Tet transcription factor under the control a p53-regulated promoter that can be inducibly controlled via doxycycline to regulate the expression of the essential viral protein that has been deleted from viral E2 unit.

Providing herein are synthetic p53-selective adenoviruses contain a p53-responsive promoter operably linked to the tetracycline repressor (TetR), and a synthetic CMV-Tet-O promoter linked to the adenovirus DNA binding protein (DBP). In cells with p53 transcriptional activity, TetR expression is induced by the p53-responsive promoter, and TetR protein suppresses activity of the CMV-Tet-O promoter, preventing expression of DBP. In the absence of DBP expression, adenovirus is unable to replicate in the host cell. In cells lacking p53 transcriptional activity (such as tumor cells, such as cancer cells), TetR is not expressed, which allows for expression of DBP and adenovirus replication.

Also provided herein are recombinant adenovirus genomes that include an E1B region encoding a modified 55 k protein, wherein p53 degradation activity of the modified 55 k protein is reduced compared to a wild-type 55 k protein; an E2 region comprising a deletion of the DBP open reading frame (ORF); an E3 region comprising an adenovirus death protein (ADP) ORF and comprising a deletion of the 12.5 k, 6.7 k, 19 k, RIDα, RIDβ and 14.7 k ORFs; an E4 region; L1, L2, L3, L4 and L5 regions; a first exogenous nucleic acid sequence comprising a CMV-Tet-O promoter operably linked to an adenovirus DBP ORF; and a second exogenous nucleic acid sequence comprising a p53-responsive promoter operably linked to a TetR protein ORF. In some embodiments, the recombinant adenoviruses further include a reporter gene, one or more modifications that detarget the virus from the liver, or a chimeric fiber protein.

Also provided are isolated cells, such as tumor or cancer cells, that include a recombinant adenovirus genome disclosed herein. Further provided are compositions that include a recombinant adenovirus genome disclosed herein and a pharmaceutically acceptable carrier.

Synthetic adenoviruses that include a recombinant adenovirus genome disclosed herein, and compositions that include a synthetic adenovirus and a pharmaceutically acceptable carrier are also provided.

Further provided are methods of reducing or inhibiting tumor progression, or reducing tumor volume, or both, in a subject having a tumor deficient in p53 transcriptional activity. In some embodiments, the method includes administering to the subject a therapeutically effective amount of a recombinant adenovirus genome, a synthetic adenovirus, or a composition disclosed herein.

Methods of treating a cancer in a subject having a cancer deficient in p53 transcriptional activity are also provided. In some embodiments, the method includes administering to the subject a therapeutically effective amount of a recombinant adenovirus genome, a synthetic adenovirus, or a composition disclosed herein.

The disclosed methods can be used alone or in combination with other anti-cancer therapies, such as chemotherapy, radiation therapy, biologic therapy (e.g., monoclonal antibody therapy), surgery, or combinations thereof.

The foregoing and other objects and features of the disclosure will become more apparent from the following detailed description, which proceeds with reference to the accompanying figures.

BRIEF DESCRIPTION OF THE DRAWINGS

(FIG. 1A) Schematic diagram of the genome modifications of CMBT-1064. Expression of DBP is controlled by the CMV-Tet-O promoter and the TetR protein is also driven by a CMV promoter. (FIG. 1B) Cell viability assay in the presence and absence of Dox. (FIGS. 1C and 1D) Kinetics curves in the absence of Dox (FIG. 1C) and in the presence of Dox (FIG. 1D). CMBT-1064: ΔE2-DBP, Δ12.5 k, Δ6.7 k, Δ19 k, mCherry-P2A-ADP, ΔRIDα, ΔRIDβ, Δ14.7 k, SV40 Poly-A on L5 side, CMV-TetO::DBP (for), CMV::TetR (for), Tet-On Poly-A.

(FIG. 2A) Schematic and cell viability assay of a recombinant adenovirus engineered to control expression of DBP with the Tet-On system. (FIG. 2B) Schematic and cell viability assay of a recombinant adenovirus engineered to control expression of DBP with the TetR system.

(FIG. 8A) A549 and A549p53KO cells infected with CMBT-1065 (WT E1B-55 k, Δ12.5 k, Δ6.7 k, Δ19 k, mCherry-P2A-ADP, ΔRIDα, ΔRIDβ, Δ14.7 k, SV40 Poly-A on L5 side, CMV-Tet-O::DBP (for), PrMin::TetR (for), Tet-On Poly-A). (FIG. 8B) A549 and A549p53KO cells infected with CMBT-1066 (E1B-55 k[M1V, I90stop], ΔE2-DBP, Δ12.5 k, Δ6.7 k, Δ19 k, mCherry-P2A-ADP, ΔRIDα, ΔRIDβ, Δ14.7 k, SV40 Poly-A on L5 side, CMV-Tet-O::DBP (for), PrMin::TetR (for), Tet-On Poly-A). (FIG. 8C) A549 and A549p53KO cells infected with CMBT-1093 (E1B-55 k[H260A], ΔE2-DBP, Δ12.5 k, Δ6.7 k, Δ19 k, mCherry-P2A-ADP, ΔRIDα, ΔRIDβ, Δ14.7 k, SV40 Poly-A on L5 side, CMV-Tet-O::DBP (for), PrMin::TetR (for), Tet-On Poly-A). (FIG. 8D) A549 and A549p53KO cells infected with CMBT-1094 (E1B-55 k[R240A], ΔE2-DBP, Δ12.5 k, Δ6.7 k, Δ19 k, mCherry-P2A-ADP, ΔRIDα, ΔRIDβ, Δ14.7 k, SV40 Poly-A on L5 side, CMV-Tet-O::DBP (for), PrMin::TetR (for), Tet-On Poly-A).

SEQUENCE LISTING

Figure 1A:
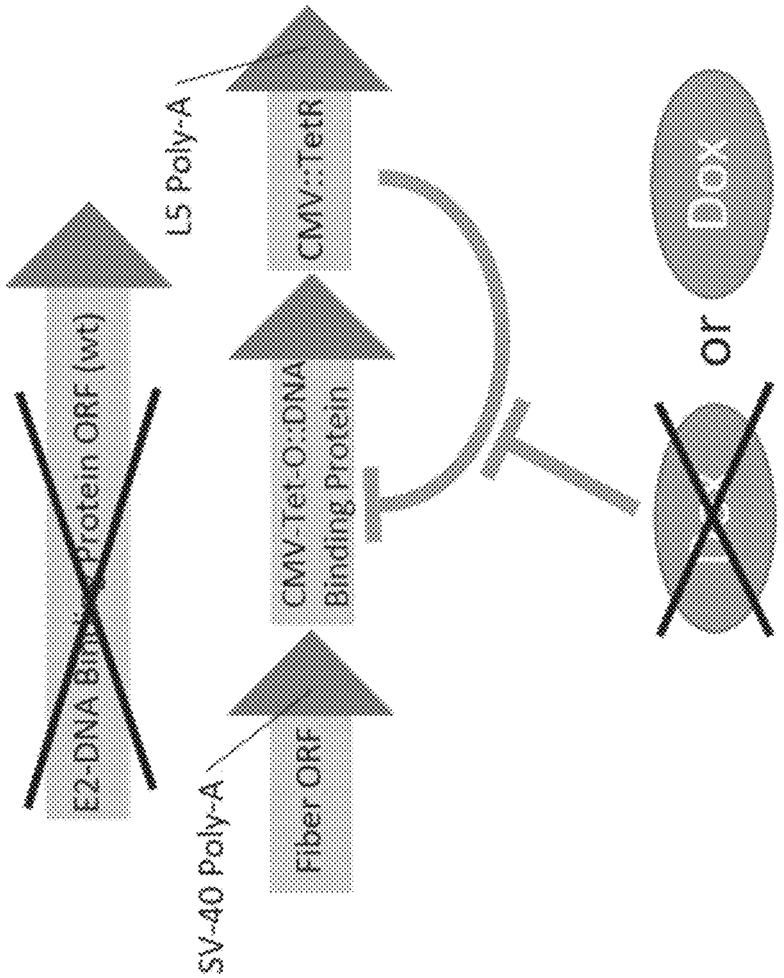
FIGS. 1A-1D: Recombinant adenovirus with DBP placed under direct control of CMV-Tet-O promoter.
Figure 1B:
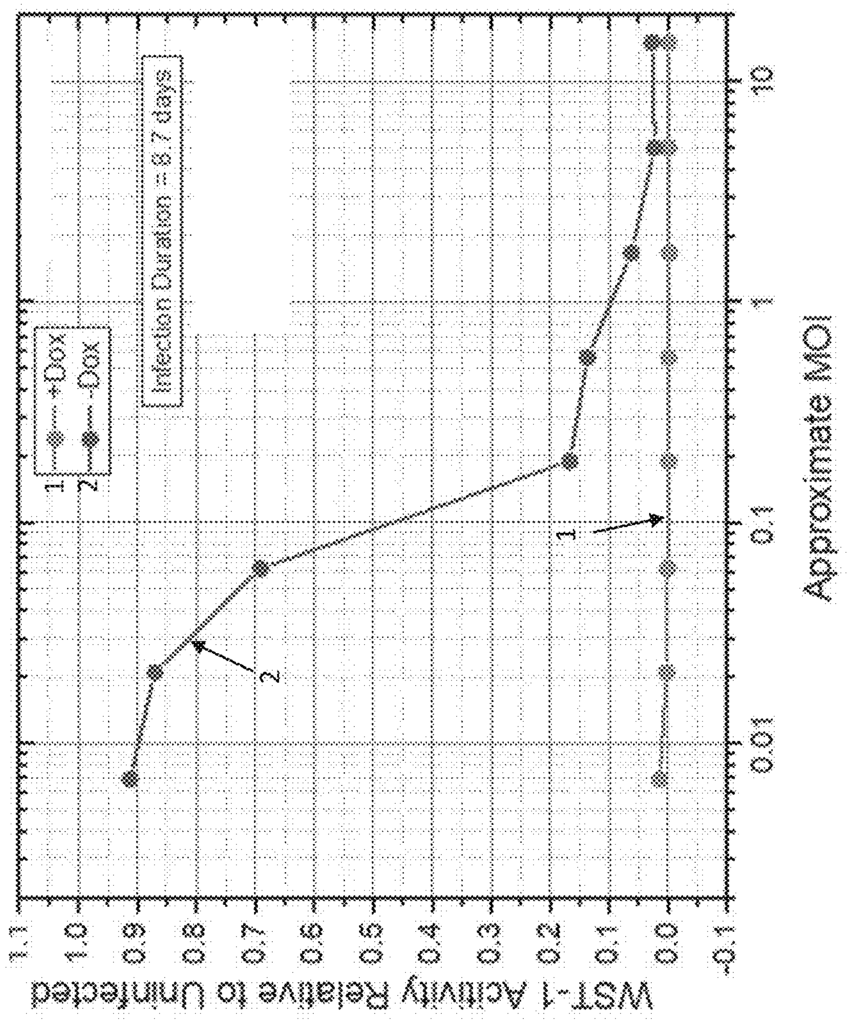
Figure 1C:
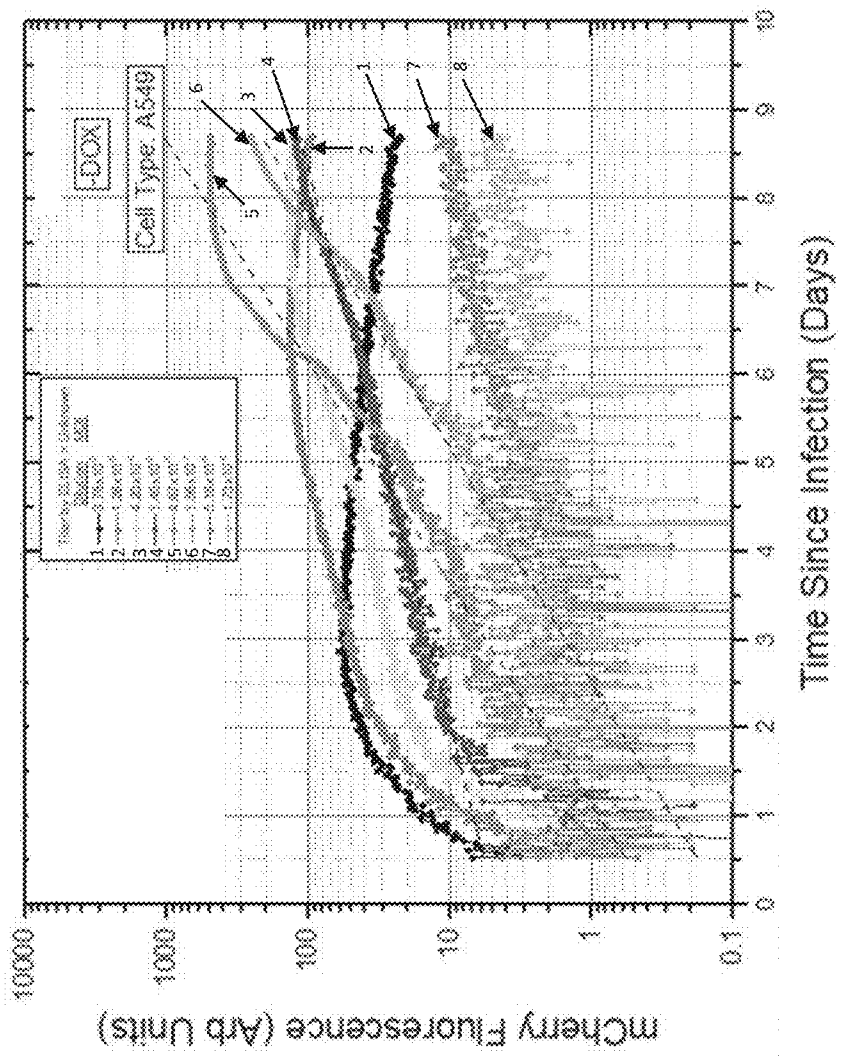
Figure 1D:
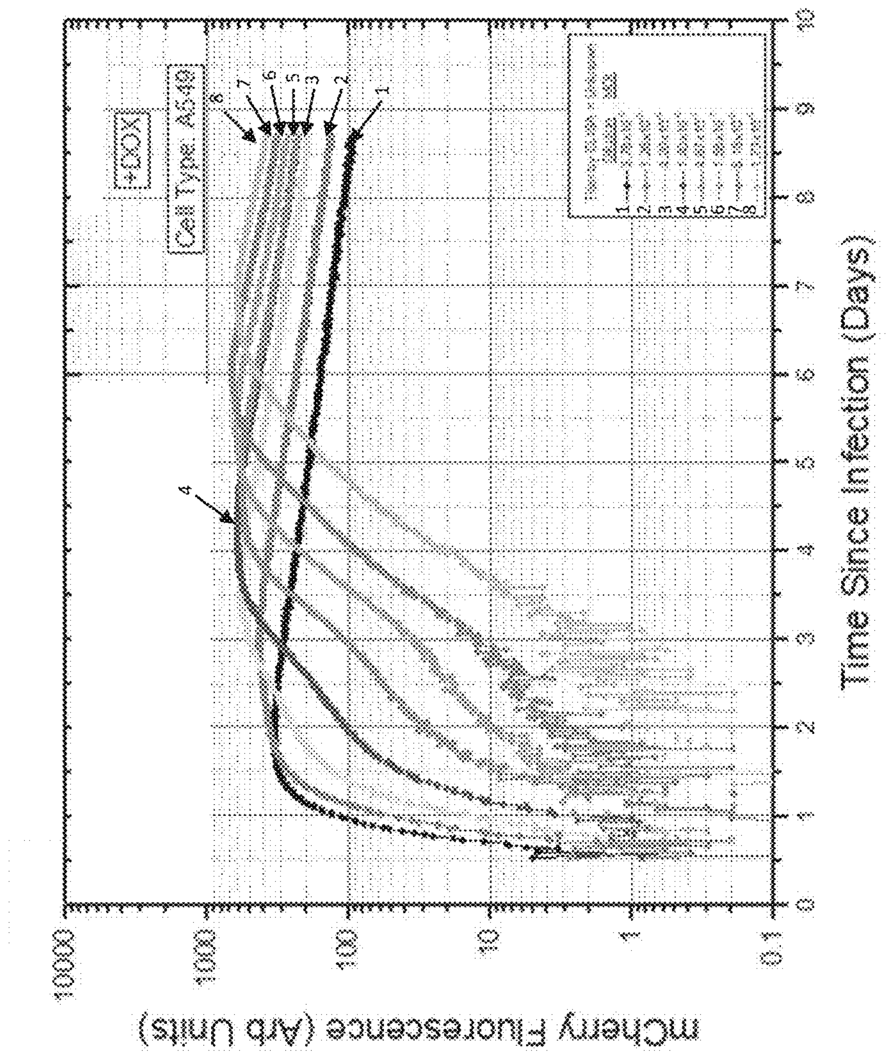

The nucleic and amino acid sequences listed in the accompanying sequence listing are shown using standard letter abbreviations for nucleotide bases, and single letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the nucleotide sequence of synthetic adenovirus CMBT-1065.

SEQ ID NO: 2 is the nucleotide sequence of synthetic adenovirus CMBT-1066.

SEQ ID NO: 3 is the nucleotide sequence of synthetic adenovirus CMBT-1093.

SEQ ID NO: 4 is the nucleotide sequence of synthetic adenovirus CMBT-1094.

SEQ ID NO: 5 is the nucleotide sequence of synthetic adenovirus CMBT-1254.

SEQ ID NO: 6 is the amino acid sequence of the Ad5 E1B-55 k protein.

SEQ ID NO: 7 is the amino acid sequence of P2A.

SEQ ID NO: 8 is the amino acid sequence of F2A.

SEQ ID NO: 9 is the amino acid sequence of E2A.

SEQ ID NO: 10 is the amino acid sequence of T2A.

SEQ ID NO: 11 is the amino acid sequence of a modified P2A comprising GSG at the N-terminus.

SEQ ID NO: 12 is the amino acid sequence of a modified F2A comprising GSG at the N-terminus.

SEQ ID NO: 13 is the amino acid sequence of a modified E2A comprising GSG at the N-terminus.

SEQ ID NO: 14 is the amino acid sequence of a modified T2A comprising GSG at the N-terminus.

SEQ ID NO: 15 is the amino acid sequence of the Ad5 hexon protein.

SEQ ID NO: 16 is the nucleotide sequence of a synthetic polyA sequence.

DETAILED DESCRIPTION

I. Abbreviations

Ad adenovirus
ADP adenovirus death protein
CAR coxsackie adenovirus receptor
CMV cytomegalovirus
DBP DNA binding protein
miR microRNA
ORF open reading frame
Tet tetracycline TetR tetracycline repressor
UTR untranslated region
WT wild-type II. Terms and Methods Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of May 18, 2018) are herein incorporated by reference in their entireties.

In order to facilitate review of the various embodiments of the disclosure, the following explanations of specific terms are provided:

2A peptide: A type of self-cleaving peptide encoded by some RNA viruses, such as picornaviruses. 2A peptides function by making the ribosome skip the synthesis of a peptide bond at the C-terminus of a 2A element, leading to separation between the end of the 2A sequence and the downstream peptide (Kim et al., *PLoS One* 6(4):e18556, 2011). The "cleavage" occurs between the glycine and proline residues found on the C-terminus of the 2A peptide. Exemplary 2A peptides include, but are not limited to, the 2A peptides encoded by Thosea asigna virus (TaV), equine rhinitis A virus (ERAV), porcine teschovirus-1 (PTV1) and foot and mouth disease virus (FMDV), which are set forth herein as SEQ ID NOs: 7-10. In some embodiments, the 2A peptide comprises Gly-Ser-Gly at the N-terminus to improve cleavage efficiency (SEQ ID NOs: 11-14).

Adenovirus: A non-enveloped virus with a liner, double-stranded DNA genome and an icosahedral capsid. There are at least 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G).

Adenovirus death protein (ADP): A protein synthesized in the late stages of adenovirus infection that mediates lysis of cells and release of adenovirus to infect other cells. ADP is an integral membrane glycoprotein of 101 amino acids that localizes to the nuclear membrane, endoplasmic reticulum and Golgi. ADP was previously named E3-11.6K.

Administration: To provide or give a subject an agent, such as a therapeutic agent (e.g. a recombinant virus or recombinant virus genome), by any effective route. Exemplary routes of administration include, but are not limited to, injection (such as subcutaneous, intramuscular, intradermal, intraperitoneal, intratumoral, intraosseous, and intravenous), oral, intraductal, sublingual, rectal, transdermal, intranasal, vaginal and inhalation routes.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth, such as psoriasis. In one embodiment, a chemotherapeutic agent is a radioactive compound. In one embodiment, a chemotherapeutic agent is a biologic, such as a therapeutic monoclonal antibody (e.g., specific for PD-1, PDL-1, CTLA-4, EGFR, VEGF, and the like). One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy,* 2nd ed. St. Louis, Mosby-Year Book, 1995; Fischer, D. S., Knobf, M. F., Durivage, H. J. (eds)*: The Cancer Chemotherapy Handbook,* 4th ed. St. Louis, Mosby-Year Book, 1993). Combination chemotherapy is the administration of more than one agent to treat cancer. In some examples, a subject treated with the disclosed synthetic adenoviruses was previously treated with a chemotherapy. In some examples, the disclosed synthetic adenoviruses are used in combination with one or more chemotherapeutic agents to treat a cancer, for example by reducing or inhibiting tumor progression, decreasing tumor volume, or both.

Chimeric: Composed of at least two parts having different origins. In the context of the present disclosure, a "chimeric adenovirus" is an adenovirus having genetic material and/or proteins derived from at least two different serotypes (such as from Ad5 and a second serotype of adenovirus). In this context, a "capsid-swapped" adenovirus refers to a chimeric adenovirus in which the capsid proteins are derived from one serotype of adenovirus and the remaining proteins are derived from another adenovirus serotype. Similarly, a "chimeric fiber" is a fiber protein having amino acid sequence derived from at least two different serotypes of adenovirus. For example, a chimeric fiber can be composed of a fiber shaft from Ad5 and a fiber knob from a second serotype of adenovirus (such as Ad34).

Contacting: Placement in direct physical association; includes both in solid and liquid form.

Deletion: An adenovirus genome comprising a "deletion" of an adenovirus protein coding sequence refers to an adenovirus having a complete deletion of the protein coding sequence, or a partial deletion that results in the absence of detectable expression of the protein.

Detargeted: As used herein, a "detargeted" adenovirus is a recombinant or synthetic adenovirus comprising one or more modifications that alter tropism of the virus such that is no longer infects, or no longer substantially infects, a particular cell or tissue type. In some embodiments, the recombinant or synthetic adenovirus comprises a capsid mutation, such as a mutation in the hexon protein (for example, E451Q) that detargets the virus from the liver. In some embodiments, the recombinant or synthetic adenovirus comprises a native capsid from an adenovirus that naturally does not infect, or does not substantially infect, a particular cell or tissue type. In some embodiments herein, the recombinant or synthetic adenovirus is liver detargeted and/or spleen detargeted.

DNA-binding protein (DBP): This adenovirus protein binds to single-stranded DNA and RNA. DBP, a 72-kilodalton protein, is essential for replication of adenoviral DNA.

E1A region: A region of the adenovirus genome that includes the early region 1A (E1A) gene. The E1A protein plays a role in viral genome replication by driving cells into the cell cycle. As used herein, "E1A protein" refers to any protein(s) expressed from the E1A gene and the term includes E1A proteins produced by any adenovirus serotype.

E1B region: A region of the adenovirus genome that includes the early region 1B (E1B) gene. The E1B gene encodes two proteins, referred to as the 55 k and 19 k proteins, both of which are involved in blocking apoptosis in adenovirus-infected cells. The 19 k protein blocks a p53-independent apoptosis pathway, whereas the 55 k protein blocks p53-dependent apoptosis by promoting degradation of p53. Described herein are mutations in the E1B-55 k protein that diminish its ability to promote p53 degradation. In some examples, the 55 k mutation is selected from H260R, H260A, H260D, R240A, R240E and R240H with respect to wild-type Ad5 E1B-55 k, set forth herein as SEQ ID NO: 6 (residues 240 and 260 are underlined):

```
MERRNPSERGVPAGFSGHASVESGCETQESPATVVFRPPGDNTDGGAAAA
AGGSQAAAAGAEPMEPESRPGPSGMNVVQVAELYPELRRILTITEDGQGL
KGVKRERGACEATEEARNLAFSLMTRHRPECITFQQIKDNCANELDLLAQ
KYSIEQLTTYWLQPGDDFEEAIRVYAKVALRPDCKYKISKLVNIRNCCYI
SGNGAEVEIDTEDRVAFRCSMINMWPGVLGMDGVVIMNVRFTGPNFSGTV
FLANTNLILHGVSFYGFNNTCVEAWTDVRVRGCAFYCCWKGVVCRPKSRA
SIKKCLFERCTLGILSEGNSRVRHNVASDCGCFMLVKSVAVIKHNMVCGN
CEDRASQMLTCSDGNCHLLKTIHVASHSRKAWPVFEHNILTRCSLHLGNR
RGVFLPYQCNLSHTKILLEPESMSKVNLNGVFDMTMKIWKVLRYDETRTR
CRPCECGGKHIRNQPVMLDVTEELRPDHLVLACTRAEFGSSDEDTD.
```

E2A region: A region of the adenovirus genome that includes the early region 2 A (E2A) gene. The E2A gene encodes the DNA binding protein (DBP).

E2B region: A region of the adenovirus genome that includes the early region 2 B (E2B) gene. The E2B gene encodes the DNA polymerase protein and terminal protein.

E3 region: A region of the adenovirus genome that includes the early region 3 (E3) gene. In human adenoviruses, there are seven E3 proteins (encoded from 5' to 3'): 12.5 k (also known as gp12.5 kDa), 6.7 k (also known as CR1α), 19 k (also known as gp19 k), ADP (also known as CR1β or 11.6 k), RIDα (10.4 k), RIDβ (14.9 k), and 14.7K. The RIDα, RIDβ, and 14.7 k proteins make up the receptor internalization and degradation complex (RID), which localizes to the nuclear membrane and causes the endocytosis and degradation of a variety of receptors including CD95 (FasL receptor), and TNFR1 and 2 (TNF/TRAIL receptors) to protect infected cells from host antiviral responses. The 6.7 k protein is involved in apoptosis modulation of infection cells and the 19 k protein is known to inhibit insertion of class I MHC proteins in the infected host-cell membrane. ADP mediates lysis of infected cells. The function of the 12.5 k protein is unknown.

E4 region: A region of the adenovirus genome that includes the early region 4 (E4) gene. In human adenoviruses, the E4 region encodes at least six proteins, including E4orf1, E4orf2, E4orf3, E4orf4, E4orf6 and E4orf6/7.

Exogenous: Produced or originating from outside of an organism or system. In the context of the present disclosure, an "exogenous nucleic acid" is a nucleic acid molecule that is synthetically produced and inserted into an adenovirus genome. In some examples, an "exogenous nucleic acid" is a nucleic acid molecule that does not occur naturally in the organism, such as an adenovirus or mammalian cell.

Fiber: The adenovirus fiber protein is a trimeric protein that mediates binding to cell surface receptors. The fiber protein is comprised of a long N-terminal shaft and globular C-terminal knob. The fiber protein is encoded by the L5 region of the adenovirus genome.

Fluorescent protein: A protein that emits light of a certain wavelength when exposed to a particular wavelength of light. Fluorescent proteins include, but are not limited to, green fluorescent proteins (such as GFP, EGFP, AcGFP1, Emerald, Superfolder GFP, Azami Green, mWasabi, TagGFP, TurboGFP, YPet and ZsGreen), blue fluorescent proteins (such as EBFP, EBFP2, Sapphire, T-Sapphire, Azurite and mTagBFP), cyan fluorescent proteins (such as ECFP, mECFP, Cerulean, CyPet, AmCyanl, Midori-Ishi Cyan, mTurquoise and mTFP1), yellow fluorescent proteins (EYFP, Topaz, Venus, mCitrine, YPet, TagYFP, PhiYFP, ZsYellowl and mBanana), orange fluorescent proteins (Kusabira Orange, Kusabira Orange2, mOrange, mOrange2 and mTangerine), red fluorescent proteins (mRuby, mApple, mStrawberry, AsRed2, mRFP1, JRed, mCherry, HcRed1, mRaspberry, dKeima-Tandem, HcRed-Tandem, mPlum, AQ143, tdTomato and E2-Crimson), orange/red fluorescence proteins (dTomato, dTomato-Tandem, TagRFP, TagRFP-T, DsRed, DsRed2, DsRed-Express (T1) and DsRed-Monomer) and modified versions thereof.

Heterologous: A heterologous protein or polypeptide refers to a protein or polypeptide derived from a different source or species.

Hexon: A major adenovirus capsid protein. The sequence of the wild-type Ad5 hexon protein is set forth herein as SEQ ID NO: 15. In some embodiments, the hexon comprises an E451Q substitution. The wild-type Ad5 hexon sequence is shown below, with position 451 underlined:

```
MATPSMMPQWSYMHISGQDASEYLSPGLVQFARATETYFSLNNKFRNPTV
APTHDVTTDRSQRLTLRFIPVDREDTAYSYKARFTLAVGDNRVLDMASTY
FDIRGVLDRGPTFKPYSGTAYNALAPKGAPNPCEWDEAATALEINLEEED
DDNEDEVDEQAEQQKTHVFGQAPYSGINITKEGIQIGVEGQTPKYADKTF
QPEPQIGESQWYETEINHAAGRVLKKTTPMKPCYGSYAKPTNENGGQGIL
VKQQNGKLESQVEMQFFSTTEATAGNGDNLTPKVVLYSEDVDIETPDTHI
SYMPTIKEGNSRELMGQQSMPNRPNYIAFRDNFIGLMYYNSTGNMGVLAG
QASQLNAVVDLQDRNTELSYQLLLDSIGDRTRYFSMWNQAVDSYDPDVRI
IENHGTEDELPNYCFPLGGVINTETLTKVKPKTGQENGWEKDATEFSDKN
EIRVGNNFAMEINLNANLWRNFLYSNIALYLPDKLKYSPSNVKISDNPNT
YDYMNKRVVAPGLVDCYINLGARWSLDYMDNVNPFNHHRNAGLRYRSMLL
GNGRYVPFHIQVPQKFFAIKNLLLLPGSYTYEWNFRKDVNMVLQSSLGND
LRVDGASIKFDSICLYATFFPMAHNTASTLEAMLRNDTNDQSFNDYLSAA
```

-continued

```
NMLYPIPANATNVPISIPSRNWAAFRGWAFTRLKTKETPSLGSGYDPYYT

YSGSIPYLDGTFYLNHTFKKVAITFDSSVSWPGNDRLLTPNEFEIKRSVD

GEGYNVAQCNMTKDWFLVQMLANYNIGYQGFYIPESYKDRMYSFFRNFQP

MSRQVVDDTKYKDYQQVGILHQHNNSGFVGYLAPTMREGQAYPANFPYPL

IGKTAVDSITQKKFLCDRTLWRIPFSSNFMSMGALTDLGQNLLYANSAHA

LDMTFEVDPMDEPTLLYVLFEVFDVVRVHRPHRGVIETVYLRTPFSAGNA

TT
```

Isolated: An "isolated" biological component (such as a nucleic acid molecule, protein, virus or cell) has been substantially separated or purified away from other biological components in the cell or tissue of the organism, or the organism itself, in which the component occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Late gene regions: The region of the adenovirus genome that include the late genes L1, L2, L3, L4 and L5. The L5 gene encodes the fiber protein.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). MicroRNAs modulate gene expression by promoting cleavage of target mRNAs or by blocking translation of the cellular transcript. In the context of the present disclosure, a "liver-specific microRNA" is a microRNA that is preferentially expressed in the liver, such as a microRNA that is expressed only in the liver, or a microRNA that is expressed significantly more in the liver as compared to other organs or tissue types.

Modification: A change in a nucleic acid sequence or protein sequence. For example, amino acid sequence modifications include, for example, substitutions, insertions and deletions, or combinations thereof. Insertions include amino and/or carboxyl terminal fusions as well as intrasequence insertions of single or multiple amino acid residues. Deletions are characterized by the removal of one or more amino acid residues from the protein sequence. In some embodiments herein, the modification (such as a substitution, insertion or deletion) results in a change in function, such as a reduction or enhancement of a particular activity of a protein. As used herein, "Δ" or "delta" refer to a deletion. For example, ΔE2-DBP refers to deletion of the DBP ORF of the E2 gene. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final mutant sequence. These modifications can be prepared by modification of nucleotides in the DNA encoding the protein, thereby producing DNA encoding the modification. Techniques for making insertion, deletion and substitution mutations at predetermined sites in DNA having a known sequence are well known in the art. A "modified" protein, nucleic acid or virus is one that has one or more modifications as outlined above.

Neoplasia, malignancy, cancer and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that invades the surrounding tissue and/or can metastasize is referred to as "malignant." Malignant tumors are also referred to as "cancer."

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In some cases, lymphomas are considered solid tumors.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, human papilloma virus (HPV)-infected neoplasias, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

Oncolytic virus: A virus that selectively kills cells of a proliferative disorder, e.g., cancer/tumor cells. Killing of the cancer cells can be detected by any method established in the art, such as determining viable cell count, or detecting cytopathic effect, apoptosis, or synthesis of viral proteins in the cancer cells (e.g., by metabolic labeling, immunoblot, or RT-PCR of viral genes necessary for replication), or reduction in size of a tumor.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

p53: A transcription factor that regulates expression of a variety genes with diverse biological functions, including genes responsible for cell-cycle checkpoint and apoptosis. This protein is a tumor suppressor that is often mutated in tumor cells. p53 is also known as tumor protein 53, cellular tumor antigen p53, phosphoprotein 53, tumor suppressor 53, antigen NY-CO-13 and transformation-related protein 53 (TRP53). The adenovirus E1B-55 k protein is known to bind p53 and promote its degradation. Thus, in the context of the present disclosure, "p53 degradation activity" refers to the ability of the 55 k protein to promote degradation of p53. A tumor or cancer "deficient in p53 transcriptional activity" refers to a tumor or cancer in which the cells include at least one modification that results in downregulation of p53 transcriptional activity. The deficiency need not be a complete abolishment of transcriptionally activity, but rather can be decreased to varying degrees compared to non-tumor cells, such as a decrease of at least 10%, at least 20%, at least 30%, at least 40%, at least 50%, at least 60%, at least 70% or at least 80%.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, PA, 15th Edition (1975), describes compositions and formulations suitable for pharmaceutical delivery of one or more therapeutic compounds, molecules or agents (e.g. a recombinant virus or recombinant virus genome disclosed herein). In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms "polypeptide," "peptide" and "protein" are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription. A "constitutive promoter" is a promoter that is continuously active and is not subject to regulation by external signals or molecules. In contrast, the activity of an "inducible promoter" is regulated by an external signal or molecule (for example, a transcription factor or tetracycline). In some embodiments herein, the promoter is a native adenovirus promoter. In other instances, the promoter is a heterologous promoter, such as a p53-responsive promoter or a cytomegalovirus (CMV) promoter. A "p53-responsive promoter" is a promoter whose activity is regulated by the presence or absence of functional p53 (the promoter activates transcription of operably linked genes when p53 is present and the promoter is inactive in the absence of p53). In some embodiments herein, the p53-responsive promoter is prMinRGC, which is an artificial promoter that includes thirteen p53 binding sites combined with a minimal CMV promoter (Kühnel et al., *Cancer Gene Ther* 11(1):28-40, 2004).

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, deletion, or combinations thereof, of a portion of the natural nucleic acid molecule, protein or virus.

Replication defects: An adenovirus that exhibits "replication defects" in a non-tumor cell (compared to a tumor cell) refers to an adenovirus that exhibits reduced viral replication in normal cells compared to tumor cells. Replication defects are evidenced by, for example, a lack of viral late protein expression, a reduction in viral DNA synthesis, a reduced ability to induce E2F target genes (e.g. cyclin A and B), a reduced ability to elicit S phase entry and/or a reduced ability to induce cell killing in normal cells compared to tumor cells.

RGD peptide: A peptide with the tri-amino acid motif arginine-glycine-aspartate. The RGD motif is found in many matrix proteins, such as fibronectin, fibrinogen, vitronectin and osteopontin and plays a role in cell adhesion to the extracellular matrix.

Self-cleaving peptides: Peptides that induce the ribosome to skip the synthesis of a peptide bond at the C-terminus, leading to separation of the peptide sequence and a downstream polypeptide. Virally encoded 2A peptides are a type of self-cleaving peptide. Virally encoded 2A peptides include, for example, 2A peptides from porcine teschovirus-1 (PTV1), foot and mouth disease virus (FMDV), equine rhinitis A virus (ERAV) and Thosea asigna virus (TaV).

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Subject: Living multi-cellular vertebrate organisms, a category that includes human and non-human mammals, such as veterinary subjects (e.g., mice, rats, rabbits, cats, dogs, pigs, and non-human primates). In one example, the subject is a mammal with a cancer.

Synthetic: Produced by artificial means in a laboratory, for example a synthetic nucleic acid or protein can be chemically synthesized in a laboratory.

TetR: The tetracycline repressor protein. In the context of the present disclosure, the TetR protein binds to the CMV-TetO promoter and inhibits its transcriptional activation. The CMV-Tet-O promoter is a promoter that has been optimized for high activity in the absence of TetR and maximum repression in the presence of the TetR protein (Urlinger et al., *Proc Natl Acad Sci USA* 97(14):7963-7968, 2000).

Therapeutic agent: A chemical compound, small molecule, recombinant virus or other composition, such as an antisense compound, antibody, peptide or nucleic acid molecule capable of inducing a desired therapeutic or prophylactic effect when properly administered to a subject. For example, therapeutic agents for cancer include agents that prevent or inhibit development or metastasis of the cancer.

Therapeutically effective amount: A quantity of a specified pharmaceutical or therapeutic agent (e.g. a recombinant virus) sufficient to achieve a desired effect in a subject, or in a cell, being treated with the agent. The effective amount of the agent can be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

III. Introduction

All normal cells contain transcriptionally active p53, while a large fraction of tumor cells are either deleted for p53 entirely or express mutant forms that are no longer transcriptionally active. Thus, an oncolytic virus that replicates only in the absence of transcriptionally active p53 would be a useful clinical tool against nearly all cancer types.

Because of the tremendous promise of a p53-selective oncolytic virus, considerable work has gone into its development. Because E1B-55 k mediates degradation of p53 (Yew Berk, *Nature* 357:82-85, 1992), the earliest studies involved deletion of the E1B-55 k gene from the Ad5 genome (Bischoff et al., *Science* 274(5286):373-376, 19; Heise et al., *Nat. Med.* 3(6):639-645, 1997). It was thought that deletion of E1B-55 k would make Ad5 replication dependent on the status of p53 in the infected cell. However, this predicted p53-dependence was not borne out (Goodrum and Ornelles, *J. Virol.* 72(12):9479-9490, 1998; O'Shea et al., *Cancer Cell* 6:611-623, 2004).

As an alternate approach, exogenous p53-dependent repressive control was added to adenovirus to impart p53-selective replication. One such example was expression of an E2F antagonist driven by a p53-dependent promoter (Ramachandra et al., *Nat. Biotech.* 19:1035-1041, 2001). Since both the E1A and E2 promoters are activated by the E2F transcription factor, it was hypothesized that expressing an E2F antagonist in a p53-dependent fashion would render the Ad5 replication dependent on the absence of p53 in the infected cell. Another study involved expression of a shRNA against one of the endogenous adenovirus proteins and expression of this shRNA was driven with a p53-dependent promoter (Gurlevik et al., *Nucleic Acids Res.* 37(12):e84, 2009). An adenovirus genome in which expression of the I-secI meganuclease was driven by a p53-dependent promoter and the 18-base pair I-secI target sequence was inserted into the adenovirus genome has also been described (Goez G, Generating an oncolytic adenovirus with optimized p53-dependent replication. Dissertation, Hannover Medical School. 2012; Gurlevik et al., *Mol. Ther.* 21(9):1738-1748, 2013). Since the I-secI target sequence is not found in the human genome (Belfort and Roberts, *Nucleic Acids Res.* 25(17):3379-3388, 1997), this meganuclease should not cut any DNA except for the adenovirus genome and do so in a p53-dependent manner. If the Ad genome is cleaved by I-secI in a p53-depenent fashion, then adenovirus replication would become dependent on the absence of transcriptionally active p53.

Other adenovirus studies involved a p53-sensitive promoter driving expression of a factor that represses another promoter within the adenovirus genome. One example of this scheme is a p53-dependent promoter driving a gal4-KRAB fusion which represses the CMV-gal4 promoter inserted into the Ad5 genome in place of the E1A promoter (Kühnel et al., *Mol. Ther.* 18(5):936-946, 2010). A similar example employs the same repression mechanism, but in this case applied to a promoter consisting of gal4 binding sites surrounding the hTERT promoter, again replacing the E1A promoter (Gurlevik et al., *Mol. Ther.* 18(11):1972-1982, 2010).

Previously described synthetic adenoviruses, such as those described above, generated for the purpose of p53-selectivity failed to demonstrate the properties critical for a therapeutic/oncolytic adenovirus. In particular, previously developed recombinant adenoviruses have exhibited significantly diminished virus replication (required for tumor cell killing) and/or have lacked p53-selectivity. The present disclosure solves these problems by providing synthetic adenoviruses that selectively replicate in cells lacking p53 transcriptional activity and retain near wild-type levels of virus replication.

IV. Overview of Several Embodiments

Disclosed herein are synthetic adenoviruses that selectively replicate in cells, such as tumor cells, lacking p53 transcriptional activity. The synthetic p53-selective adenoviruses described herein contain a synthetic p53-responsive two step transcriptional activation (TSTA) circuit. In some embodiments, the TSTA module is inserted into the adenoviral genome between the L5 and E4 transcript units. An essential viral protein, such as E2A DNA binding protein (DBP), is deleted from the viral genome and placed under the control of the TSTA circuit. A transcriptional activator or repressor, such as Tet, is expressed in the TSTA circuit under the control of a p53-regulated promoter. The transcription factor repressor or activator regulates the promoter and expression of the essential viral protein. In one embodiment, the TSTA transcriptional circuit includes a doxycycline regulated Tet transcription factor under the control a p53-regulated promoter that can be inducibly controlled via doxycycline to regulate the expression of the essential viral protein that has been deleted from viral E2 unit.

In some embodiments, the synthetic p53-selective adenoviruses described herein contain a p53-responsive promoter operably linked to the tetracycline repressor (TetR), and a synthetic CMV-Tet-O promoter linked to the adenovirus DNA binding protein (DBP). In cells with p53 transcriptional activity, TetR expression is induced by the p53-responsive promoter, and the TetR protein suppresses activity of the CMV-Tet-O promoter, preventing expression of DBP. In the absence of DBP, adenovirus is unable to replicate. In cells lacking p53 transcriptional activity, TetR is not expressed, which allows for expression of DBP and adenovirus replication. The synthetic adenoviruses also contain a mutation in E1B-55 k that inhibits the ability of the 55 k protein to degrade cellular p53. To enhance virus replication kinetics and provide space in the Ad genome for exogenous genes, the synthetic adenoviruses also include deletions of six E3 genes (Δ12.5 k, Δ6.7 k, Δ19 k, ΔRIDα, ΔRIDβ and Δ14.7 k).

The specific modifications disclosed herein are described with reference to the adenovirus 5 (Ad5) genome sequence. However, the same (or equivalent) modifications and deletions could be made in any human adenovirus serotype. Adenovirus modifications for tumor-selectivity, liver detargeting, inducible retargeting, retargeting via chimeric fiber proteins, and other modifications are described in detail in PCT Publication No. WO 2016/049201, which is herein incorporated by reference in its entirety.

Provided herein are recombinant adenovirus genomes that include an E1B region encoding a modified 55 k protein, wherein p53 degradation activity of the modified 55 k protein is reduced compared to a wild-type 55 k protein (such as a reduction of at least 10%, at least 20%, at least 30%, at least 40%, at least 50%, at least 75%, at least 80%, at least 90%, at least 95%, at least 96%, at least 97%, at least 98%, at least 99%, at least 99.5%, or 100%); an E2 region comprising a deletion of the DBP ORF; an E3 region comprising an ADP ORF and comprising a deletion of the 12.5 k, 6.7 k, 19 k, RIDα, RIDβ and 14.7 k ORFs; an E4 region; L1, L2, L3, L4 and L5 regions; a first exogenous nucleic acid sequence comprising a TSTA circuit in which a synthetic promoter is operably linked to an adenovirus DBP ORF; and a second exogenous nucleic acid sequence comprising a p53-responsive promoter operably linked to a transcriptional repressor or activator that controls the synthetic promoter.

Also provided herein are recombinant adenovirus genomes that include an E1B region encoding a modified 55 k protein, wherein p53 degradation activity of the modified 55 k protein is reduced compared to a wild-type 55 k protein (such as a reduction of at least 10%, at least 20%, at least 30%, at least 40%, at least 50%, at least 75%, at least 80%, at least 90%, at least 95%, at least 96%, at least 97%, at least 98%, at least 99%, at least 99.5%, or 100%); an E2 region comprising a deletion of the DBP ORF; an E3 region comprising an ADP ORF and comprising a deletion of the 12.5 k, 6.7 k, 19 k, RIDα, RIDβ and 14.7 k ORFs; an E4 region; L1, L2, L3, L4 and L5 regions; a first exogenous nucleic acid sequence comprising a CMV-Tet-O promoter operably linked to an adenovirus DBP ORF; and a second exogenous nucleic acid sequence comprising a p53-responsive promoter operably linked to a TetR protein ORF.

In some embodiments, the first and second exogenous nucleic acid sequences are located between the L5 and E4 regions of the adenovirus genome. In other embodiments, the first and second exogenous nucleic acid sequences are located between the E1A and E1B transcripts, or between the E1B and U gene transcripts.

In some embodiments, the first exogenous nucleic acid sequence precedes the second exogenous nucleic acid sequence. In other embodiments, the second exogenous nucleic acid sequence precedes the first exogenous nucleic acid sequence.

In some embodiments, the first exogenous nucleic acid sequence further includes a first heterologous polyA sequence following the DBP ORF. In some examples, the first heterologous polyA sequence is a synthetic polyA sequence, for example aataaacaagt-taacaacaacacaaaaataatgctttattt (SEQ ID NO: 16, referred to herein as the "Tet-On polyA sequence").

In some embodiments, the second exogenous nucleic acid sequence further includes a second heterologous polyA sequence following the TetR ORF. In some examples, the second heterologous polyA sequence is a synthetic polyA sequence, for example aataaacaagt-taacaacaacacaaaaataatgctttattt (SEQ ID NO: 16).

In some embodiments, the recombinant adenovirus genome further includes a third heterologous polyA sequence following the L5 region and preceding the first and second exogenous nucleic acid sequences. In some examples, the third heterologous polyA sequence is a SV40 polyA sequence.

In some embodiments, the p53-responsive promoter is prMinRGC.

In some embodiments, the modified 55 k protein comprises a mutation selected from H260R, H260A, H260D, R240A, R240E and R240H with respect to Ad5 wild-type E1B-55 k set forth as SEQ ID NO: 6.

In some embodiments, the recombinant adenovirus genome further includes a reporter gene. In some examples, the reporter gene encodes a fluorescent protein. In particular examples, the fluorescent protein is YPet or mCherry. In specific examples, the reporter gene is operably linked to and in the same reading frame as a self-cleaving peptide coding sequence and the ADP ORF. In non-limiting examples, the self-cleaving peptide is a 2A peptide, such as a P2A, F2A, E2A or T2A sequence, or modified version thereof, such as any of the 2A sequences set forth herein as SEQ ID NOs: 7-14.

In some embodiments, the recombinant adenovirus genome includes at least one modification to detarget an adenovirus from the liver. In some examples, the recombinant adenovirus genome includes a mutation in the hexon protein coding sequence, such as a mutation resulting in an E451Q substitution (relative to wild-type Ad5 hexon protein set forth herein as SEQ ID NO: 15). In some examples, the recombinant adenovirus genome includes one or more binding sites for a liver-specific microRNA. In particular examples, the one or more binding sites for the liver-specific microRNA are located in the 3-UTR of E1A. The liver-specific microRNA can be, for example, miR-122, miR-30 or miR-192.

In some embodiments, the genome encodes a chimeric fiber protein. In some examples, the chimeric fiber protein comprises a fiber shaft from a first adenovirus serotype and a fiber knob from a second adenovirus serotype. In specific examples, the first adenovirus serotype is Ad5 and the second adenovirus serotype is Ad3, Ad9, Ad11, Ad12, Ad34 or Ad37. In one non-limiting example, the first adenovirus serotype is Ad5 and the second adenovirus serotype is Ad34.

In some embodiments, the genome encodes a fiber protein modified to include an RGD peptide.

In some embodiments, the nucleotide sequence of the recombinant adenovirus genome is at least 90%, at least 95%, at least 96%, at least 97%, at least 98%, at least 99% or at least 99.5% identical to SEQ ID NO: 3, SEQ ID NO: 4 or SEQ ID NO: 5. In some examples, the nucleotide sequence of the genome comprises or consists of SEQ ID NO: 3, SEQ ID NO: 4, or SEQ ID NO: 5.

Also provided here are isolated cells (such as mammalian cells, such as a mammalian tumor cell) that include a recombinant adenovirus genome disclosed herein.

Further provided are compositions that include a recombinant adenovirus genome disclosed herein and a pharmaceutically acceptable carrier.

Also provided are isolated adenoviruses that include a recombinant adenovirus genome disclosed herein. Compositions that include an isolated adenovirus and a pharmaceutically acceptable carrier are further provided.

Further provided is a method of inhibiting tumor cell viability (of a tumor cell lacking p53 transcriptional activity) by contacting the tumor cell with a recombinant adenovirus genome, an adenovirus, or a composition described herein. In some embodiments, the method is an in vitro method. In other embodiments, the method is an in vivo method and contacting the tumor cell includes administering a therapeutically effective amount of the recombinant adenovirus genome, the adenovirus, or the composition, to a subject with a tumor characterized by lacking p53 transcriptional activity.

Also provided is a method of inhibiting tumor progression or reducing tumor volume in a subject having a tumor deficient in p53 transcriptional activity. The method includes administering to the subject a therapeutically effective amount of a recombinant adenovirus genome, an adenovirus, or a composition described herein.

Further provided is a method of treating cancer in a subject having a tumor deficient in p53 transcriptional activity. The method includes administering to the subject a therapeutically effective amount of a recombinant adenovirus genome, a recombinant adenovirus, or a composition disclosed herein.

Also provided herein is a recombinant adenovirus genome, wherein the nucleotide sequence of the genome is at least 90%, at least 95%, at least 96%, at least 97%, at least 98%, at least 99% or at least 99.5% identical to any one of SEQ ID NOs: 1-5. In some embodiments, the nucleotide sequence of the genome comprises or consists of any one of SEQ ID NOs: 1-5. Isolated adenoviruses comprising a recombinant adenovirus genome are further provided.

V. Synthetic Adenoviruses

The Adsembly, AdSLICr and RapAD technologies enable the modular design and production of adenoviruses with unique capabilities (see PCT Publication Nos. WO 2012/024351 and WO 2013/138505, which are herein incorporated by reference in their entireties). The ability to design custom viruses with novel functions and properties expands the utility of adenoviruses as therapeutic agents, and/or as vehicles to deliver therapeutic proteins or genes.

The specific modifications disclosed herein are described with reference to the adenovirus 5 (Ad5) genome sequence, but may be used with any adenovirus serotype. Adenovirus is a natural multi-gene expression vehicle. The E1, E3, and E4 regions are either not necessary for replication in culture or can be complemented with available cell lines. Each of these regions has independent promoter elements that can be replaced with cellular promoters if necessary to drive the expression of multiple gene products via alternative splicing.

The synthetic adenoviruses disclosed herein have been engineered to selectively replicate in cells (such as tumor cells) lacking p53 transcriptional activity. The p53 selectivity of the disclosed viruses is a result of a modified E1B-55 k protein that has a reduced ability to promote degradation of p53, and the presence of exogenous nucleic acid sequences that result in repression of adenovirus replication in cells with p53 transcriptional activity (and conversely, that allow for adenovirus replication in cells lacking p53 transcriptional activity). Deletion of six E3 ORFs (12.5 k, 6.7 k, 19 k, RIDα, RIDβ and 14.7 k) enhances virus replication in permissive cells and creates room in the Ad genome for the addition of exogenous genes.

The synthetic adenoviruses disclosed herein may further include modifications that detarget the virus from the liver and/or modifications to prevent transgene expression in the liver. Ad5 hexon can bind to Factor X in the blood, which can lead to its absorption by Kuppfer cells in the liver, thereby preventing systemic dissemination. To overcome this, synthetic adenoviruses can be engineered to include additional genomic modifications that prevent uptake and expression in the liver, as described further below.

A. Chimeric Fiber Proteins for Retargeting

While the fiber proteins of Ad5 and many other serotypes bind to coxsackie adenovirus receptor (CAR) for cellular attachment, other serotypes use CD46 (Gaggar et al., *Nat Med* 9:1408-1412, 2003), desmoglein 2 (Wang et al., *Nat Med* 17:96-104, 2011), sialic acid (Nilsson et al., *Nat Med* 17:105-109, 2011), or others (Arnberg, *Trends Pharmacol Sci* 33:442-448, 2012). The receptor usage of many serotypes has not been thoroughly examined and CD46 is not thought to be expressed in mature mice. Since the globular knob at the C-terminus of the fiber protein is typically responsible for receptor binding, chimeras can be created by replacing the Ad5 fiber knob with fiber knob of another serotype, such as Ad3, Ad9, Ad11, Ad12, or Ad34 (see, for example, PCT Publication No. WO 2017/062511, which is herein incorporated by reference).

B. Liver Detargeting and Silencing Modifications

Natural adenovirus type 5 vectors primarily infect the lungs (via inhalation) or liver (via intravenous administration). Ad5 hexon binds to Factor X in the blood, which leads its absorption by Kuppfer cells in the liver, preventing systemic dissemination and inducing virus-limiting inflammation. To overcome this and enable intravenous delivery of viruses that travel systemically, synthetic adenoviruses can be engineered to include additional genomic modifications that prevent uptake and expression in the liver.

To prevent virus uptake and sequestration in the liver through Ad5 hexon binding to Factor X, viruses can be engineered with an additional mutation in hexon (E451Q) that prevents liver uptake. Thus, in some embodiments herein, the synthetic adenovirus comprises a modified hexon protein with an E451Q substitution. Other mutations to the adenovirus hexon gene are contemplated herein to prevent adenovirus accumulation in the liver. For example, a synthetic adenovirus could be detargeted from the liver by replacing the nine hypervariable regions of hexon with those from different serotypes.

To prevent off-target expression of the transgene in the liver, viruses can be engineered to include in the 3' untranslated region (UTR) of the transgene binding sites for microRNAs that are specifically expressed in the liver. Inclusion of the liver-specific miRNA binding sites leads to silencing of the transgene in liver. In particular embodiments, miR122 is the liver-specific microRNA (expression and binding sites of miR122 are conserved in both human and mouse liver cells). In some examples, two micro-RNA binding sites for liver-specific miR122 are inserted in the 3'UTR of the transgene to prevent transgene expression in the liver. In other embodiments, the liver-specific microRNA is miR-30 or miR-192.

C. Capsid Swaps for Evading Neutralizing Antibodies

The majority of humans have antibodies that recognize Ad5, the serotype most frequently used in research and therapeutic applications. Moreover, once a particular adenovirus serotype is used in a patient, new antibodies that recognize the viral capsid will be generated, making repeated administration of the same vector problematic. Therefore, the present disclosure further contemplates exploiting natural adenovirus modularity to create chimeric viruses capable of evading existing neutralizing antibodies. For example, a synthetic adenovirus may further have a complete 'capsid' module swap (almost 60% of genome), which renders the virus 'invisible' to pre-existing antibodies and enables repeated inoculations. Thus, in some examples, the disclosed methods of treating cancer can further include determining if a subject to be treated has antibodies to a particular adenovirus serotype, such as Ad5, Ad11, Ad3, Ad9 or Ad34.

In some embodiments, the E1, E3 and E4 regions of the genome are derived from a first adenovirus serotype and the E2B, L1, L2, L3, E2A and L4 regions of the genome are derived from a second adenovirus serotype, such as Ad11, Ad3, Ad9 or Ad34. In some examples, the E1 region of the first adenovirus serotype is modified to encode a pIX protein from the second adenovirus serotype; and/or the E3 region of the first adenovirus serotype is modified to encode Uexon and fiber proteins from the second adenovirus serotype. In particular examples, the first adenovirus serotype is Ad5 and the second adenovirus serotype is Ad11, Ad3, Ad9 or Ad34.

D. Expression of Transgenes

In some embodiments, the synthetic adenoviruses disclosed herein include a transgene, such as a reporter gene. For example, the reporter gene may be a fluorescent reporter that enables detection of virus expression. In some embodiments, the synthetic adenoviruses encode on or more reporter genes selected from a luciferase, a GFP, a yellow fluorescent protein (YFP), a cyan fluorescent protein (CFP), a red fluorescent protein (RFP)(such as mCherry), blue fluorescent protein (BFP) and orange fluorescent protein (such as mOrange).

In some embodiments, the transgene is inserted into the E1 or E3 region. Appropriate transgene insertion sites have been described (see, for example, PCT Publication No. WO 2012/024351, which is incorporated herein by reference).

The transgene is operably linked to a promoter. In some embodiments, the promoter is a heterologous promoter. In some examples, the promoter is the EF1α promoter. The selection of promoter is within the capabilities of one of skill in the art. In some cases, the promoter is an inducible promoter or a tissue-specific promoter. In some cases, a single promoter is used to regulate expression of multiple genes, which can be achieved by use of an internal ribosomal entry site (IRES) or 2A peptide.

In some embodiments, the transgene (such as a reporter gene) is operably linked to and in the same reading frame as an endogenous adenovirus ORF (such as ADP), and the reporter gene ORF and endogenous ORF are separated by a self-cleaving peptide coding sequence.

VI. Self-Cleaving Peptide Sequences

Self-cleaving peptides are peptides that induce the ribosome to skip the synthesis of a peptide bond at the C-terminus, leading to separation of the peptide sequence and a downstream polypeptide. The use of self-cleaving peptides allows for expression of multiple proteins flanking the self-cleaving peptide from a single ORF. Virally encoded 2A peptides are one type of self-cleaving peptide.

As with other self-cleaving peptides, 2A peptides function by making the ribosome skip the synthesis of a peptide bond at the C-terminus of a 2A element, leading to separation between the end of the 2A sequence and the downstream peptide (Kim et al., *PLoS One* 6(4):e18556, 2011). The "cleavage" occurs between the glycine and proline residues found on the C-terminus of the 2A peptide. Exemplary 2A peptides include, but are not limited to, the 2A peptides encoded by TaV, ERAV, PTV1 and FMDV, or modified versions thereof.

In particular examples, the 2A peptide comprises PTV1 2A (P2A), FMDV 2A (F2A), ERAV 2A (E2A) or TaV 2A (T2A), the sequences of which are shown below and are set forth herein as SEQ ID NOs: 7-10.

(SEQ ID NO: 7)
P2A: ATNFSLLKQAGDVEENPGP (SEQ ID NO: 8)
F2A: VKQTLNFDLLKLAGDVESNPGP (SEQ ID NO: 9)
E2A: QCTNYALLKLAGDVESNPGP (SEQ ID NO: 10)
T2A: EGRGSLLTCGDVEENPGP

In some examples, the 2A peptide is modified to include Gly-Ser-Gly at the N-terminus to improve cleavage efficiency. The sequences of modified P2A, F2A, E2A and T2A are shown below and are set forth herein as SEQ ID NOs: 11-14.

(SEQ ID NO: 11)
Modified P2A: GSGATNFSLLKQAGDVEENPGP (SEQ ID NO: 12)
Modified F2A: GSGVKQTLNFDLLKLAGDVESNPGP -continued (SEQ ID NO: 13)
Modified E2A: GSGQCTNYALLKLAGDVESNPGP (SEQ ID NO: 14)
Modified T2A: GSGEGRGSLLTCGDVEENPGP In some embodiments, the 2A polypeptide is a variant of a 2A polypeptide disclosed herein. Variants can include polypeptide sequences having at least 80%, at least 85%, at least 90%, at least 95%, at least 96%, at least 97%, at least 98%, at least 99%, or more, sequence identity to a wild-type or modified 2A polypeptide disclosed herein. Variants can include, for example, a deletion of at least one N-terminal amino acid from the 2A polypeptide of any one of SEQ ID NOs: 7-14, for example a deletion of 1, 2, 3, 4 or 5 amino acids. Variants can include a deletion of at least one C-terminal amino acid from the 2A polypeptide of any one of SEQ ID NOs: 7-14, for example a deletion of 1, 2, 3, 4 or 5 amino acids. Variants can also include, for example, at least 1, 2, 3, 4 or 5 amino acid substitutions, such as conservative amino acid substitutions.

VII. Pharmaceutical Compositions

Provided herein are compositions comprising a recombinant adenovirus or recombinant adenovirus genome disclosed herein. The compositions are, optionally, suitable for formulation and administration in vitro or in vivo. Optionally, the compositions comprise one or more of the provided agents and a pharmaceutically acceptable carrier. Suitable carriers and their formulations are described in *Remington: The Science and Practice of Pharmacy,* 22nd Edition, Loyd V. Allen et al., editors, Pharmaceutical Press (2012). Pharmaceutically acceptable carriers include materials that are not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The recombinant viruses or recombinant adenovirus genomes are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral, or inhalation routes. The administration may be local or systemic. The compositions can be administered via any of several routes of administration, including topically, orally, parenterally, intravenously, intra-articularly, intraperitoneally, intramuscularly, subcutaneously, intracavity, transdermally, intrahepatically, intracranially, intratumorally, intraosseously, nebulization/inhalation, or by installation via bronchoscopy. Thus, the compositions can be administered in a number of ways depending on whether local or systemic treatment is desired, and on the area to be treated.

In some embodiments, the compositions for administration include a recombinant adenovirus (or recombinant genome) as described herein dissolved in a pharmaceutically acceptable carrier, such as an aqueous carrier. A variety of aqueous carriers can be used, e.g., buffered saline and the like. These solutions are sterile and generally free of undesirable matter. These compositions may be sterilized. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the recombinant viruses or recombinant adenovirus genomes can be prepared by mixing the recombinant adenovirus (or recombinant adenovirus genome) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives, low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The recombinant adenovirus (or one or more nucleic acids encoding the recombinant adenovirus) can be formulated at any appropriate concentration of infectious units.

Formulations suitable for oral administration can consist of (a) liquid solutions, such as an effective amount of the recombinant adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The recombinant adenovirus or recombinant adenovirus genome, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

The pharmaceutical preparation can be in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

In some embodiments, the compositions include at least two different recombinant adenoviruses or recombinant adenovirus genomes, such as recombinant adenoviruses that bind different cellular receptors. For example, at least one of the recombinant adenoviruses in the composition could express a chimeric fiber protein. In some examples, the composition includes two, three, four, five or six different recombinant adenoviruses or recombinant adenovirus genomes.

VIII. Methods of Treatment

The recombinant adenovirus and recombinant adenovirus genome compositions disclosed herein can be administered for therapeutic or prophylactic treatment. In particular, provided are methods of inhibiting tumor cell viability in a subject, reducing or inhibiting tumor progression in a subject, reducing tumor volume in a subject, reducing the number of metastases in a subject, and/or treating cancer in a subject. In some embodiments, the tumor lacks p53 transcriptional activity. Thus, in some examples, the methods reduce tumor cell viability, reduce tumor progression, reduce tumor volume, reduce tumor size, reduce tumor weight, reduce the number of metastases, or combinations thereof, by at least 20%, at least 50%, at least 75%, at least 80%, at least 90%, at least 95%, at least 96%, at least 97%, at least 98%, at least 99%, or at least 99.5%, for example relative to no treatment (e.g., before treatment with the recombinant adenovirus or recombinant adenovirus genome compositions disclosed herein).

The methods include administering a therapeutically effective amount of a recombinant adenovirus or recombinant adenovirus genome (or composition thereof) to the subject. As described throughout, the adenovirus or pharmaceutical composition is administered in any number of ways including, but not limited to, intravenously, intravascularly, intrathecally, intramuscularly, subcutaneously, intratumorally, intraperitoneally, or orally. Optionally, the method further comprising administering to the subject one or more additional therapeutic agents. In some embodiments, the therapeutic agent is a chemotherapeutic agent. In other embodiments, the therapeutic agent is an immune modulator. In yet other embodiments, the therapeutic agent is a CDK inhibitor, such as a CDK4 inhibitor.

In some embodiments, the cancer or tumor is a lung, prostate, colorectal, breast, thyroid, renal, or liver cancer or tumor, or is a type of leukemia. In some cases, the cancer is metastatic. In some examples, the tumor is a tumor of the mammary, pituitary, thyroid, or prostate gland; a tumor of the brain, liver, meninges, bone, ovary, uterus, or cervix; monocytic or myelogenous leukemia; adenocarcinoma, adenoma, astrocytoma, bladder tumor, brain tumor, Burkitt's lymphoma, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, lymphoma, liposarcoma cell, mammary tumor, medulloblastoma, myeloma, plasmacytoma, neuroblastoma, neuroglioma, osteogenic sarcoma, pancreatic tumor, pituitary tumor, retinoblastoma, rhabdomyosarcoma, sarcoma, testicular tumor, thymoma, or Wilms tumor. Tumors include both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects, solid tumors may be treated that arise from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, treatments may be useful in the prevention of metastases from the tumors described herein.

In therapeutic applications, recombinant adenoviruses or recombinant adenovirus genomes, or compositions thereof, are administered to a subject in a therapeutically effective amount or dose. Amounts effective for this use will depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus, the methods are applicable to both human therapy and veterinary applications.

An effective amount of a synthetic adenovirus having a modified sequence is determined on an individual basis and is based, at least in part, on the particular recombinant adenovirus used; the individual's size, age, gender; and the size and other characteristics of the proliferating cells. For example, for treatment of a human, at least $10^3$ plaque forming units (PFU) of a recombinant virus is used, such as at least $10^4$, at least $10^5$, at least $10^6$, at least $10^7$, at least $10^8$, at least $10^9$, at least $10^{10}$, at least $10^{11}$, or at least $10^{12}$ PFU, for example approximately $10^3$ to $10^{12}$ PFU of a recombinant virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight).

A recombinant adenovirus or recombinant adenovirus genome is administered in a single dose or in multiple doses (e.g., two, three, four, six, or more doses). Multiple doses can be administered concurrently or consecutively (e.g., over a period of days or weeks).

In some embodiments, the provided methods include administering to the subject one or more additional therapeutic agents, such as an anti-cancer agent or other therapeutic treatment (such as surgical resection of the tumor). Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens), anti-angiogenesis agents and CDK inhibitors. Other anti-cancer treatments include radiation therapy and antibodies that specifically target cancer cells (such as therapeutic monoclonal antibodies).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of chemotherapy drugs that can be used in combination with disclosed adenoviruses include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used in combination with the disclosed adenoviruses include AS-101 (Wyeth-Ayerst Labs.), bropirimine (Upjohn), gamma interferon (Genentech), GM-CSF (granulocyte macrophage colony stimulating factor; Genetics Institute), IL-2

(Cetus or Hoffman-LaRoche), human immune globulin (Cutter Biological), IMREG (from Imreg of New Orleans, La.), SK&F 106528, and TNF (tumor necrosis factor; Genentech).

In some examples, the additional therapeutic agent administered is a biologic, such as a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, Zalutumumab, or combinations thereof. In some examples, the therapeutic antibody is specific for PD-1 or PDL-1 (such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, or MSB-0010718C).

In some examples, the additional therapeutic is a CTLA-4, LAG-3, or B7-H3 antagonist, such as Tremelimumab, BMS-986016, and MGA271, respectively.

In some examples, the additional therapeutic is an antagonist of PD-1 or PDL-1. Another treatment that can be used in combination with the disclosed adenoviruses is surgical treatment, for example surgical resection of the cancer or a portion of it. Another treatment that can be used in combination with the disclosed adenoviruses is radiotherapy, for example administration of radioactive material or energy (such as external beam therapy) to the tumor site to help eradicate the tumor or shrink it prior to surgical resection or treatment with the disclosed adenoviruses.

CDK (cyclin-dependent kinase) inhibitors are agents that inhibit the function of CDKs. Non-limiting examples of CDK inhibitors that can be used in combination with the disclosed adenoviruses include AG-024322, AT7519, AZD5438, flavopiridol, indisulam, P1446A-05, PD-0332991, and P276-00 (see e.g., Lapenna et al., *Nature Reviews,* 8:547-566, 2009). Other CDK inhibitors include LY2835219, Palbociclib, LEE011 (Novartis), pan-CDK inhibitor AT7519, seliciclib, CYC065, butyrolactone I, hymenialdisine, SU9516, CINK4, PD0183812 or fascaplysin.

In some examples, the CDK inhibitor is a broad-range inhibitor (such as flavopiridol, olomoucine, roscovitine, kenpaullone, SNS-032, AT7519, AG-024322, (S)-Roscovitine or R547). In other examples, the CDK inhibitor is a specific inhibitor (such as fascaplysin, ryuvidine, purvalanol A, NU2058, BML-259, SU 9516, PD0332991 or P-276-00).

The choice of agent and dosage can be determined readily by one of skill in the art based on the given disease being treated. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions (such as the disclosed adenoviruses and another anti-cancer agent).

According to the methods disclosed herein, the subject is administered an effective amount of one or more of the agents provided herein. The effective amount is defined as any amount necessary to produce a desired physiologic response (e.g., killing of a cancer cell). Therapeutic agents are typically administered at the initial dosage of about 0.001 mg/kg to about 1000 mg/kg daily. A dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the subject, the severity of the condition being treated, and the compound being employed. For example, dosages can be empirically determined considering the type and stage of cancer diagnosed in a particular subject. The dose administered to a subject, in the context of the provided methods should be sufficient to affect a beneficial therapeutic response in the patient over time. Determination of the proper dosage for a particular situation is within the skill of the practitioner. Thus, effective amounts and schedules for administering the agent may be determined empirically by one skilled in the art. The dosage should not be so large as to cause substantial adverse side effects, such as unwanted cross-reactions, anaphylactic reactions, and the like. The dosage can be adjusted by the individual physician in the event of any contraindications. Guidance can be found in the literature for appropriate dosages for given classes of pharmaceutical products.

Provided herein is a method of reducing or inhibiting tumor cell viability by contacting the tumor cell with a recombinant adenovirus or recombinant adenovirus genome, or composition thereof, as disclosed herein. In some embodiments, the method is an in vitro method. In other embodiments, the method is an in vivo method and contacting the tumor cell comprises administering the recombinant adenovirus or recombinant adenovirus genome or composition to a subject with a tumor, such as a tumor lacking p53 transcriptional activity.

Further provided is a method of reducing or inhibiting tumor progression, or reducing tumor volume, or both, in a subject having a tumor lacking p53 transcriptional activity, by administering to the subject a therapeutically effective amount of a recombinant adenovirus or recombinant adenovirus genome (or composition thereof) disclosed herein.

Also provided is a method of treating cancer in a subject, wherein the cancer lacks p53 transcriptional activity, by administering to the subject a therapeutically effective amount of a recombinant adenovirus or recombinant adenovirus genome (or composition thereof) disclosed herein.

The following examples are provided to illustrate certain particular features and/or embodiments. These examples should not be construed to limit the disclosure to the particular features or embodiments described.

EXAMPLES

Example 1: Negatively Regulated Selective Oncolytic Adenovirus

This example describes the development of a synthetic adenovirus that selectively replicates in cells lacking p53 transcriptional activity.

Description of Synthetic Adenoviruses

The synthetic p53-selective adenoviruses described in this example contain a synthetic p53-responsive two step transcriptional activation (TSRA) circuit. A TSTA module was inserted in the viral genome between the L5-E4 synthetic split poly-A unit. An essential viral protein, E2A DNA binding protein (DBP), was deleted from the virus genome transcriptional unit and placed under the control of the TSTA circuit. A transcriptional repressor, TetR, was expressed in the TSTA circuit under the control of a p53 regulated promoter (PrMin). TetR is inducibly controlled via doxycycline to regulate the expression of DBP that was deleted from the viral E2 transcriptional unit. In cells with p53 transcriptional activity, TetR expression is induced by the p53-responsive promoter, and TetR protein suppresses activity of the CMV-Tet-O promoter, preventing expression of DBP. In the absence of DBP, adenovirus is unable to replicate. In cells lacking p53 transcriptional activity, TetR is not expressed, which allows for expression of DBP and adenovirus replication.

The synthetic adenoviruses also contain a mutation in E1-55 k that inhibits the ability of the E1E55 k protein to bind, inactivate or degrade cellular p53 and have deletions in six E3 genes (Δ12.5 k, Δ6.7 k, A39 k, ΔRIDα, ΔRIDβ, Δ14.7 k), which enhances replication of the virus and provides space in the Ad genome for the addition of exogenous genes. A summary of the virus mutations relative to wild-type Ad5 are listed in Table 1.

possible with the TetR system, CMV-Tet-O::DBP and CMV::TetR were inserted following the major late transcript (MLT). The CMV-Tet-O promoter is optimized for high expression in the absence of TetR and maximum repression by the TetR protein (Urlinger et al., *Proc Natl Acad Sci USA* 97(14):7963-7968, 2000). A schematic of this circuit and the resulting control authority is shown in FIG. 1A.

Figure 2A:
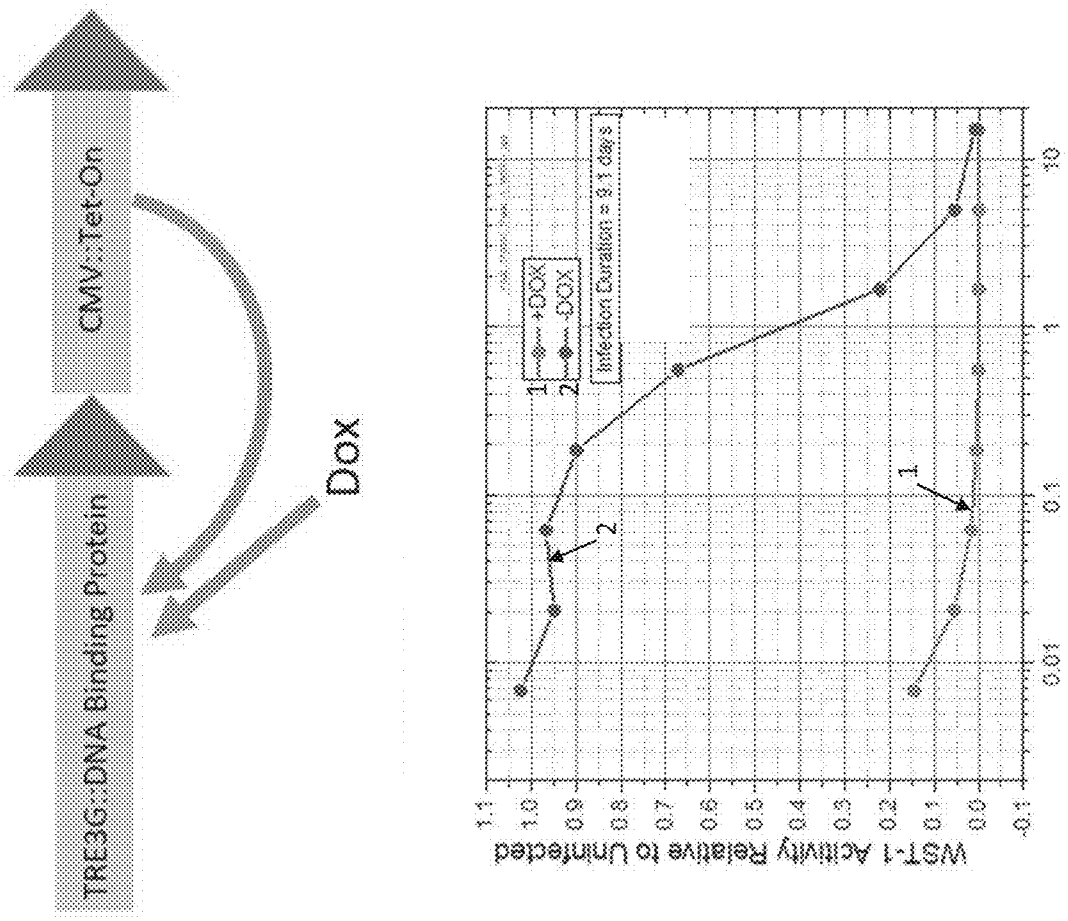
FIGS. 2A and 2B: A side-by-side comparison of the Tet-On and TetR systems used to control Ad5 replication.
Figure 2B:
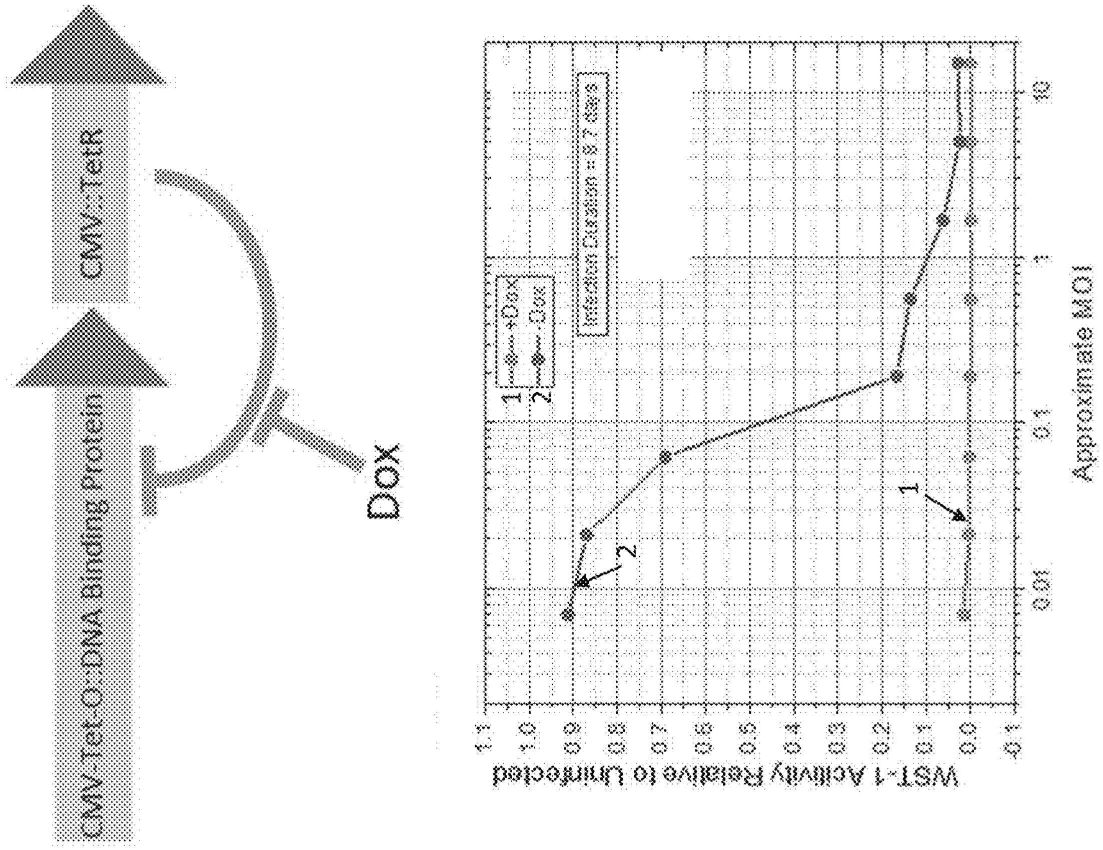

Comparing the TetR system performance to that of the Tet-On system highlights two differences (FIGS. 2A-2B). The off-state of the TetR system is not as complete as that of the Tet-On system, and the on-state of the Tet-On system is not as complete as that of the TetR system. Both of these observations make sense in light of the control mechanisms of the Tet-On and TetR systems. To generate the off-state in the TetR system, the TetR protein must first be transcribed, translated, and accumulate in the cell, causing an initial delay in suppression of the CMV-Tet-O promoter. During this delay, some amount of DBP mRNA is transcribed. Conversely, the Tet-O system begins in the off-state and there is a time delay associated with the transcription, translation, and accumulation of the Tet-On protein required for activating the TRE3G promoter, thus the on-state of the Tet-On system is slower than that of the TetR system.

p53-Sensitive Promoter

Figure 3:
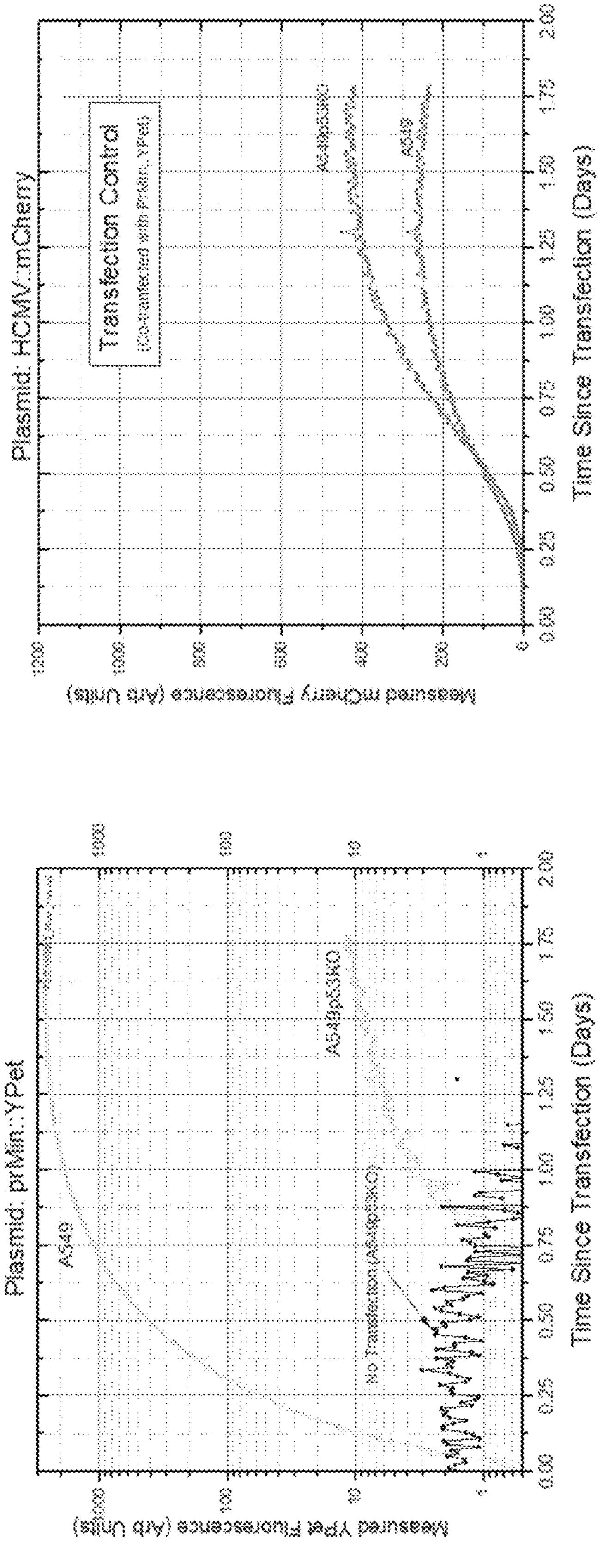
FIG. 3: YPet fluorescence produced by PrMin::YPet plasmid transfected into A549 and A549p53KO cells. Also shown is measured mCherry fluorescence produced by a co-transfected CMV::mCherry plasmid.

To convert the TetR-controlled virus into a p53-selective virus, the CMV promoter driving TetR expression was replaced with a p53-sensitive promoter referred to as prMin-RGC (Kühnel et al., *Cancer Gene Ther.* 11:28-40, 2004). This promoter consists of 13 p53-binding sites in combination with a minimal CMV promoter. This promoter was reconstituted on a plasmid driving YPet expression. Transfecting this plasmid into A549 and A549p53KO cell lines demonstrated the p53-selective nature of this promoter (FIG. 3). The A549p53KO cell line is a $p53^{-/-}$ version of the A549 cell line generated using CRISPR.

The prMin-RGC promoter exhibits a dynamic range of approximately 200× between $p53^{+/+}$ and $p53^{-/-}$ cell lines. To measure the performance of this promoter in the context of

TABLE 1

Synthetic Adenovirus

| Virus Name | SEQ ID NO: | Mutations Relative to WT Ad5 |
|---|---|---|
| CMBT-1065 | 1 | ΔE2-DBP, Δ12.5k, Δ6.7k, Δ19k, mCherry-P2A-ADP, ΔRIDα, ΔRIDβ, Δ14.7k, SV40-PolyA on L5 side, CMV-Tet-O::DNA Binding Protein, PrMin::TetR, Tet-On Poly-A |
| CMBT-1066 | 2 | ΔE1B-55k, ΔE2-DBP, Δ12.5k, Δ6.7k, Δ19k, mCherry-P2A-ADP, ΔRIDα, ΔRIDβ, Δ14.7k, SV40-PolyA on L5 side, CMV-Tet-O::DNA Binding Protein, PrMin::TetR, Tet-On Poly-A |
| CMBT-1093 | 3 | E1B-55k[H260A], ΔE2-DBP, Δ12.5k, Δ6.7k, Δ19k, mCherry-P2A-ADP, ΔRIDα, ΔRIDβ, Δ14.7k, SV40-PolyA on L5 side, CMV-Tet-O::DNA Binding Protein, PrMin::TetR, Tet-On Poly-A |
| CMBT-1094 | 4 | E1B-55k[R240A], ΔE2-DBP, Δ12.5k, Δ6.7k, Δ19k, mCherry-P2A-ADP, ΔRIDα, ΔRIDβ, Δ14.7k, SV40-PolyA on L5 side, CMV-Tet-O::DNA Binding Protein, PrMin::TetR, Tet-On Poly-A |
| CMBT-1254 | 5 | E1B-55k[H260R], ΔE2-DBP, Δ12.5k, Δ6.7k, Δ19k, mCherry-P2A-ADP, ΔRIDα, ΔRIDβ, Δ14.7k, SV40-PolyA on L5 side, CMV-Tet-O::DNA Binding Protein, PrMin::TetR, Tet-On Poly-A |

Virus Regulated by the TetR System

Figure 4:
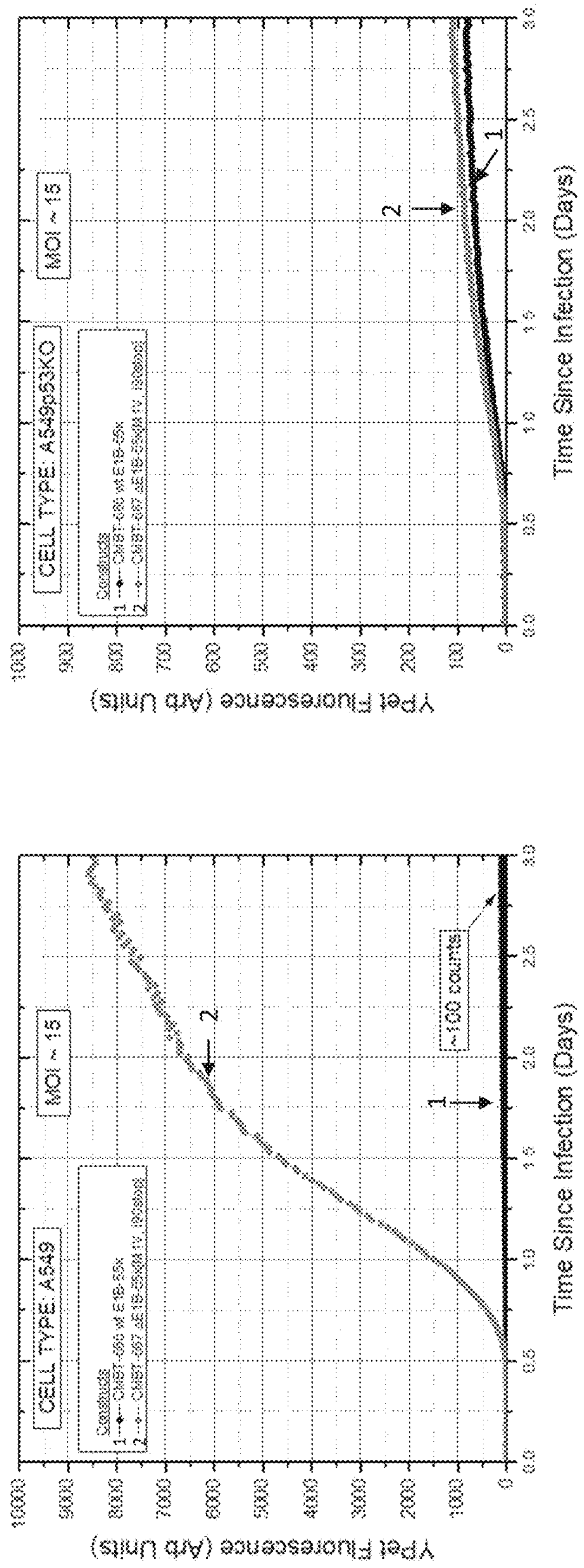
FIG. 4: YPet fluorescence produced by sensor viruses after infection of A549 and A549p53KO cell lines. YPet fluorescence produced by a virus with WT E1B-55 k (CMBT-666) and for virus with a deletion of E1B-55 k (CMBT-667) is shown. CMBT-666: Δ12.5 k, Δ6.7 k, Δ19 k, mCherry-P2A-ADP, ΔRIDα, ΔRIDβ, Δ14.7 k, SV40 Poly-A on L5 side, PrMin::YPet (rev). CMBT-667: E1B-55 k[M1V, I90stop], Δ12.5 k, Δ6.7 k, Δ19 k, mCherry-P2A-ADP, ΔRIDα, ΔRIDβ, Δ14.7 k, SV40 Poly-A on L5 side, PrMin::YPet (rev).

An adenovirus engineered to control expression of the DNA binding protein (DBP) with a TSTA circuit has been shown to exhibit an approximate 1000-fold difference in tissue culture infectious dose 50% (TCID50) between cells cultured in the presence of doxycycline and cells cultured in the absence of doxycycline. To test what level of control is an adenovirus infection, PrMin::YPet was cloned into the region between L5 poly-A and E4 poly-A. Two "sensor" viruses were produced, one with WT E1B-55 k (CMBT-666) and another with ΔE1B-55 k (CMBT-667). When A549 cells were infected, a large YPet signal was produced only with the ΔE1B-55 k virus (FIG. 4). When A549p53KO cells were infected, neither of the sensor viruses produced significant YPet signal. With ΔE1B-55 k, the PrMin promoter exhibits a dynamic range of about 80×. This data shows how efficiently the WT E1B-55 k protein of Ad5 degrades p53. No significant signal was produced by the sensor virus containing WT E1B-55 k. Many of the previously described p53-selective viruses were constructed with WT E1B55 k. Because of the efficient degradation of p53 by WT E1B-55 k, one should not expect high expression of any Ad5 gene using a p53-sensitive promoter and thus the repressive effects of these p53-driven gene products are minimal.

Figure 5:
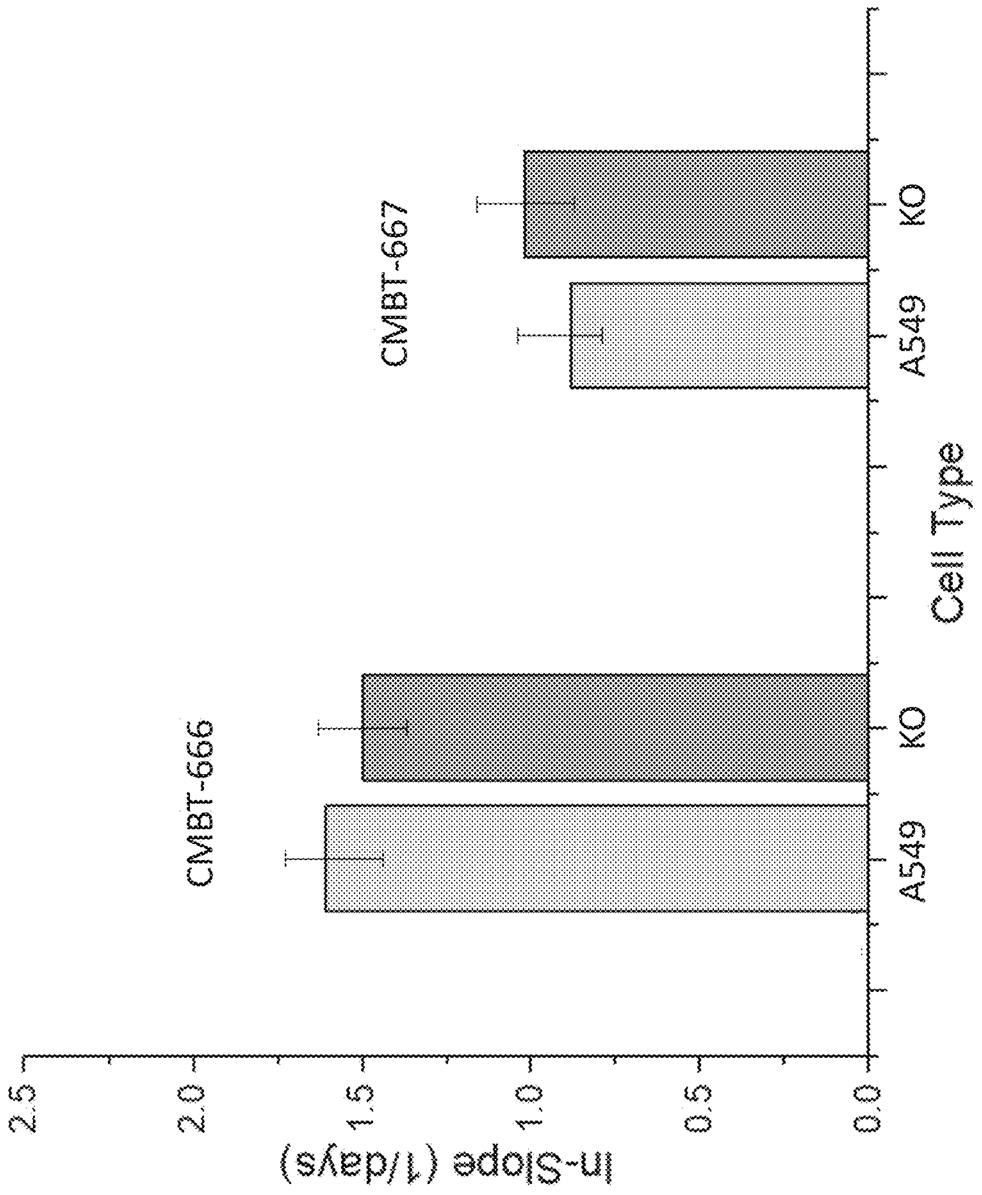
FIG. 5: Replication kinetics of sensor viruses with WT E1B-55 k or ΔE1B-55 k. Replication of CMBT-666 and CMBT-667 was tested in A549 and A549p53KO cell lines.

However, there is a high cost in replication kinetics when deleting E1B-55 k completely from Ad5. Each of the sensor viruses described above also contain mCherry-P2A-ADP as a kinetics readout. FIG. 5 shows the measured replication kinetics for the sensor viruses when infecting A549 and A549p53KO cells. This data confirms that a significant kinetic defect occurs with deletion of E1B-55 k.

Figure 6:
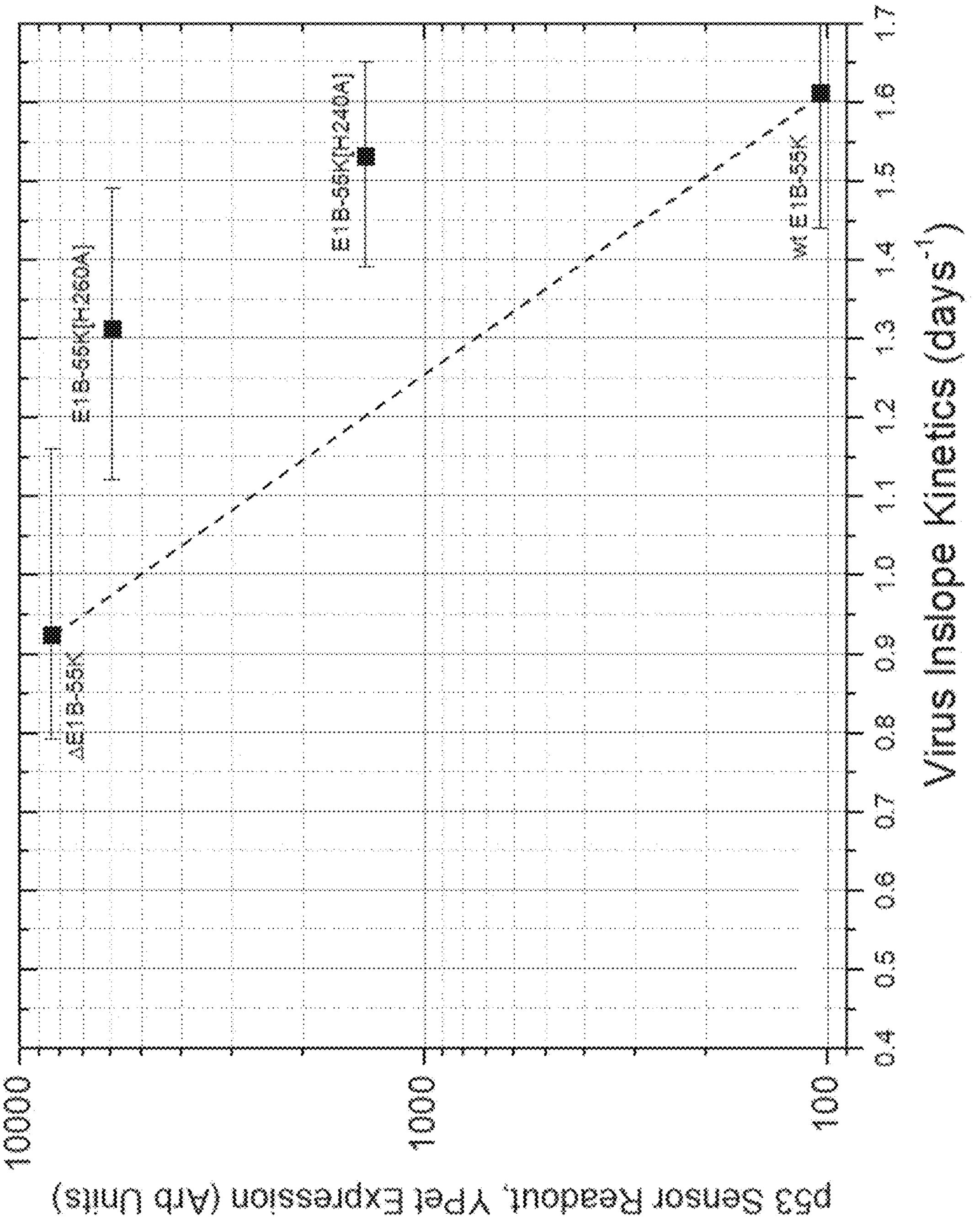
FIG. 6: p53 transcriptional activity (YPet signal) compared with virus replication kinetics for sensor viruses when infecting A549 cells. The sensor viruses have either wild-type E1B-55 k, a full deletion of E1B-55 k, E1B-55 k[H260A] or E1B-55 k[R240A].

Binding and inactivation of p53 by E1B-55 k must be mitigated in order to achieve activation of a p53-sensitive promoter placed within the Ad5 genome, but wholesale deletion of E1B-55 k incurs a high cost in kinetics. Point mutations in E1B-55 k have been described that abrogate to some extent the interaction between E1B-55 k and p53 while mostly maintaining the other functions of E1B-55 k (Shen et al., *J. Virol.* 75(9):4297-4307, 2001). Two exemplary mutations described herein are: E1B-55 k[H260A] and E1B-55 k[R240A]. These mutations were cloned into sensor viruses and the resulting p53 transcriptional activity vs. virus kinetics was measured (FIG. 6).

p53-Selective, Negatively-Regulated Ad

Figure 7:
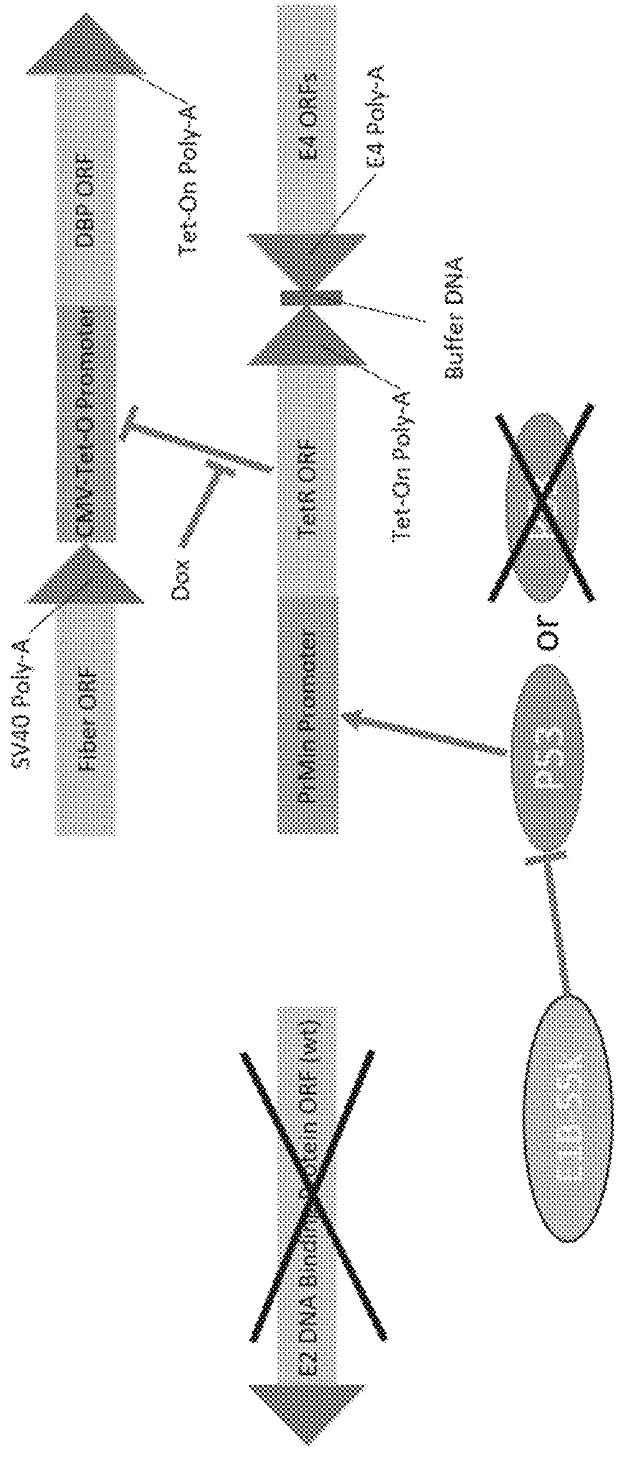
FIG. 7: Schematic of p53-selective, negative control of Ad5 replication. The E1B-55 k protein is either wild-type, completely deleted, or contains an H260A or R240A point mutation. Testing is performed in $p53^{+/+}$ or $p53^{-/-}$ cell lines.
Figure 8A:
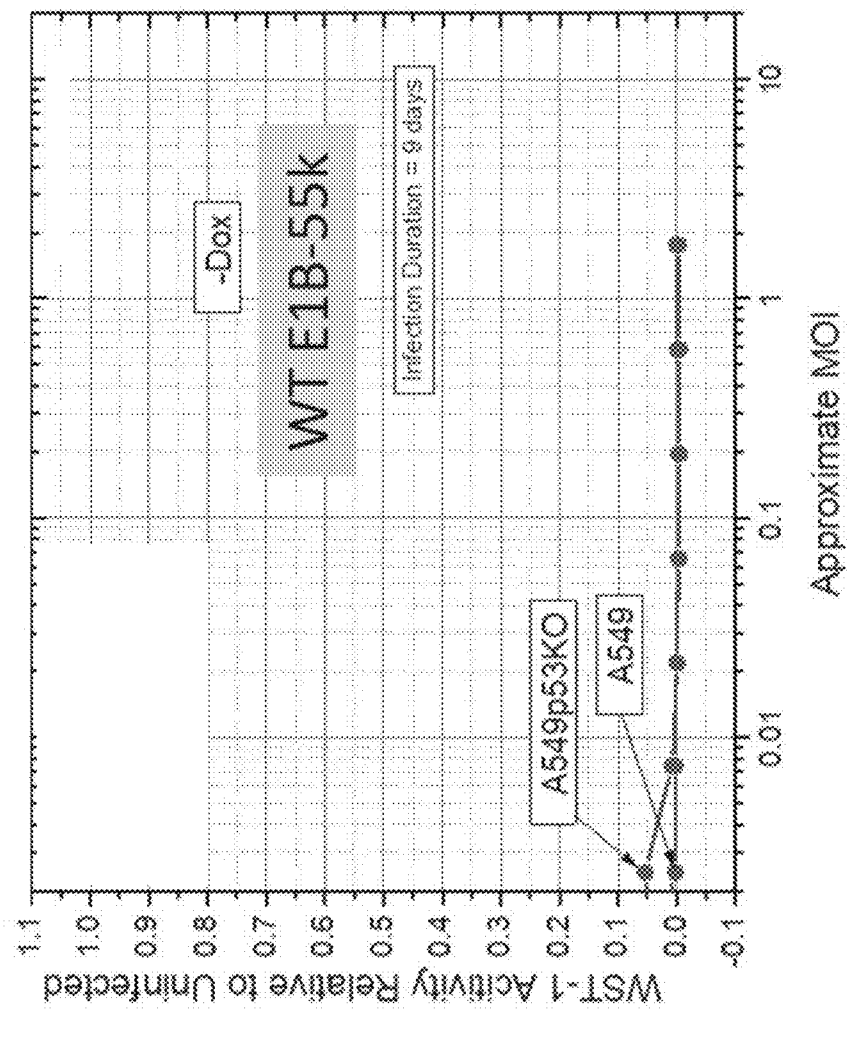
FIGS. 8A-8D: Cell viability 9 days post-infection in A549 and A549p53KO cells infected with p53-selective viruses containing various mutations in E1B-55 k.
Figure 8B:
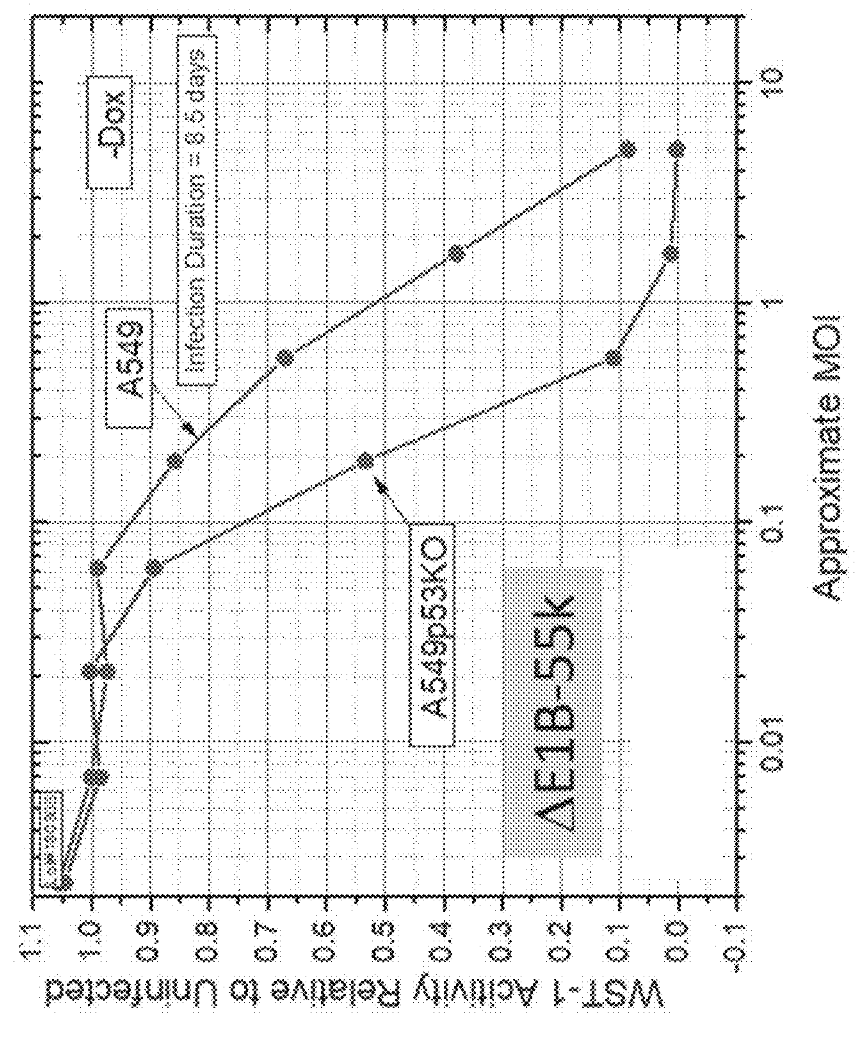
Figure 8C:
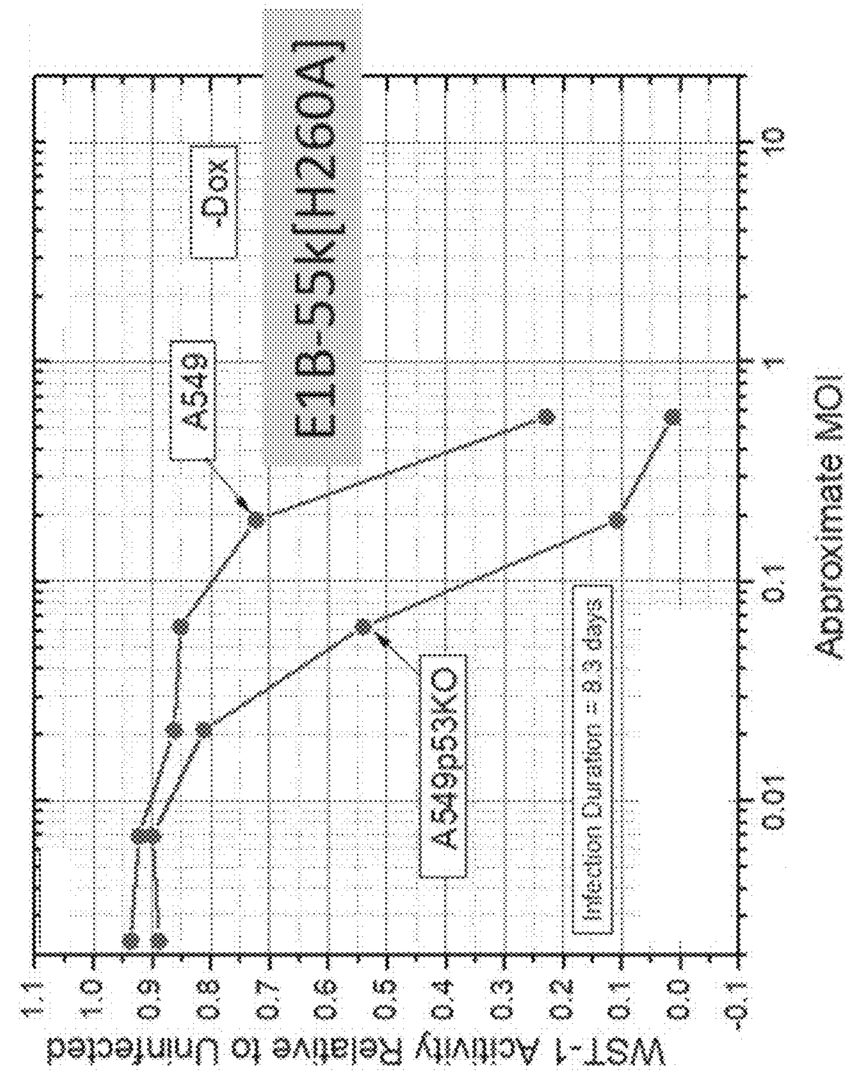
Figure 8D:
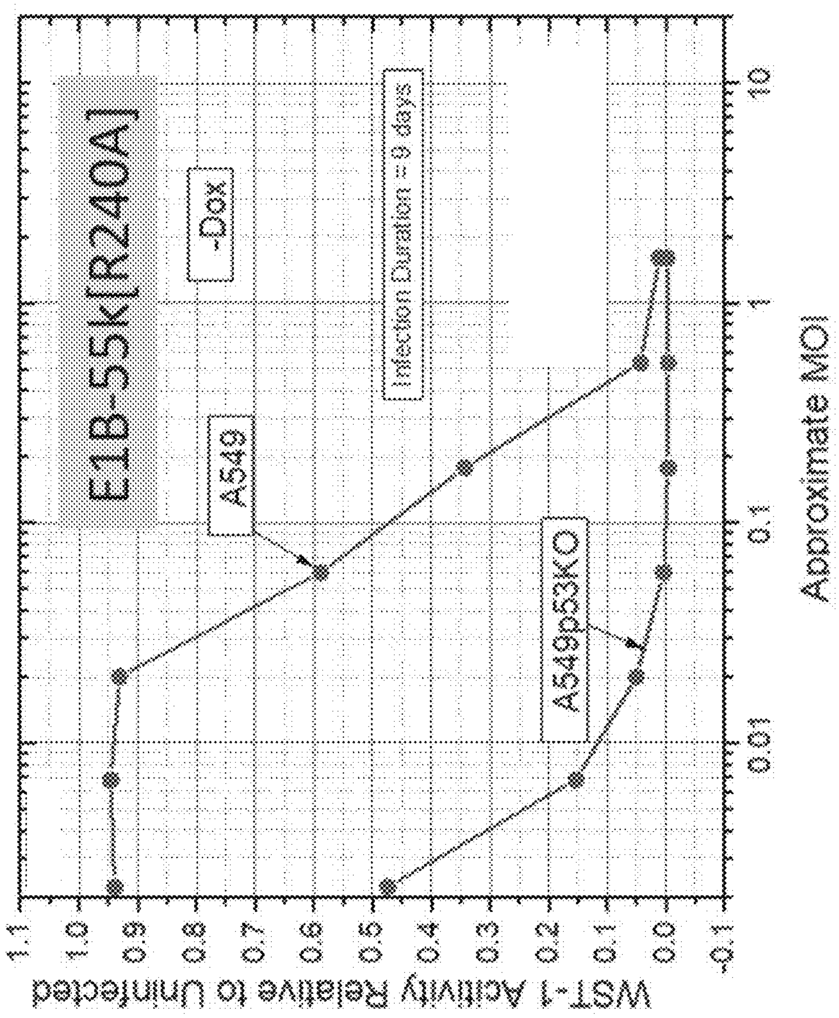
Figure 9:
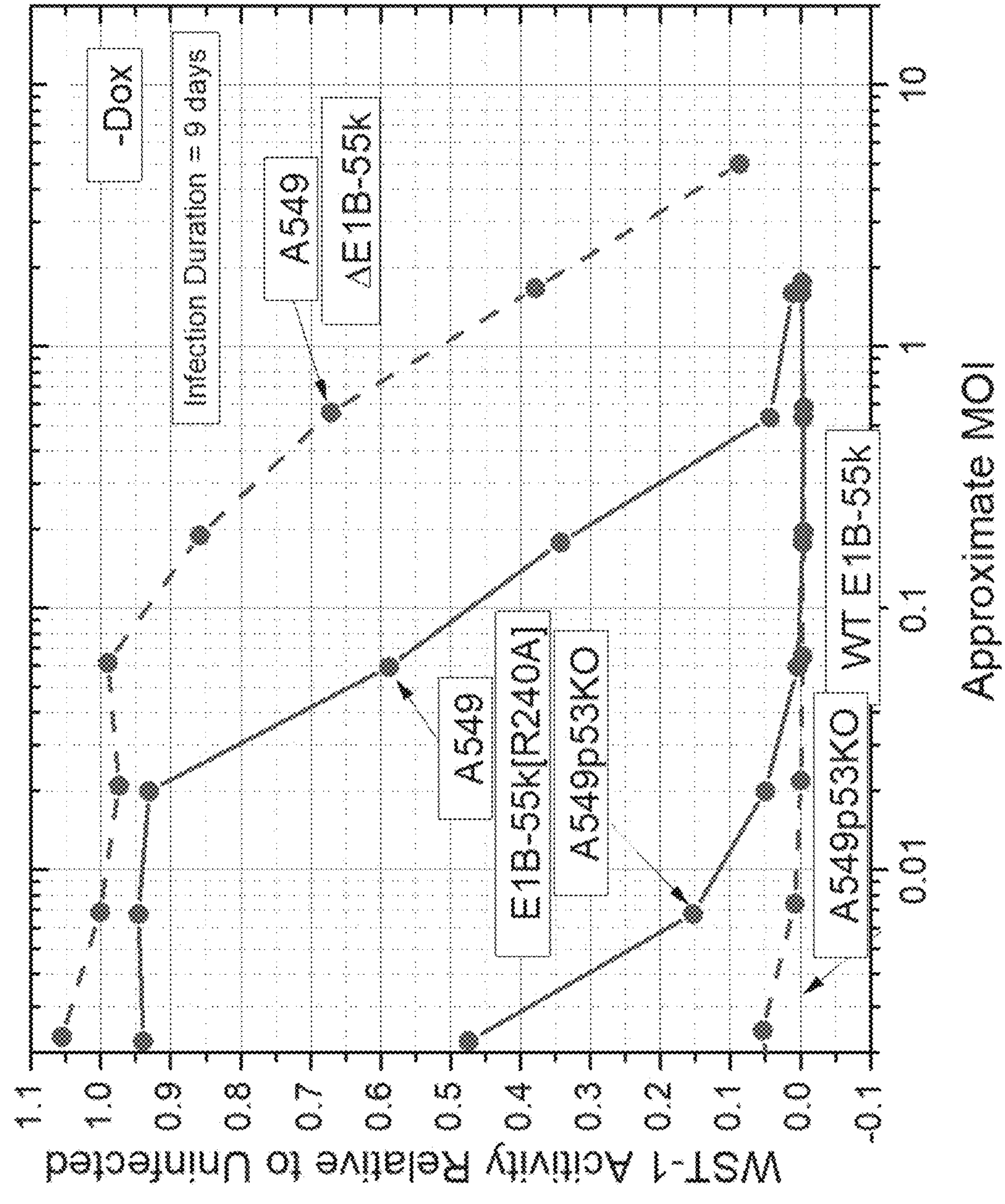
FIG. 9: Comparison of cell viability between E1B-55 k[R240A] virus (CMBT-1094) shown with solid lines and that of WT E1B-55 k virus (CMBT-1065) in A549p53KO cells and ΔE1B-55 k virus in A549 cells shown with dashed lines.

To further evaluate the effect of mutations in E1B-55 k, four versions of E1B-55 k (WT, ΔE1B-55 k, E1B-55 k[H260A] and E1B-55 k[R240A]) were cloned into the p53-selective virus shown schematically in FIG. 7. The resulting synthetic adenoviruses are referred to as CMBT-1065 (SEQ ID NO: 1), CMBT-1066 (SEQ ID NO: 2), CMBT-1093 (SEQ ID NO: 3) and CMBT-1094 (SEQ ID NO: 4) (see Table 1). The p53 selectivity of these viruses is shown in FIGS. 8A-8D using a cell viability assay to determine cell killing versus initial MOI when infecting A549 and A549p53KO cells. The virus with WT E1-55 k (FIG. 8A) showed no selectivity because WT E1B-55 k is so effective at degrading p53. The virus with ΔE1B-55 k (FIG. 8B) showed some differential between A549 and A549p53KO. This virus exhibited an excellent off state, but a very weak on state, due to the kinetic hit caused by deletion of E1B-55 k. The virus with E1B-55 k[H260A] (FIG. 8C) showed an improved on state compared to the ΔE1B-55 k virus, but a slightly worse off state. The best results were obtained with the E1B-55 k[R240A] virus (FIG. 8D). Though the off state for this virus was slightly worse that the H260A mutation, the on state is significantly improved. The TCID50 for this virus is about 100× different between $p53^{+/+}$ and $p53^{-/-}$ cell lines. FIG. 9 shows the performance of the E1B-55 k[R240A] virus in both A549p53KO and A549 cells overlaid with that of the WT E1B-55 k virus in A549p53KO cells and ΔE1B-55 k virus in A549 cells. A synthetic adenovirus having an H260R in E1B-55 k (CMBT-1254; SEQ ID NO: 5) is expected to exhibit results similar or superior to CMBT-1094.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A recombinant adenovirus genome, comprising:

an E1B region encoding a modified 55k protein, wherein p53 degradation activity of the modified 55k protein is reduced compared to a wild-type 55k protein;

an E2A region comprising a deletion of the DNA binding protein (DBP) open reading frame (ORF);

an E3 region comprising an adenovirus death protein (ADP) ORF and comprising a deletion of the 12.5k, 6.7k, 19k, RIDα, RIDβ and 14.7k ORFs;

an E4 region;

L1, L2, L3, L4 and L5 regions;

a first exogenous nucleic acid sequence comprising a CMV-Tet-O promoter operably linked to an adenovirus DBP ORF; and a second exogenous nucleic acid sequence comprising a p53-responsive promoter operably linked to a tetracycline repressor (TetR) protein ORF.

2. The recombinant adenovirus genome of claim 1, wherein the first and second exogenous nucleic acid sequences are located between the L5 and E4 regions of the adenovirus genome.

3. The recombinant adenovirus genome of claim 2, wherein the first exogenous nucleic acid sequence precedes the second exogenous nucleic acid sequence.

4. The recombinant adenovirus genome of claim 1, wherein the first exogenous nucleic acid sequence further comprises a first heterologous polyA sequence following the DBP ORF.

5. The recombinant adenovirus genome of claim 4, wherein the second exogenous nucleic acid sequence further comprises a second heterologous polyA sequence following the TetR ORF.

6. The recombinant adenovirus genome of claim 5, further comprising a third heterologous polyA sequence following the L5 region and preceding the first and second exogenous nucleic acid sequences.

7. The recombinant adenovirus genome of claim 1, wherein the p53-responsive promoter is prMinRGC.

8. The recombinant adenovirus genome of claim 1, wherein the modified 55k protein comprises a mutation selected from H260R, H260A, H260D, R240A, R240E and R240H with respect to SEQ ID NO: 6.

9. The recombinant adenovirus genome of claim 1, further comprising a reporter gene.

10. The recombinant adenovirus genome of claim 9, wherein the reporter gene is operably linked to and in the same reading frame as a self-cleaving peptide coding sequence and the ADP ORF.

11. The recombinant adenovirus genome of claim 1, comprising at least one modification to detarget an adenovirus from the liver.

12. The recombinant adenovirus genome of claim 11, further comprising one or more binding sites for a liver-specific microRNA.

13. The recombinant adenovirus genome of claim 12, wherein the liver-specific microRNA is miR-122.

14. The recombinant adenovirus genome of claim 1, wherein the genome encodes a chimeric fiber protein comprising a fiber shaft from a first adenovirus serotype and a fiber knob from a second adenovirus serotype.

15. The recombinant adenovirus genome of claim 14, wherein the first adenovirus serotype is Ad5 and the second adenovirus serotype is Ad3, Ad9, Ad11, Ad12, Ad34 or Ad37.

16. The recombinant adenovirus genome of claim 1, wherein the genome encodes a fiber protein modified to include an RGD peptide.

17. The recombinant adenovirus genome of claim 1, wherein the nucleotide sequence of the genome is at least 95% identical to SEQ ID NO: 3, SEQ ID NO: 4 or SEQ ID NO: 5.

18. An isolated cell comprising the recombinant adenovirus genome of claim 1.

19. A composition comprising the recombinant adenovirus genome of claim 1 and a pharmaceutically acceptable carrier.

20. An isolated adenovirus comprising the recombinant adenovirus genome of claim 1.

21. A composition comprising the adenovirus of claim 20 and a pharmaceutically acceptable carrier.

22. A method of reducing or inhibiting tumor progression, reducing tumor volume, or both, in a subject having a tumor deficient in p53 transcriptional activity, comprising administering to the subject a therapeutically effective amount of the recombinant adenovirus of claim 20, thereby reducing or inhibiting tumor progression, reducing tumor volume, or both, in the subject.

23. A method of treating a cancer in a subject having a cancer deficient in p53 transcriptional activity, comprising administering to the subject a therapeutically effective amount of the recombinant adenovirus of claim 20, thereby treating cancer in the subject.

* * * * *